US009493436B2

(12) United States Patent
Zhang et al.

(10) Patent No.: US 9,493,436 B2
(45) Date of Patent: Nov. 15, 2016

(54) **TYROSINE PHOSPHATASE INHIBITORS AND USES THEREOF TO MODULATE THE ACTIVITY OF ENZYMES INVOLVED IN THE PATHOLOGY OF *MYCOBACTERIUM TUBERCULOSIS***

(75) Inventors: Zhong-Yin Zhang, Carmel, IN (US); Yantao He, Indianapolis, IN (US); Li-Fan Zeng, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/114,077

(22) PCT Filed: Apr. 25, 2012

(86) PCT No.: PCT/US2012/035039
§ 371 (c)(1),
(2), (4) Date: Nov. 26, 2013

(87) PCT Pub. No.: WO2012/149049
PCT Pub. Date: Nov. 1, 2012

(65) Prior Publication Data
US 2014/0179735 A1     Jun. 26, 2014

Related U.S. Application Data

(60) Provisional application No. 61/479,092, filed on Apr. 26, 2011.

(51) Int. Cl.
*C07D 417/12* (2006.01)
*C07D 413/12* (2006.01)
(Continued)

(52) U.S. Cl.
CPC .......... *C07D 307/80* (2013.01); *C07D 209/42* (2013.01); *C07D 307/84* (2013.01);
(Continued)

(58) Field of Classification Search
None
See application file for complete search history.

(56) References Cited

U.S. PATENT DOCUMENTS 6,867,200 B1    3/2005 Allen et al.
6,998,415 B2    2/2006 Talley et al.
(Continued)

FOREIGN PATENT DOCUMENTS

| WO | WO2008002674 A2 | 1/2008 |
| WO | WO2009049098 A2 | 4/2009 |
| WO | WO2010118241 A2 | 10/2010 |

OTHER PUBLICATIONS

Danziger, Automated Site-Directed Drug Design: A General Algorithm for Knowledge Acquisition about Hydrogen-Bonding Regions at Protein Surfaces, Proceedings of the Royal Society of London. Series B, Biological Sciences, 1989, 236(1283), pp. 101-113.*

(Continued)

*Primary Examiner* — San-Ming Hui
*Assistant Examiner* — Andrew Lee
(74) *Attorney, Agent, or Firm* — Faegre Baker Daniels LLP

(57) ABSTRACT

A variety of benzofurans and indole derivatives some with an alkynyl linker are disclosed herein. These compounds are not highly charged at physiological pH and have good bioavailability characteristics. These compounds exhibit selective or at least preferential affinity for the active sites of various sub-sets of protein tyrosine phosphatases. Some of these compounds are excellent inhibitors of *Mycobacterium* protein tyrosine phosphatase B (mPTPB) a protein tyrosine phosphatase expressed in *Mycobacterium tuberculosis* and characterized as a virulence factor in the causal agent of tuberculosis. Accordingly, many of these compounds and pharmaceutically acceptable salts thereof are useful for the treatment of diseases such as tuberculosis.

17 Claims, 14 Drawing Sheets

Reagents and conditions: a) ICl, AcOH, rt; b) Acetone, TFA, TFAA, rt;
c) MeI, K₂CO₃, DMSO, rt; d) Pd(PPh₃)₂Cl₂, CuI, , DMF, rt; e) I₂, NaHCO₃, MeCN;
f) Pd(PPh₃)₂Cl₂, CuI, DMF, rt; g) KOH, THF/H₂O, reflux; h) Lindalar catalysis, H₂, THF/MeOH, rt,; i) H₂, Pd/C, THF/MeOH, rt,

(51) Int. Cl.

| | | |
|---|---|---|
| C07D 407/06 | (2006.01) | |
| C07D 307/80 | (2006.01) | |
| C07D 401/12 | (2006.01) | |
| C07D 405/12 | (2006.01) | |
| C07D 407/12 | (2006.01) | |
| C07D 409/06 | (2006.01) | |
| C07D 209/42 | (2006.01) | |
| C07D 307/84 | (2006.01) | |

(52) U.S. Cl.
CPC ........... C07D401/12 (2013.01); C07D 405/12 (2013.01); C07D 407/06 (2013.01); C07D 407/12 (2013.01); C07D 409/06 (2013.01); C07D 413/12 (2013.01); C07D 417/12 (2013.01)

(56) References Cited

U.S. PATENT DOCUMENTS

| | | |
|---|---|---|
| 7,547,794 B2 | 6/2009 | Green et al. |
| 7,589,232 B2 | 9/2009 | Swinnen et al. |
| 7,772,216 B2 | 8/2010 | Hangauer et al. |
| 2005/0137234 A1 | 6/2005 | Bressi et al. |
| 2007/0232682 A1 | 10/2007 | Beard et al. |
| 2011/0136807 A1 | 6/2011 | Hangauer |
| 2011/0212947 A1 | 9/2011 | Maddaford et al. |
| 2012/0088720 A1 | 4/2012 | Zhang et al. |

OTHER PUBLICATIONS

International Search Report and Written Opinion mailed Aug. 3, 2012 in the related International Application No. PCT/US2012/035039.

Zhang et al., A salicylic acid-based small molecule inhibitor for the oncogenic Src homology-2 domain containing protein tyrosine phosphatase-2 (SHP2), J. Med. Chem. Mar. 25, 2010, 53 (6), 2482-2403 especially figure 1.

Grudner et al. Structural Basis for Selective Inhibition of *Mycobacterium tuberculosis* Protein Tyrosine Phosphatase PtpB. Cell, Structure, 2007, pp. 499-509; Elsevier doi: 10.1016/j.str.2007.03.003 [online] retrieved on Jul. 10, 2012 from internet, <URL: http://www.ncbi.nlm.nih.gov/pmc/articles/PMC2775457/?tool=pubmed>, abstract.

Beresford et al. MptpB, a virulence factor from *Mycobacterium tuberculosis*, exhibits triple-specificity phosphatase activity. Biochem. J., 2007, vol. 406, pp. 13-18; doi:10.1042/BJ20070670 [online] retrieved on Jul. 10, 2012 from internet,<URL: http://www.biochemj.org/bj/406/0013/4060013.pdf>, abstract.

\* cited by examiner

Reagents and conditions: a) ICl, AcOH, rt; b) Acetone, TFA, TFAA, rt;
c) MeI, K$_2$CO$_3$, DMSO, rt; d) Pd(PPh$_3$)$_2$Cl$_2$, CuI, , DMF, rt; e) I$_2$, NaHCO$_3$, MeCN;
f) Pd(PPh$_3$)$_2$Cl$_2$, CuI, DMF, rt; g) KOH, THF/H$_2$O, reflux; h) Lindalar catalysis, H$_2$, THF/MeOH, rt.; i) H$_2$, Pd/C, THF/MeOH, rt.$_1$ Conditions: a) Me₂SO₄, Na₂CO₃, acetone, r.t.; b) (CHO)n, NaCNBH₃, AcOH, r.t.; then R₂-Br, NaHCO₃, c) I₂, K₂CO₃, water, r.t.; d) , Pd(PPh₃)₂Cl₂, CuI, Et₃N, DMF; e) I₂, CH₂Cl₂, r.t; f) R₁- containing alkyne, Pd(PPh₃)₂Cl₂, CuI, Et₃N, DMF, r.t.; g) LiOH, THF/H₂O, reflux.

TYROSINE PHOSPHATASE INHIBITORS AND USES THEREOF TO MODULATE THE ACTIVITY OF ENZYMES INVOLVED IN THE PATHOLOGY OF *MYCOBACTERIUM TUBERCULOSIS*

PRIORITY CLAIM

This application is a 35 U.S.C. §371 National Stage Filing base on PCT Application No. PCT/US2012/35039 filed Apr. 25, 2012, which claims the benefit of U.S. Provisional Patent Application No. 61/479,092 filed on Apr. 26, 2011 each of these Applications is incorporated herein by reference in its entirety.

STATEMENT OF GOVERNMENT RIGHTS

This invention was made with government support under grant numbers CA69202 and CA152194 awarded by the National Institutes of Health. The government has certain rights in the invention.

FIELD OF THE INVENTION

Aspects of this disclosure relate to the synthesis and use of salicylic acid derivatives to selectively inhibit various tyrosine phosphatases.

BACKGROUND AND SUMMARY

According to the World Health Organization, about one third of the world's population is infected with *Mycobacterium tuberculosis* (Mtb), the causative agent of Tuberculosis (TB). Stewart G R, Robertson B D, Young D B: Tuberculosis: a problem with persistence. Nat. Rev. Microbiol. 2003, 1:97-105. In 2007 there were an estimated 13.7 million chronic active cases, 9.3 million new cases, and 1.8 million deaths of TB in the worldwide. The standard treatment of TB takes a period of six to nine months and uses multiple antibiotics targeting several metabolic processes, RNA transcription and cell wall synthesis. Because of the increasing ineffectiveness against multidrug-resistant (MDR) and extremely drug resistant (XDR) Mtb strains, new targets and drugs for anti-TB treatments are in urgent demand to shorten the treatment period and combat TB infections. Clatworthy A. E.; Pierson, E.; Hung, D. T. Targeting virulence: A new paradigm for antimicrobial therapy. Nat. Chem. Biol. 2007, 3,541-548. Objects of the instant invention include developing and using compounds that selectively inhibit tyrosine phosphatases to treat diseases such as tuberculosis and other conditions that involve pathologic tyrosine phosphatase activity.

BRIEF SUMMARY OF THE INVENTION

The present disclosure relates to the synthesis and use of salicylic acid derivatives to selectively inhibit various tyrosine phosphatases.

Some embodiments of the disclosure include a compound according to Formula A,

Formula A 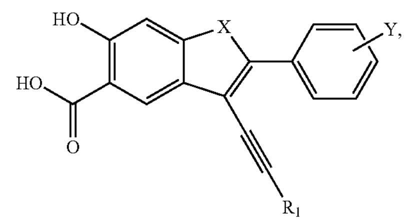 or a pharmaceutically acceptable salt thereof, wherein X is O and $R_1$ is selected from the group consisting of 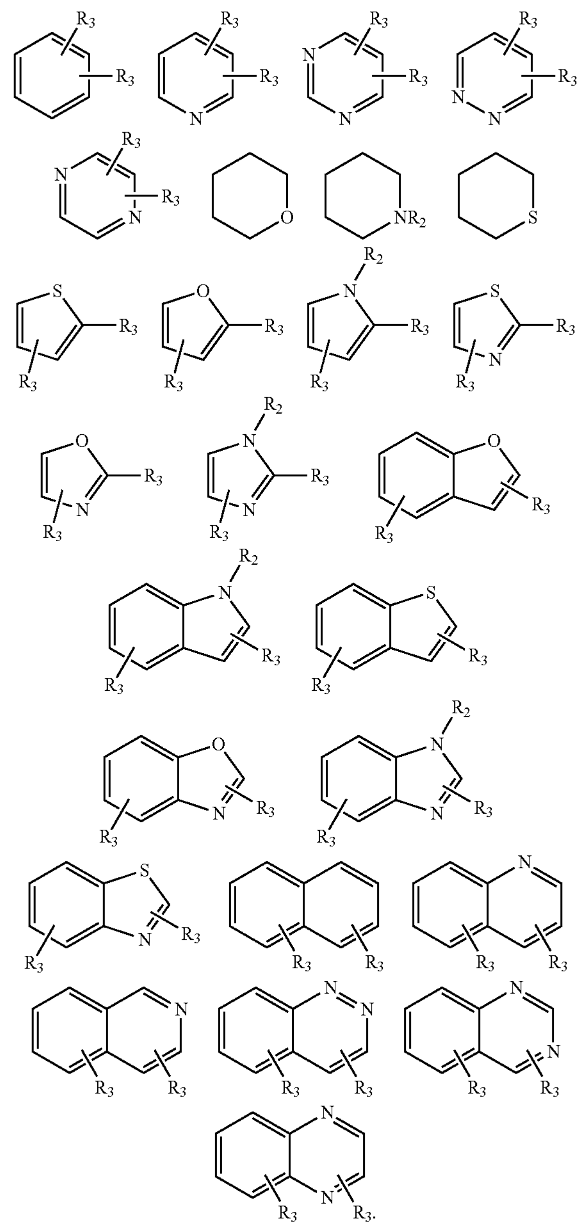 or hydrogen.

According to these embodiments, $R_3$ may be the same or different and is selected from the group consisting of H, halogen, hydroxyl, NR₂R₂, substituted or unsubstituted C₁-C₆ alkyl, substituted or unsubstituted C₁-C₆ alkenyl, substituted or unsubstituted C₁-C₆ alkynyl, O-(substituted or unsubstituted C₁-C₆ alkyl), S-(substituted or unsubstituted C₁-C₆ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, SO₂-(substituted or unsubstituted C₁-C₆ alkyl), SO₂NR₂R₂, C(O)-(substituted or unsubstituted C₁-C₆ alkyl), C(O)-(substituted or unsubstituted aryl), C(O)-(substituted or unsubstituted heteroaryl), (CH₂)ₙCO₂H, and O(CH₂)ₙCO₂H.

According to these embodiments, R₂ can be the same or different and is H or C₁-C₆ alkyl.

Additionally, according to these embodiments, Y may be H, halogen, hydroxyl, NR₂R₂, substituted or unsubstituted C₁-C₆ alkyl, substituted or unsubstituted C₁-C₆ alkenyl, substituted or unsubstituted C₁-C₆ alkynyl, O-(substituted or unsubstituted C₁-C₆ alkyl), S-(substituted or unsubstituted C₁-C₆ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, SO₂C₁-C₆ alkyl, SO₂NR₂R₂, C(O)-(substituted or unsubstituted C₁-C₆ alkyl), C(O)-(substituted or unsubstituted aryl), C(O)-(substituted or unsubstituted heteroaryl), —(CH₂)ₙCOZ, or —O—(CH₂)n-COZ; and n is selected from one of 1, 2, 3, and 4; and Z is one of OH, or N(R₄)₂, wherein each occurrence of R₄ may be the same or different and is selected from the group consisting of H, substituted or unsubstituted C₁-C₆ alkyl, substituted or unsubstituted C₃-C₈ cycloalkyl, substituted or unsubstituted C₁-C₆ alkenyl, substituted C₁-C₆ alkynyl, substituted or unsubstituted aryl, substituted or unsubstituted heteroaryl,

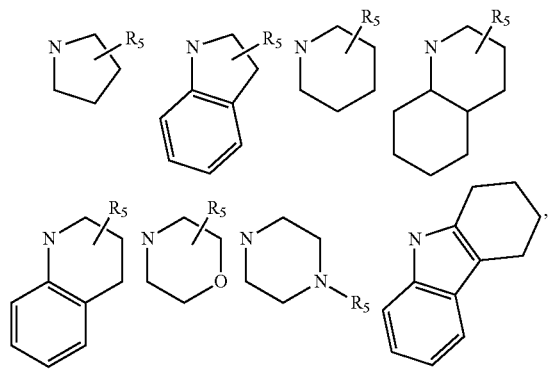

OR₅, and NHR₅, wherein R₅ is substituted or unsubstituted C₁-C₆ alkyl, substituted or unsubstituted aryl, substituted or unsubstituted heteroaryl, C(O)-(substituted or unsubstituted C₁-C₆alkyl), C(O)-(substituted or unsubstituted aryl), C(O)-(substituted or unsubstituted heteroaryl), or C(O)-(substituted or unsubstituted C₃-C₈ cycloalkyl).

In other embodiments of the present, R₁ of the compound described above is

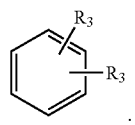

In some embodiments of the present disclosure, R₃ of the compound described above is selected from the group consisting of H, Cl, F; OCH₃, CF₃, OCF₃, OPh, and OCH₂CO₂H; Y is selected from the group consisting of H, CF₃, OCF₃, Cl, Ph, OPh, and —OCH₂COZ; and Z is selected from the group consisting of:

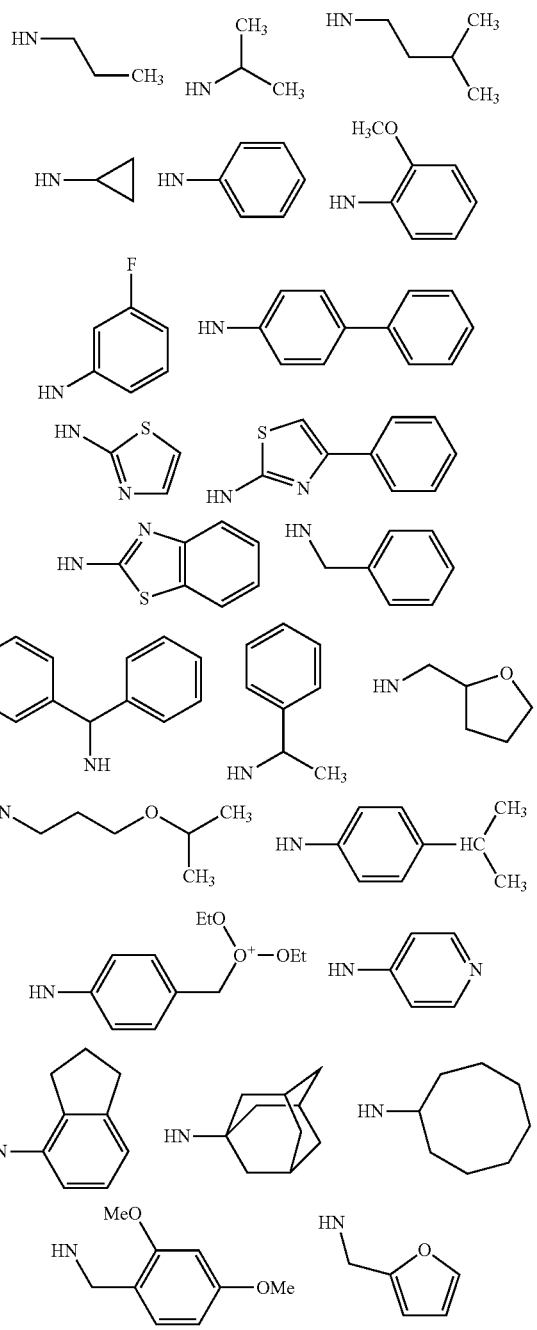

-continued
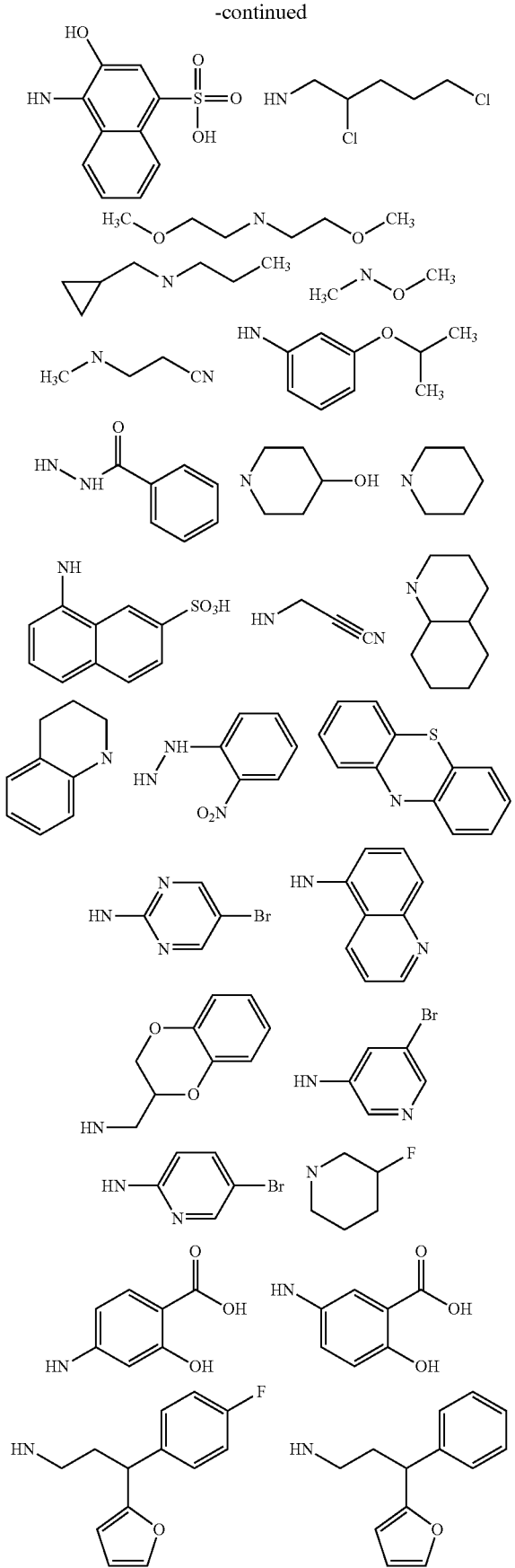
-continued
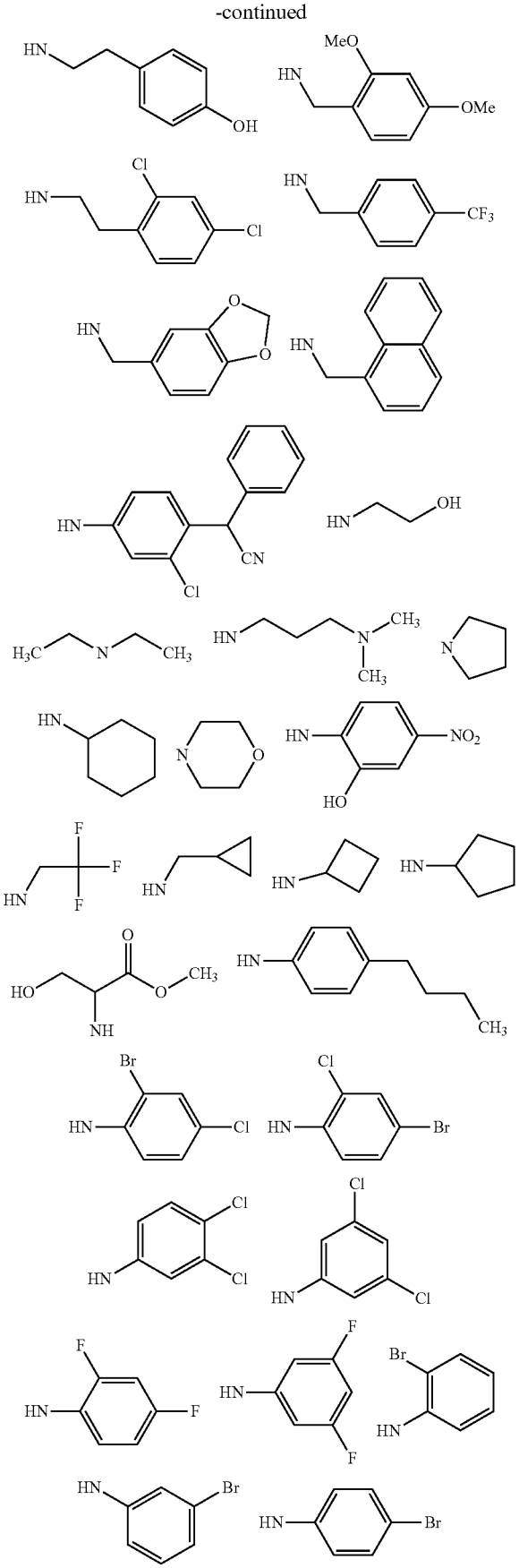

-continued
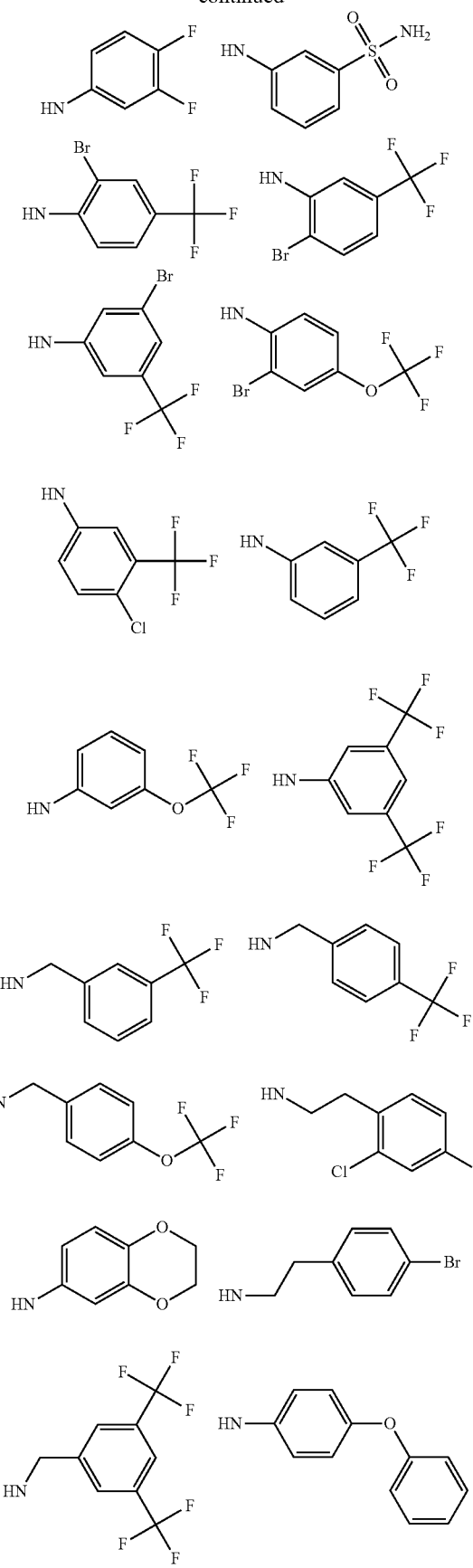
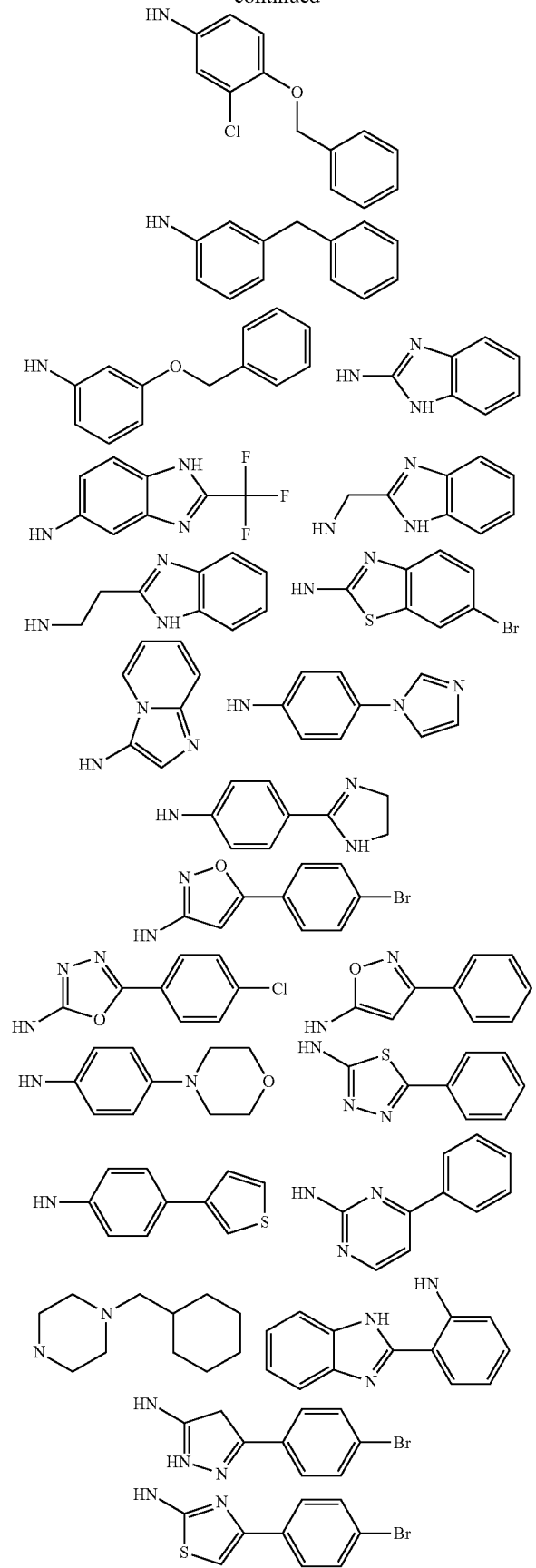

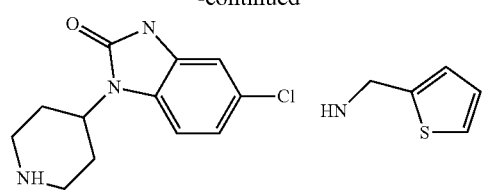
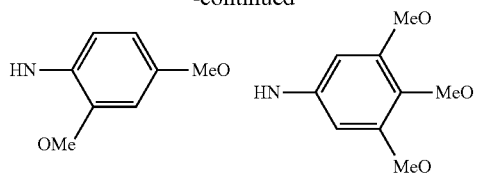
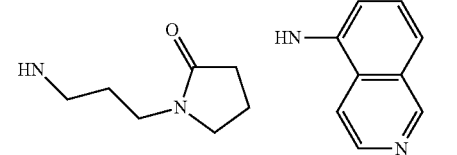
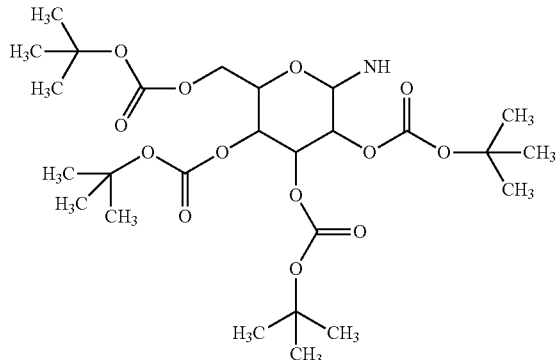
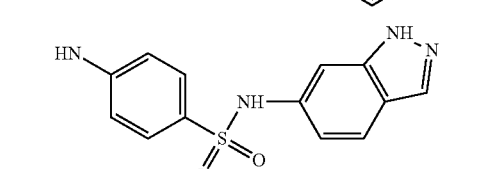
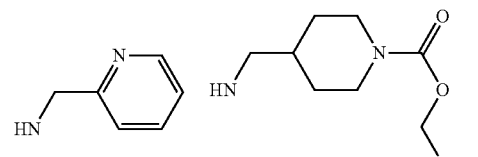
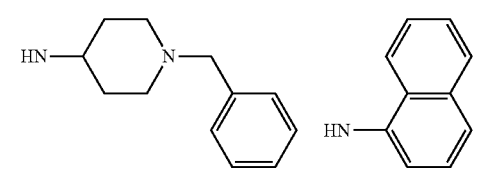
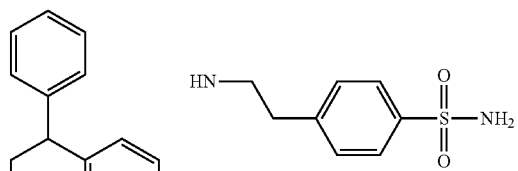
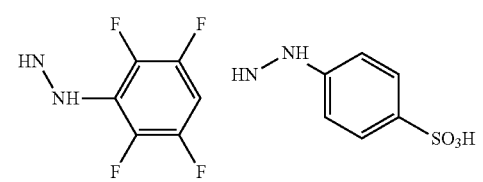
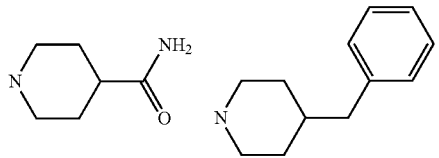

-continued
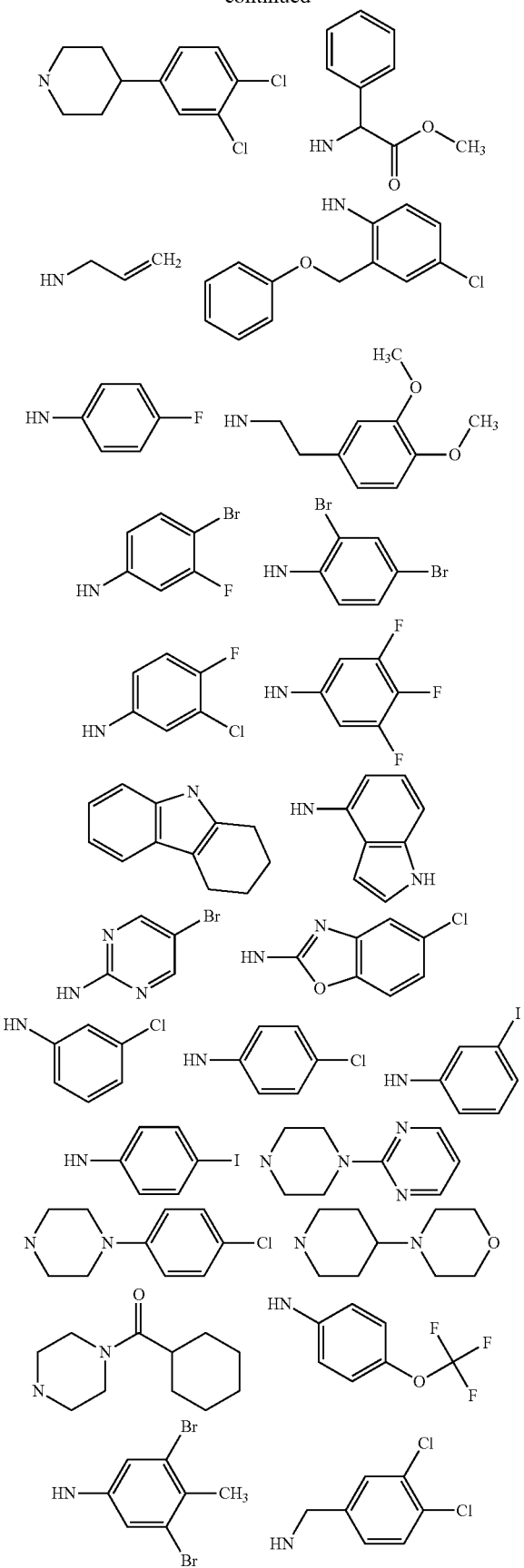
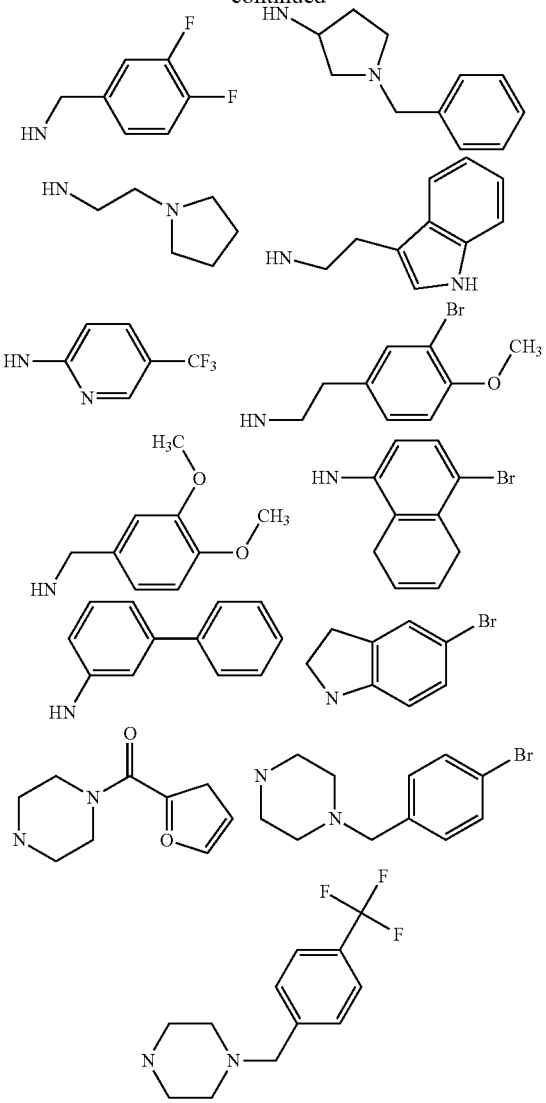
and —OH.
In still other embodiments, the present disclosure provides a compound comprising the formula,
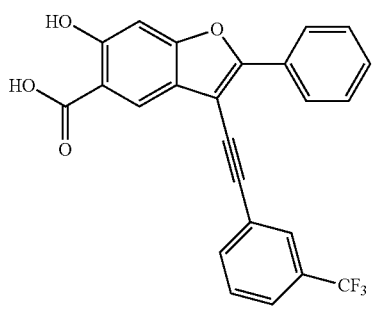 [SMILES: O=C(O)c1cc2c(C#Cc3cccc(C(F)(F)F)c3)c(-c3ccccc3)oc2cc1O]
(6-hydroxy-2-phenyl-3-(3-trifluoromethyl-phenylethynyl)-benzofuran-5-carboxylic acid), or a pharmaceutically acceptable salt thereof.
In still other embodiments, the present disclosure provides a compound comprising the formula,

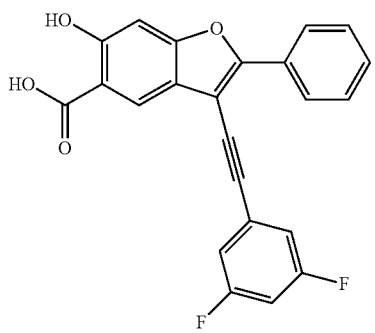 [SMILES: O=C(O)c1cc2c(C#Cc3cc(F)cc(F)c3)c(-c3ccccc3)oc2cc1O]

(3-(3,5-difluoro-phenylethynyl)-6-hydroxy-2-phenyl-benzofuran-5-carboxylic acid), or a pharmaceutically acceptable salt thereof.

In other embodiments, the present disclosure provides a compound comprising the formula:

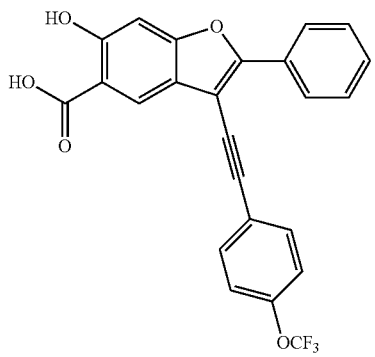 [SMILES: O=C(O)c1cc2c(C#Cc3ccc(OC(F)(F)F)cc3)c(-c3ccccc3)oc2cc1O]

(6-hydroxy-2-phenyl-3-(4-trifluoromethoxy-phenylethynyl)-benzofuran-5-carboxylic acid), or a pharmaceutically acceptable salt thereof.

The present disclosure includes a compound comprising the formula:

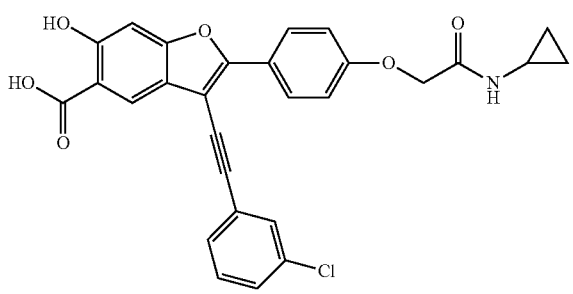 [SMILES: O=C(COc1ccc(-c2oc3cc(O)c(C(=O)O)cc3c2C#Cc2cccc(Cl)c2)cc1)NC1CC1]

(3-(3-Chloro-phenylethynyl)-2-(4-cyclopropylcarbamoylmethoxy-phenyl)-6-hydroxy-benzofuran-5-carboxylic acid), or a pharmaceutically acceptable salt thereof.

The following compound is an inhibitor of mPTPB inhibitor with an $IC_{50}$ value of about 25 nM.

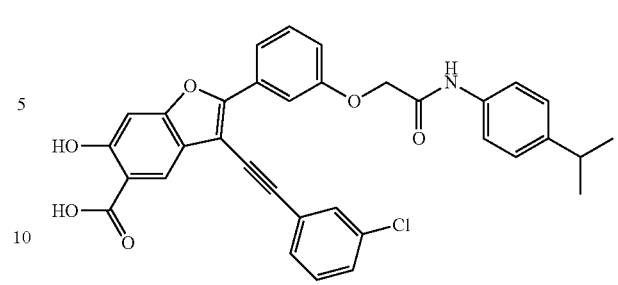

Some other embodiments of the disclosure include a compound according to Formula A,

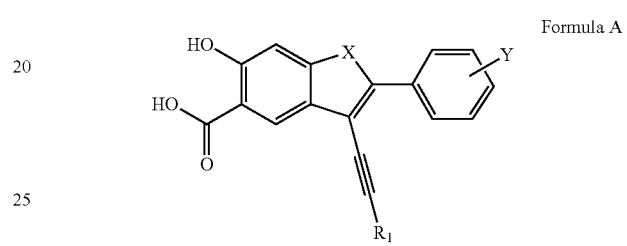

or a pharmaceutically acceptable salt thereof, wherein X is $NR_2$ and $R_1$ is selected from the group consisting of:

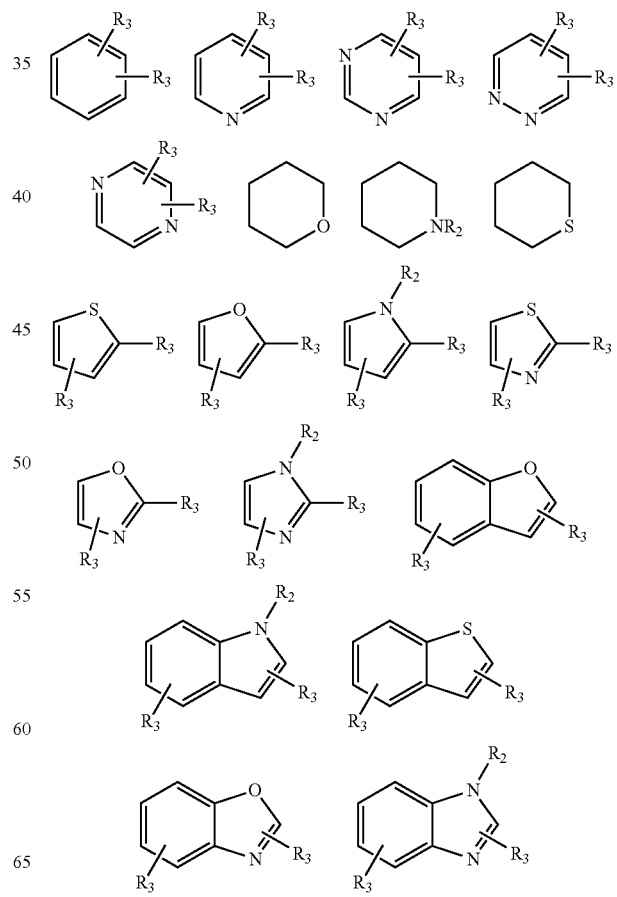

-continued

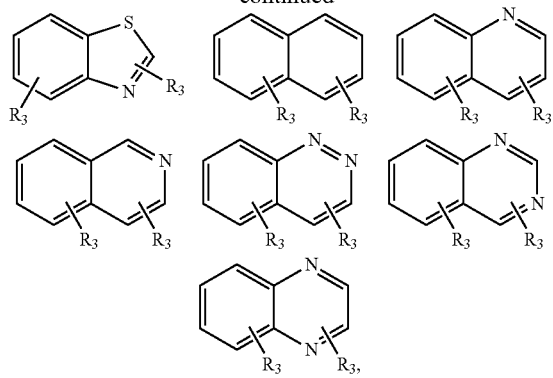

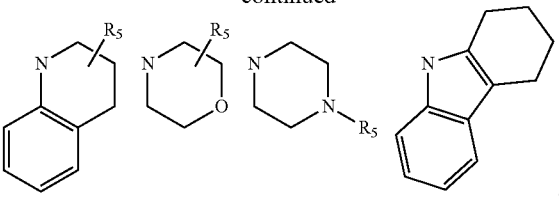

or hydrogen, wherein each occurrence of $R_2$ may be the same or different and is H or $C_1-C_6$ alkyl.

According to these embodiments, $R_3$ may be the same or different and is selected from the group consisting of H, halogen, hydroxyl, $NR_2R_2$, substituted or unsubstituted $C_1-C_6$ alkyl, substituted or unsubstituted $C_1-C_6$ alkenyl, substituted or unsubstituted $C_1-C_6$ alkynyl, O-(substituted or unsubstituted $C_1-C_6$ alkyl), S-(substituted or unsubstituted $C_1-C_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, $SO_2$-(substituted or unsubstituted $C_1-C_6$ alkyl), $SO_2NR_2R_2$, C(O)-(substituted or unsubstituted $C_1-C_6$ alkyl), C(O)-(substituted or unsubstituted aryl), C(O)-(substituted or unsubstituted heteroaryl), $(CH_2)_nCO_2H$, and $O(CH_2)_nCO_2H$.

Additionally, according to these embodiments, Y is H, halogen, hydroxyl, $NR_2R_2$, substituted or unsubstituted $C_1-C_6$ alkyl, substituted or unsubstituted $C_1-C_6$ alkenyl, substituted or unsubstituted $C_1-C_6$ alkynyl, O-(substituted or unsubstituted $C_1-C_6$ alkyl), S-(substituted or unsubstituted $C_1-C_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, $SO_2C_1-C_6$ alkyl, $SO_2NR_2R_2$, C(O)-(substituted or unsubstituted $C_1-C_6$ alkyl), C(O)-(substituted or unsubstituted aryl), C(O)-(substituted or unsubstituted heteroaryl), —$(CH_2)_nCOZ$, or —O—$(CH_2)_n$—COZ; and n is selected from one of 1, 2, 3, and 4; and Z is one of OH, or $N(R_4)_2$, wherein each occurrence of $R_4$ may be the same or different and is selected from the group consisting of H, substituted or unsubstituted $C_1-C_6$ alkyl, substituted or unsubstituted $C_3-C_8$ cycloalkyl, substituted or unsubstituted $C_1-C_6$ alkenyl, substituted or unsubstituted $C_1-C_6$ alkynyl, substituted or unsubstituted aryl, substituted or unsubstituted heteroaryl,

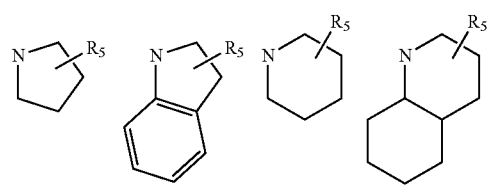

$OR_5$, and $NHR_5$, wherein $R_5$ is substituted or unsubstituted $C_1-C_6$ alkyl, substituted or unsubstituted aryl, substituted or unsubstituted heteroaryl, C(O)-(substituted or unsubstituted $C_1-C_6$alkyl), C(O)-(substituted or unsubstituted aryl), C(O)-(substituted or unsubstituted heteroaryl), or C(O)-(substituted or unsubstituted $C_3-C_8$ cycloalkyl).

In other embodiments of the present, $R_1$ of the compound described above is

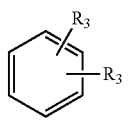

In some embodiments of the present disclosure, each occurrence of $R_3$ of the compound described can be the same or different is selected from the group consisting of H, Cl, F, $OCH_3$, $CF_3$, $OCF_3$, OPh, and $OCH_2CO_2H$; Y is selected from the group consisting of H, $CF_3$, $OCF_3$, Cl, Ph, OPh, and —$OCH_2COZ$; and Z is selected from the group consisting of:

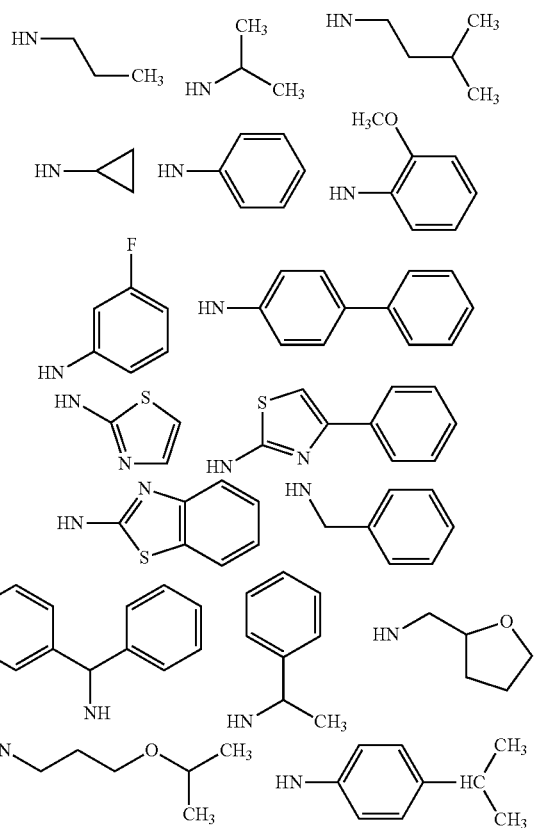

-continued
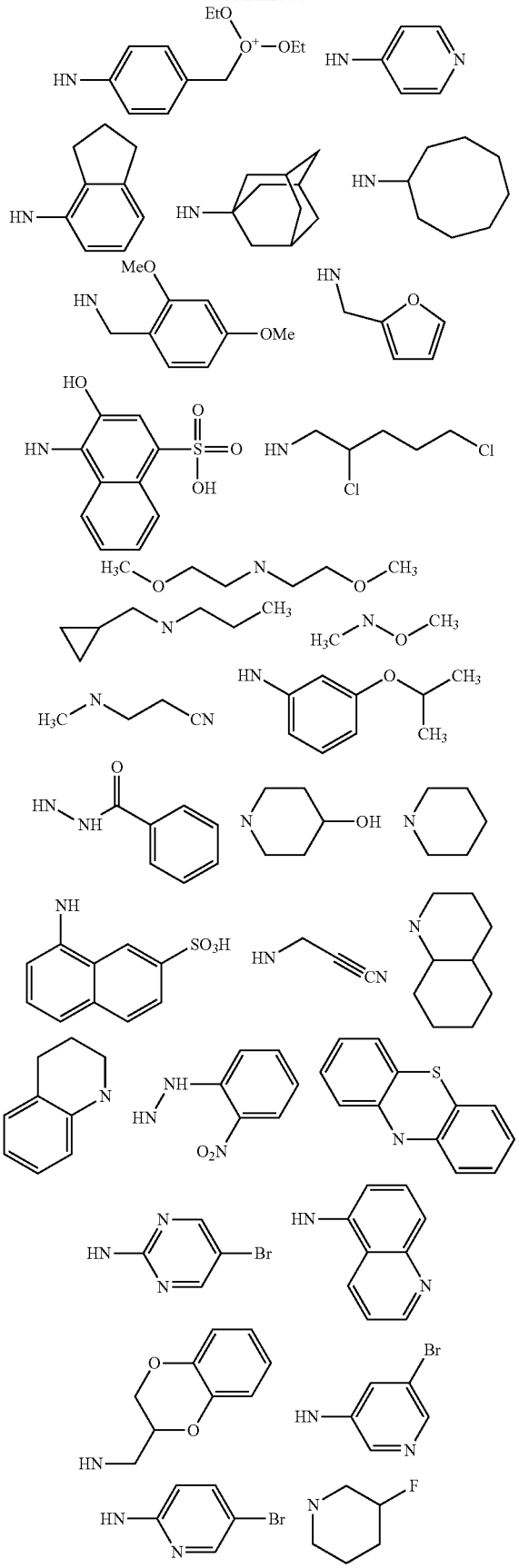
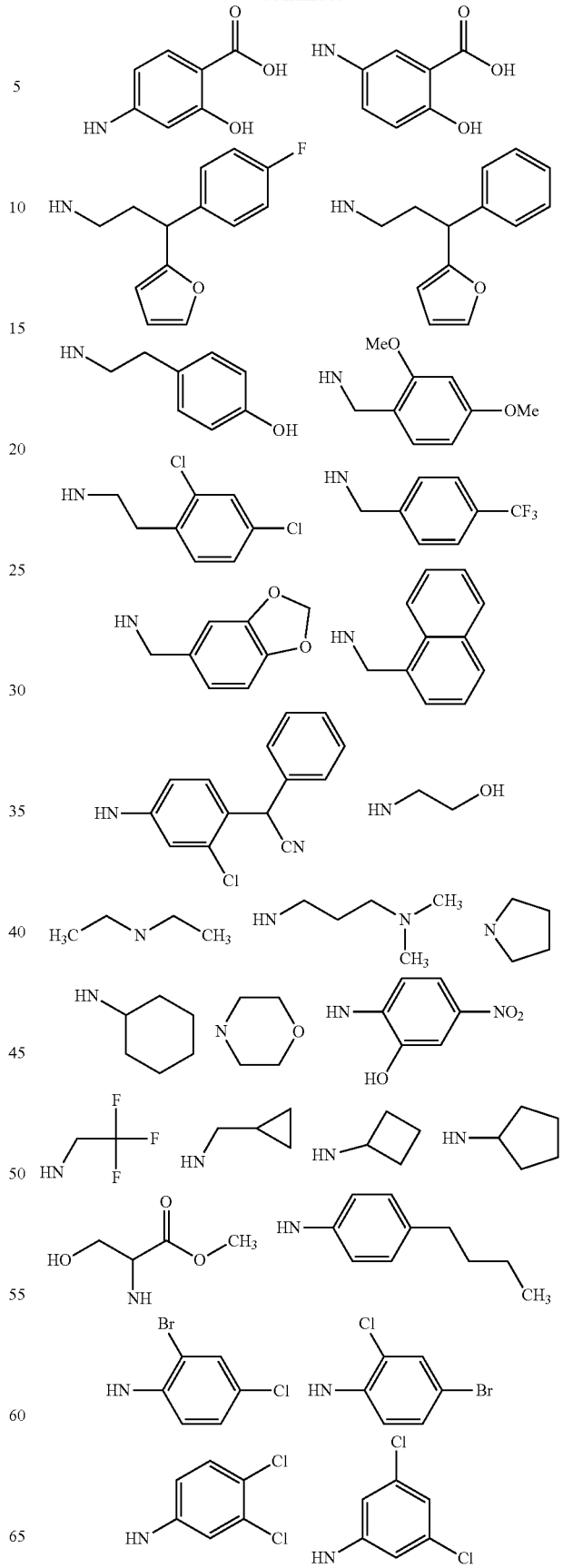

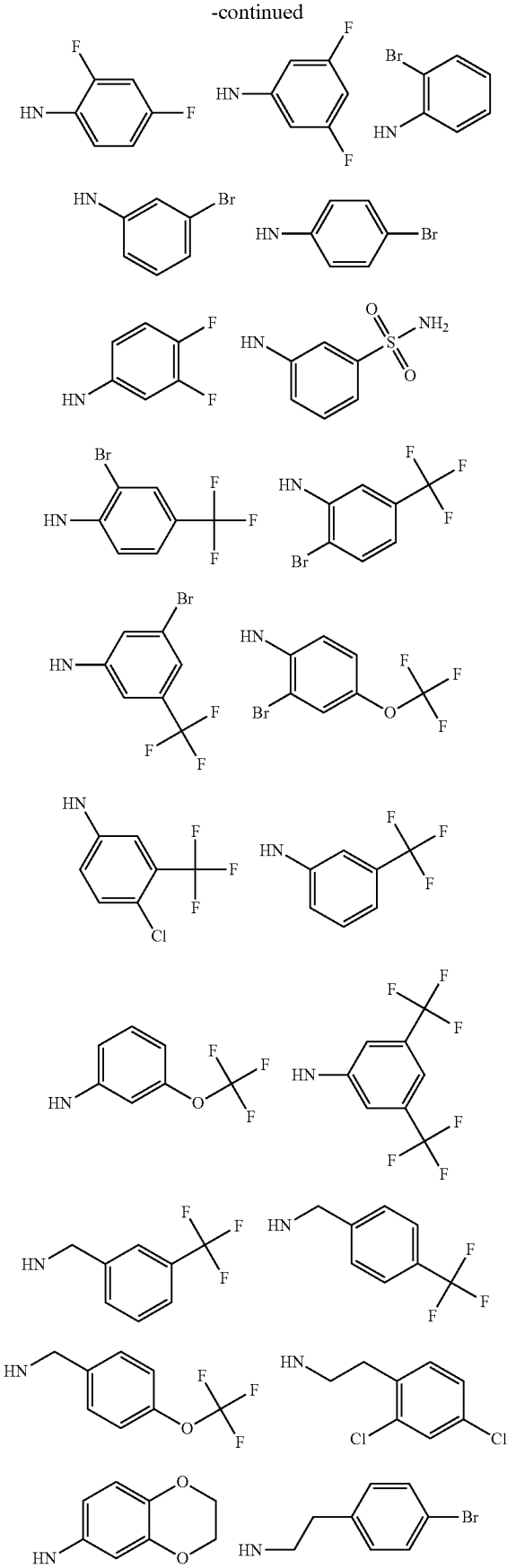
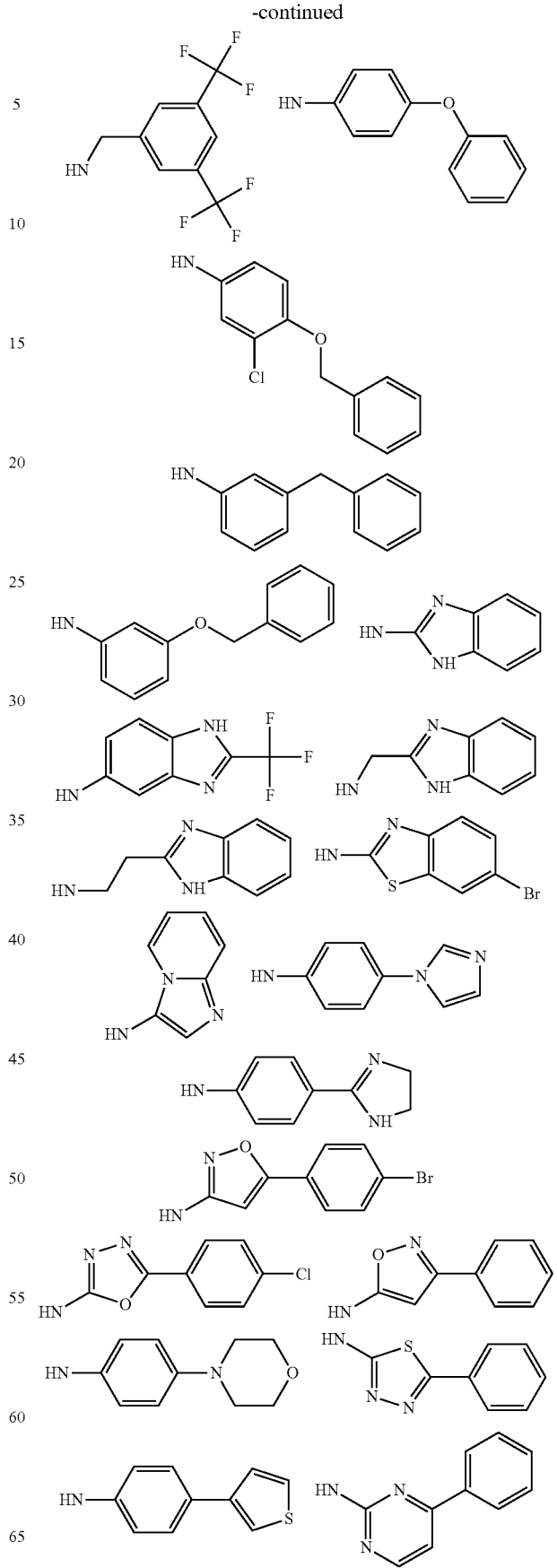

-continued
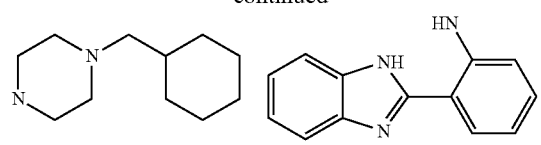
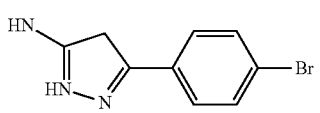
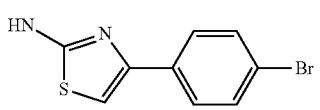
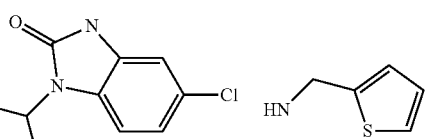
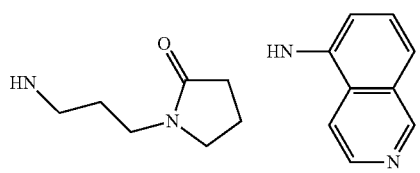
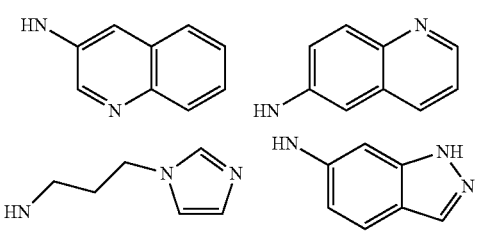
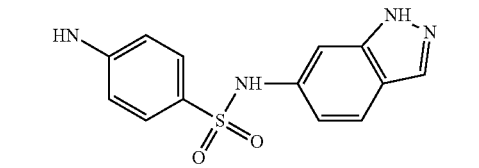
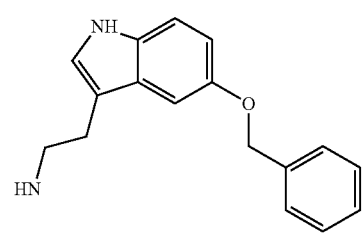
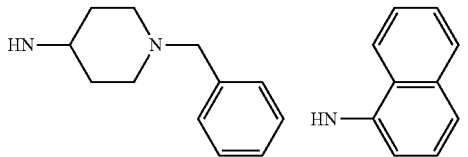
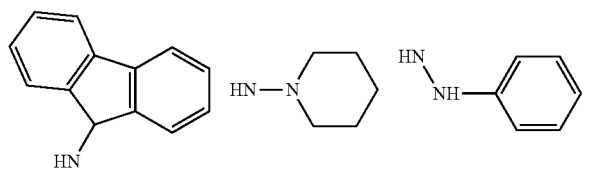
-continued
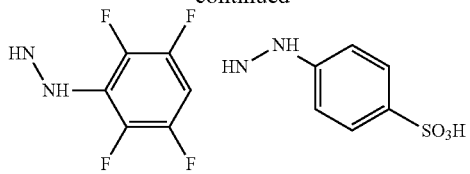
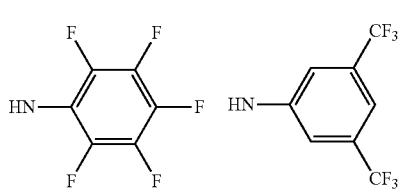
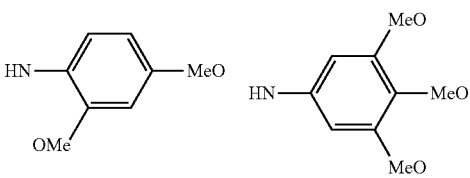
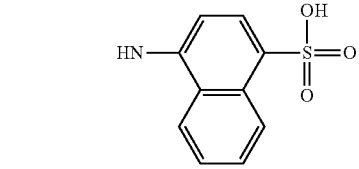
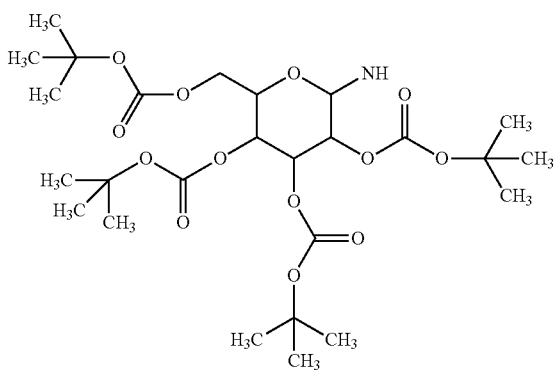
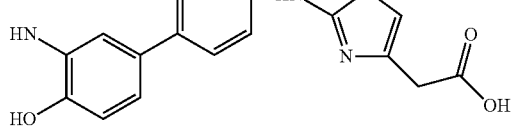
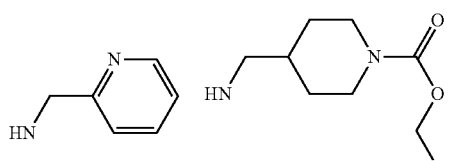
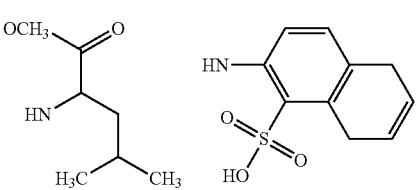

-continued
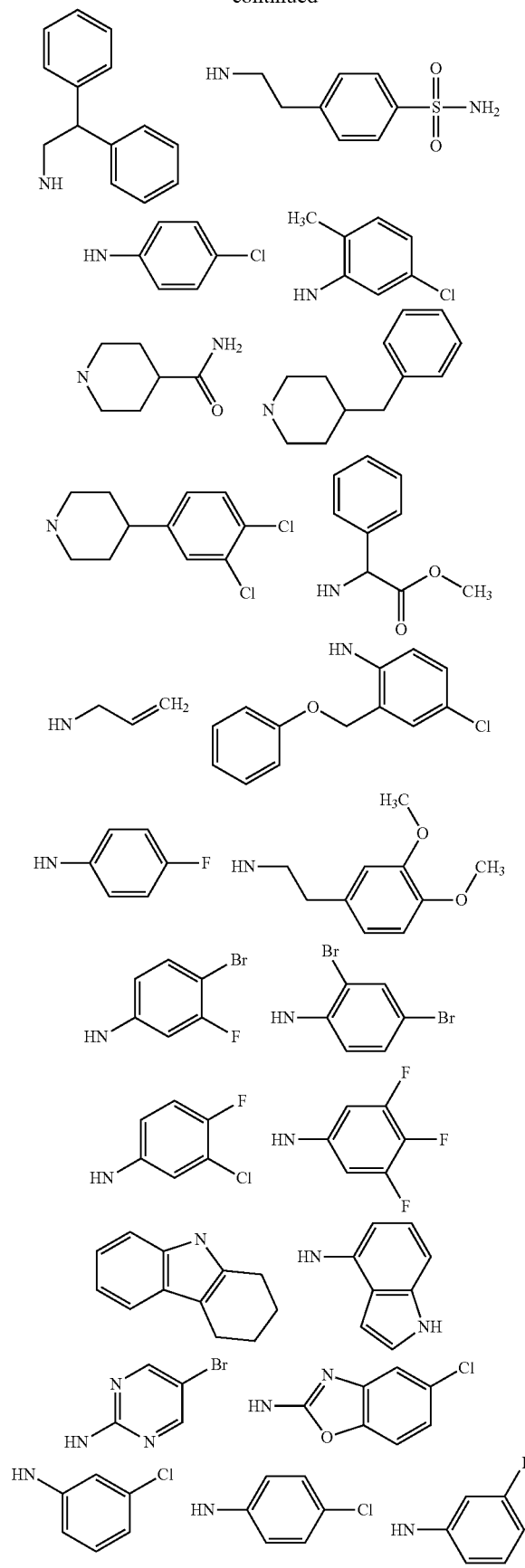
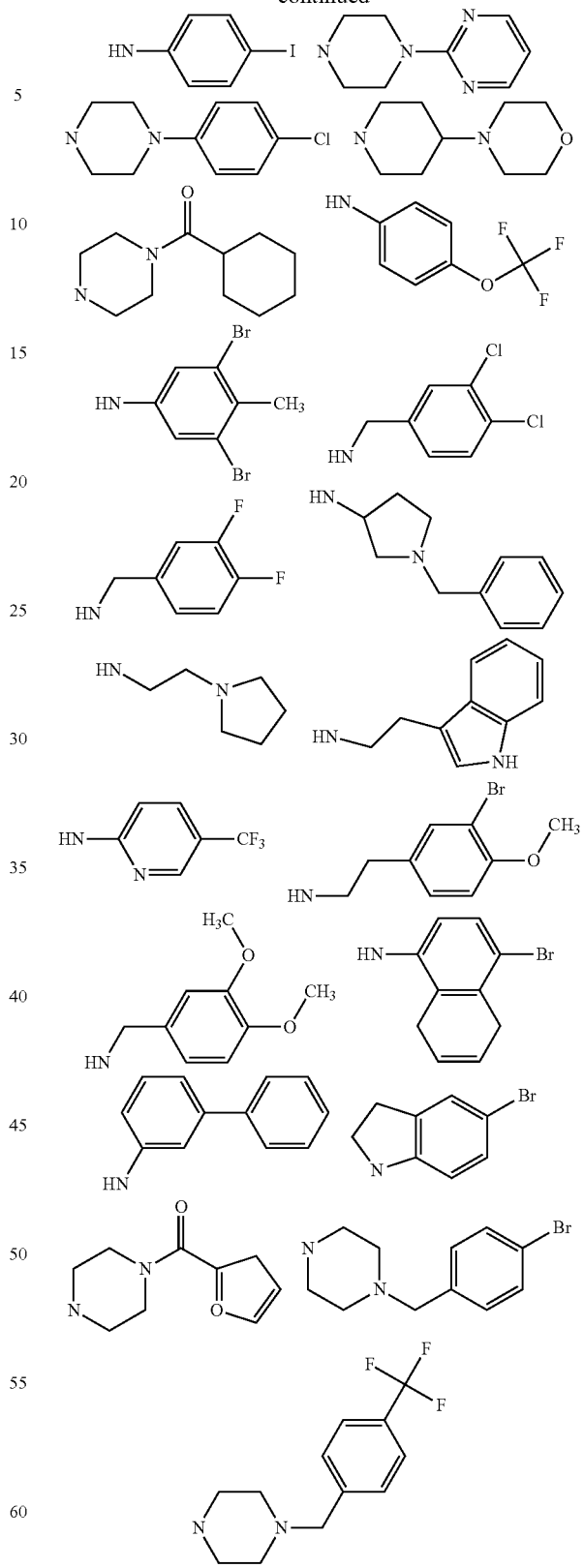
and —OH.
In still other embodiments, the present disclosure provides a compound comprising the formula,

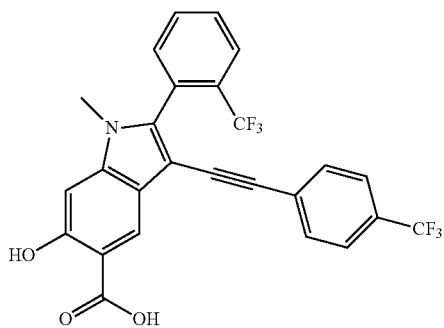 [SMILES: Cn1c(-c2ccccc2C(F)(F)F)c(C#Cc2ccc(C(F)(F)F)cc2)c2cc(C(=O)O)c(O)cc21]

6-Hydroxy-1-methyl-2-(2-trifluoromethyl-phenyl)-3-(4-trifluoromethyl-phenylethynyl)-1H-indole-5-carboxylic acid, and pharmaceutically acceptable salts thereof.

Other embodiments of the disclosure described herein include a compound according to Formula B,

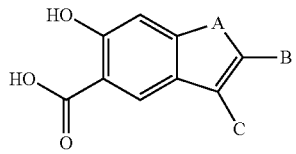

Formula B and a pharmaceutically acceptable salt thereof, wherein A is O.

Some embodiments of the compounds described herein, according to Formula B disclosed above, include B comprising one of a substituted or unsubstituted aryl, substituted or unsubstituted heteroaryl, or substituted or unsubstituted $C_3$-$C_8$ cycloalkyl; C comprising one of I, Br, and Cl.

Some embodiments of the compounds described herein, according to Formula B include B comprising one of cyclohexyl and

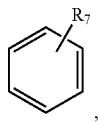

, wherein $R_7$ is selected from the group consisting of H, Ph, F, $CF_3$, $OCF_3$, and OH; and C is I.

Still other embodiments of the disclosure described herein include a compound according to Formula B,

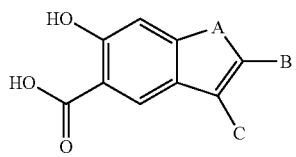

Formula B and a pharmaceutically acceptable salt thereof, wherein A is $NR_6$ with $R_6$ comprising one of H and $C_1$-$C_6$ alkyl.

Some embodiments of the compounds described herein, according to Formula B comprise one cyclohexyl

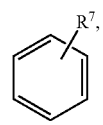

wherein $R_7$ is selected from the group consisting of H, Ph, F, $CF_3$, $OCF_3$, and OH; C is I; and $R_6$ is $CH_3$.

Still further embodiments of the present disclosure include compounds according to Formula C:

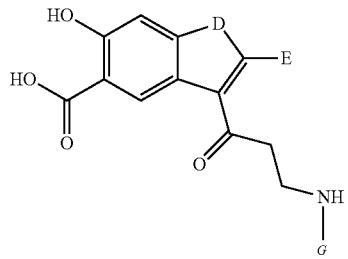

Formula C or a pharmaceutically acceptable salt thereof, wherein D is O; E is one of a substituted or unsubstituted aryl, substituted or unsubstituted heteroaryl, and a substituted or unsubstituted $C_3$-$C_8$ cycloalkyl; and G is one of C(O)-(substituted or unsubstituted $C_1$-$C_6$ alkyl), C(O)-(substituted or unsubstituted $C_3$-$C_8$ cycloalkyl), C(O)-(substituted or unsubstituted $C_1$-$C_6$ alkenyl), C(O)-(substituted or unsubstituted $C_1$-$C_6$ alkynyl), C(O)-(substituted or unsubstituted aryl), and C(O)-(substituted or unsubstituted heteroaryl).

Some embodiments of the compounds described herein, according to Formula C include:
E comprising one of cyclohexyl and

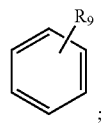

;

$R_9$ comprising one of H, Ph, F, $CF_3$, $OCF_3$, and OH; and G is selected from the group comprising:

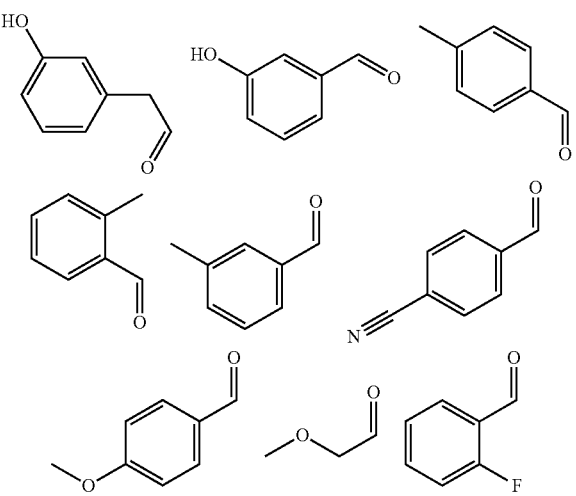

27
-continued
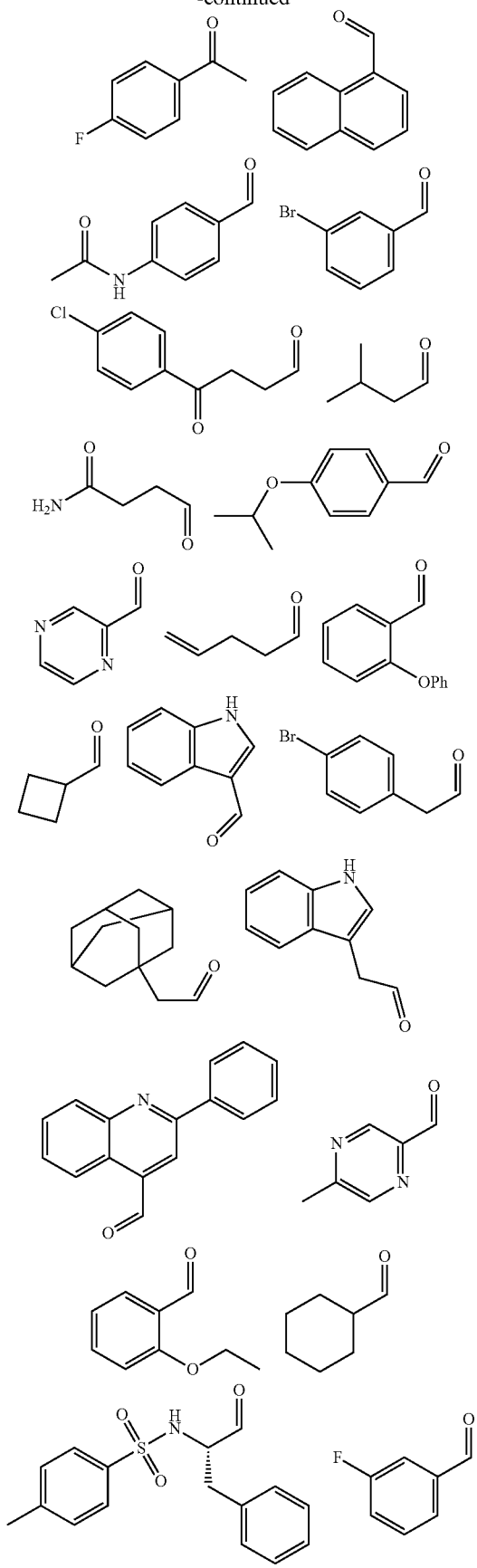
28
-continued
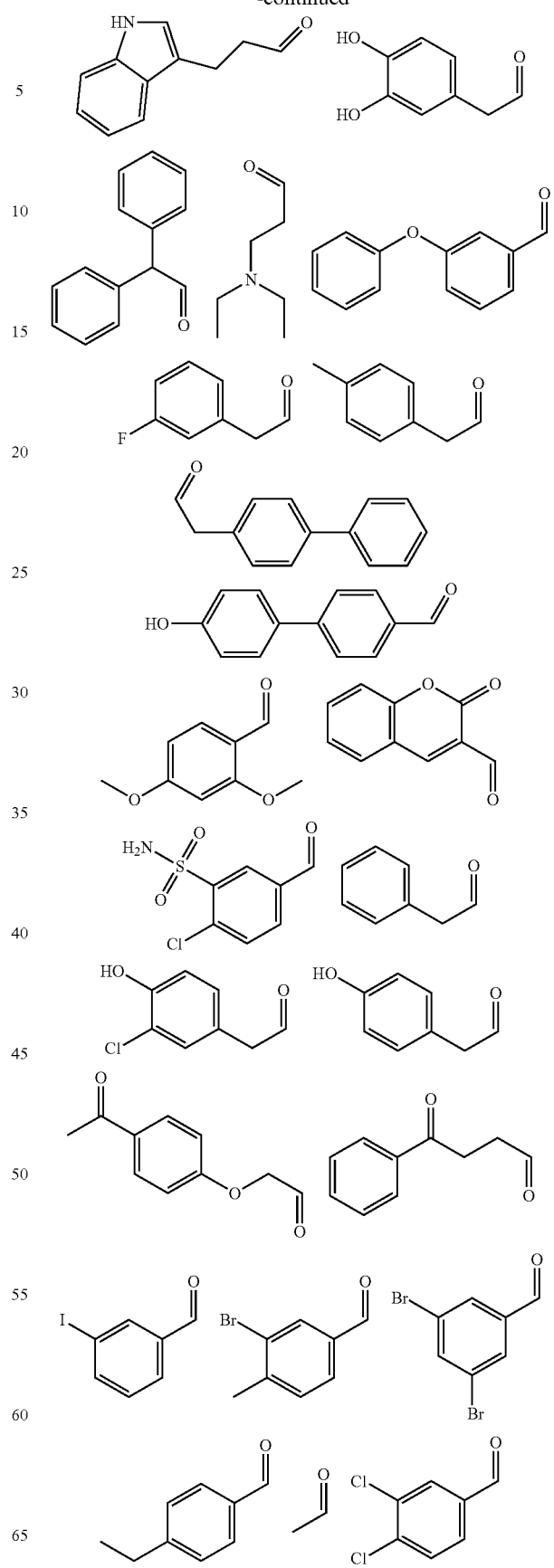

29
-continued
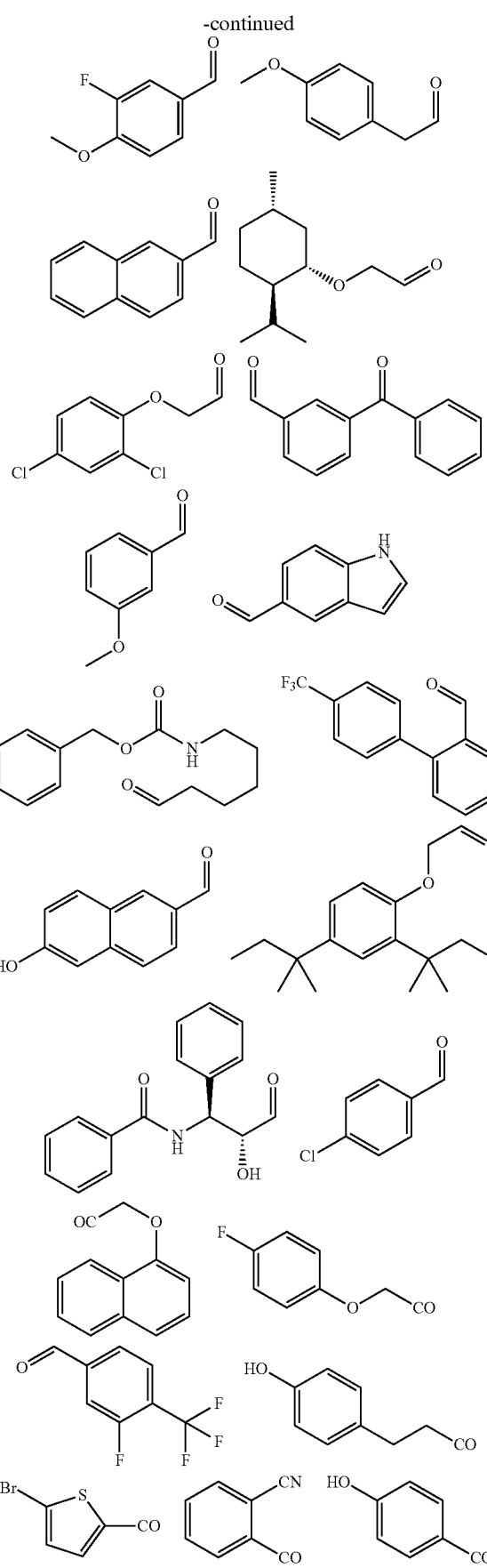
30
-continued
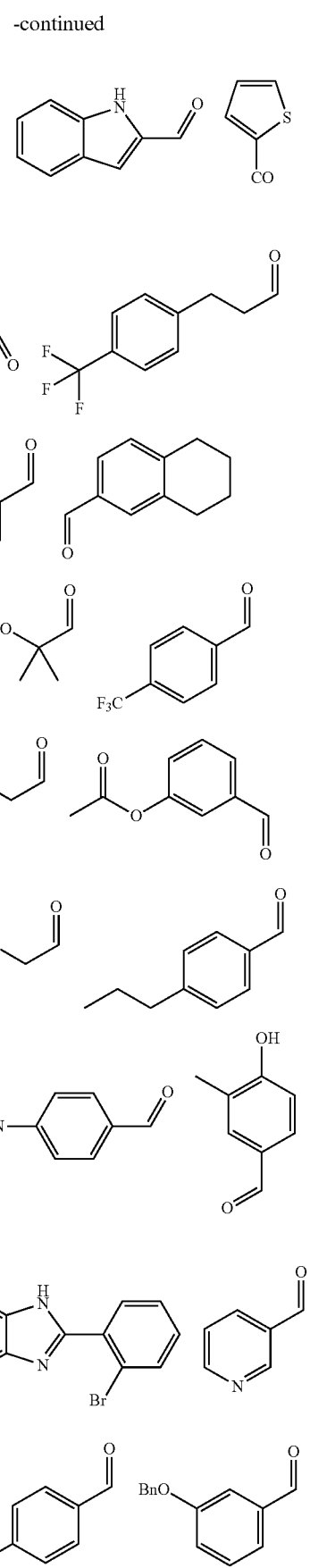

-continued

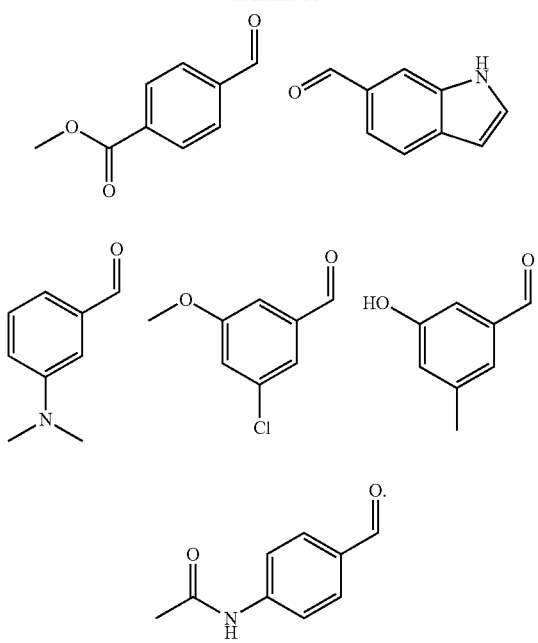

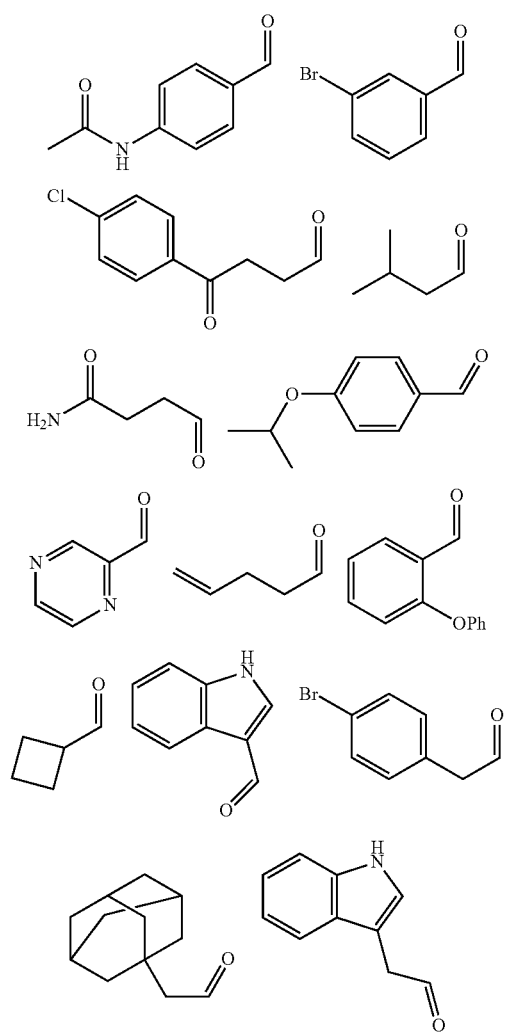

Other embodiments of the present disclosure include compounds according to Formula C:

Formula C

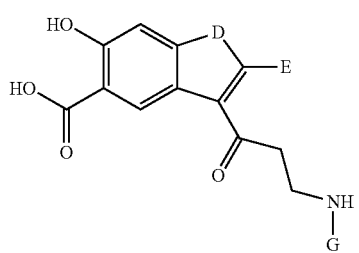

or a pharmaceutically acceptable salt thereof, wherein D is $NR_8$; $R_8$ is one of a H and a $C_1$-$C_6$ alkyl; E is one of a substituted or unsubstituted aryl, substituted or unsubstituted heteroaryl, and a substituted or unsubstituted $C_3$-$C_8$ cycloalkyl; and G is one of C(O)-(substituted or unsubstituted $C_1$-$C_6$ alkyl), C(O)-(substituted or unsubstituted $C_3$-$C_8$ cycloalkyl), C(O)-(substituted or unsubstituted $C_1$-$C_6$ alkenyl), C(O)-(substituted or unsubstituted $C_1$-$C_6$ alkynyl), C(O)-(substituted or unsubstituted aryl), and C(O)-(substituted or unsubstituted heteroaryl).

Some embodiments of the compounds described herein, according to Formula C include: $NR_8$ comprising $CH_3$; E comprising one of cyclohexyl and

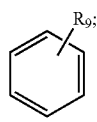

$R_9$ comprising one of H, Ph, F, $CF_3$, $OCF_3$, and OH; and G is selected from the group comprising:

33
-continued
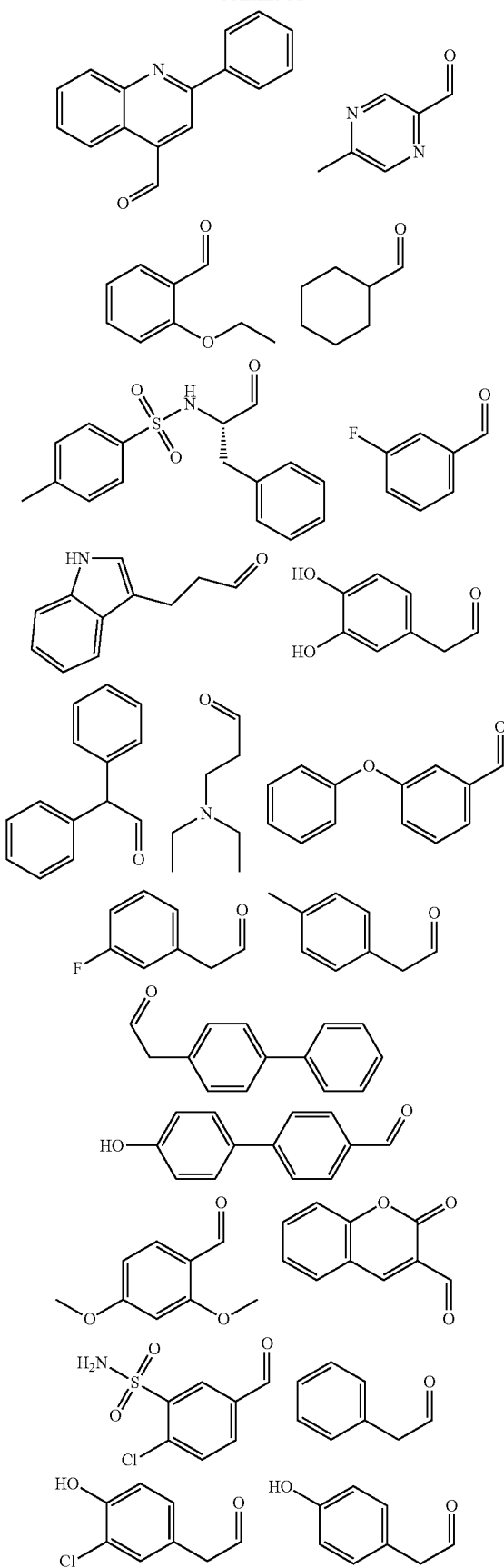
34
-continued
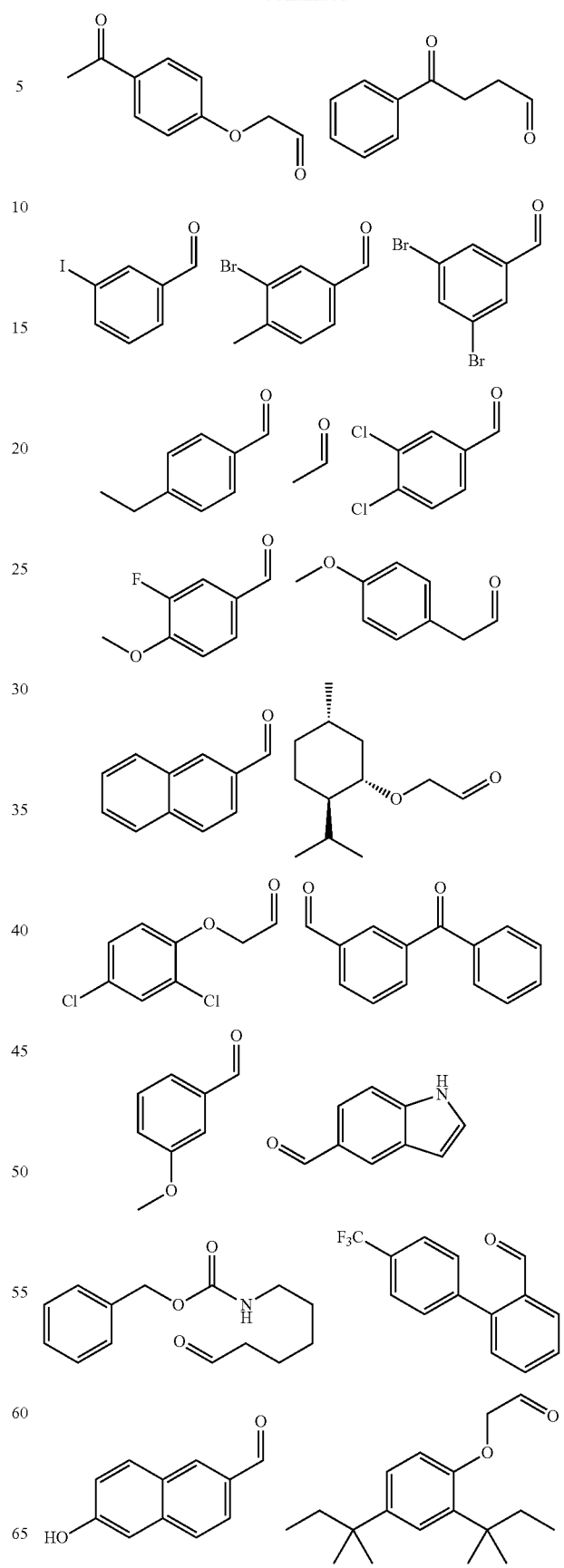

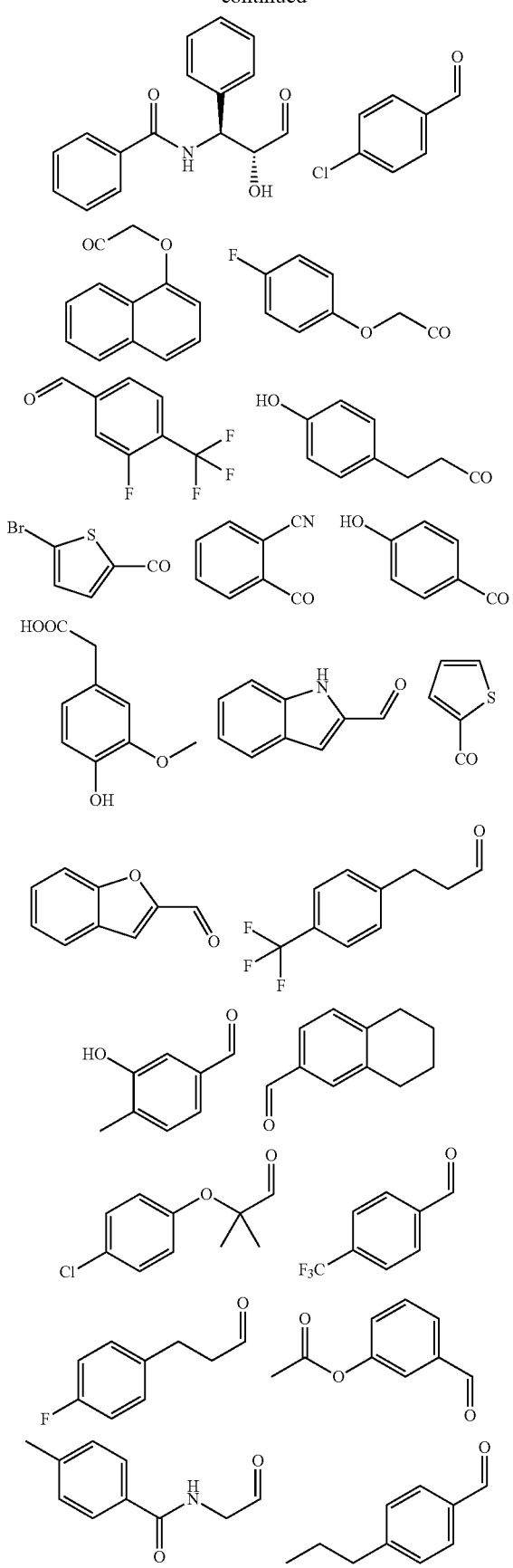
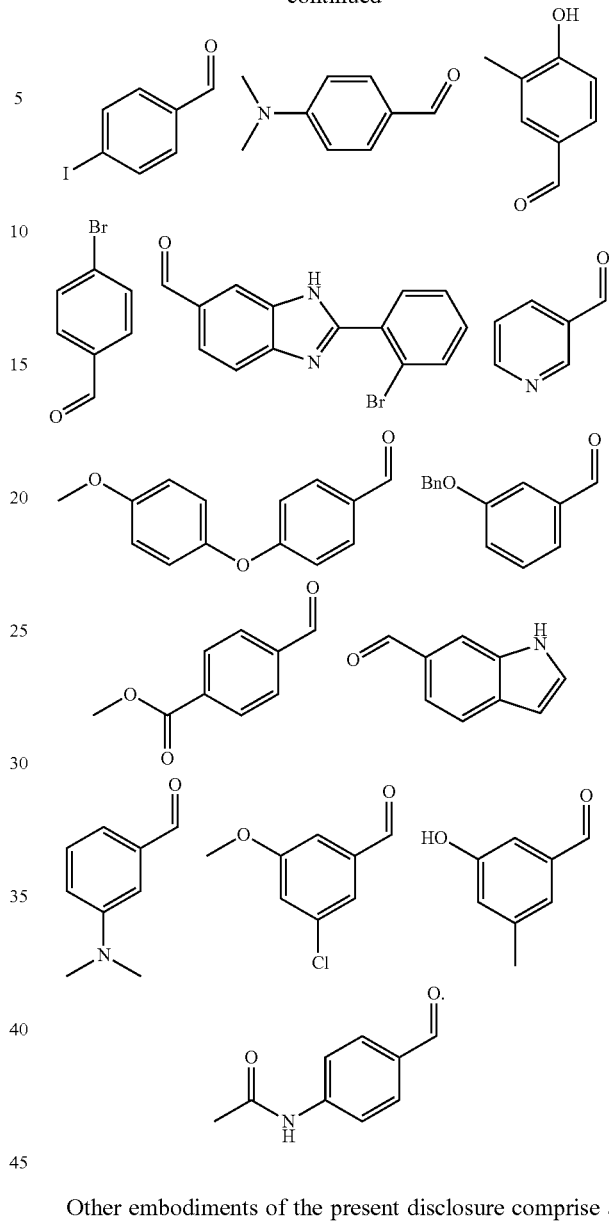
Other embodiments of the present disclosure comprise a compound having the formula:
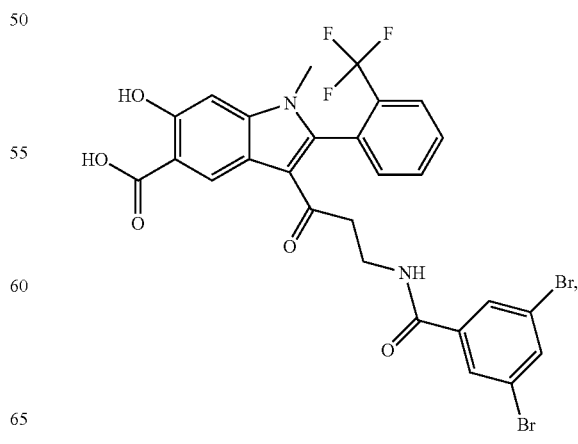

(3-[3,5-dibromo-benzoylamino)-propionyl]-6-hydroxy-1-methyl-2-(2-trifluoromethyl-phenyl)-1H-indole-5-carboxylic acid), or a pharmaceutically acceptable salt thereof.

In addition to providing the compounds disclosed above, embodiments of the present disclosure further include a method of reducing the activity of a tyrosine phosphatase comprising providing at least one of the compounds disclosed above, or a pharmaceutically acceptable salt thereof.

Some of embodiments of the method of this disclosure comprise providing at least one compound selected from one of:

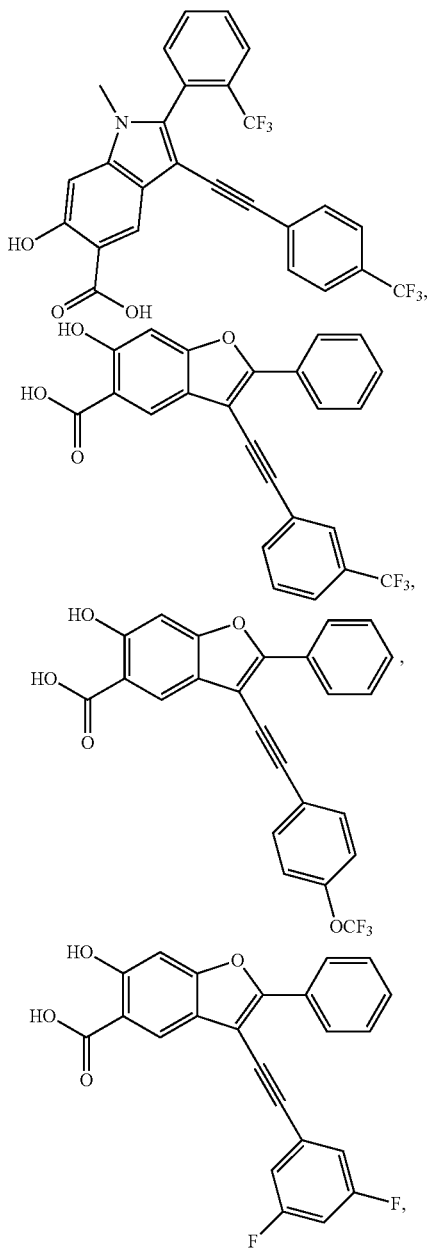

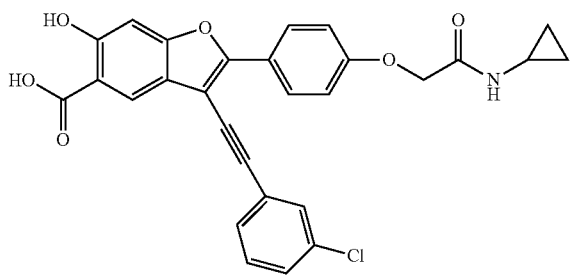 [SMILES: O=C(COc1ccc(-c2oc3cc(O)c(C(=O)O)cc3c2C#Cc2cccc(Cl)c2)cc1)NC1CC1]

or a pharmaceutically acceptable salt thereof, and wherein said tyrosine phosphatase is lymphoid-specific tyrosine phosphatase (Lyp).

Other aspects of the disclosure include compounds according to the following formula:

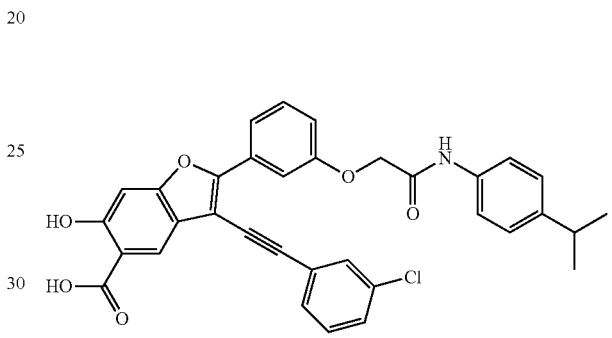

The present disclosure includes methods for treating physiological diseases, disorder, or conditions associated with inappropriate activity of a protein tyrosine phosphatase comprising administering to an individual in need thereof a therapeutically effective amount of at least one compound disclosed herein, or a pharmaceutically acceptable salt thereof. Some of these methods include treating type 1 or type 2 diabetes, obesity, metabolic syndrome, Crohn's disease, rheumatoid arthritis, Graves' disease, systemic lupus erythematosus, juvenile idiopathic arthritis, myasthenia gravis, generalized vitiligo, Wegener's granulomatosis, cancer, leukemia, or tuberculosis.

An embodiment according to the disclosed method of treating a physiological disease comprises the disease, disorder, or condition being tuberculosis, and the at least one compound being selected from

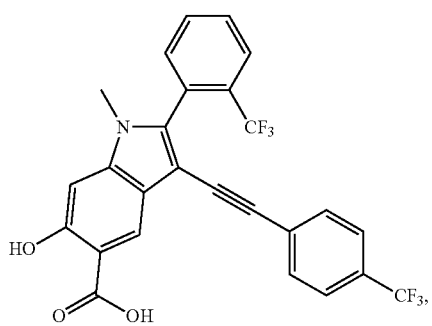

or a pharmaceutically acceptable salts thereof, wherein said tyrosine phosphatase is *Mycobacterium* protein tyrosine phosphatase B (mPTPB).

Also disclosed herein are methods that include the step of providing a compound according to the following formula, -continued

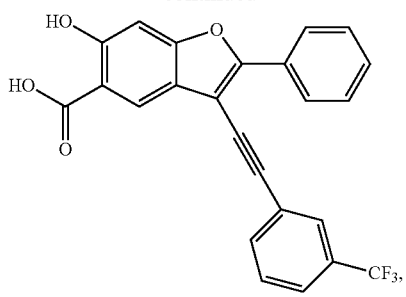

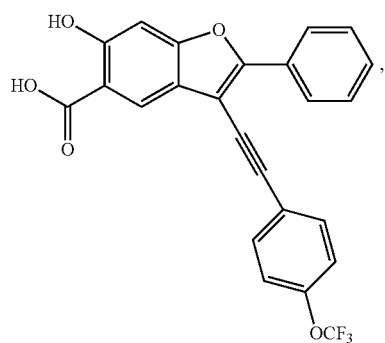

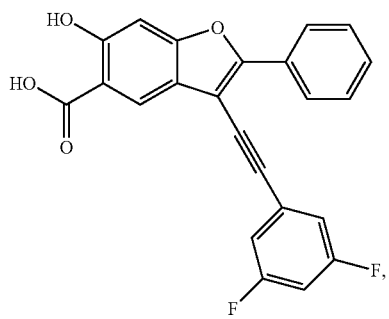

or a pharmaceutically acceptable salt thereof.

Also disclosed herein are methods of treating diseases, disorders, or conditions related to autoimmunity, some of these methods include using a compound according to the following formula, or a pharmaceutically acceptable salts thereof:

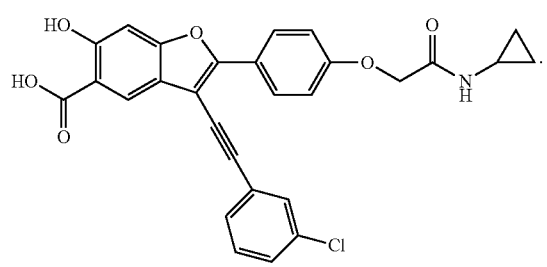 [SMILES: O=C(COc1ccc(-c2oc3cc(O)c(C(=O)O)cc3c2C#Cc2cccc(Cl)c2)cc1)NC1CC1]

Some aspects include compounds such as the following, or pharmaceutically acceptable salts thereof:

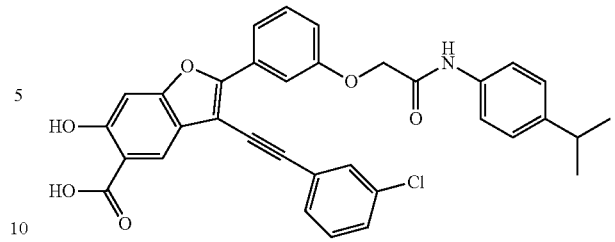

Compounds such as this compound are especially useful in the treatment of diseases such as tuberculosis and other disease caused by infection with some species of *mycobacterium*.

Some aspects of the invention include compounds of Formula A, or a pharmaceutically acceptable salt thereof, Formula A

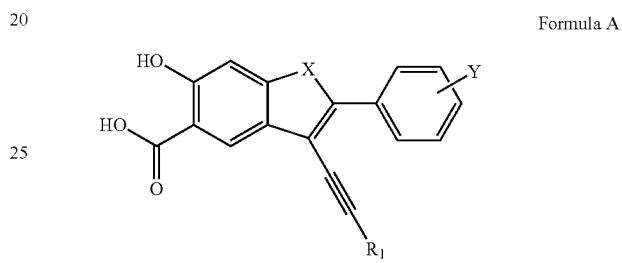

wherein X is O or $NR_2$; $R_1$ is, selected from the group consisting of:

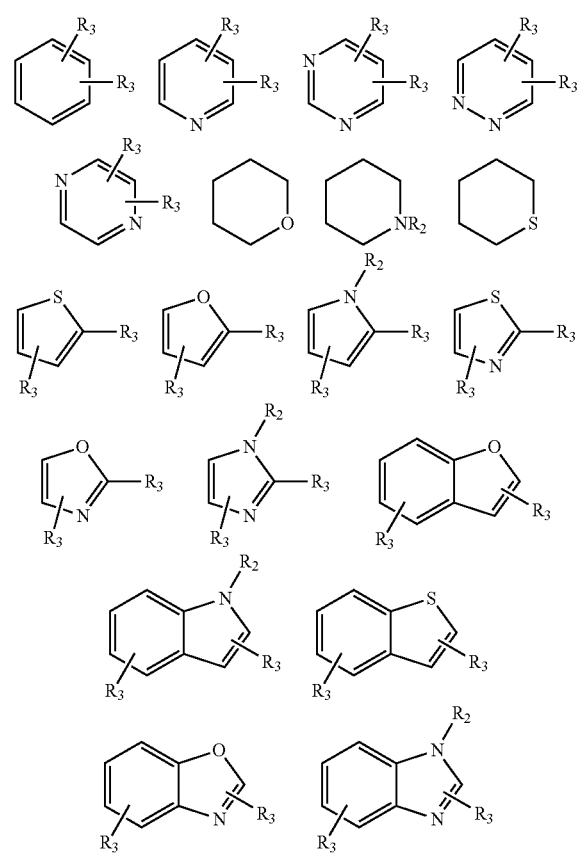

-continued

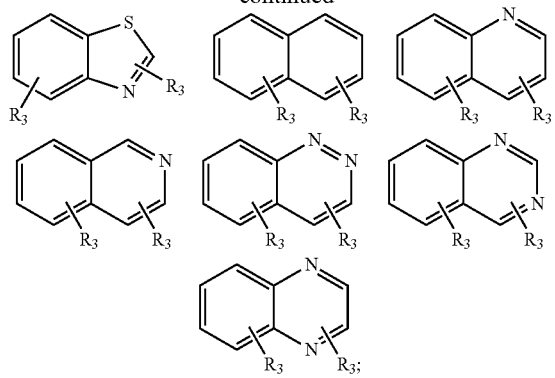

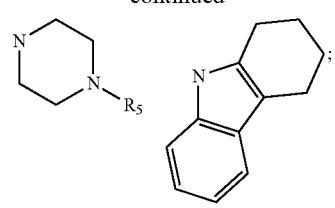

or hydrogen, each occurrence of $R_2$ can be the same or different and is H or $C_1$-$C_6$ alkyl; each occurrence of $R_3$ can be the same or different and is H, halogen, hydroxyl, $NR_2R_2$, substituted or unsubstituted $C_1$-$C_6$ alkyl, substituted or unsubstituted $C_1$-$C_6$ alkenyl, substituted or unsubstituted $C_1$-$C_6$ alkynyl, O-(substituted or unsubstituted $C_1$-$C_6$ alkyl), S-(substituted or unsubstituted $C_1$-$C_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, $SO_2$-(substituted or unsubstituted $C_1$-$C_6$ alkyl), $SO_2NR_2R_2$, C(O)-(substituted or unsubstituted $C_1$-$C_6$ alkyl), C(O)-(substituted or unsubstituted aryl), C(O)-(substituted or unsubstituted heteroaryl), $(CH_2)_nCO_2H$, or $O(CH_2)_nCO_2H$; Y is H, halogen, hydroxyl, $NR_2R_2$, substituted or unsubstituted $C_1$-$C_6$ alkyl, substituted or unsubstituted $C_1$-$C_6$ alkenyl, substituted or unsubstituted $C_1$-$C_6$ alkynyl, O-(substituted or unsubstituted $C_1$-$C_6$ alkyl), S-(substituted or unsubstituted $C_1$-$C_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, $SO_2C_1$-$C_6$ alkyl, $SO_2NR_2R_2$, C(O)-(substituted or unsubstituted $C_1$-$C_6$ alkyl), C(O)-(substituted or unsubstituted aryl), C(O)-(substituted or unsubstituted heteroaryl); —$(CH_2)_nCOZ$, or —O—$(CH_2)_n$-COZ; n can be the same or different at each occurrence and is 1, 2, 3, or 4; Z is —OH, or $N(R_4)_2$; each occurrence of $R_4$ can be the same or different and is H, substituted or unsubstituted $C_1$-$C_6$ alkyl, substituted or unsubstituted $C_3$-$C_8$ cycloalkyl, substituted or unsubstituted $C_1$-$C_6$ alkenyl, substituted $C_1$-$C_6$ alkynyl, substituted or unsubstituted aryl, substituted or unsubstituted heteroaryl, $OR_5$, $NHR_5$,

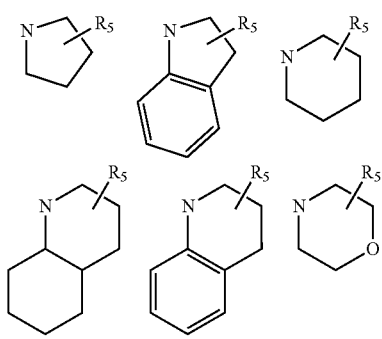

and $R_5$ is substituted or unsubstituted $C_1$-$C_6$ alkyl, substituted or unsubstituted aryl, substituted or unsubstituted heteroaryl, C(O)-(substituted or unsubstituted $C_1$-$C_6$ alkyl), C(O)-(substituted or unsubstituted aryl), C(O)-(substituted or unsubstituted heteroaryl), or C(O)-(substituted or unsubstituted $C_3$-$C_8$ cycloalkyl).

In some embodiments Formula is such that Y is H, halogen, hydroxyl, NR2R2, substituted or unsubstituted C1-C6 alkyl, substituted or unsubstituted C1-C6 alkenyl, substituted or unsubstituted C1-C6 alkynyl, O-(substituted or unsubstituted C1-C6 alkyl), S-(substituted or unsubstituted C1-C6 alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, SO2C1-C6 alkyl, SO2NR2R2, C(O)-(substituted or unsubstituted C1-C6 alkyl), C(O)-(substituted or unsubstituted aryl), or C(O)-(substituted or unsubstituted heteroaryl). In some embodiments X is O. In still other embodiments X is $NR_2$ In some embodiments when X is $NR_2$ in Formula A, $R_1$ is

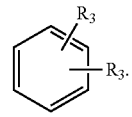

and in still other embodiments $R_1$ is

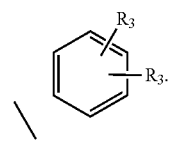

In some embodiments each occurrence of $R_3$ can be the same or different and is H, Cl, F, $OCH_3$, $CF_3$, $OCF_3$, OPh, or $OCH_2CO_2H$, and Y is H, $CF_3$, $OCF_3$, Cl, Ph, or OPh. In still other embodiments wherein each occurrence of $R_3$ can be the same or different and is H, Cl, F, $OCH_3$, $CF_3$, $OCF_3$, OPh, or $OCH_2CO_2H$, and Y is H, $CF_3$, $OCF_3$, Cl, Ph, or OPh. In some embodiments $R_1$ is hydrogen. In some embodiments Y is Ph, Cl, $OCF_3$, or OPh. In still other embodiments Y is Ph, Cl, $OCF_3$, or OPh Some aspects of the invention include compounds of formula:

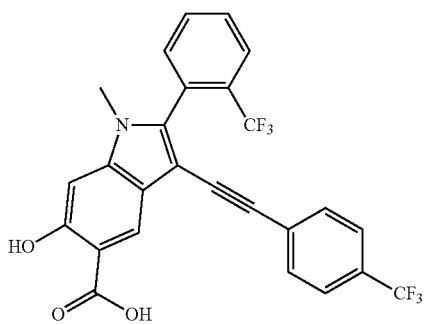 [SMILES: Cn1c(-c2ccccc2C(F)(F)F)c(C#Cc2ccc(C(F)(F)F)cc2)c2cc(C(=O)O)c(O)cc21]

6-Hydroxy-1-methyl-2-(2-trifluoromethyl-phenyl)-3-(4-trifluoromethyl-phenylethynyl)-1H-indole-5-carboxylic acid, or a pharmaceutically acceptable salt thereof.

Some aspects include compound of the formula

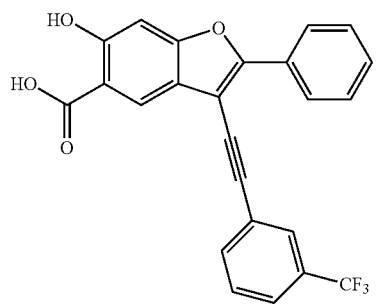 [SMILES: O=C(O)c1cc2c(C#Cc3cccc(C(F)(F)F)c3)c(-c3ccccc3)oc2cc1O]

(6-hydroxy-2-phenyl-3-(3-trifluoromethyl-phenylethynyl)-benzofuran-5-carboxylic acid), or a pharmaceutically acceptable salt thereof.

In some aspects of the invention include compounds of the formula

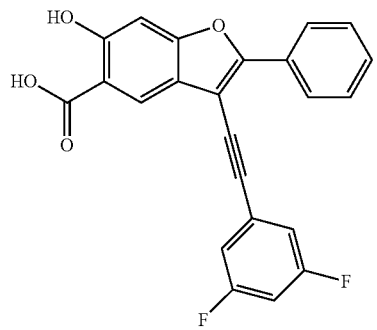 [SMILES: O=C(O)c1cc2c(C#Cc3cc(F)cc(F)c3)c(-c3ccccc3)oc2cc1O]

3-(3,5-difluoro-phenylethynyl)-6-hydroxy-2-phenyl-benzofuran-5-carboxylic acid), or a pharmaceutically acceptable salt thereof.

Still other embodiments of the invention include compounds of the formula

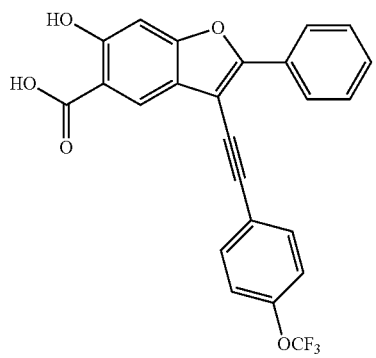 [SMILES: O=C(O)c1cc2c(C#Cc3ccc(OC(F)(F)F)cc3)c(-c3ccccc3)oc2cc1O]

(6-hydroxy-2-phenyl-3-(4-trifluoromethoxy-phenylethynyl)-benzofuran-5-carboxylic acid), or a pharmaceutically acceptable salt thereof.

Some aspects of the invention include compounds of Formula B, or a pharmaceutically acceptable salts thereof, Formula B

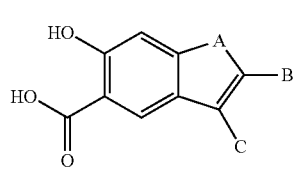

wherein A is O or $NR_6$; B is substituted or unsubstituted aryl, substituted or unsubstituted heteroaryl, or substituted or unsubstituted $C_3$-$C_8$ cycloalkyl; C is I, Br, or Cl; and $R_6$ is H or $C_1$-$C_6$ alkyl.

In some embodiments wherein A is O or $NR_6$. Some embodiments of the invention include compounds wherein B is cyclohexyl or

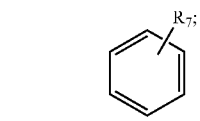

each occurrence of $R_7$ can be the same or different and is H, Ph, F, $CF_3$, $OCF_3$, or OH; and C is I. In some embodiments wherein B is cyclohexyl or

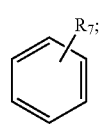

$R_7$ is H, Ph, F, $CF_3$, $OCF_3$, or OH, C is I, and $R_6$ is $CH_3$.

Some embodiments include compounds of Formula C, or a pharmaceutically acceptable salt thereof,

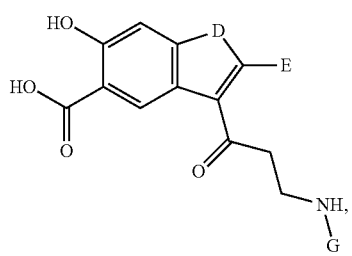

Formula C wherein D is O or NR$_8$; R$_8$ is H or C$_1$-C$_6$ alkyl; E is substituted or unsubstituted aryl, substituted or unsubstituted heteroaryl, or substituted or unsubstituted C$_3$-C$_8$ cycloalkyl; and G is C(O)-(substituted or unsubstituted C$_1$-C$_6$ alkyl), C(O)-(substituted or unsubstituted C$_3$-C$_8$ cycloalkyl), C(O)-(substituted or unsubstituted C$_1$-C$_6$ alkenyl), C(O)-(substituted or unsubstituted C$_1$-C$_6$ alkynyl), C(O)-(substituted or unsubstituted aryl), or C(O)-(substituted or unsubstituted heteroaryl). In some embodiments D is O. In still other embodiments D is NR$_8$. In some embodiments E is cyclohexyl or

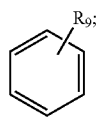

R$_9$ is H, Ph, F, CF$_3$, OCF$_3$, or OH, and G is

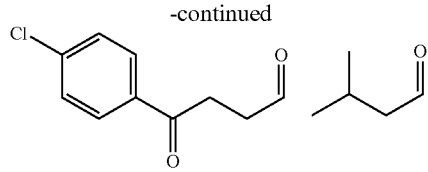
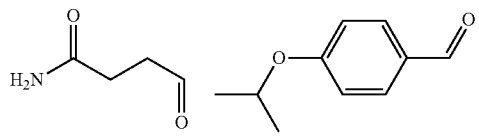
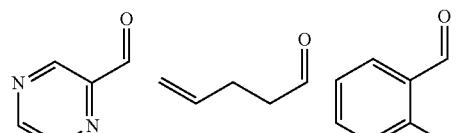
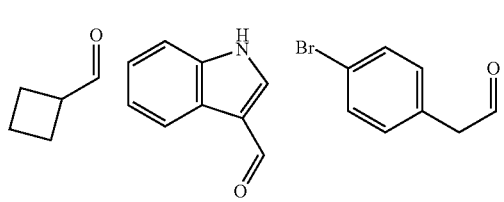
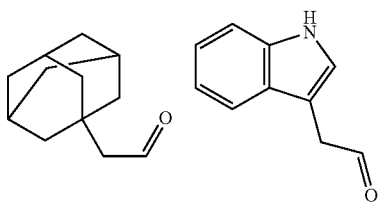
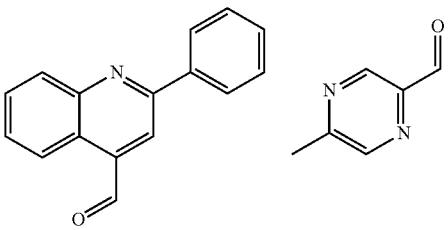
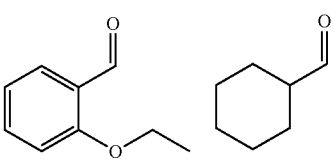
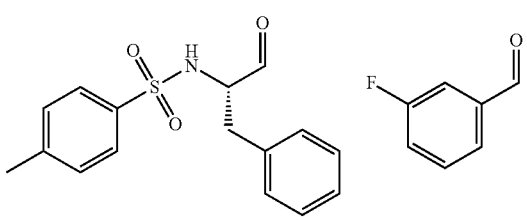
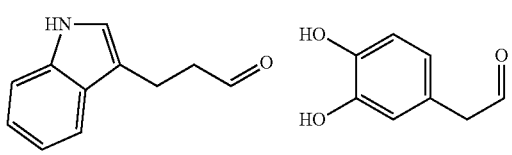

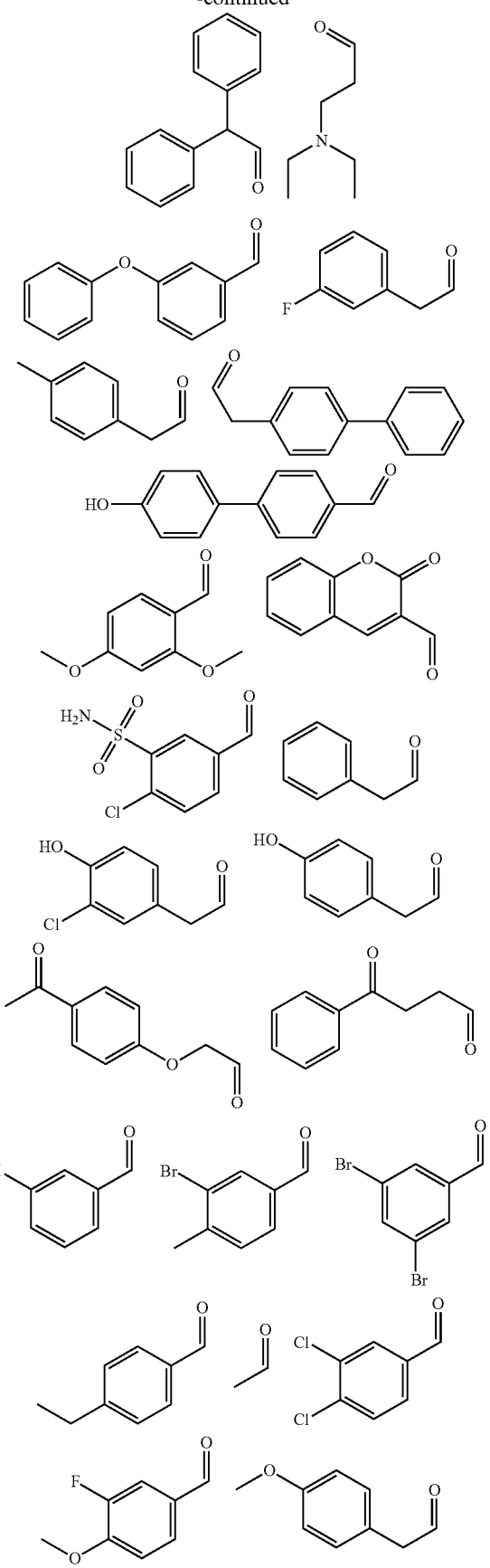
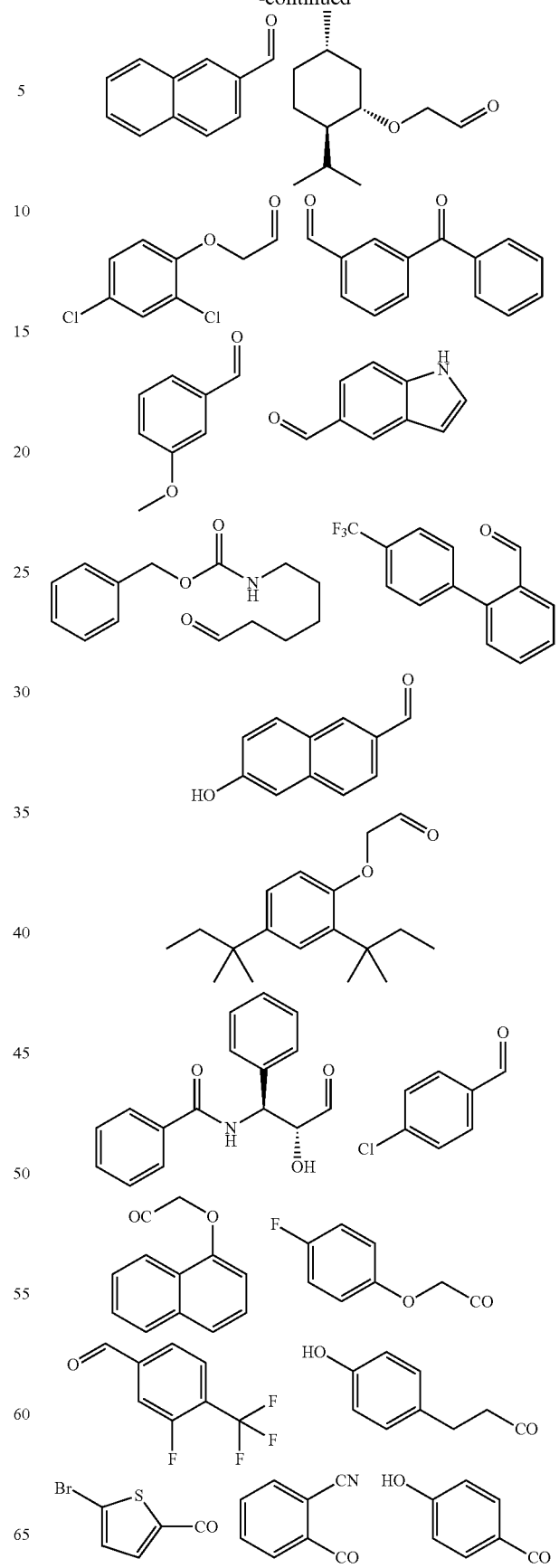

-continued
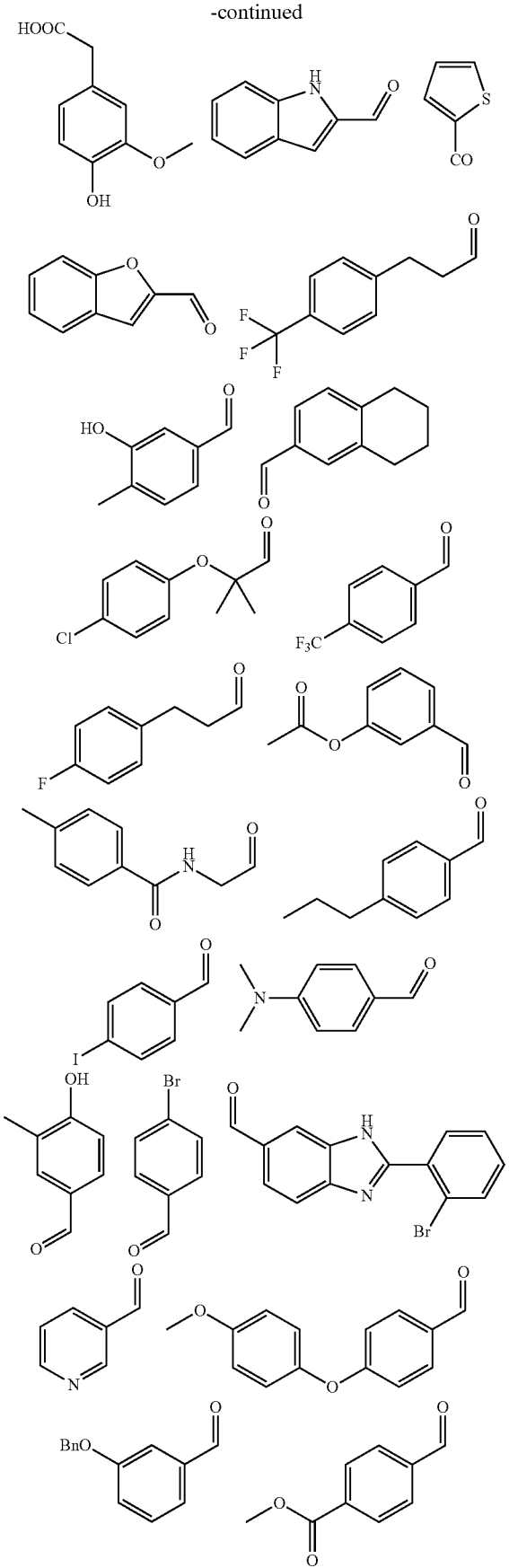
-continued
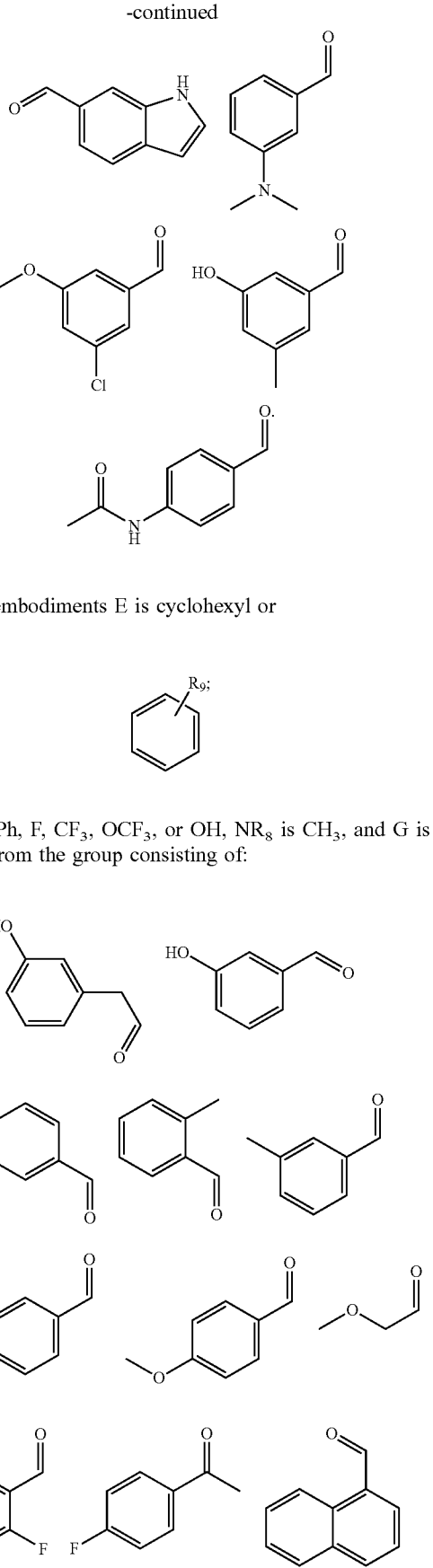
In some embodiments E is cyclohexyl or
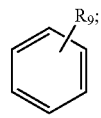
$R_9$ is H, Ph, F, $CF_3$, $OCF_3$, or OH, $NR_8$ is $CH_3$, and G is selected from the group consisting of:
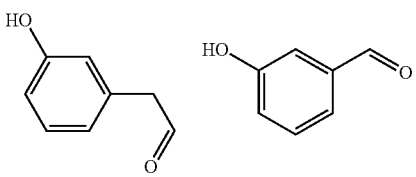
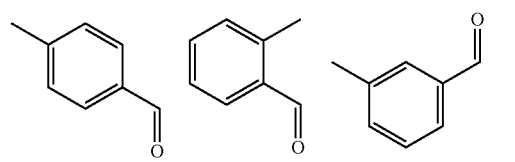
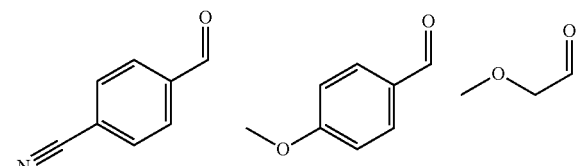
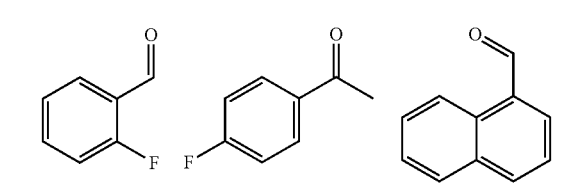

51
-continued
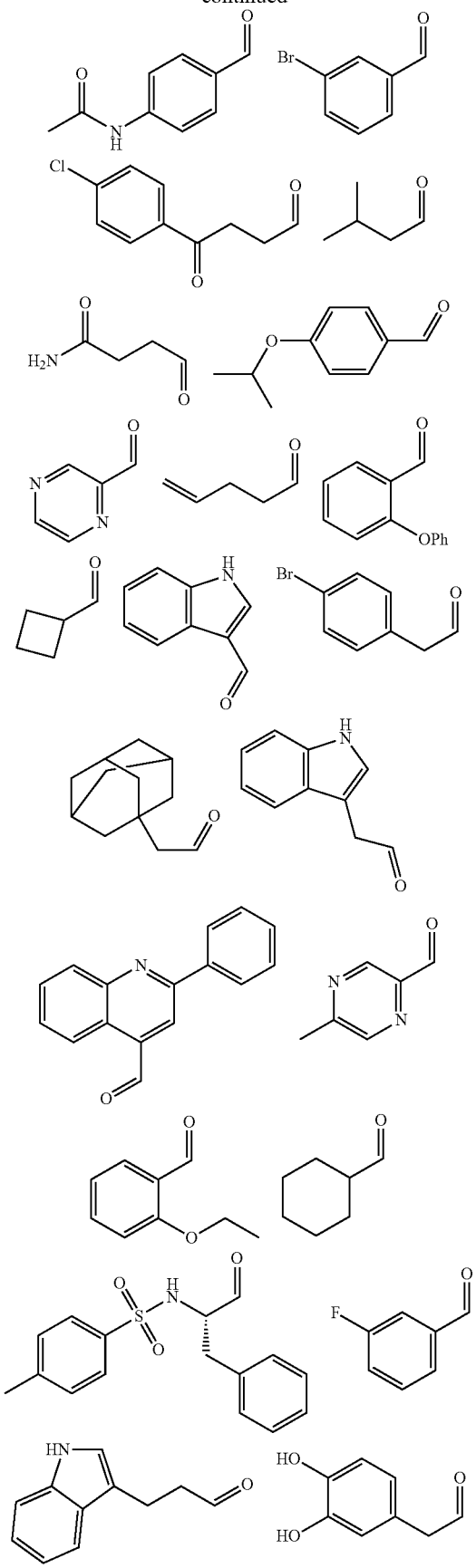
52
-continued
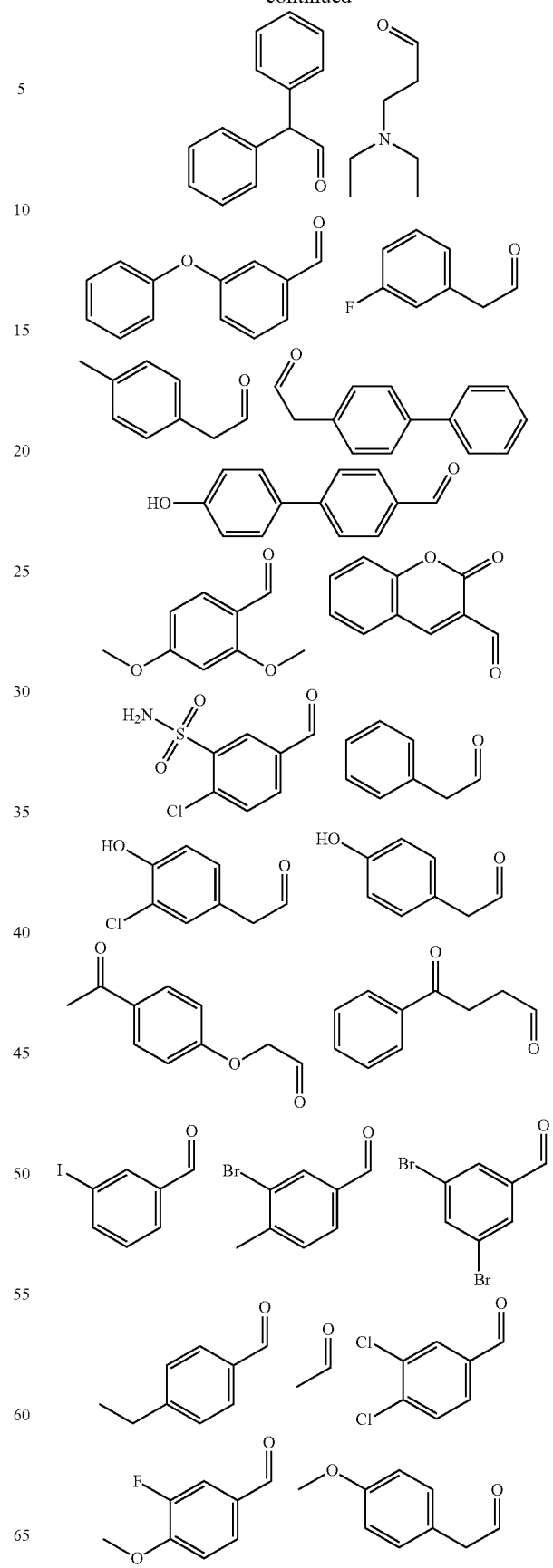

-continued
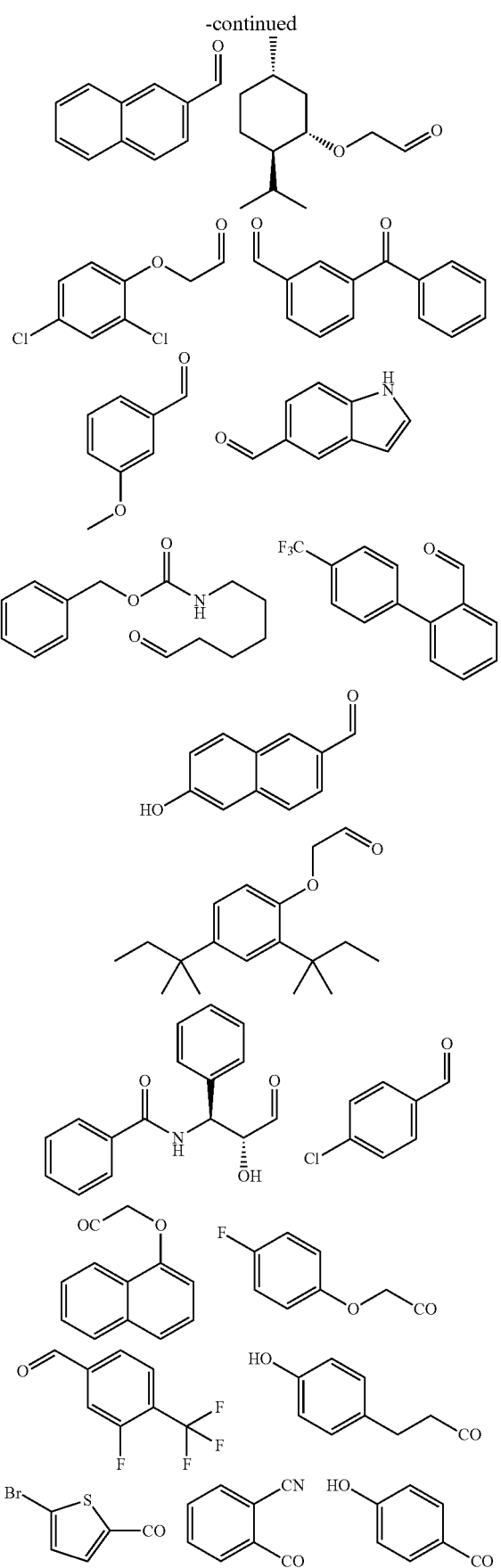
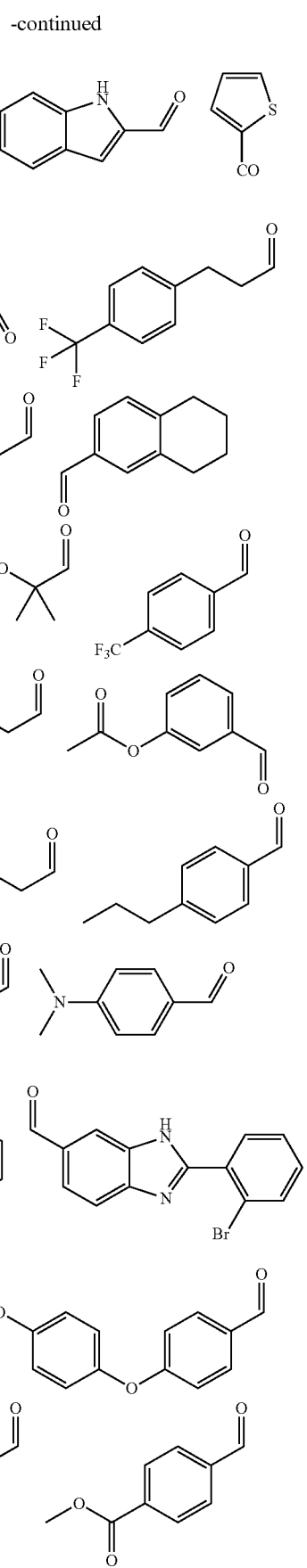

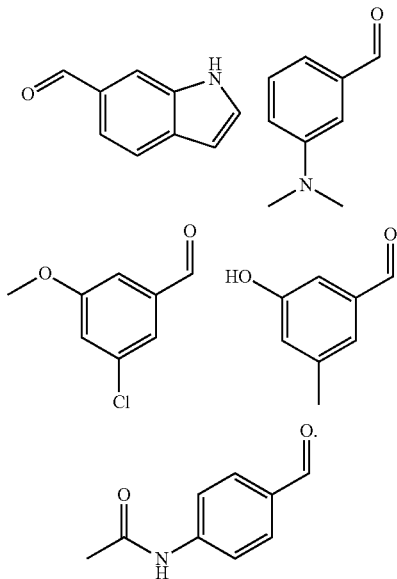

Some aspects of the invention include compound shaving the following formula:

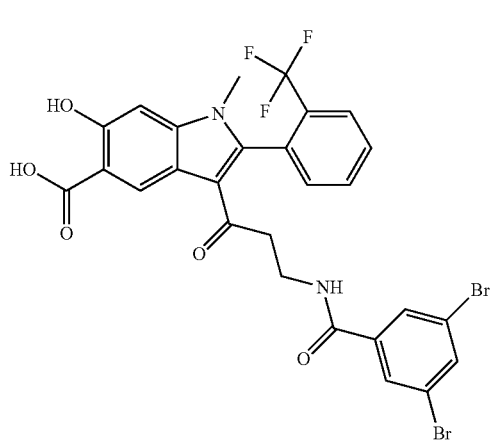 [SMILES: Cn1c(-c2ccccc2C(F)(F)F)c(C(=O)CCNC(=O)c2cc(Br)cc(Br)c2)c2cc(C(=O)O)c(O)cc21]

(3-[3-(3,5-dibromo-benzoylamino)-propionyl]-6-hydroxy-1-methyl-2-(2-trifluoromethyl-phenyl)-1H-indole-5-carboxylic acid), or a pharmaceutically acceptable salt thereof.

Some embodiments of the disclosure include a compound according to Formula D,

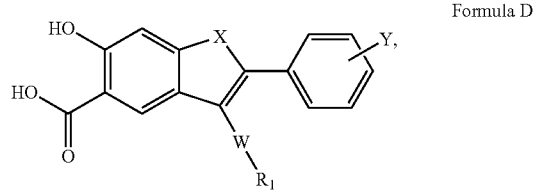

Formula D or a pharmaceutically acceptable salt thereof, wherein X is O, W is CH=CH or CH$_2$CH$_2$, and R$_1$ is selected from the group consisting of

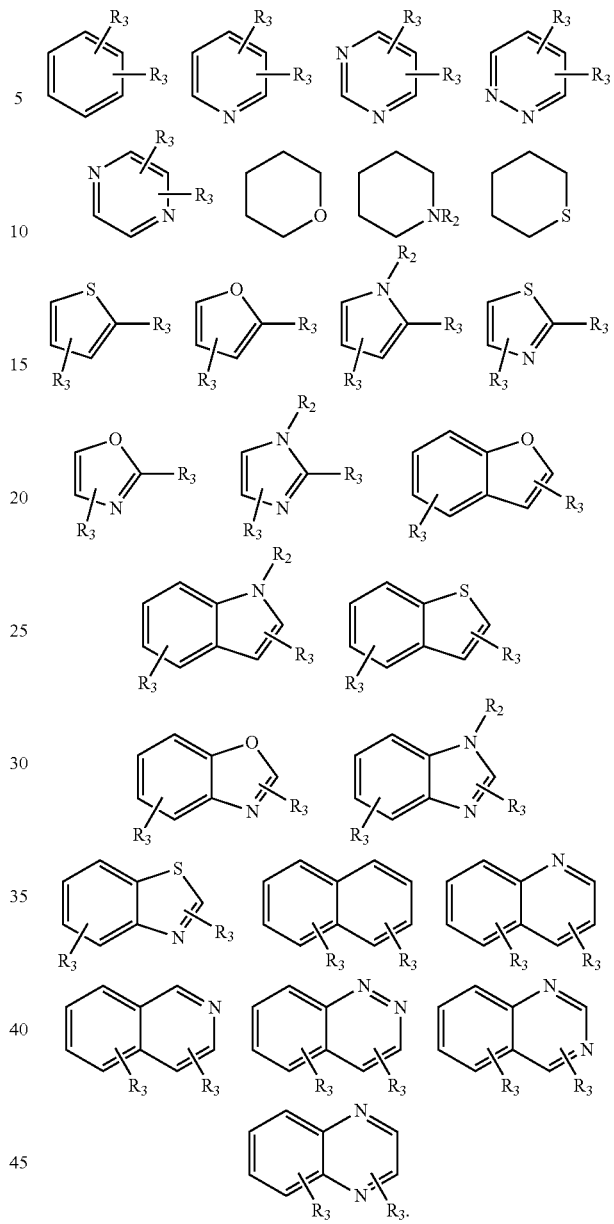

or hydrogen.

According to these embodiments, R$_3$ may be the same or different and is selected from the group consisting of H, halogen, hydroxyl, NR$_2$R$_2$, substituted or unsubstituted C$_1$-C$_6$ alkyl, substituted or unsubstituted C$_1$-C$_6$ alkenyl, substituted or unsubstituted C$_1$-C$_6$ alkynyl, O-(substituted or unsubstituted C$_1$-C$_6$ alkyl), S-(substituted or unsubstituted C$_1$-C$_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, SO$_2$-(substituted or unsubstituted C$_1$-C$_6$ alkyl), SO$_2$NR$_2$R$_2$, C(O)-(substituted or unsubstituted C$_1$-C$_6$ alkyl), C(O)-(substituted or unsubstituted aryl), C(O)-(substituted or unsubstituted heteroaryl), (CH$_2$)$_n$CO$_2$H, and O(CH$_2$)$_n$CO$_2$H.

According to these embodiments, R$_2$ can be the same or different and is H or C$_1$-C$_6$ alkyl.

Additionally, according to these embodiments, Y may be H, halogen, hydroxyl, NR$_2$R$_2$, substituted or unsubstituted C$_1$-C$_6$ alkyl, substituted or unsubstituted C$_1$-C$_6$ alkenyl, substituted or unsubstituted C$_1$-C$_6$ alkynyl, O-(substituted or unsubstituted C$_1$-C$_6$ alkyl), S-(substituted or unsubstituted C$_1$-C$_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, SO$_2$C$_1$-C$_6$ alkyl, SO$_2$NR$_2$R$_2$, C(O)-(substituted or unsubstituted C$_1$-C$_6$ alkyl), C(O)-(substituted or unsubstituted aryl), C(O)-(substituted or unsubstituted heteroaryl), —(CH$_2$)$_n$COZ, or —O—(CH$_2$) n-COZ; and n is selected from one of 1, 2, 3, and 4; and Z is one of OH, or N(R$_4$)$_2$, wherein each occurrence of R$_4$ may be the same or different and is selected from the group consisting of H, substituted or unsubstituted C$_1$-C$_6$ alkyl, substituted or unsubstituted C$_3$-C$_8$ cycloalkyl, substituted or unsubstituted C$_1$-C$_6$ alkenyl, substituted C$_1$-C$_6$ alkynyl, substituted or unsubstituted aryl, substituted or unsubstituted heteroaryl,

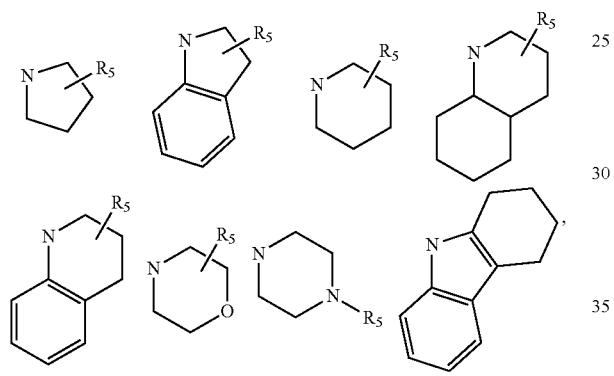

OR$_5$, and NHR$_5$, wherein R$_5$ is substituted or unsubstituted C$_1$-C$_6$ alkyl, substituted or unsubstituted aryl, substituted or unsubstituted heteroaryl, C(O)-(substituted or unsubstituted C$_1$-C$_6$alkyl), C(O)-(substituted or unsubstituted aryl), C(O)-(substituted or unsubstituted heteroaryl), or C(O)-(substituted or unsubstituted C$_3$-C$_8$ cycloalkyl).

In other embodiments of the present, R$_1$ of the compound described above is

In some embodiments of the present disclosure, R$_3$ of the compound described above is selected from the group consisting of H, Cl, F, OCH$_3$, CF$_3$, OCF$_3$, OPh, and OCH$_2$CO$_2$H; Y is selected from the group consisting of H, CF$_3$, OCF$_3$, Cl, Ph, OPh, and —OCH$_2$COZ; and Z is selected from the group consisting of:

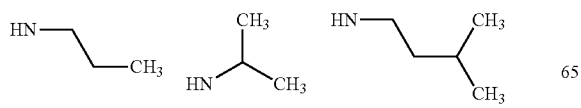

-continued

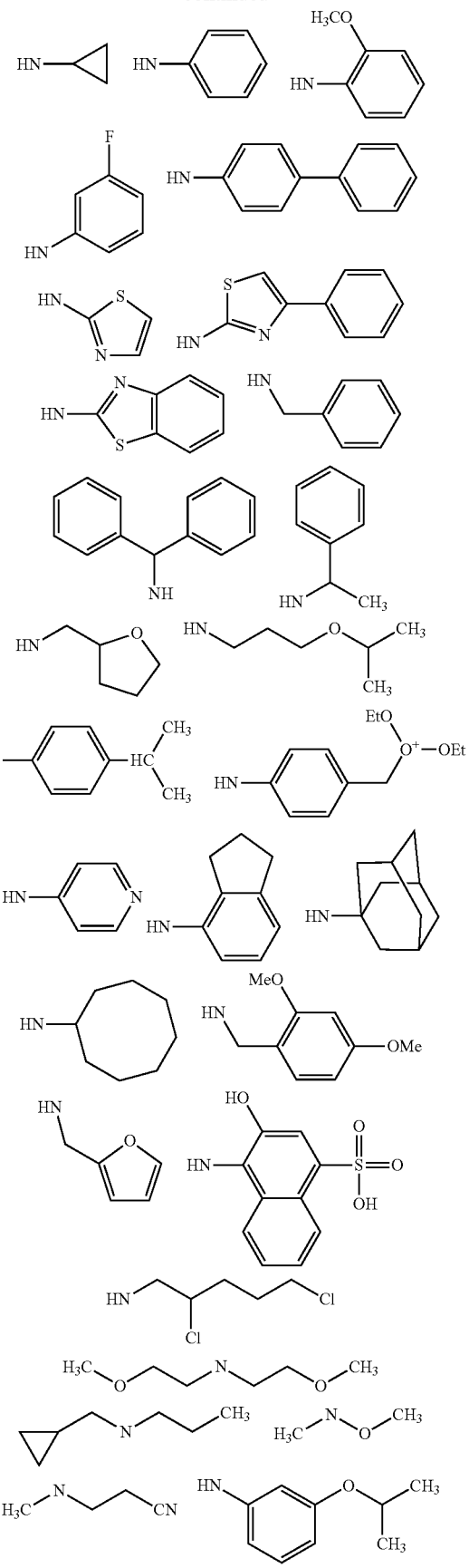

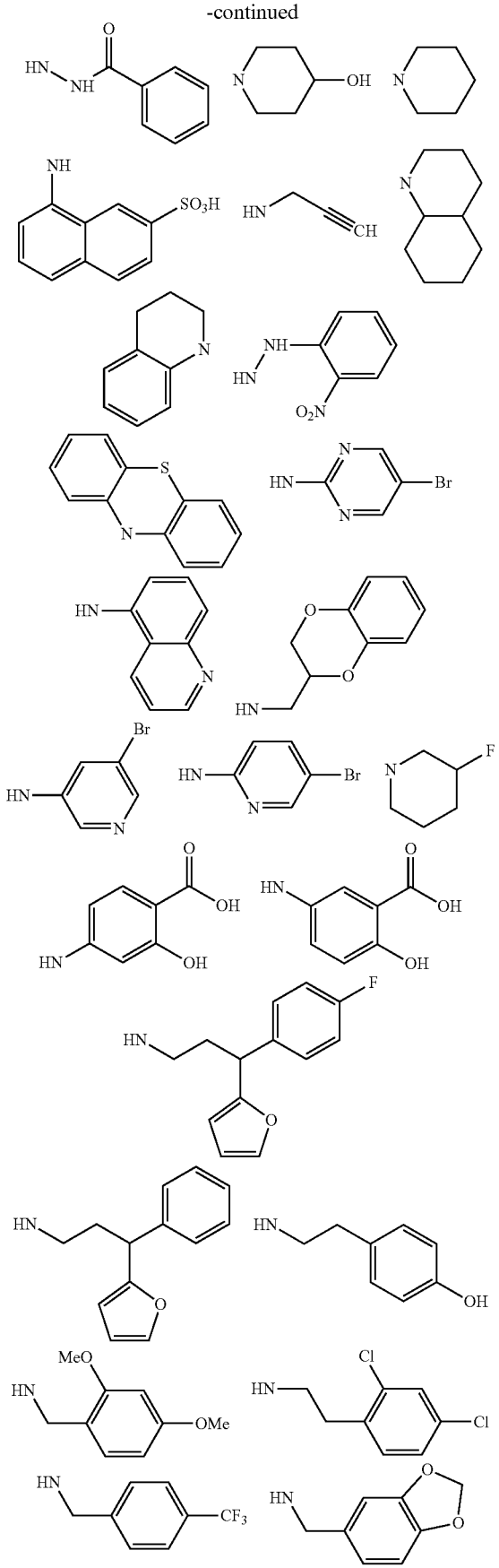
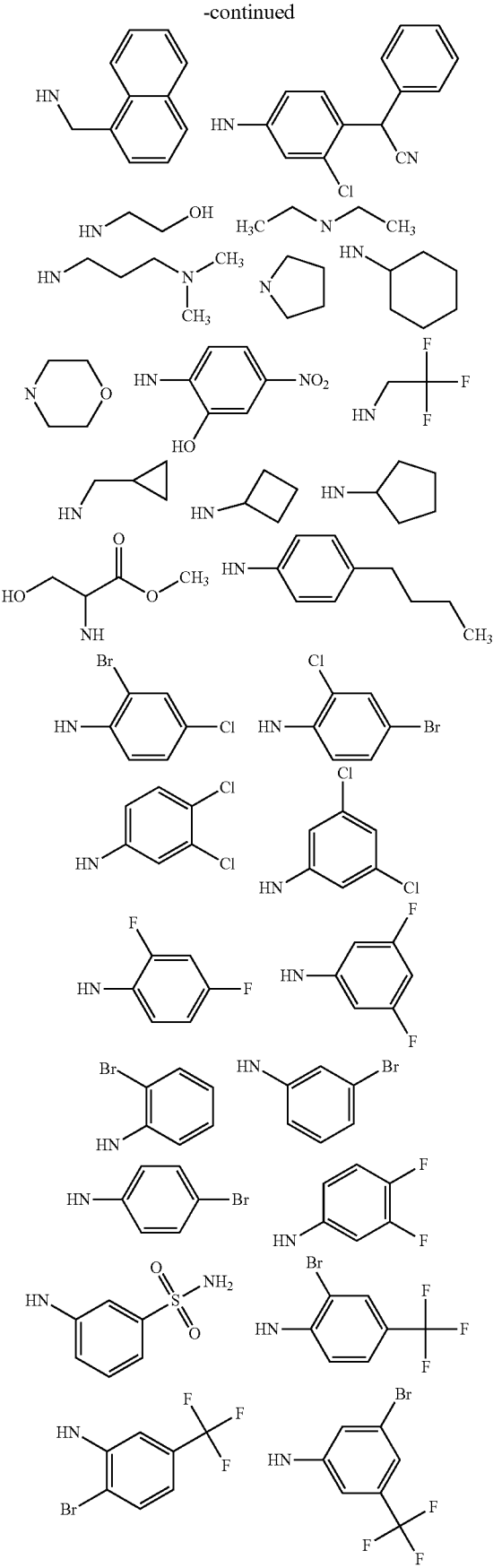

-continued
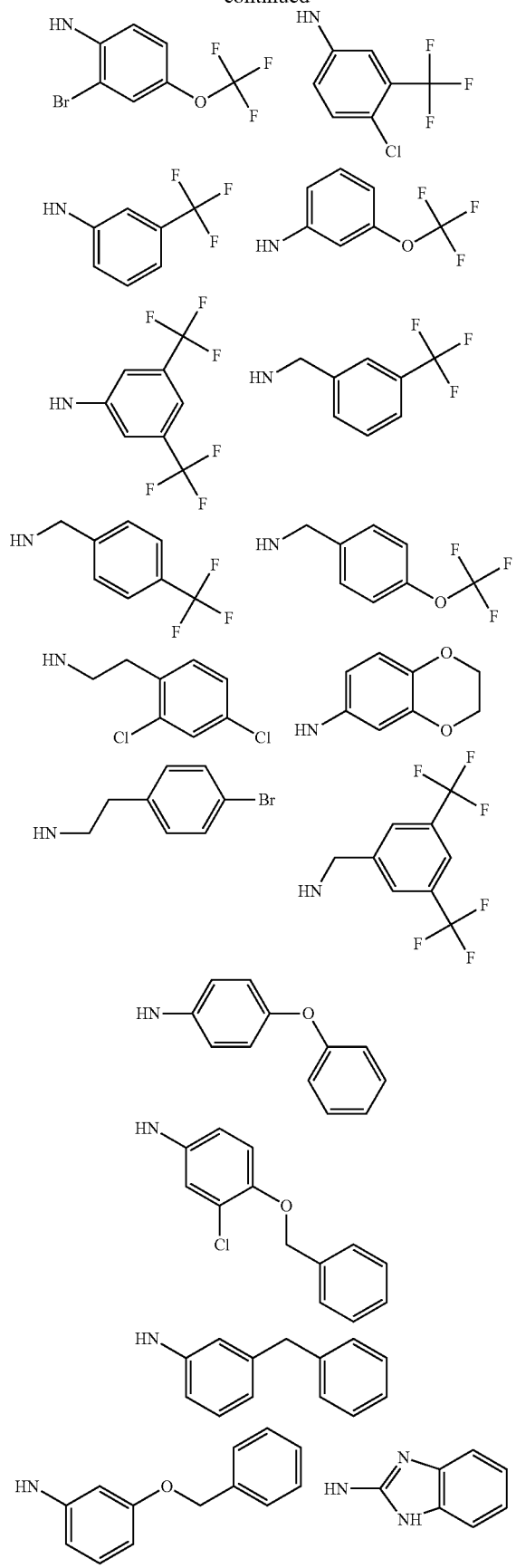
-continued
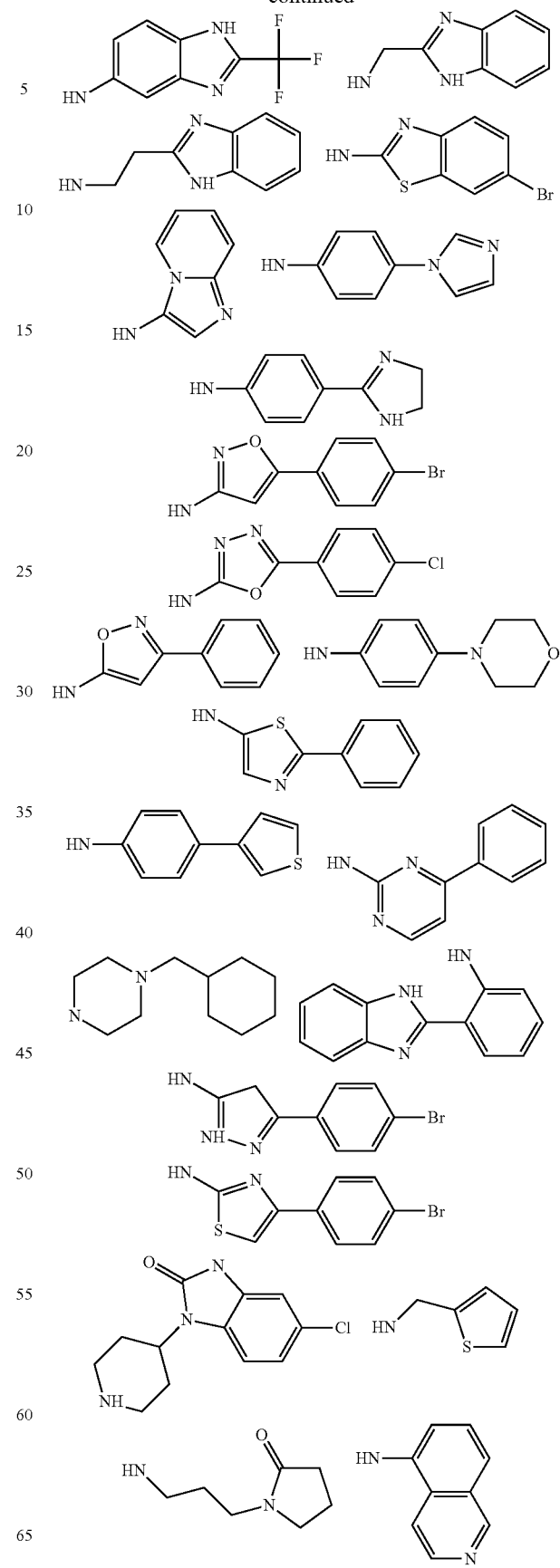

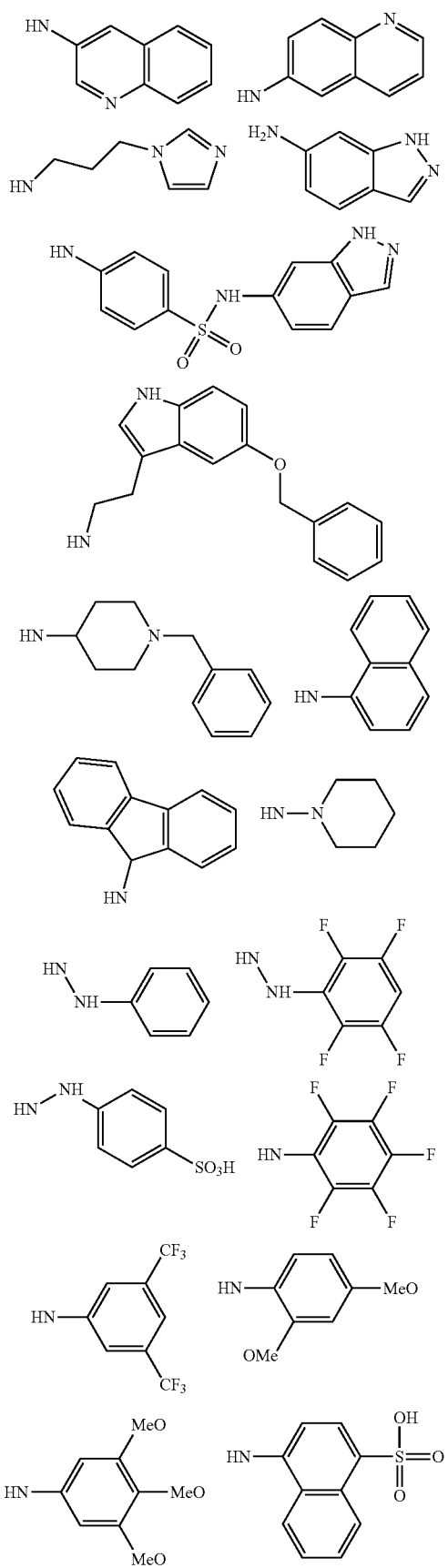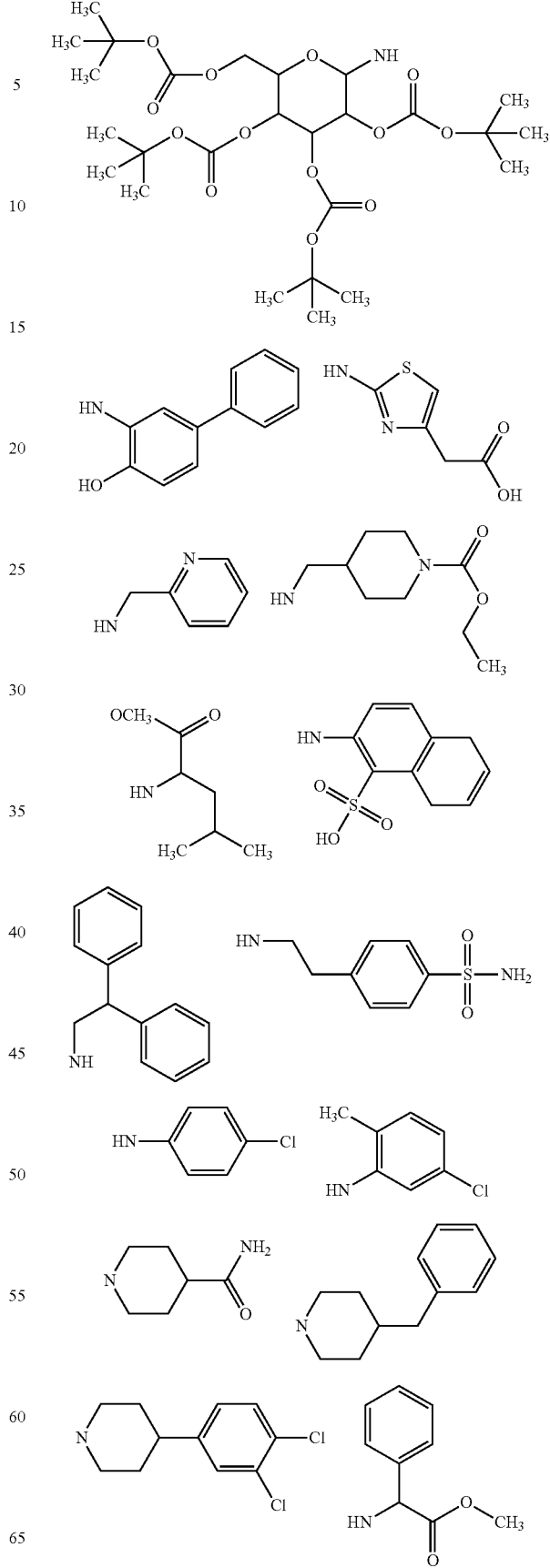

-continued
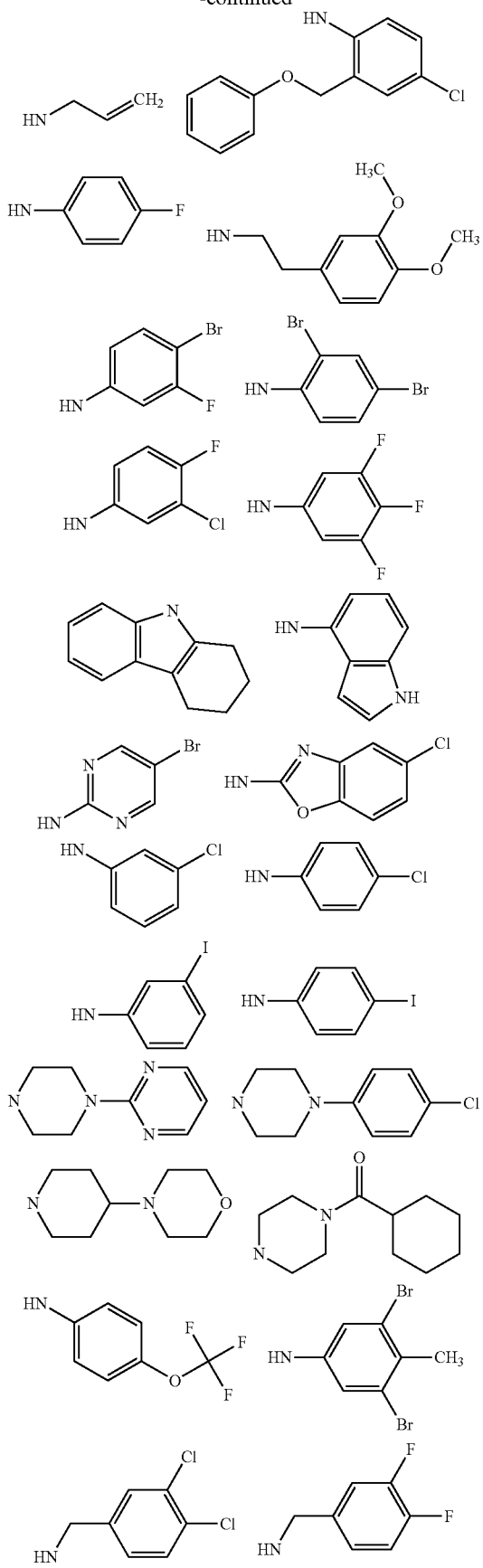
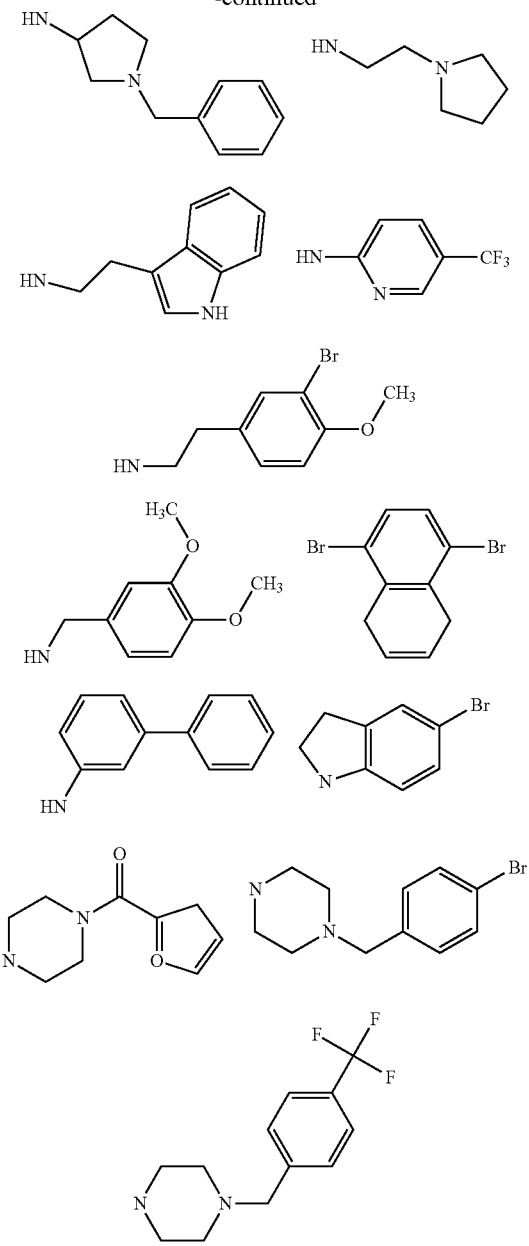
and —OH.
Some other embodiments of the disclosure include a compound according to Formula D,
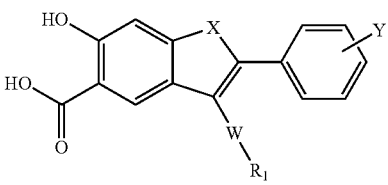
Formula D
or a pharmaceutically acceptable salt thereof, wherein X is $NR_2$, W is CH=CH or $CH_2CH_2$, and $R_1$ is selected from the group consisting of:

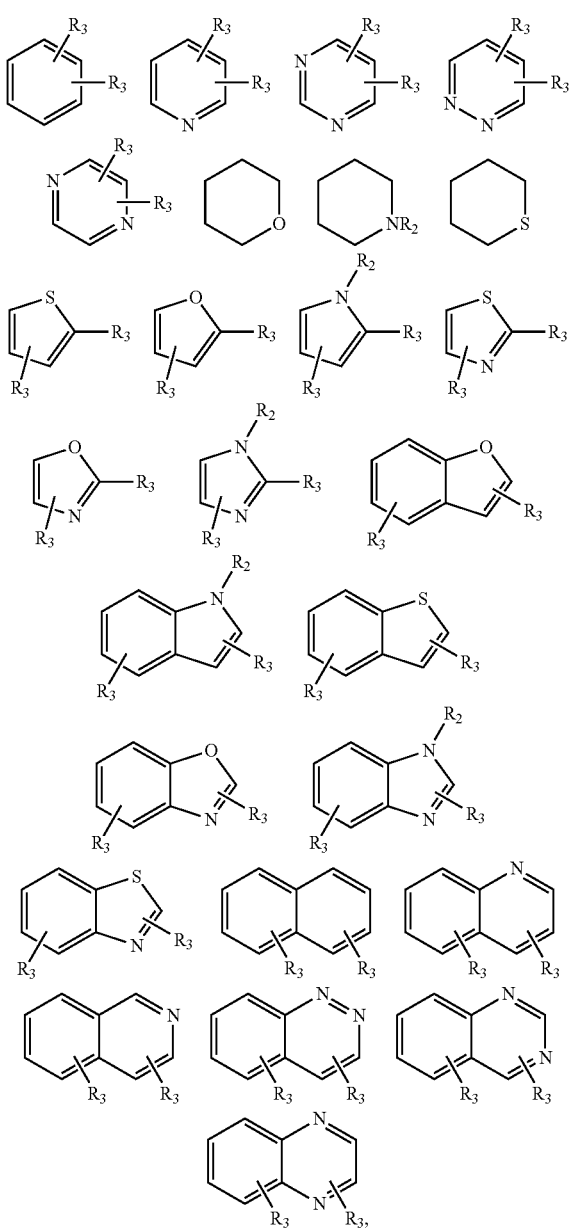

and hydrogen, wherein each occurrence of $R_2$ may be the same or different and is H or $C_1$-$C_6$ alkyl.

According to these embodiments, $R_3$ may be the same or different and is selected from the group consisting of H, halogen, hydroxyl, $NR_2R_2$, substituted or unsubstituted $C_1$-$C_6$ alkyl, substituted or unsubstituted $C_1$-$C_6$ alkenyl, substituted or unsubstituted $C_1$-$C_6$ alkynyl, O-(substituted or unsubstituted $C_1$-$C_6$ alkyl), S-(substituted or unsubstituted $C_1$-$C_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, $SO_2$-(substituted or unsubstituted $C_1$-$C_6$ alkyl), $SO_2NR_2R_2$, C(O)-(substituted or unsubstituted $C_1$-$C_6$ alkyl), C(O)-(substituted or unsubstituted aryl), C(O)-(substituted or unsubstituted heteroaryl), $(CH_2)_nCO_2H$, and $O(CH_2)_nCO_2H$.

Additionally, according to these embodiments, Y is H, halogen, hydroxyl, $NR_2R_2$, substituted or unsubstituted $C_1$-$C_6$ alkyl, substituted or unsubstituted $C_1$-$C_6$ alkenyl, substituted or unsubstituted $C_1$-$C_6$ alkynyl, O-(substituted or unsubstituted $C_1$-$C_6$ alkyl), S-(substituted or unsubstituted $C_1$-$C_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, $SO_2C_1$-$C_6$ alkyl, $SO_2NR_2R_2$, C(O)-(substituted or unsubstituted $C_1$-$C_6$ alkyl), C(O)-(substituted or unsubstituted aryl), C(O)-(substituted or unsubstituted heteroaryl), $—(CH_2)_nCOZ$, or $—O—(CH_2)$n-COZ; and n is selected from one of 1, 2, 3, and 4; and Z is one of OH, or $N(R_4)_2$, wherein each occurrence of $R_4$ may be the same or different and is selected from the group consisting of H, substituted or unsubstituted $C_1$-$C_6$ alkyl, substituted or unsubstituted $C_3$-$C_8$ cycloalkyl, substituted or unsubstituted $C_1$-$C_6$ alkenyl, substituted $C_1$-$C_6$ alkynyl, substituted or unsubstituted aryl, substituted or unsubstituted heteroaryl,

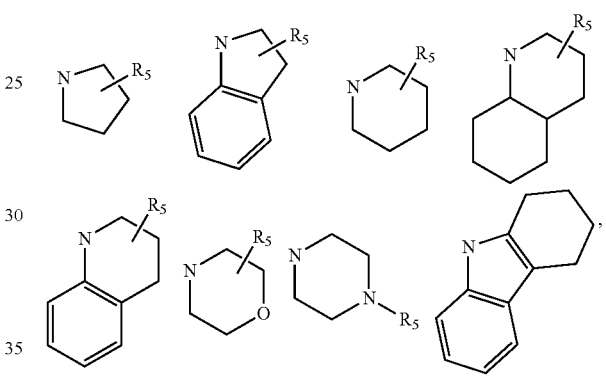

$OR_5$, and $NHR_5$, wherein $R_5$ is substituted or unsubstituted $C_1$-$C_6$ alkyl, substituted or unsubstituted aryl, substituted or unsubstituted heteroaryl, C(O)-(substituted or unsubstituted $C_1$-$C_6$alkyl), C(O)-(substituted or unsubstituted aryl), C(O)-(substituted or unsubstituted heteroaryl), or C(O)-(substituted or unsubstituted $C_3$-$C_8$ cycloalkyl).

In other embodiments of the present, $R_1$ of the compound described above is

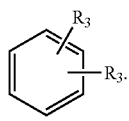

In some embodiments of the present disclosure, each occurrence of $R_3$ of the compound described can be the same or different is selected from the group consisting of H, Cl, F, $OCH_3$, $CF_3$, $OCF_3$, OPh, and $OCH_2CO_2H$; Y is selected from the group consisting of H, $CF_3$, $OCF_3$, Cl, Ph, OPh, and $—OCH_2COZ$; and Z is selected from the group consisting of:

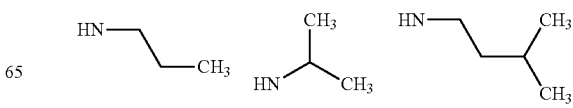

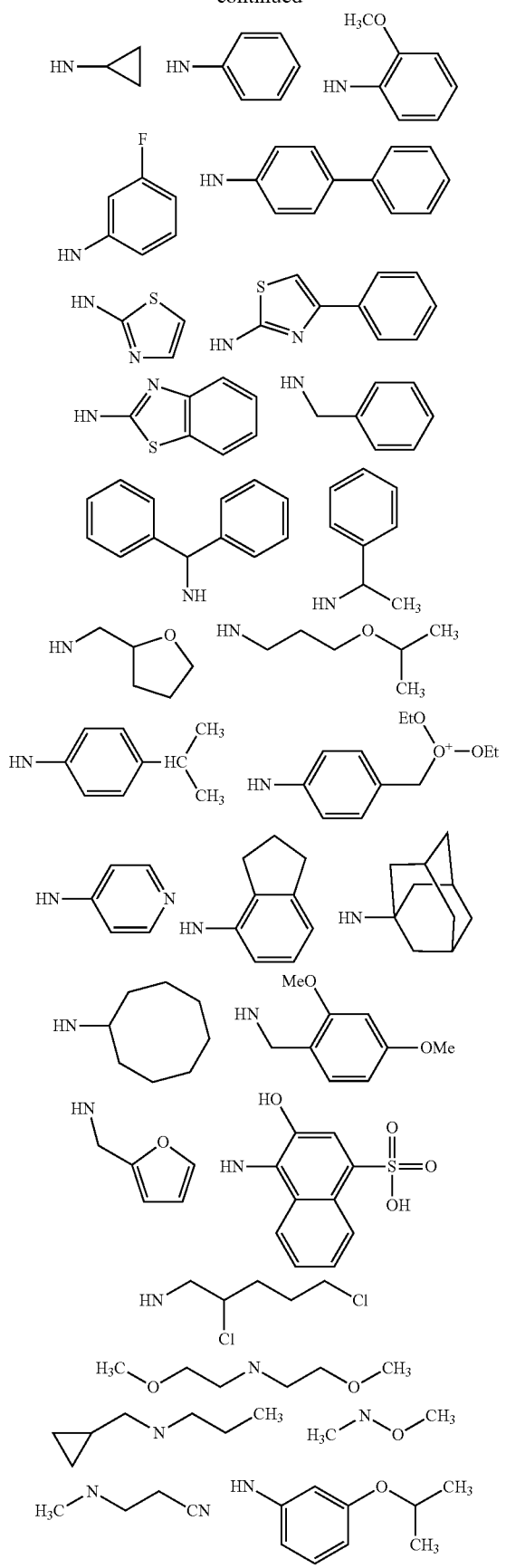
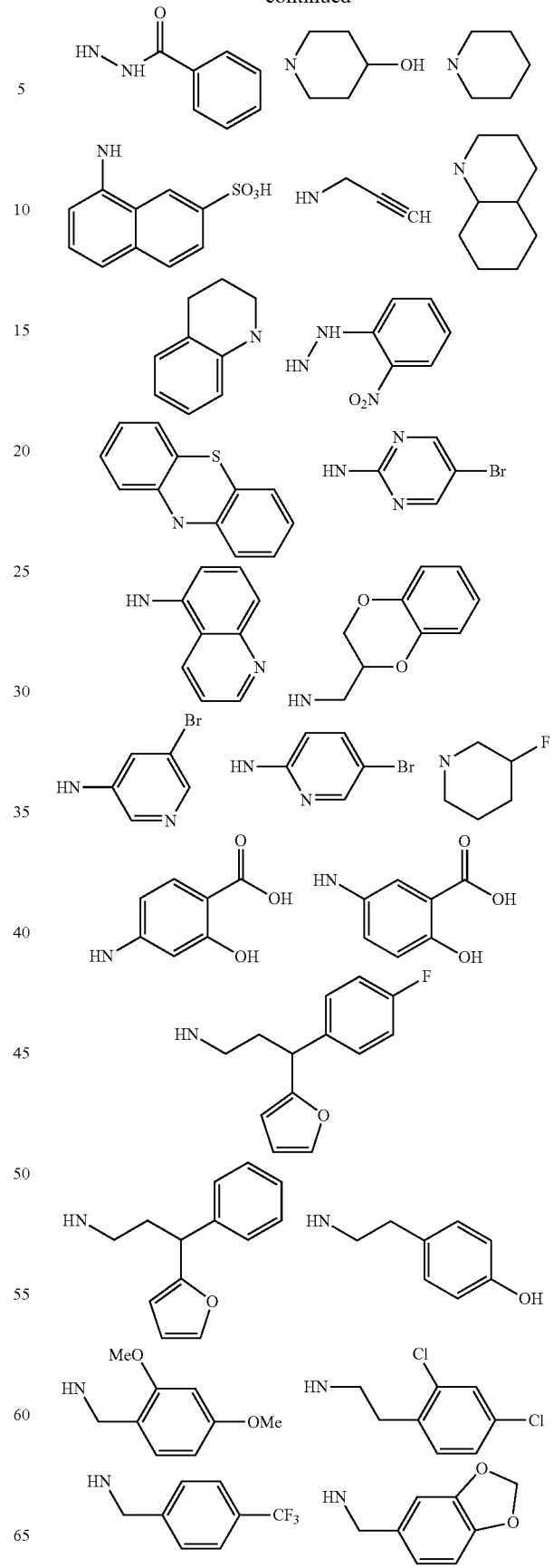

71
-continued
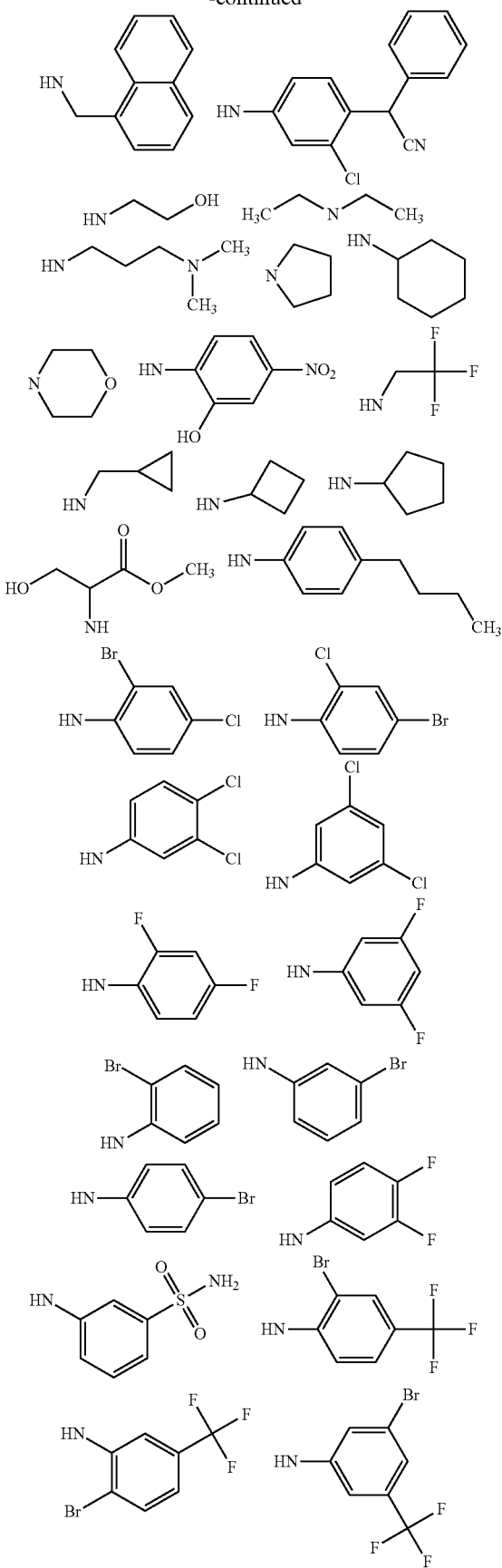
72
-continued
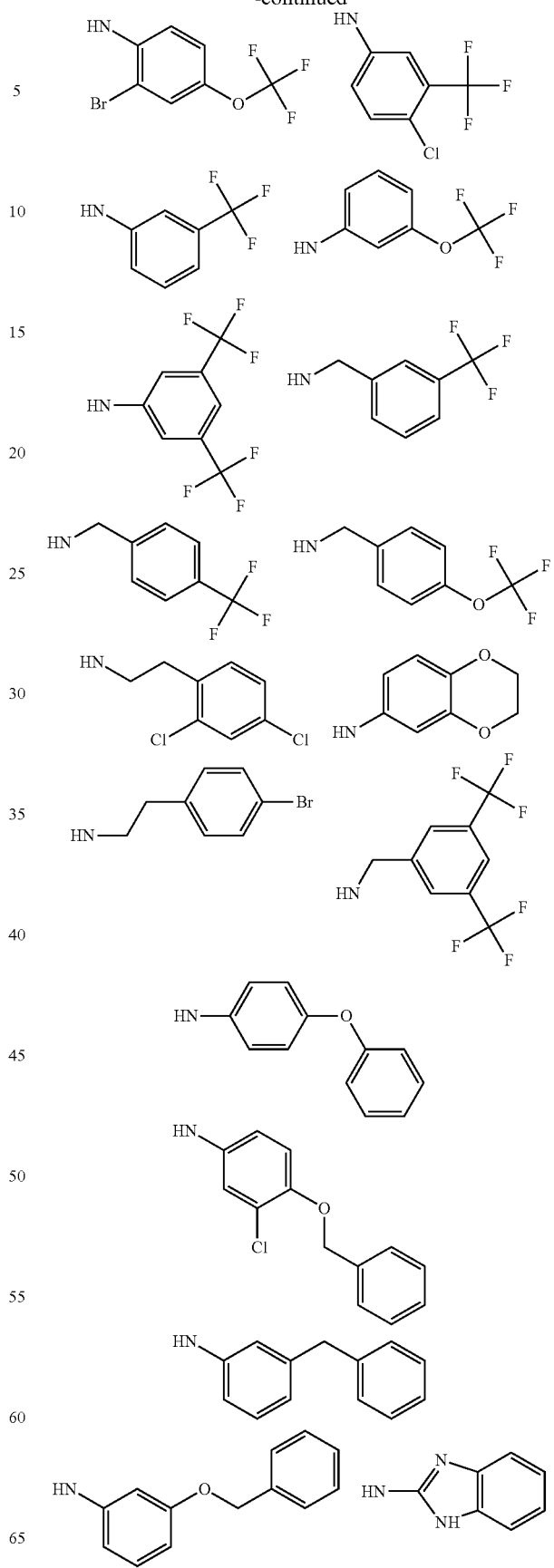

73
-continued
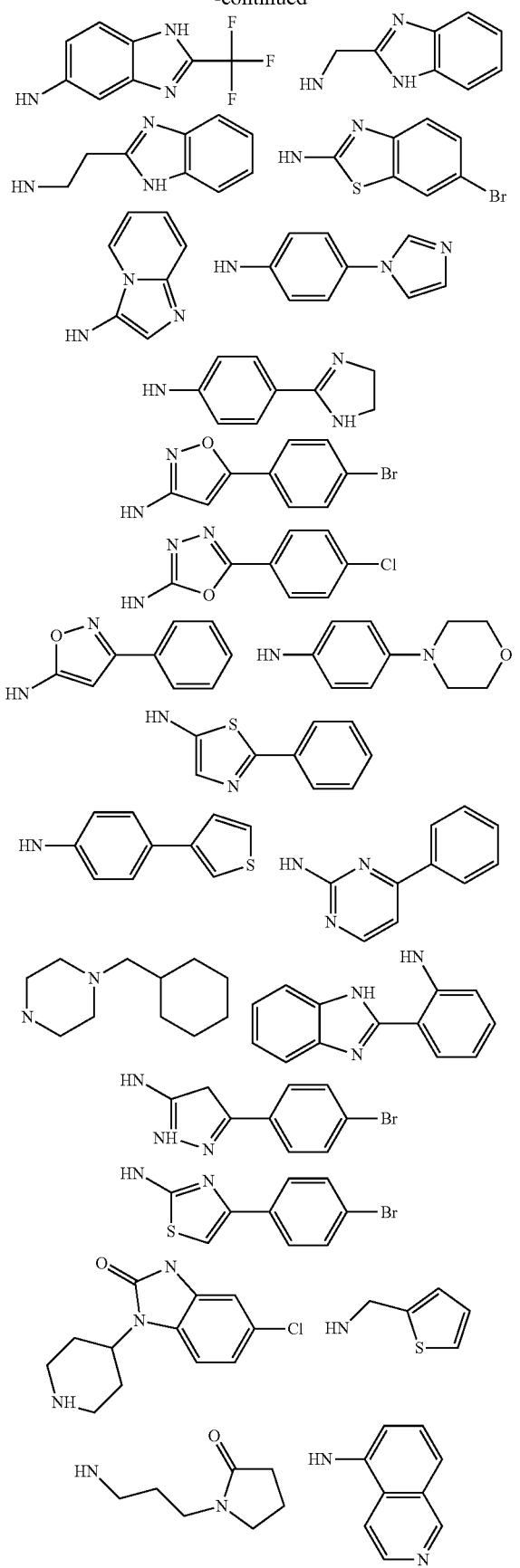
74
-continued
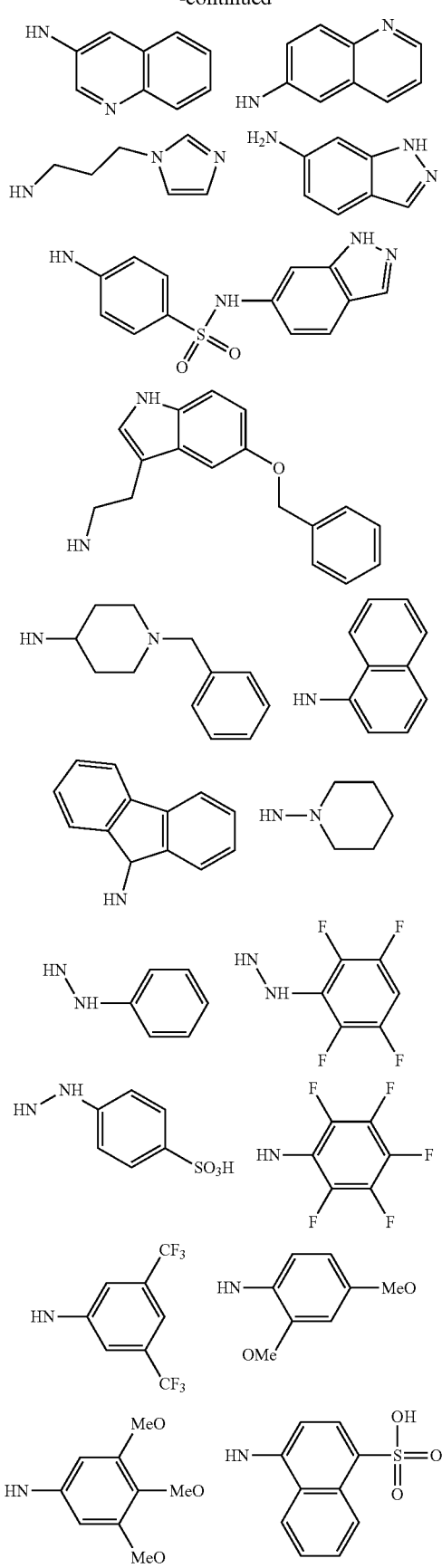

75
-continued
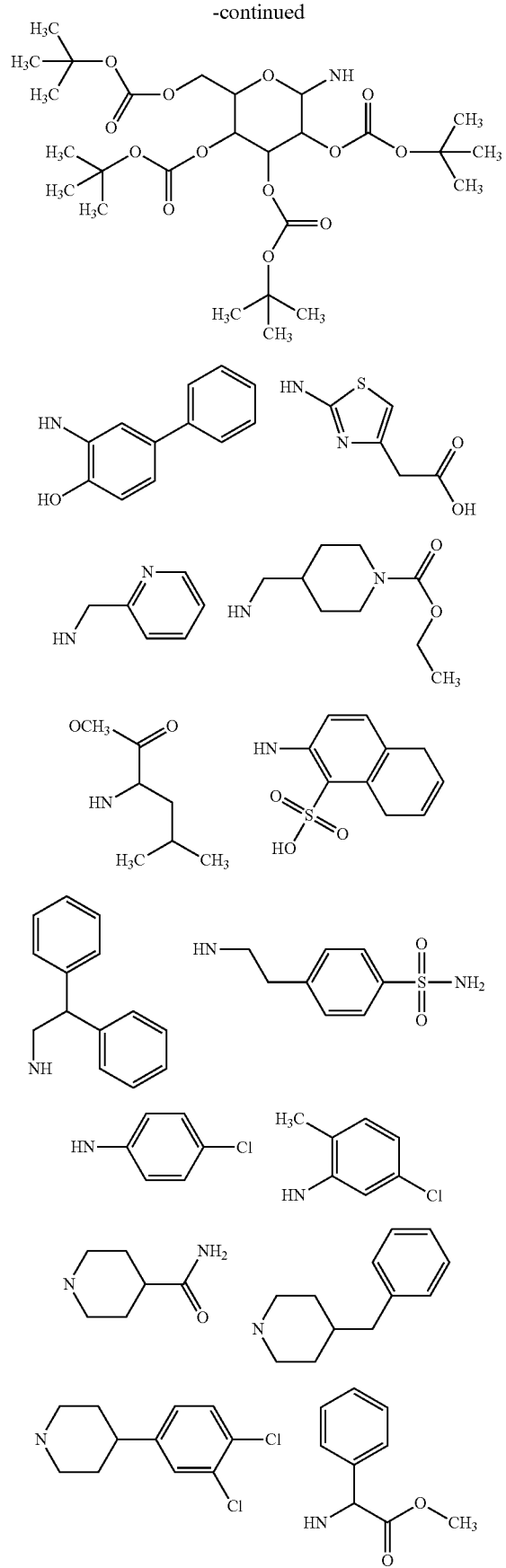
76
-continued
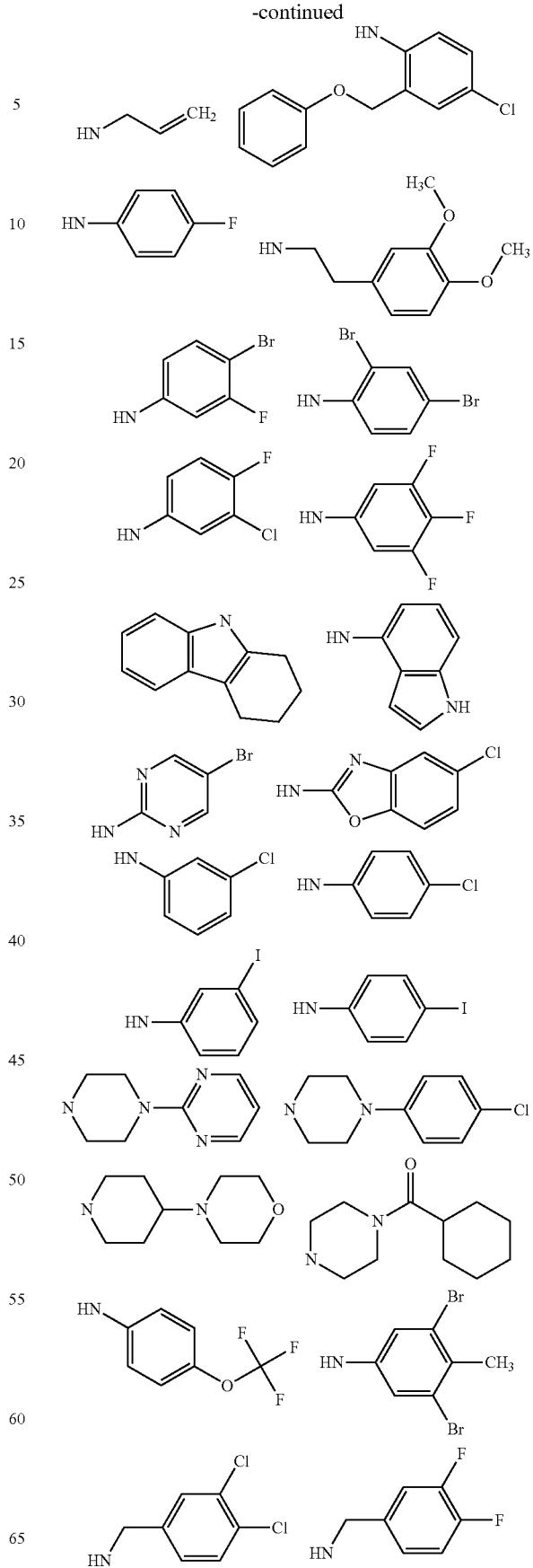

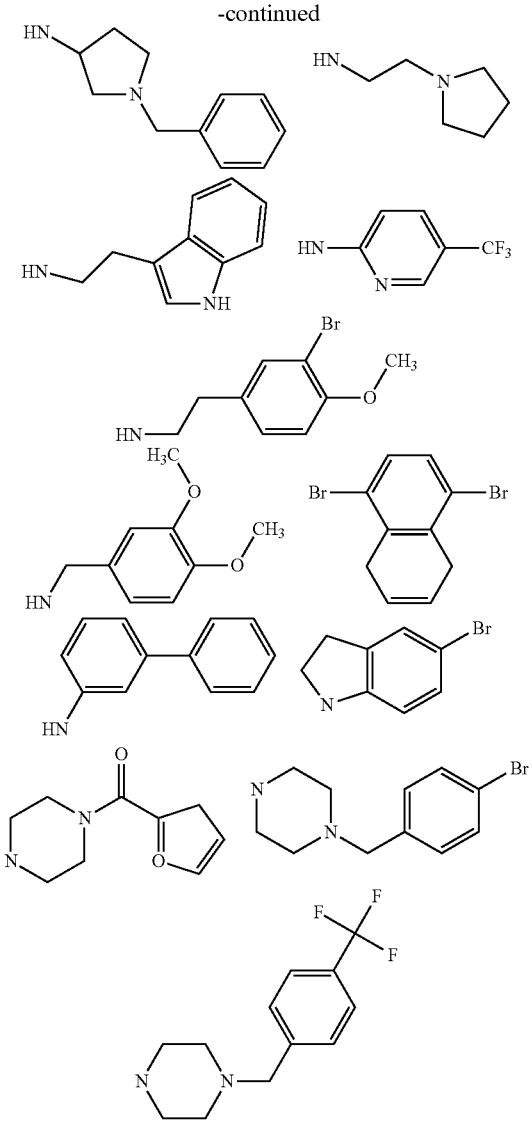

and —OH.

Some aspects of the invention include methods of reducing the activity of a tyrosine phosphatase comprising providing at least one compound according to any of the compounds disclosed herein or a pharmaceutically acceptable salt thereof. In some embodiment that tyrosine phosphatase is *Mycobacterium* protein tyrosine phosphatase B (mPTPB).

Also disclosed herein are methods and/or compounds for treating diseases, disorders, and/or condition associated with inappropriate activity of a protein tyrosine phosphatase comprising administering to an individual in need thereof a therapeutically effective amount of at least one compound of claim 2, or a pharmaceutically acceptable salt thereof. In some embodiments the e or condition is type 1 or type 2 diabetes, obesity, metabolic syndrome, Crohn's disease, rheumatoid arthritis, Graves' disease, systemic lupus erythematosus, juvenile idiopathic arthritis, myasthenia gravis, generalized vitiligo, Wegener's granulomatosis, cancer, leukemia, or tuberculosis.

Some aspects of the invention include pharmaceutical formulations comprising at least one compound disclosed herein or a pharmaceutically acceptable salt thereof, and a pharmaceutically acceptable carrier therefore.

Yet another embodiment of the present disclosure includes a pharmaceutical formulation of at least one compound disclosed here and further comprising at least one additional therapeutic agent.

DESCRIPTION

Figure 1:
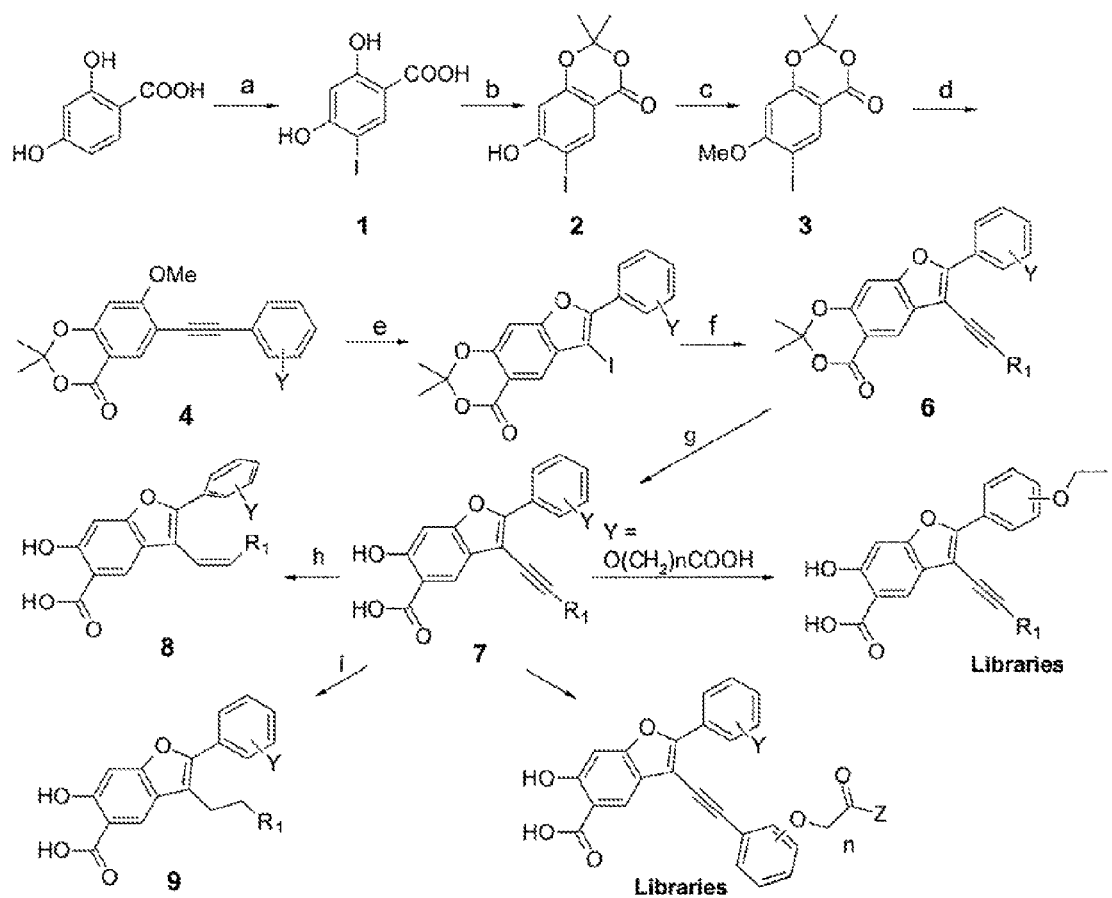
FIG. 1 is a schematic illustrating the creation of a benzofuran salicylic acid based library.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

As used herein, unless explicitly stated otherwise or clearly implied otherwise the term 'about' refers to a range of values plus or minus 10 percent, e.g. about 1.0 encompasses values from 0.9 to 1.1.

As used herein, unless explicitly stated otherwise or clearly implied otherwise the terms 'therapeutically effective dose,' 'therapeutically effective amounts,' and the like, refers to a portion of a compound that has a net positive effect on the health and well being of a human or other animal. Therapeutic effects may include an improvement in longevity, quality of life and the like these effects also may also include a reduced susceptibility to developing disease or deteriorating health or well being. The effects may be immediate realized after a single dose and/or treatment or they may be cumulative realized after a series of doses and/or treatments.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For addition information on some pharmaceutically acceptable salts that can be used to practice the invention please reviews such as Berge, et al., 66 J. PHARM. SCI. 1-19 (1977), Haynes, et al, J. Pharma. Sci., Vol. 94, No. 10, October 2005, pgs. 2111-2120 and the like.

Halogens that may be used to practice the invention include Fluoride (F), Chloride (Cl), Bromide (Br), and Iodine (I).

As used herein, the term, "substituted or unsubstituted alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl tert butyl, n-pentyl, isopentyl, neopentyl, heptyl, hexyl, octyl, nonyl, decyl, undecyl, dodecyl, tridecyl, tetradecyl and the like. These alkyl groups may be substituted with groups including, but not limited to, amines, nitriles, halogens, aldehydes, ketones, carboxylic acids, aryl and heteroaryl groups, cyclic alkanes, heterocyclic alkanes, and the like.

The term "substituted or unsubstituted alkenyl" as used herein represents an olefinically unsaturated branched or linear group having at least one double bond. Examples of such groups include radicals such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl as well as dienes and trienes of straight and branched chains. These alkenyl groups may be substituted with groups including, but not limited to, amines, nitriles, halogens, aldehydes, ketones, carboxylic acids, aryl and heteroaryl groups, cyclic alkanes, heterocyclic alkanes, and the like.

The term "alkynyl" denotes such radicals as ethynyl, propynyl, butynyl, pentynyl, hexynyl, heptynyl as well as di- and tri-ynes. These alkynyl groups may be substituted with groups including, but not limited to, amines, nitriles, halogens, aldehydes, ketones, carboxylic acids, aryl and heteroaryl groups, cyclic alkanes, heterocyclic alkanes, and the like.

The term "cycloalkyl" includes groups such as cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, adamantyl, and the like. Such cycloalkyls may be unsaturated, as in, cyclohexenyl, cyclohexadienyl, cyclopentenyl, and the like. Cycloalkyl cyclic compounds that may include cyclic structures that include atoms other than carbon such as nitrogen and sulfur and the like, and include, but not limited to, morpholine, piperidine, tetrahydrofuran, pyrrolidine and the like. These cycloalkyl groups may be substituted with groups including, but not limited to, amines, nitriles, halogens, aldehydes, ketones, carboxylic acids, aryl and heteroaryl groups, cyclic alkanes, heterocyclic alkanes, and the like.

The term "aryl" denotes 5- and 6-membered stable, organic, saturated or unsaturated, carbocyclic bicyclic rings, which may be substituted with groups including, but not limited to, amines, nitriles, halogens, aldehydes, ketones, carboxylic acids, aryl and heteroaryl groups, cyclic alkanes, heterocyclic alkanes, and the like. Typical "aryl" groups are phenyl, naphthyl, toluoyl, xylenyl, indanyl, tetralinyl, and the like.

The term "heteroaryl" includes 5- and 6-membered stable, organic, saturated or unsaturated, heterocyclic monocyclic rings having 1 to 4 hetero atoms selected from S, O, and N; and 7 to 10 membered stable, organic saturated or unsaturated, bicyclic rings having 1 to 5 hetero atoms selected from S, O, N; both of which may be substituted with groups including, but not limited to, amines, nitriles, halogens, aldehydes, ketones, carboxylic acids, aryl and heteroaryl groups, cyclic alkanes, heterocyclic alkanes, and the like. Typical "heteroaryl" groups are pyridyl, thienyl, pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, indazolyl, imidazo(1.2-A)pyridinyl, benzotriazolyl, 1,2-benzisoxazolyl, benzoxazolyl, benzothiazolyl, purinyl, pyrimidinyl, quinolinyl, phthalazinyl, quinazolinyl, quinoxalinyl, tedtrahydrobenzofuranyl, dihydroindolyl, and the like.

The term, "treating" as used herein unless stated or implied otherwise, includes administering to a human or an animal patient at least one dose of a compounds, treating includes preventing or lessening the likelihood and or severity of a at least one disease as well as limiting the length of an illness or the severity of an illness it may or may not result in a cure of the disease.

Physiological diseases, disorders, and/or conditions, that can be treated with the inventive compounds and/or treatments disclosed herein involve pathological activity of at least one protein tyrosine phosphatase, includes, but is not limited to, diseases, disorder, conditions and the like that are initiated, propagated, worsened and/or prolonged by the activity of at least one protein tyrosine phosphatase.

The term, "Pharmaceutically acceptable salts" as used herein unless defined otherwise refers to: Pharmaceutically acceptable salts, and common methodology for preparing them, are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

Pharmaceutical formulation: The compounds of the invention and their salts may be formulated as pharmaceutical compositions for administration. Such pharmaceutical compositions and processes for making the same are known in the art for both humans and non-human mammals. See, e.g., REMINGTON: THE SCIENCE AND PRACTICE OF PHARMACY, (A. Gennaro, et al., eds., $19^{th}$ ed., Mack Publishing Co., 1995).

Formulations can be administered through various means, including oral administration, parenteral administration such as injection (intramuscular, subcutaneous, intravenous, intraperitoneal) or the like; transdermal administration such as dipping, spray, bathing, washing, pouring-on and spotting-on, and dusting, or the like. Additional active ingredients may be included in the formulation containing a compound of the invention or a salt thereof.

Pharmaceutically acceptable carrier: Pharmaceutically acceptable carrier, unless stated or implied otherwise, is used herein to describe any ingredient other than the active component(s) that maybe included in a formulation. The choice of carrier will to a large extent depend on factors such as the particular mode of administration, the effect of the carrier on solubility and stability, and the nature of the dosage form.

The term, "treating" as used herein unless stated or implied otherwise, includes administering to a human or an animal patient at least one dose of a compounds, treating includes preventing or lessening the likelihood and or severity of a at least one disease as well as limiting the length of an illness or the severity of an illness it may or may not result in a cure of the disease.

Physiological diseases, disorders, and/or conditions, that can be treated with the inventive compounds and/or treatments disclosed herein involve pathological activity of at least one protein tyrosine phosphatase, includes, but is not limited to, diseases, disorder, conditions and the like that are initiated, propagated, worsened and/or prolonged by the activity of at least one protein tyrosine phosphatase.

'Pharmaceutically acceptable salts" as used herein unless defined otherwise refers to: Pharmaceutically acceptable salts, and common methodology for preparing them, are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

Pharmaceutical formulation: The compounds of the invention and their salts may be formulated as pharmaceutical compositions for administration. Such pharmaceutical compositions and processes for making the same are known in the art for both humans and non-human mammals. See, e.g., REMINGTON: THE SCIENCE AND PRACTICE OF PHARMACY, (A. Gennaro, et al., eds., $19^{th}$ ed., Mack Publishing Co., 1995). Formulations can be administered through various means, including oral administration, parenteral administration such as injection (intramuscular, subcutaneous, intravenous, intraperitoneal) or the like; transdermal administration such as dipping, spray, bathing, washing, pouring-on and spotting-on, and dusting, or the like. Additional active ingredients may be included in the formulation containing a compound of the invention or a salt thereof.

The pharmaceutical formulations of the present invention include those suitable for oral, parenteral (including subcutaneous, intradermal, intramuscular and intravenous) and rectal administration. The formulations may be presented in unit dosage form and may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or non-aqueous liquid such as a syrup, elixir or a draught, or as an oil-in-water liquid emulsion or a water-in-oil liquid emulsion. The formulation may also be a bolus, electuary or paste.

Pharmaceutically acceptable carrier: Pharmaceutically acceptable carrier, unless stated or implied otherwise, is used herein to describe any ingredient other than the active component(s) that maybe included in a formulation. The choice of carrier will to a large extent depend on factors such as the particular mode of administration, the effect of the carrier on solubility and stability, and the nature of the dosage form.

A tablet may be made by compressing or moulding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqueous sterile injection solutions, and may also include an antioxidant, buffer, a bacteriostat and a solution which renders the composition isotonic with the blood of the recipient, and aqueous and non-aqueous sterile suspensions which may contain, for example, a suspending agent and a thickening agent. The formulations may be presented in a single unit-dose or multi-dose containers, and may be stored in a lyophilized condition requiring the addition of a sterile liquid carrier prior to use.

As used herein, the term "pharmaceutically acceptable salt" is defined as a salt wherein the desired biological activity of the PTP inhibitor is maintained and which exhibits a minimum of undesired toxicological effects. Non-limiting examples of such a salt are (a) acid addition salts formed with inorganic acids (e.g., hydrochloric acid, hydrobromic acid, sulphuric acid, phosphoric acid, nitric acid, and the like), and salts formed with organic acids (such as e.g. acetic acid, oxalic acid, tartaric acid, succinic acid, malic acid, ascorbic acid, benzoic acid, tannic acid, palmitic acid, polyglutamic acid, naphthalene sulphonic acid, naphthalene disulphonic acid, polygalacturonic acid and the like); (b) base additional salts formed with metal cations such as zinc, calcium, bismuth, barium, magnesium, aluminum, copper, cobalt, nickel, cadmium, sodium, potassium and the like, or with a cation formed from ammonia, N,N-dibenzylethylenediamine, D-glucosamine, tetraethylammonium or ethylenediamine; or (c) combinations of (a) and (b); e.g. a zinc tannate or the like.

As used herein, "inhibition" or "inhibitory activity" each encompass whole or partial reduction of activity or effect of an enzyme.

A "therapeutically effective amount" in general means the amount that, when administered to a subject or animal for treating a disease, is sufficient to affect the desired degree of treatment for the disease. Effective amounts of a compound of this invention or composition thereof for treatment of a mammalian subject are about 0.1 to about 1000 mg/Kg of body weight of the subject/day, such as from about 1 to about 100 mg/Kg/day, especially from about 10 to about 100 mg/Kg/day.

A "selective" PTP inhibitor is one that has at least 2, 5, 10, 20, 50, 100, or 200 fold greater inhibitory activity (for example, as determined by calculation of $IC_{50}$, $K_i$, or other measure of affinity or effect) for a particular isozyme of PTP compared to other members of the PTP enzyme family. For example, a selective mPTPB and Lyp inhibitor is a compound that has a least 2, 5, 10, 20, 50, or 100 fold greater activity (determined by calculation of IC50, $K_i$) at mPTPB and Lyp compared to other PTPs.

The term "associated with inappropriate activity of a protein tyrosine phosphatase" encompasses all diseases, disorders, or conditions in which symptoms are in part related to excessive activity of a protein tyrosine phosphatase or deficient activity of a protein tyrosine kinase.

PTPs have been classified into sub-families: classical PTPs, dual specificity PTPs, and low molecular weight PTPs. Examples of classical PTPs include RPTPα, RPTPβ, CD45, LCA, RPTPδ, RPTPε, RPTPγ, LAR, SAP1, DEP1, DC148, RPTPη, RPTPκ, RPTPμ, IA-2, PTPRP, RPTPπ, IA-2β, phogrin, GLEPP1/PTP-U2/PTPROτ, PTPS31, PTP-SL, PCPTP, PTPBR7, PC12-PTP1, RPTPσ; RPTPσPTPJ/PTP-U1/PTPRomicron, OST-PTP, RPTPζ, PTP1B, TCPTP, MPTP, PTP-S, PTPH1, PTP-MEG1, TEP, STEP, SHP1, PTP1C, SH-PTP1, HCP, HePTP, LCPTP, PTP-MEG2, SHP2, SH-PTP2, Syp, PTP1D, PTP2C, SH-PTP3, PTP-PEST, PTP-P19, PTPG1, PTP-BAS, FAP-1, PTP1E, RIP, PTPL1, PTP-BL, PTP36, PEZ, PTPD2, PTP-HSCF, PTP20, BDP, TypPTP, PTPD1, PTP2E, PTP-RL10, LYP, PEP, HD-PTP, HDPTP, PTP-TD14, KIAA1471, and DKFZP564F0923. The PTPs have proven to be exceptionally challenging targets for the development of new therapeutic agents.

Protein tyrosine phosphatases (PTPs) are an enzyme family comprising multiple enzyme subtypes, or isozymes, with differential activity and various distributions in the body. PTPs are important regulators playing critical roles in many cellular functions such as proliferation, differentiation, migration, apoptosis, and immune responses. Increasing evidence suggests that a growing number of PTPS are associated with cancers, metabolic syndromes, and autoimmune disorders.

Lymphoid-specific tyrosine phosphatase (Lyp) is a member of the PTP family. The A620W mutant of Lyp, encoded by PTPN22 gene (comprising a single nucleotide polymorphism), is more effective in reducing T cell antigen receptor (TCR) signalling than the wild-type enzyme. The A620W mutant is associated with several autoimmune diseases, including type I diabetes, rheumatoid arthritis, juvenile idiopathic arthritis, systemic lupus erythematosus, Graves' disease, myasthenia gravis, generalized vitiligo, and Wegener's granulomatosis, for example. Because LYP*W620 is a gain-of-function variant, chemical inhibition of this activating mutant may be therapeutically useful in autoimmune disease treatment.

Over-expression of Tyrosine Phosphatase PTPN22 has also been reported to enhance anti-apoptotic B-cell receptor signalling in chronic lymphocytic leukemia CLL cells. Roberto Negro, et al., "Biology and Pathophysiology, excluding Therapy: Receptor Signalling in CLL," presentation, Dec. 12, 2011.

A PEST-domain enriched tyrosine phosphatase PEP has also been identified as being positive regulator of anaphylaxis. Obiri, et al., "PEST-domain enriched tyrosine phosphates and glucocorticoids as regulators of anaphylaxis in mice," Eur. Journal of Allergy and Clinical. Immunology. 67 (2012) 175-182. Treating mice with both a PEP inhibitor and compounds such as dexamethasone almost completely blocked anaphylaxis in mice.

One example of a disease that involves PTP activity is Tuberculosis. The pathogen *Mycobacterium tuberculosi*, the causal agent of Tuberculosis, produces the protein tyrosine phosphatase B (mPTPB). This PTP is secreted by mycobacterial cells into the cytoplasm macrophages, can mediate *mycobacterium* survival in host by targeting host proteins involved in related pathways of immune system. A. Koul, T. Herget, B. Klebl, A. Ullrich, Nat. Rev. Microbiol.2004, 2, 189-202; R. Singh, V. Rao, H. Shakila, R. Gupta, A. Khera, N. Dhar, A. Singh, A. Koul, Y. Singh, M. Naseema, P. R. Narayanan, C. N. Paramasivan, V. D. Ramanathan, A. K. Tyagi, Mol. Microbiol.2003, 50, 751-762; N. J. Beresford, D. Mulhearn, B. Szczepankiewicz, G. Liu, M. E. Johnson, A. Fordham-Skelton, C. Abad-Zapatero, J. S. Cavet, L. Tabernero, J. Antimicrob. Chemother. 2009, 63, 928-936; and B. Zhou, Y. He, X. Zhang, J. Xu, Y. Luo, Y. Wang, S. G. Franzblau, Z. Yang, R. J. Chan, Y. Liu, J. Zheng, Z.-Y. Zhang, Proc. Natl. Acad. Sci. USA 2010, 107, 4573-4578. The genetic knockout of mPTPB suppressed the growth and the virulence of Mtb in interferon-γ (IFN-γ) activated macrophages and severely reduces the bacterial load in guinea pig model of TB infection. Chen, L.; Zhou, B.; Zhang, S.; Wu, L.; Wang, Y.; Franzblau, S. G.; Zhang, Z.-Y. Identification and Characterization of Novel Inhibitors of mPTPB, an Essential Virulent Phosphatase from *Mycobacterium tuberculosis*. ACS Med. Chem. Lett., 2010, 1, 355-399. Small molecular mPTPB inhibitors were observed to reverse the altered host immune responses induced by-mPTPB and prevent TB growth in host cells. These experimental results demonstrated mPTPB to be an effective anti-TB target.

*Mycobacterium* protein tyrosine phosphatase B (mPTPB) is also a member of the PTP family. The enzyme mPTPB functions as a bacterial virulence factor, essential for the survival of *mycobacterium tuberculosis* (Mtb) in host macrophage cells of humans and animals. Because of mPTPB's role in the survival of Mtb in humans, inhibition of mPTPB function may impair the ability of Mtb to survive in macrophage cells and maybe therapeutically useful in tuberculosis (TB) treatment.

The lack of mPTPB counterpart in human may minimize the side effect on the host when treated with mPTPB inhibitors. Furthermore, as the enzyme is secreted into macrophage, mPTPB inhibitor is not required to penetrate the waxy mycobacterial cell wall. Consequently, mPTPB inhibitor may have great therapeutic value for speeding up the treatment of TB. Currently, there is considerable interest in development of mPTPB inhibitor. Müller, D.; Krick, A.; Kehraus, S.; Mehner, C.; Hart, M.; Küpper, F. C.; Saxena, K.; Prinz, H.; Schwalbe, H.; Janning, P.; Waldmann, H.; Konig, G. M. Brunsvicamides A-C: Spongerelated cyanobacterial peptides with *Mycobacterium tuberculosis* protein tyrosine phosphatase inhibitory activity. J. Med. Chem. 2006, 49, 4871-4878; Nören-Müller, A.; Reis-Corréa, I., Jr.; Prinz, H.; Rosenbaum, C.; Saxena, K.; Schwalbe, H. J.; Vestweber, D.; Cagna, G.; Schunk, S.; Schwarz, O.; Schiewe, H.; Waldmann, H. Discovery of protein phosphatase inhibitor classes by biology-oriented synthesis. Proc. Natl. Acad. Sci. U.S.A. 2006, 103, 10606-10611; Grundner, C.; Perrin, D.; Hooft van Huijsduijnen, R.; Swinnen, D; Gonzalez, J.; Gee, C. L.; Wells, T. N.; Alber, T. Structural basis for selective inhibition of *Mycobacterium tuberculosis* protein tyrosine phosphatase PtpB. Structure 2007, 15, 499-509; Soellner, M. B.; Rawls, K. A.; Grundner, C.; Alber, T.; Ellman, J. A. Fragment-based substrate activity screening method for the identification of potent inhibitors of the *Mycobacterium tuberculosis* phosphatase PtpB. J. Am. Chem. Soc. 2007, 129, 9613-9615; Beresford, N. J.; Mulhearn, D.; Szczepankiewicz, B.; Liu, G.; Johnson, M. E.; Fordham-Skelton, A.; Abad-Zapatero, C.; Cavet, J. S.; Tabernero, L. Inhibition of MptpB phosphatase from *Mycobacterium tuberculosis* impairs mycobacterial survival in macrophages. J. Antimicrob. Chemother. 2009, 63, 928-936; Tan, L. P.; Wu, H.; Yang, P. Y.; Kalesh, K. A.; Zhang, X.; Hu, M.; Srinivasan, R.; Yao, S. Q. High-throughput discovery of *Mycobacterium tuberculosis* protein tyrosine phosphatase B (MptpB) inhibitors using click chemistry. Org. Lett. 2009, 11, 5102-5105; and Vintonyak, V. V.; Warburg, K.; Kruse, H.; Grimme, S.; Hübel, K.; Rauh, D.; and Waldmann, H. Identification of Thiazolidinones Spiro-Fused to Indolin-2-ones as Potent and Selective Inhibitors of the *Mycobacterium tuberculosis* Protein Tyrosine Phosphatase B. Angew. Chem. Int. Ed. 2010, 49, 1-5.

Unfortunately, the conserved PTP active site (pTyr-binding pocket) is highly positively charged, which limit the development of inhibitors owing favorable pharmacological property. Continuous effort is required to identify inhibitors with highly potent enzyme activity and in vivo efficacy. As disclosed herein, using a both a focused library design and an combinatorial library approach it is possible to synthesis and identify indole salicylic acid derivatives that act as highly potent and selective mPTPB inhibitors.

Disclosed herein are salicylic acid derivatives, and methods of synthesizing them, for use in inhibiting various tyrosine phosphatases. In contrast to many tyrosine phosphatase inhibitors, many of the compounds disclosed herein selectively inhibit specific tyrosine phosphatises and have exceptional cellular efficacy. In addition to sharing the salicylic acid moiety (Formula 1) many of these compounds also include a 5 membered aromatic ring, according to Formula 2.

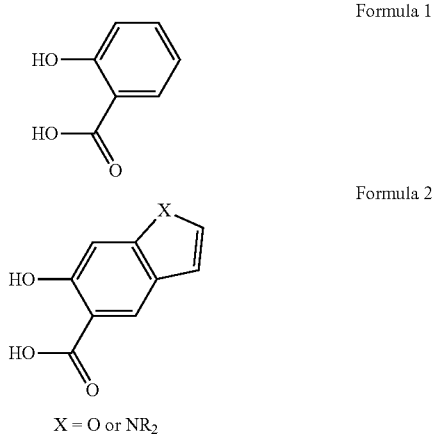

Formula 1

Formula 2

X = O or NR$_2$

Compounds capable of selectively inhibiting particular PTPs provide useful tools for studying the role of specific PTPs in normal and disease processes. Therapeutic compounds that can selectively inhibit specific PTPs are advantageous for treating diseases associated with excessive activity of a particular PTP. Use of a selective PTP can reduce the potential for undesirable effects due to nonselective inhibition of PTPs. However, the development of selective PTP inhibitors is problematic, in part due to the common architecture of the active site (i.e. pTyr-binding pocket) shared by members of the PTP family.

Developing and identifying compounds that inhibit specific for PTPs is difficult, in part because the target is a member of a large protein family and these proteins are thought to have many of the same structural features. Among the factors contributing factors to the difficulty of creating drugs that target specific PTPs are 1) the catalytic site is highly conserved, so it is not trivial to obtain drugs that can inhibit single PTPs with good selectivity; and 2) the requirement for charged phosphate analogs to pass through the hydrophobic cell membrane to reach the intracellular PTP target. To this end, most of the reported PTP inhibitors contain negatively charged nonhydrolyzable phosphotyrosine (pTyr) mimetics, due primarily to the intrinsic positively charged nature of the active site evolved to bind pTyr. Consequently, poor membrane permeability and lack of cellular efficacy of existing PTP inhibitors have limited further advancement of such compounds as drug candidates. Consequently, there is continued interest in developing pTyr mimetics with more acceptable physicochemical properties.

It was recently found using an in silico DOCK screening campaign, that the natural product salicylic acid can serve as a pTyr mimetic (Sarmiento, M.; Wu, L.; Keng, Y.-F.; Song, L.; Luo, Z.; Huang, Z.; Wu, G.-Z.; Yuan, A. K.; Zhang, Z.-Y. Structure-based discovery of small molecule inhibitors targeted to protein tyrosine phosphatase 1B. J. Med. Chem. 2000, 43, 146-155.). It was further demonstrated that naphthyl and polyaromatic salicylic acid derivatives exhibit enhanced affinity for PTPs relative to the corresponding single ring compounds. (Liang, F.; Huang, Z.; Lee, S.-Y.; Liang, J.; Ivanov, M. I.; Alonso, A.; Bliska, J. B.; Lawrence, D. S.; Mustelin, T.; Zhang, Z.-Y. Aurintricarboxylic acid blocks in vitro and in vivo activity of YopH, an essential virulent factor of *Yersinia pestis*, the agent of plague. J. Biol. Chem. 2003, 278, 41734-41741.) An effort was made to develop bicyclic salicylic acid based PTP inhibitors that carry sufficient polar and nonpolar interactions with the active site and yet possess improved pharmacological properties. It is disclosed herein that many benzofuran-based and indole-based salicylic acids are potent PTP active-site directed pTyr mimetics.

Methods for synthesizing, identifying and/or using PTP inhibitor compounds that are selective for the enzymes mPTPB and/or Lyp are described herein. Compounds within the scope of the instant disclosure include salicylic acid derivatives which selectively or at least preferentially inhibit Lyp. Small molecule inhibitors of Lyp have been reported in the literature, but these agents have proven either not sufficiently potent as inhibitors or as lacking sufficient specificity. Herewith are disclosed compounds, and the methods of synthesizing them, and in some cases using them. Further, in vitro and in vivo activity of these compounds is disclosed, demonstrating that some of these compounds are potent and preferential inhibitors of Lyp, making them useful for the treatment of autoimmune diseases and/or conditions.

Additional compounds within the scope of the instant disclosure include salicylic acid derivatives which selectively or at least preferentially inhibit mPTPB. These compounds, and the methods of synthesizing them, are disclosed wherein these compounds demonstrate, through in vitro and in vivo studies, that these compounds are potent and selective inhibitors of mPTPB. As such, these novel compounds may have potential for use in treatment of tuberculosis.

Some embodiments of the compounds described herein are benzofuran derivatives of salicylic acid, according to Formula 3.

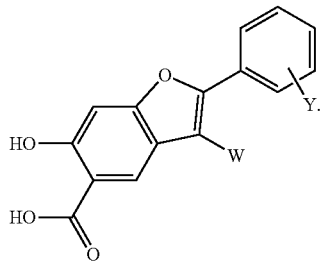

Formula 3

EXPERIMENTAL

A benzofuran salicylic acid based library constructed according to the methods depicted in FIG. 1 was screened for individual compounds that specifically or at least preferentially target various PTPs. For example, mPTPB inhibitors 7, 8 and 9 were prepared using the methods outlined in FIG. 1. Briefly, the commercially available compound 4-hydroxysalicylic acid is reacted with iodine monochloride to afford compound 1 in good yield. The compound 1 was selectively protected in the presence of acetone and TFAA/TFA to finish dioxanone 2 in modest yield. Then dioxanone 2 reacted with MeI at room temperature in the presence of $K_2CO_3$/DMSO to give the methylation product 3 with quantitative yield. Compound 3 coupled with Y-containing acetylene in the presence of catalytic amounts of Pd(PPh$_3$)$_2$Cl$_2$ and CuI to furnish 4 which was then subjected to $I_2$ induced cyclization. Cyclization of 4 proceeded exceedingly well and afforded 5 in high yield on a multigram scale. The efficiency and operational simplicity of this key cyclization step makes it possible to quickly prepare a large number of different 2,3-disubstituted benzofuran from a common intermediate 5. The key compounds 5 is modified by introducing a side chain at the 3-position of compound 5. The iodination product 5 coupled with substituted acetylene to give compound 6. After deprotection of 6 in the presence of KOH/THF/H$_2$O, 6-hydroxy-benzofuran-5-carboxylic acid 7 were obtained in a high yield. Hydrogenation of the alkyne 7 produced 8 and 9 (FIG. 1).

Protein Expression and Purification.

The full-length mPTPB with a N-terminal His6-tag was expressed and purified as described previously (Grundner C, Ng H-L, Alber T. (2005) *Mycobacterium tuberculosis* protein tyrosine phosphatase PtpB structure reveals a diverged fold and a buried active site. *Structure* 13:1625-1634.) with minor modification. Briefly, pET28b-mPTPB (a generous gift from Dr. Christoph Grunder, University of California, Berkeley) was used to transform into *E. coli* BL21/DE3 and grown in LB medium containing 50 μg/ml kanamycin at 37° C. to an OD600 of 0.5. Following the addition of IPTG to a final concentration of 20 μM, the culture was incubated at 20° C. with shaking for additional 16 hr. The cells were harvested by centrifugation at 5000 rpm for 5 min at 4° C. The bacterial cell pellets were resuspended in 20 mM Tris, pH 7.9, 500 mM NaCl, 5 mM imidazole, and were lysed by passage through a French press cell at 1,200 p.s.i. twice. Cellular debris was removed by centrifugation at 16,000 rpm for 30 min at 4° C. The protein was purified form the supernatant using standard procedures of Ni-nitrilotriacetic acid-agarose (Qiagen) affinity purification. The protein eluted from Ni-NTA column was concentrated with an Amicon Ultra centrifugal filter device (Millipore) and the buffer was changed to 20 mM Tris, pH 7.5, 150 mM NaCl, 1 mM EDTA and 1 mM DTT. Protein concentration was determined using the Bradford dye binding assay (Bio-Rad) diluted according to the manufacturer's recommendations with bovine serum albumin as standard. The purified mPTPB were made to 20% glycerol and stored at −20° C.

Determination of Selected Kinetic Parameters.

The phosphatase activity of mPTPB was assayed using pNPP as a substrate at 25° C. in 50 mM 3,3-dimethylglutarate buffer, pH 7.0, containing 1 mM EDTA with an ionic strength of 0.15 M adjusted by NaCl. The reaction was initiated by the addition of 5 μl of the enzyme to 195 μl of reaction mixture containing various concentrations of pNPP and quenched after 5 min by the addition of 50 μl of 5N NaOH. The nonenzymatic hydrolysis of pNPP was corrected by measuring the control without the addition of enzyme. After quenching, 200 μl of reaction mixture was transferred to a 96-well plate. The amount of product p-nitrophenol was determined from the absorbance at 405 nm detected by a Spectra MAX340 microplate SI-22 spectrophotometer (Molecular Devices) using a molar extinction coefficient of 18,000 M-1 cm-1. The Michaelis-Menten kinetic parameters were determined from a direct fit of the velocity versus substrate concentration data to Michaelis-Menten equation using the nonlinear regression program GraFit (Erithacus Software).

Inhibition Study.

Inhibition assays are performed at 25° C. in 50 mM 3,3-dimethylglutarate buffer, pH 7.0, containing 1 mM EDTA with an ionic strength of 0.15M adjusted by NaCl. The salicylic acid based library was screened in a 96-well format at 0.25 μM compound concentration. Compounds exhibiting more than 50% of inhibitory activity against mPTPB were selected for $IC_{50}$ measurement. The reaction was started by the addition of 5 μl of the enzyme to 195 μl of reaction mixture containing 2.5 mM (the Km value) of pNPP and various concentrations of the inhibitor. The reaction was quenched after 5 min by the addition of 50 μl of 5N NaOH, and then 200 μl of reaction mixture was transferred to a 96-well plate. The absorbance at 405 nm was detected by a Spectra MAX340 microplate spectrophotometer (Molecular Devices). $IC_{50}$ values were calculated by fitting the absorbance at 405 nm versus inhibitor concentration to the following equation: $AI/A0=IC50/(IC50+[I])$; in which AI is the absorbance at 405 nm of the sample in the presence of inhibitor; A0 is the absorbance at 405 nm in the absence of inhibitor; and [I] is the concentration of the inhibitor. Inhibition constants ($K_i$) for the inhibitor for mPTPB are determined at pH 7.0 and 25° C. The mode of inhibition and $K_i$ value were determined in the following manner. At various fixed concentrations of inhibitor (0-3 $K_i$), the initial rate at a series of pNPP concentrations was measured by following the production of p-nitrophenol as describe above, ranging from 0.2- to 5-fold the apparent $K_m$ values. The data were fitted to appropriate equations using the program SigmaPlot-Enzyme Kinetics to obtain the inhibition constant and to assess the mode of inhibition.

Figure 2:
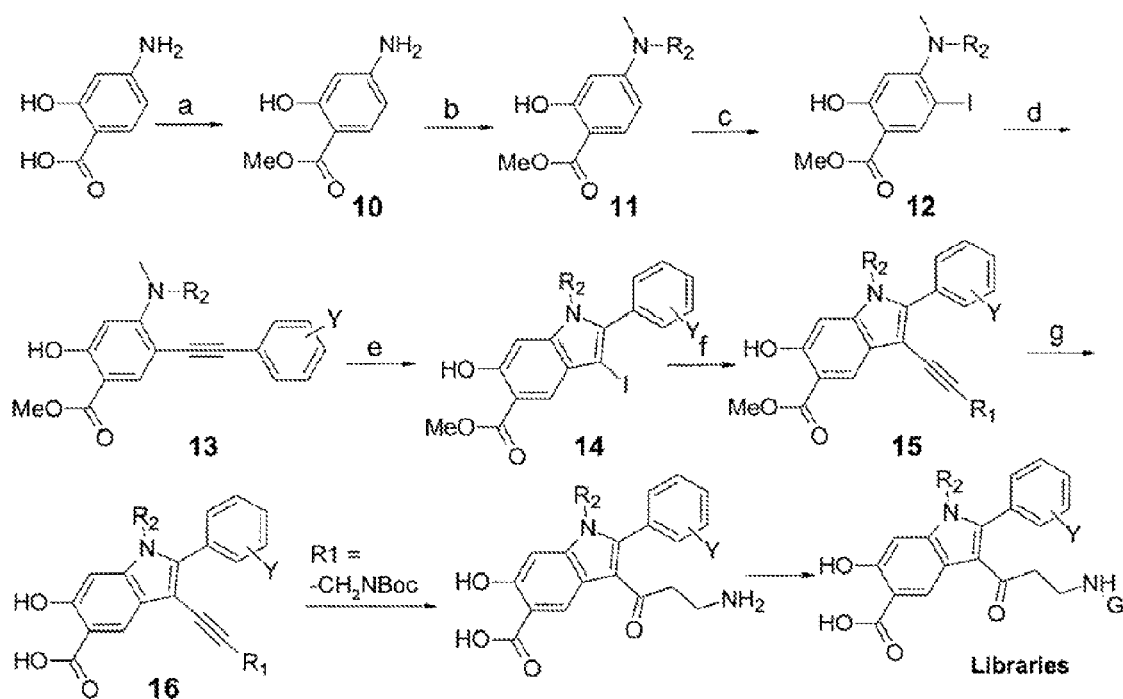
FIG. 2 is a schematic illustrating the creation of an indole salicylic acid based library.

Other embodiments of the present disclosure include indole derivatives according to Formula 4, which may be synthesized according to the method depicted in FIG. 2. Inhibitors 16 were synthesized by solution-phase parallel synthesis. The electrophilic cyclization of appropriately aromatic acetylenes promoted by iodine (Yue, D.; Larock, R. C. *Org. Lett.* 2004, 6, 1037) is used to prepare key compound 14. The synthetic route to get target inhibitors is described (FIG. 2). After esterification of the 4-aminosalicylic acid with dimethyl sulfate, compounds 10 is obtained it is treated with 1 equiv of appropriate aldehyde in the presence of NaCNBH$_3$ in AcOH, and then it is treated with paraformaldehyde and NaCNBH$_3$ to give the product 11. Selective iodination of compound II using iodine in the presence K$_2$CO$_3$ gives the compound 12. Sonogashira coupling (Sonogashira, K.; Tohda, Y.; Hagihara, N. *Tetrahedron Lett.* 1975, 16, 4467) between compound 12 and substituted alkyne was applied to prepare compound 13. Electrophilic cyclization of aromatic acetylene 13 promoted by iodine gives 3-iodoindole 14. Next, indole compound 14 is reacted with alkyne to give product 15. Deprotection of 15 releases inhibitors such as 16 (FIG. 2).

Formula 4

The indole salicylic acid based library constructed according to the method depicted in FIG. 2 is screened in order to identify individual compounds that specifically target PTPs. The phosphatase activity of mPTPB is assayed using p-nitrophenyl phosphate (pNPP) as a substrate at 25° C. in 50 mM 3,3-dimethylglutarate buffer, pH 7.0, containing 1 mM EDTA with an ionic strength of 0.15M adjusted by NaCl. The salicylic acid based library was screened in a 96-well format at 0.25 µM compound concentration. The reaction was initiated by the addition of 5 µL of the enzyme to 195 µL of reaction mixture containing 10 µM test compound and various concentrations of pNPP and quenched after 5 min by the addition of 50 µL of 5 N NaOH. The nonenzymatic hydrolysis of pNPP was corrected by measuring the control without the addition of enzyme. The amount of product p-nitrophenol was determined from the absorbance at 405 nm detected by a Spectra MAX340 microplate spectrophotometer (Molecular Devices) using a molar extinction coefficient of 18 000 M$^{-1}$ cm$^{-1}$. Compounds exhibiting more than 50% of inhibitory activity against mPTPB were selected for IC$_{50}$ measurement.

mPTPB as a Target for Impairing Mtb Ability to Survive in Host Cells

*Mycobacterium* protein tyrosine phosphate B (mPTPB) is a bacterial "virulence factor" which is active in species causing tuberculosis in humans and in animals. Generally, the protein tyrosine phosphatase mPTPB is expressed within cell, such as human macrophage cells, and acts (in response to the cytokine interferon-gamma, "IFNγ") to prevent phosphorylation of extracellular receptor kinase (ERK), thus decreasing the presence of phosphorylated ERK (ERK-P) within the cell. The decrease in ERK-P causes a decrease in the secretion of IL-6 secreted from the cell, thereby decreasing the immune response (apoptosis) towards the cell. The decrease immune response towards the cell aides in mPTPB expressing cells survival within hosts.

Figure 3:
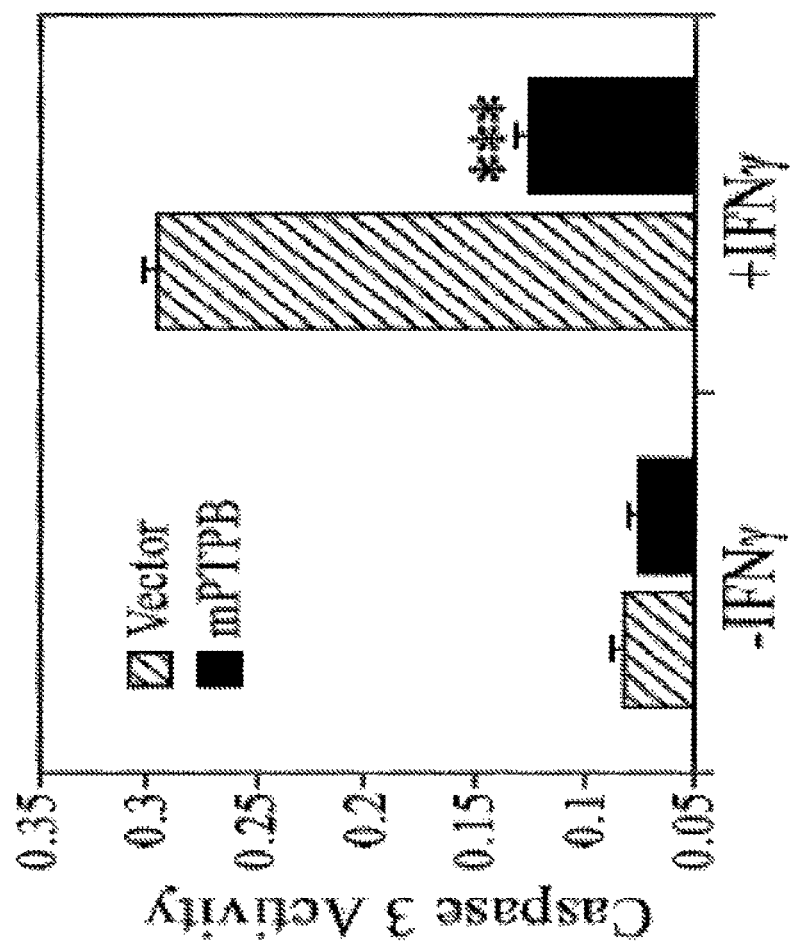
FIG. 3 is empirical data showing the effect of mPTPB expression on caspase 3 activity within a cell.
Figure 7:
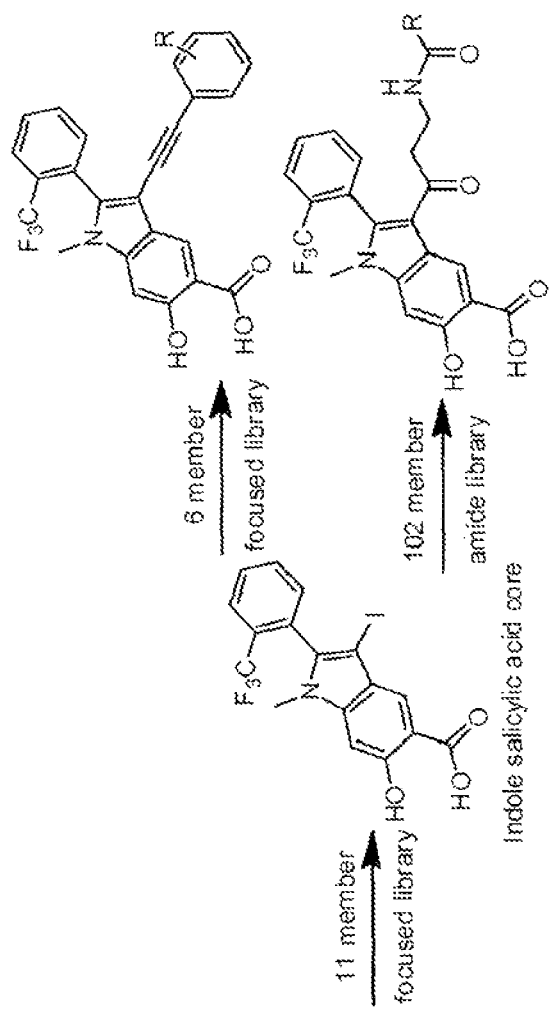
FIG. 7. A schematic depicting select intermediates in the synthesis of salicylic acid derivatives that include an acetyl linking group.

As demonstrated in FIG. 7, caspase 3 activity is also blocked by mPTPB. It should be understood that caspase 3 plays an important role in cell apoptosis. As can be seen by FIG. 3, macrophage cells expressing mPTPB and cells having only vector are treated with INFγ. The macrophage cells treated with only vector show normal caspase 3 activity whereas the cells expressing mPTPB show an approximately 60% reduction in caspase 3 activity. By blocking, or at least greatly reducing, caspase 3 activity, mPTPB further enables cell survival of Mtb infected cells. Thus, by inhibiting mPTPB activity would greatly impair the ability of Mtb to survive in host macrophage cells of humans and animals. As such, embodiments of the salicylic acid derivatives described herein target mPTPB as methods of treating Mtb infections.

Example 1

Example 2

Targeting mPTPB with mPTPB Inhibitors

Example 2.1

Synthesis of mPTPB Inhibitor Compounds

Embodiments of the instant disclosure include novel compounds having affinity and selectivity for mPTPB. Additionally, compounds for the inhibition of mPTPB, are derived from a core compound, having Formula 5.

Formula 5

Using Formula 5 as a starting point, various sets of compounds were derived and screened. The results of some of these tests are represented in Tables 2-8. mPTPB inhibitors (Formula 5) were prepared using the methods outlined in FIG. 1. Commercially available compound 4-hydroxysalicylic acid reacted with iodine monochloride to afford compound 1 in good yield. The compound 1 was selectively protected in the presence of acetone and TFAA/TFA to finish dioxanone 2 in modest yield. Then dioxanone 2 reacted with MeI at room temperature in the presence of K$_2$CO$_3$/DMSO to give the methylation product 3 with quantitative yield. Compound 3 coupled with Y-containing acetylene in the presence of catalytic amounts of Pd(PPh$_3$)$_2$Cl$_2$ and CuI to furnish 4 which was then subjected to I$_2$ induced cyclization. Cyclization of 4 proceeded exceedingly well and afforded 5 in high yield on a multigram scale. The efficiency and operational simplicity of this key cyclization make this project successful and this approach has the potential to easily prepare a large number of different 2,3-disubstituted benzofuran from a common intermediate 5. Once the key compounds 5 is made various side chains are introduced at the 3-position of compound 5. The iodination product 5 is coupled with substituted acetylene to give compound 6.

After deprotection of 6 in the presence KOH/THF/H$_2$O, 6-hydroxy-benzofuran-5-carboxylic acid 7 (Formula 5) were obtained in a high yield. Hydrogenation of the alkyne 7 produced 8 (Formula 6) and 9 (Formula 7). When Y=O(CH$_2$)nCOOH in Formula 5, the compound 7 (FIG. 1) was further reacted with amines to release sets Formula 10, 11. When R$_1$ contain a carboxylic acid group in Formula 5, it was further reacted with amines to release set Formula 12, 13.

The seven sets of compound derivatives are presented below in Tables 2-8, and further include either the IC$_{50}$ value (µM) for each compound or a "percent inhibition value at 0.25 uM" for each compound. As used in Tables 2-8 the IC$_{50}$ value is the concentration of the disclosed individual compound required for reducing mPTPB activity by 50%. Likewise, the percent inhibition defines the percent of mPTPB activity inhibition at a static concentration of 0.25 µM of the disclosed compound.

In regard to Table 2, the core structure and as such the substitutes at the R$_1$ and Y positions are based directly off of the core compound having Formula 5.

TABLE 2

| Cmpd # | Y | R$_1$ | IC50 (µM) |
|---|---|---|---|
| 25 (Core1) | H | H | 7.3 |
| 26 (L01Z01) | H | phenyl | 0.7 |
| 27 (L01Z02) | H | 2-F-phenyl | 0.18 |
| 28 (L01Z03) | H | 3-Cl-phenyl | 0.13 |
| 29 (L01Z04) | H | 3-OCH$_3$-phenyl | 0.54 |
| 30 (L01Z05) | H | 2,4-diF-phenyl | 0.26 |
| 31 (L01Z06) | H | 3,5-diF-phenyl | 0.054 |
| 32 (L01Z08) | H | 2-CF$_3$-phenyl | 0.038 |
| 33 (L01Z09) | H | 4-OCF$_3$-phenyl | 0.095 |
| 34 (L01Z12) | H | 4-phenoxy-phenyl | 0.043 |
| 35 (Core73) | 4-OCF$_3$ | H | 1.71 |
| 36 (L73Z01) | 4-OCF$_3$ | 3-Cl-phenyl | 0.082 |
| 37 (L73Z02) | 4-OCF$_3$ | 3,4-diCl-phenyl | 0.12 |
| 38 (L73Z03) | 4-OCF$_3$ | thiophenyl | 0.35 |
| 39 (L73Z05) | 4-OCF$_3$ | 3-(OCH$_2$COOH)-phenyl | 0.19 |
| 40 (Core69) | 4-OPh | H | 2.3 |
| 41 (Core71) | 4-Ph | H | 0.85 |
| 42 (Core72) | 3-Cl | H | 3.1 |

Additionally, variations of the compound derivatives generated with substitutions at the Y and Z positions of Formula 5 include compounds comprising the Formulas 12, 13:

Formula 12

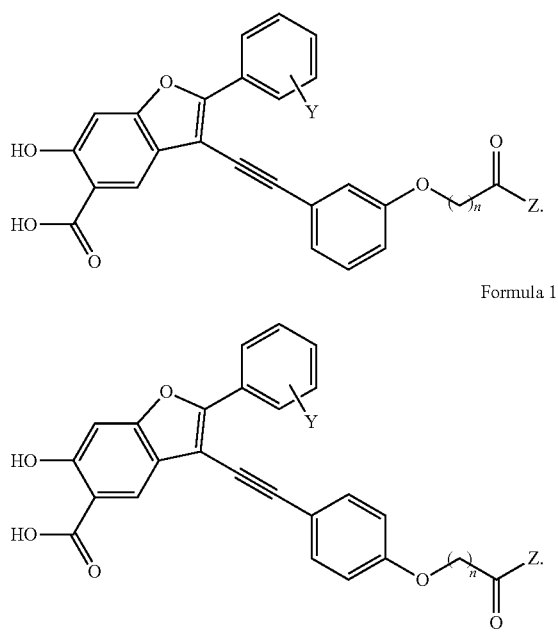

Formula 13

Additionally, a variation of the compound derivatives generated with substitutions at the Y and Z positions of Formula 6 includes compounds comprising the formula 14:

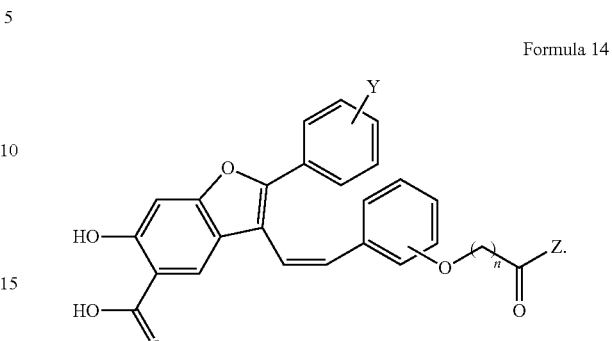

Formula 14

Referring now to table 4, a core compound having Formula 7 is used in synthesizing additional compound derivatives. The substituents at the Y and $R_1$ positioning disclosed in Table 4 refer to the core compound of Formula 7.

Formula 7

With reference to Table 3, a core compound having Formula 6 is used in synthesizing additional compound derivatives. The substituents at the Y and $R_1$ positioning disclosed in Table 3 refer to the core compound of Formula 6.

Formula 6

TABLE 4

| Cmpd # | Y | $R_1$ | IC50 (µM) |
|---|---|---|---|
| 45 (L01Y02) | H | 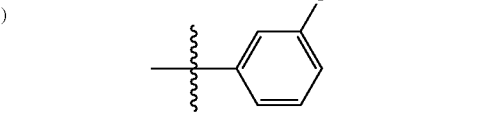 3-F-phenyl | 2.0 |
| 46 (L01Z20) | H | 3-CF$_3$-phenyl | 1.03 |
| 47 (L01Z21) | H | 4-OCF$_3$-phenyl | 3.4 |
| 48 (L01Z24) | H | 4-phenoxy-phenyl | 1.1 |

TABLE 3

| Cmpd # | Y | $R_1$ | IC$_{50}$ (µM) |
|---|---|---|---|
| 43 (L01Z25) | H | 3,5-di-F-phenyl | 1.2 |
| 44 (L01X09) | H | 3-CF$_3$-phenyl | 1.2 |

Additionally, a variation of the compound derivatives generated with substitutions at the Y and Z positioning of Formula 7 includes compounds comprising the formula:

Formula 15

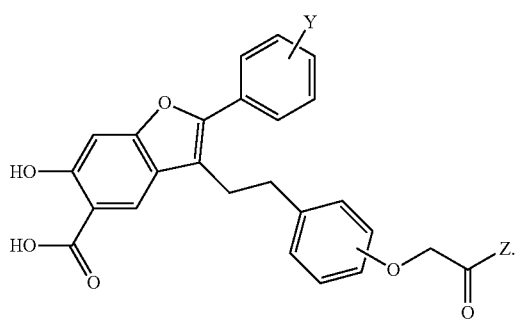

Referring now to table 5, a core compound having Formula 8 is used in synthesizing additional compound derivatives. The substituents at the $R_6$ positioning disclosed in Table 5 refer to the core compound of Formula 8.

Formula 8

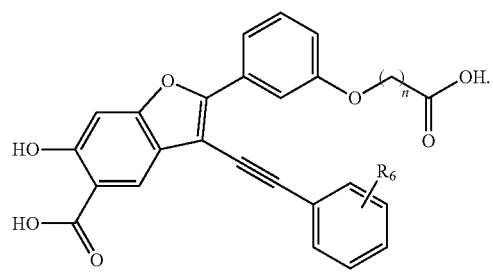

TABLE 5

| Cmpd # | n | $R_6$ | IC50 (µM) |
|---|---|---|---|
| 49 (Core 74) | 1 | 3-Cl | 0.076 |

Referring now to table 6, a core compound having Formula 9 is used in synthesizing additional compound derivatives. The substituents at the $R_6$ positioning disclosed in Table 6 refer to the core compound of Formula 9.

Formula 9

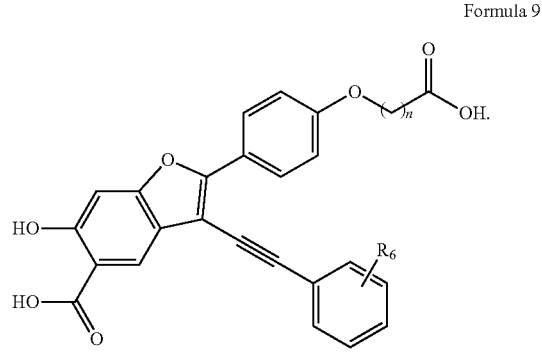

TABLE 6

| Cmpd # | n | $R_6$ | IC50 (µM) |
|---|---|---|---|
| 50 (Core 75) | 1 | 3-Cl | 0.101 |

Referring now to Table 7, a core compound having Formula 10 is used in synthesizing additional compound derivatives. The substituents at the $R_6$ and Z positioning disclosed in Table 7 refer to the core compound of Formula 10.

Formula 10

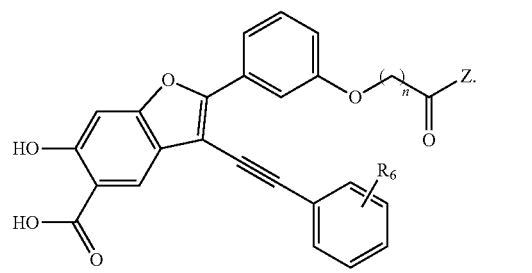

TABLE 7

| Cmpd # | n | $R_6$ | ZH | Inh % @ 0.25 µM |
|---|---|---|---|---|
| 51 (L74N05) | 1 | 3-Cl | H₂N–phenyl | 68 |
| 52 (L74N06) | 1 | 3-Cl | H₃CO-phenyl-NH₂ (2-methoxyaniline) | 64 |
| 53 (L74N07) | 1 | 3-Cl | H₂N-phenyl-F (3-fluoroaniline) | 71 |
| 54 (L74N11) | 1 | 3-Cl | H₂N-naphthyl | 81 |
| 55 (L74N13) | 1 | 3-Cl | H₂N-thiazole | 60 |
| 56 (L74N18) | 1 | 3-Cl | H₂N-CH(CH₃)-phenyl | 51 |

TABLE 7-continued
| Cmpd # | n | R6 | ZH | Inh % @ 0.25 µM |
|---|---|---|---|---|
| 57 (L74N21) | 1 | 3-Cl | 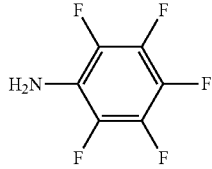 | 82 |
| 58 (L74N22) | 1 | 3-Cl | 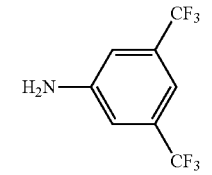 | 69 |
| 59 (L74N23) | 1 | 3-Cl | 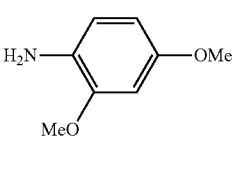 | 61 |
| 60 (L74N24) | 1 | 3-Cl | 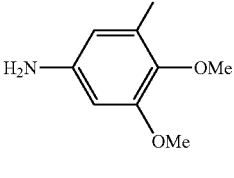 | 89 |
| 61 (L74N25) | 1 | 3-Cl | 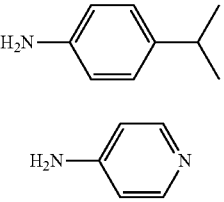 | 71 |
| 62 (L74N27) | 1 | 3-Cl |  | 81 |
| 63 (L74N29) | 1 | 3-Cl | 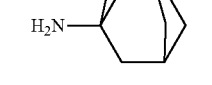 | 57 |
| 64 (L74N30) | 1 | 3-Cl | 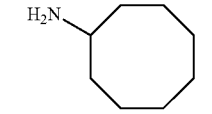 | 63 |
| 65 (L74N32) | 1 | 3-Cl | 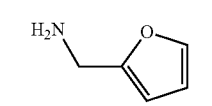 | 61 |
| 66 (L74N47) | 1 | 3-Cl | 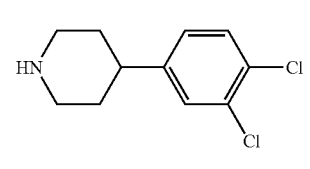 | 58 |
| 67 (L74N51) | 1 | 3-Cl | 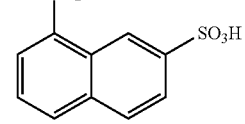 | 65 |
| 68 (L74N53) | 1 | 3-Cl | 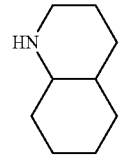 | 57 |
| 69 (L74N77) | 1 | 3-Cl | 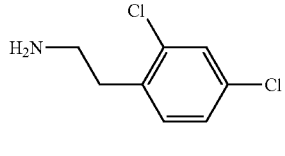 | 50 |
| 70 (L74N78) | 1 | 3-Cl | 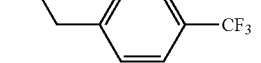 | 52 |
| 71 (L74N79) | 1 | 3-Cl | 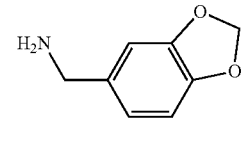 | 52 |
| 72 (L74N80) | 1 | 3-Cl | 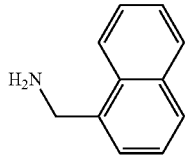 | 54 |
| 73 (L74N81) | 1 | 3-Cl | 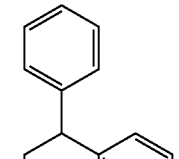 | 60 |
| 74 (L74N82) | 1 | 3-Cl | 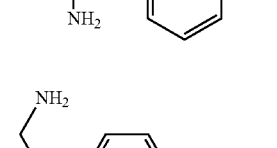 | 73 |
Referring now to Table 8, a core compound having Formula 11 is used in synthesizing additional compound derivatives. The substituents at the Z and $R_6$ positioning disclosed in Table 8 refer to the core compound of Formula 11.

Formula 11

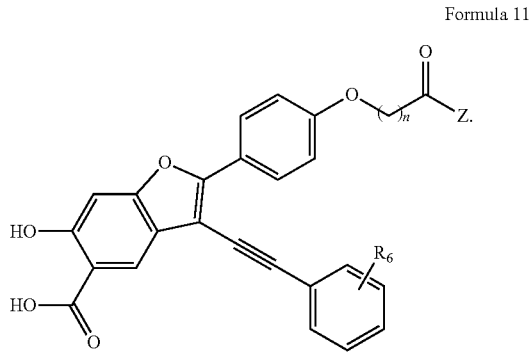

TABLE 8

| Cmpd # | n | R$_6$ | ZH | Inh % @ 0.25 μM |
|---|---|---|---|---|
| 75 (L75M06) | 1 | 3-Cl | 4-butylaniline | 81 |
| 76 (L75M08) | 1 | 3-Cl | 2-chloro-4-bromoaniline | 81 |
| 77 (L75M10) | 1 | 3-Cl | 2,4-dibromoaniline | 75 |
| 78 (L75M13) | 1 | 3-Cl | 3,4-dichloroaniline | 78 |
| 79 (L75M14) | 1 | 3-Cl | 3,5-dichloroaniline | 77 |
| 80 (L75M15) | 1 | 3-Cl | 2,4-difluoroaniline | 75 |
| 81 (L75M16) | 1 | 3-Cl | 3,5-difluoroaniline | 77 |

TABLE 8-continued

| Cmpd # | n | R$_6$ | ZH | Inh % @ 0.25 μM |
|---|---|---|---|---|
| 82 (L75M17) | 1 | 3-Cl | 2-bromoaniline | 75 |
| 83 (L75M18) | 1 | 3-Cl | 3-bromoaniline | 78 |
| 84 (L75M21) | 1 | 3-Cl | 3-chloroaniline | 76 |
| 85 (L75M22) | 1 | 3-Cl | 4-chloroaniline | 78 |
| 86 (L75M23) | 1 | 3-Cl | 3-iodoaniline | 77 |
| 87 (L75M24) | 1 | 3-Cl | 4-iodoaniline | 80 |
| 88 (L75M25) | 1 | 3-Cl | 3-sulfamoylaniline | 78 |
| 89 (L75M26) | 1 | 3-Cl | 2-bromo-4-(trifluoromethyl)aniline | 79 |
| 90 (L75M28) | 1 | 3-Cl | 3-bromo-5-(trifluoromethyl)aniline | 77 |
| 91 (L75M30) | 1 | 3-Cl | 4-chloro-3-(trifluoromethyl)aniline | 77 |

TABLE 8-continued
| Cmpd # | n | R6 | ZH | Inh % @ 0.25 μM |
|---|---|---|---|---|
| 92 (L75M37) | 1 | 3-Cl | 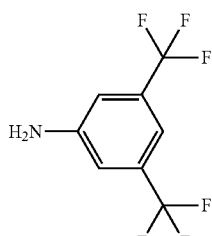 | 82 |
| 93 (L75M43) | 1 | 3-Cl | 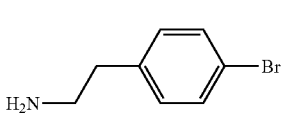 | 78 |
| 94 (L75M45) | 1 | 3-Cl | 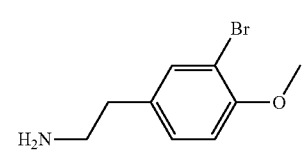 | 77 |
| 95 (L75M47) | 1 | 3-Cl | 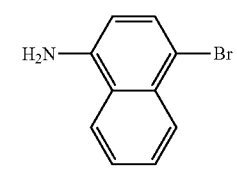 | 79 |
| 96 (L75M49) | 1 | 3-Cl | 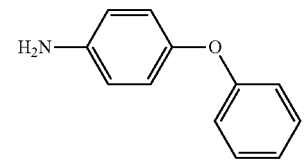 | 81 |
| 97 (L75M50) | 1 | 3-Cl | 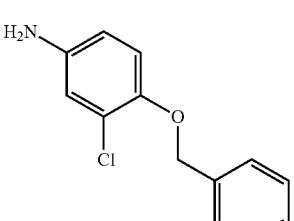 | 78 |
| 98 (L75M51) | 1 | 3-Cl | 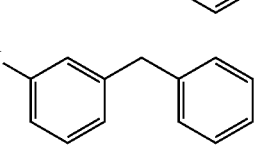 | 76 |
| 99 (L75M52) | 1 | 3-Cl | 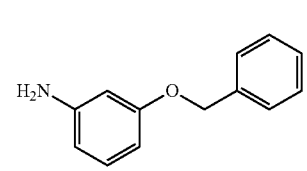 | 79 |
| 100 (L75M57) | 1 | 3-Cl | 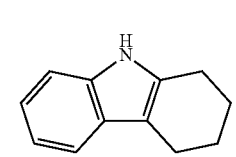 | 75 |
| 101 (L75M58) | 1 | 3-Cl | 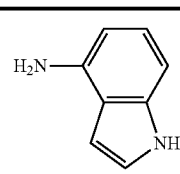 | 78 |
| 102 (L75M61) | 1 | 3-Cl | 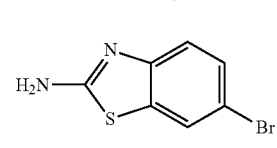 | 81 |
| 103 (L75M66) | 1 | 3-Cl | 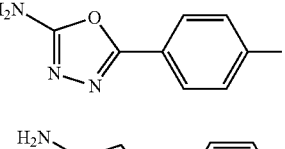 | 78 |
| 104 (L75M67) | 1 | 3-Cl | 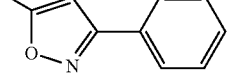 | 78 |
| 105 (L75M79) | 1 | 3-Cl | 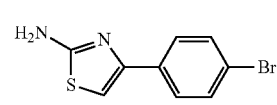 | 77 |
| 106 (L75M84) | 1 | 3-Cl | 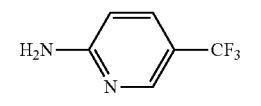 | 76 |
| 107 (L75M87) | 1 | 3-Cl | 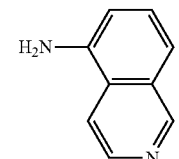 | 76 |
| 108 (L75M88) | 1 | 3-Cl | 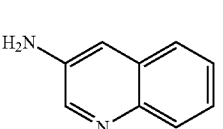 | 78 |
| 109 (L75N09) | 1 | 3-Cl | 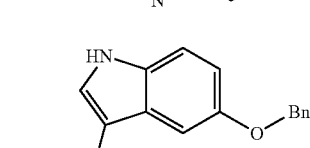 | 75 |
| 110 (L75N17) | 1 | 3-Cl | 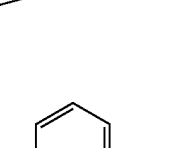 | 76 |

TABLE 8-continued

| Cmpd # | n | R6 | ZH | Inh % @ 0.25 μM |
|---|---|---|---|---|
| 111 (L75N21) | 1 | 3-Cl | | 75 |
| 112 (L75N22) | 1 | 3-Cl | | 75 |
| 113 (L75N25) | 1 | 3-Cl | | 75 |
| 114 (L75N27) | 1 | 3-Cl | | 75 |
| 115 (L75N36) | 1 | 3-Cl | | 78 |
| 116 (L75N60) | 1 | 3-Cl | | 80 |
| 117 (L75N68) | 1 | 3-Cl | | 75 |
| 118 (L75N69) | 1 | 3-Cl | | 78 |
| 119 (L77M41) | 1 | 4-OCF3 | | 53 |
| 120 (L77M48) | 1 | 4-OCF3 | | 68 |
| 121 (L77M57) | 1 | 4-OCF3 | | 73 |
| 122 (L77M91) | 1 | 4-OCF3 | | 56 |
| 123 (L77N25) | 1 | 4-OCF3 | | 58 |
| 124 (L77N36) | 1 | 4-OCF3 | | 54 |
| 125 (L77N43) | 1 | 4-OCF3 | | 50 |
| 126 (L79N60) | 1 | 3,5-di-F | | 52 |

Example 2.2

Assessment of the Selectivity and Potency of some Exemplary Compounds as Inhibitors of mPTPB Various derivatives of Formula 5, some of which are reported in this disclosure (as represented in Tables 2-8), were synthesized and screened. Of these, three representative compounds are provided below:

Compound 32 (L01Z08)

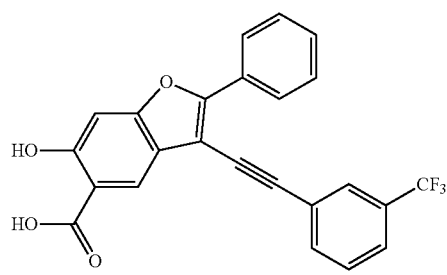

-continued

Compound 31 (L01Z06)

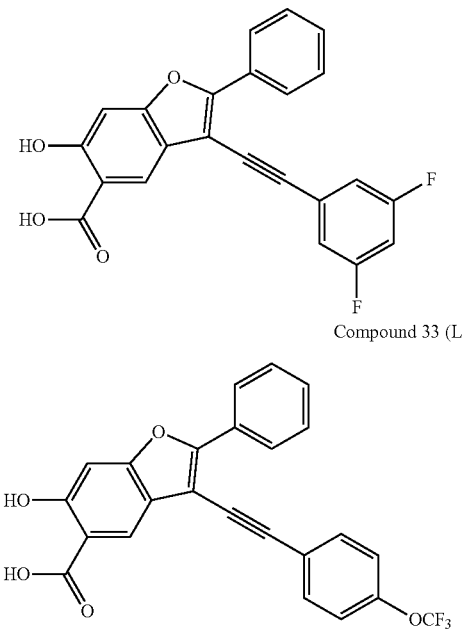

Compound 33 (L01Z09)

The selectivity and potency of Compound 32 (L01Z08) against PTPs, and specifically against mPTPB, was assessed in various ways. First, with reference to Table 9, the selectivity of Compound 32 (L01Z08) against a panel of 19 different PTPs, including mPTPB and Lyp, was accessed by a determination of the $IC_{50}$ in μM of Compound 32 (L01Z08) for each PTP. As shown in Table 9, Compound 32 (L01Z08) presented high selectivity (on the order of 2 log values) for mPTPB over the nearest PTP assayed.

TABLE 9

| PTA | $IC_{50}$ (μM) |
| --- | --- |
| mPTPB | 0.038 ± 0.002 |
| mPTPA | 2.5 ± 0.2 |
| PTP1B | 6.7 ± 0.7 |
| TC-PTP | 5.7 ± 0.4 |
| SHP2 | 1.8 ± 0.2 |
| SHP1 | 2.3 ± 0.3 |
| FAP1 | 1.3 ± 0.2 |
| Lyp | 2.0 ± 0.1 |
| Meg2 | 4.3 ± 0.5 |
| HePTP | 2.1 ± 0.3 |
| Laforin | 40 ± 10 |
| VHX | 1.4 ± 0.2 |
| VHR | 1.9 ± 0.4 |
| LMWPTP | 4.3 ± 0.6 |
| Cdc14A | 6.0 ± 1.0 |
| PTP_ | >10 |
| LAR | >10 |
| CD45 | 4.2 ± 0.5 |
| PTPRG | 2.6 ± 0.6 |

Referring next to Table 10, the selectivity of compound 31 (L01Z06) was assessed by a determination way of the $IC_{50}$ against 19 different PTPs, including mPTPB and Lyp. As shown by Table 10, of compound 31 (L01Z06) presented high selectivity (on the order of 2 log values) for mPTPB over the nearest PTP assayed.

TABLE 10

| PTP | $IC_{50}$ (μM) |
| --- | --- |
| mPTPB | 0.054 ± 0.004 |
| mPTPA | 1.6 ± 0.1 |
| PTP1B | 4.5 ± 0.2 |
| TC-PTP | 3.8 ± 0.1 |
| SHP2 | 2.2 ± 0.1 |
| SHP1 | 2.2 ± 0.1 |
| FAP1 | 1.9 ± 0.04 |
| Lyp | 1.3 ± 0.1 |
| Meg2 | 2.3 ± 0.08 |
| HePTP | 3.3 ± 0.5 |
| Laforin | >30 |
| VHX | 2.9 ± 0.3 |
| VHR | 5.3 ± 0.6 |
| LMWPTP | 2.9 ± 0.3 |
| Cdc14A | 21 ± 2 |
| PTP_ | >10 |
| LAR | >10 |
| CD45 | 4.1 ± 0.5 |
| PTPRG | 5.0 ± 0.3 |

Next, with reference to FIG. 4, the oral pK values for both Compound 32 (L01Z08) and Compound 31 (L01Z06) are presented. As shown, the disassociation constant (pK) values for both Compound 32 (L01Z08) and Compound 31 (L01Z06) remain relatively constant for the full 24 hour duration of the assay (as compared to the pK value for Compound I-A09 which undergoes a 1 log reduction over the 24 hour period).

Oral and intravenous (IV) pharmacokinetics were determined for compounds L01-Z06, L01-Z08 and L01-Z09 in mice. Drugs were administered by a single IV injection (5 mg/kg) or oral gavage (25 mg/kg) in 20% hydroxypropyl-b-cyclodextrin/2% diethanolamine and blood samples were collected at 0.5, 1, 3, 6, 9 and 24 hours later. The full pharmacokinetic parameters of compound L01-Z08 is shown in Table 11. All three compounds were readily administered by both IV and oral routes. Uptake was rapid via both routes of administration, with the peak concentrations being reached in 0.5-1 hour, except for L01-Z08, where the $T_{max}$ was at 6 hours after oral delivery. Drug levels peaked at 16-49 mM after IV injection, or 7.2-9.2 mM after oral gavage. Based on these parameters, all three compounds are classified as highly permeable with moderate-slow clearance rates. Absolute oral bioavailability for L01-Z08 was calculated to be 75.6%. Compound L01-Z08 displayed the slowest clearance of the three, with active levels (sufficient to inhibit target activity by 80% in cells) being maintained for 18.5 hours after oral delivery, demonstrating that L01-Z08 is possesses pharmacologic properties suitable for oral, daily delivery.

TABLE 11

| Pharmacokinetic parameters of L01-Z08 | | | | | | | | | |
| --- | --- | --- | --- | --- | --- | --- | --- | --- | --- |
| DOSE (mg/kg) | ROUTE | Cmax (ng/mL) | Cmax nM | Tmax (hours) | $T_{1/2}$ (hours) | Clearance (mL/hr/kg) | Clearance % LPF | Vdss (L/kg) | Absolute Bioavailability |
| 5** | IV | 10183 | 25458 | 0.5 | 4.1 | 934.9 | 28.9 | 5.53 | — |
| 25 | PO | 2883 | 7208 | 1 | 3.7 | 1236.1 | 38.2 | 6.58 | 75.6 |

**IV data normalized to 25 mg/kg dose

Referring now to Table 12, the selectivity of compound 33 (L01Z09) was also assessed by a determination of the $IC_{50}$ against 19 different PTPs, including mPTPB and Lyp. As shown by Table 11, of Compound 25 (L01Z09) presented high selectivity (on the order of 2 log values) for mPTPB over the nearest PTP assayed.

TABLE 12

| PTP | $IC_{50}$ (μM) |
|---|---|
| mPTPB | 0.090 ± 0.017 |
| mPTPA | 2.8 ± 0.3 |
| PTP1B | 5.1 ± 0.3 |
| TC-PTP | 3.8 ± 0.2 |
| SHP2 | 1.8 ± 0.6 |
| SHP1 | 2.5 ± 0.1 |
| FAP1 | 1.6 ± 0.1 |
| Lyp | 2.0 ± 0.1 |
| Meg2 | 4.0 ± 0.2 |
| HePTP | 1.9 ± 0.3 |
| Laforin | 31 ± 4 |
| VHX | 1.9 ± 0.1 |
| VHR | 2.1 ± 0.2 |
| LMWPTP | 3.0 ± 0.1 |
| Cdc14A | 6.0 ± 1.0 |
| PTP__ | >10 |
| LAR | >10 |
| CD45 | 3.6 ± 0.2 |
| PTPRG | 1.8 ± 0.1 |

Example 2.3

Inhibition of mPTPB Activity by Compound 32 (L01Z08)

Figure 4A:
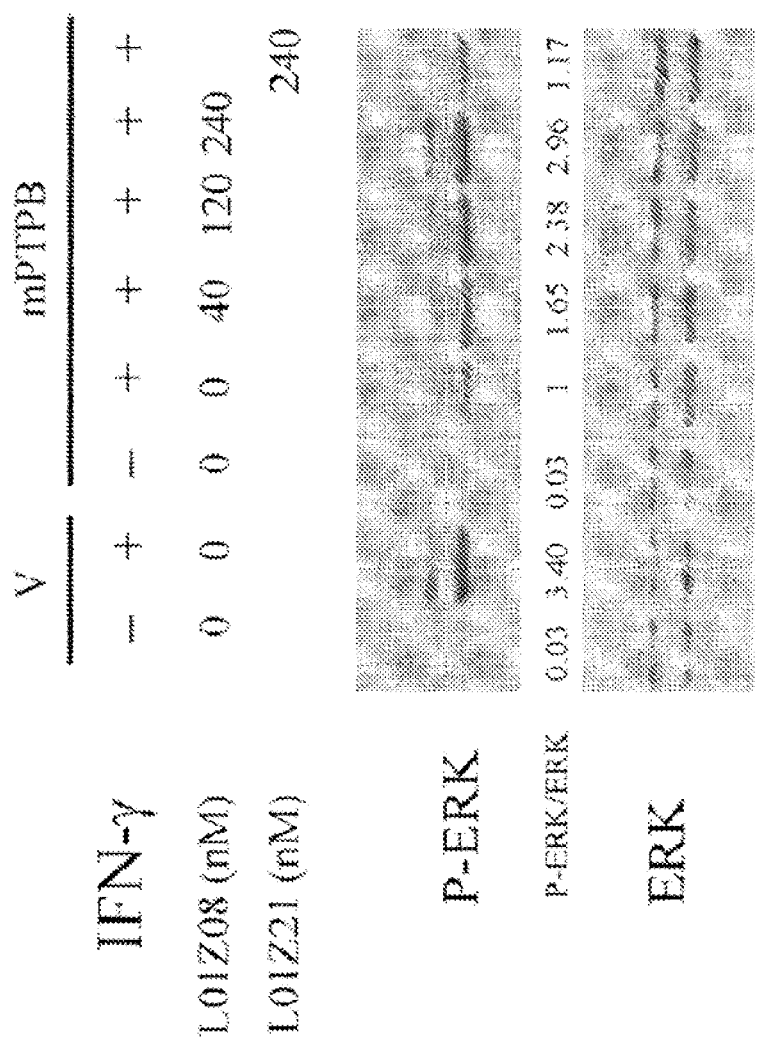
FIG. 4A is empirical data demonstrating the effect of Compound 32, L01Z08, on ERK phosphorylation in cells expressing mPTPB.
Figure 4B:
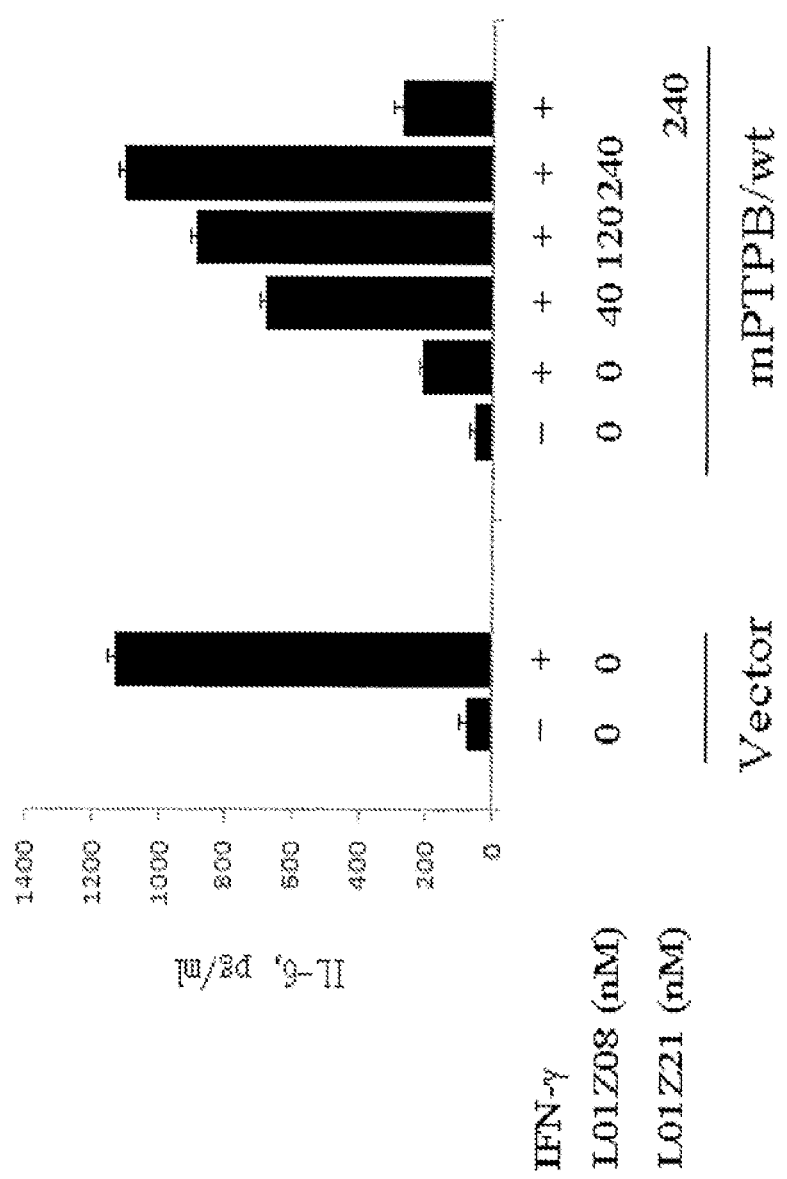
FIG. 4B is empirical data demonstrating the effect of Compound 32, L01Z08, on IL-6 secretion in cells expressing mPTPB.

With reference to FIGS. 4a and 4b, the effect of Compound 32 (L01Z08) on mPTPB expressing cells is shown in regard to ERK phosphorylation and IL-6 secretion. As explained above, ERK phosphorylation is important in the cellular secretion pathway of IL-6. However, mPTPB blocks or inhibits the phosphorylation of ERK which reduces and potentially prevents IL-6 secretion altogether.

Referring specifically to FIG. 4a, the effect of Compound 32 (L01Z08) on cells expressing mPTPB is shown. As is demonstrated, cells expressing mPTPB have reduced or eliminated ERK phosphorylation. However, addition of Compound 32 (L01Z08) (especially at 120 and 240 nM concentrations) returns to ERK phosphorylation levels to normal or near normal levels. Further, addition of compound L01Z21, which is a structurally similar but inactive compound, demonstrates the response to Compound 32 (L01Z08) is specific.

Referring specifically to FIG. 4b, the effect of Compound 32 (L01Z08) regarding IL-6 secretion in cells expressing mPTPB is shown. As is demonstrated, cells expressing mPTPB have greatly reduced IL-6 secretion from normal cells. Further shown in FIG. 4b, cells expressing mPTPB which are treated with Compound 32 (L01Z08) are returned to normal or near normal IL-6 secretion levels (especially at 120 and 240 nM concentrations). Treatment with compound L01Z21, which is a structurally similar but inactive compound, demonstrates the response to Compound 32 (L01Z08) is specific.

Figure 5A:
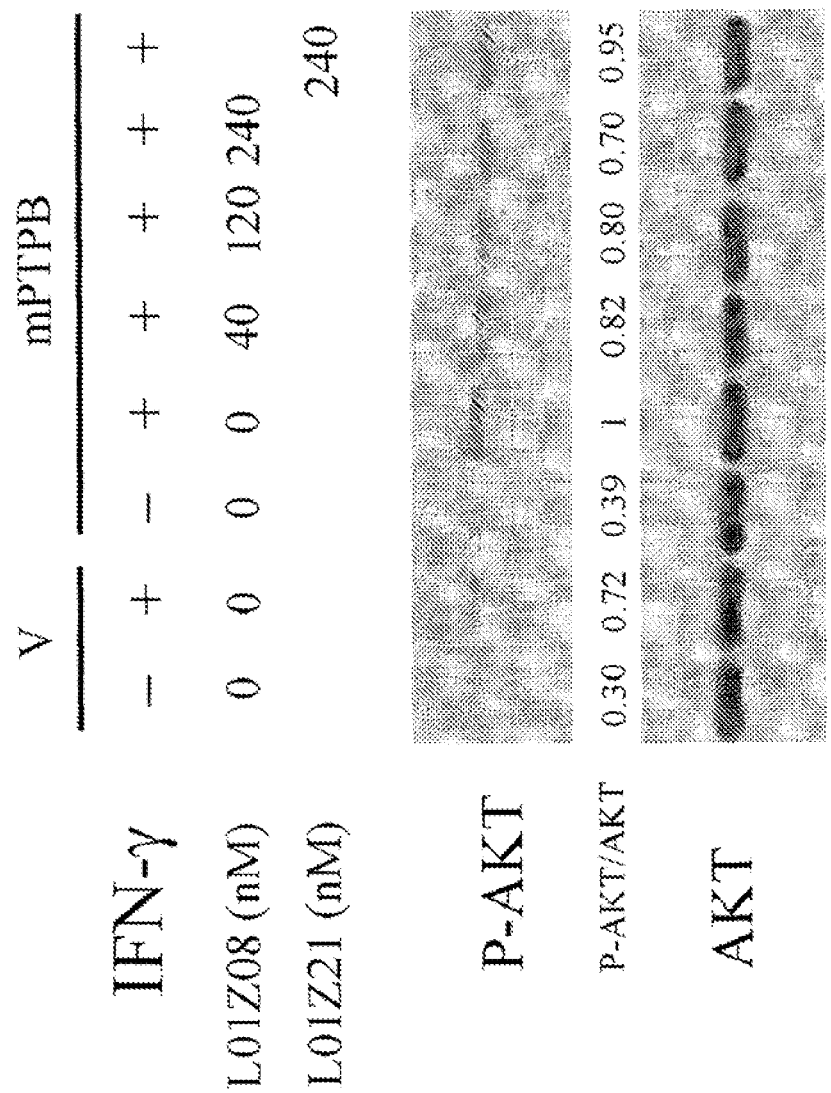
FIG. 5A. Western blots demonstrating the effect of Compound 32, L01Z08, and structurally related inactive compound L01Z21 on Caspase 3 activity in cells expressing mPTPB.
Figure 5B:
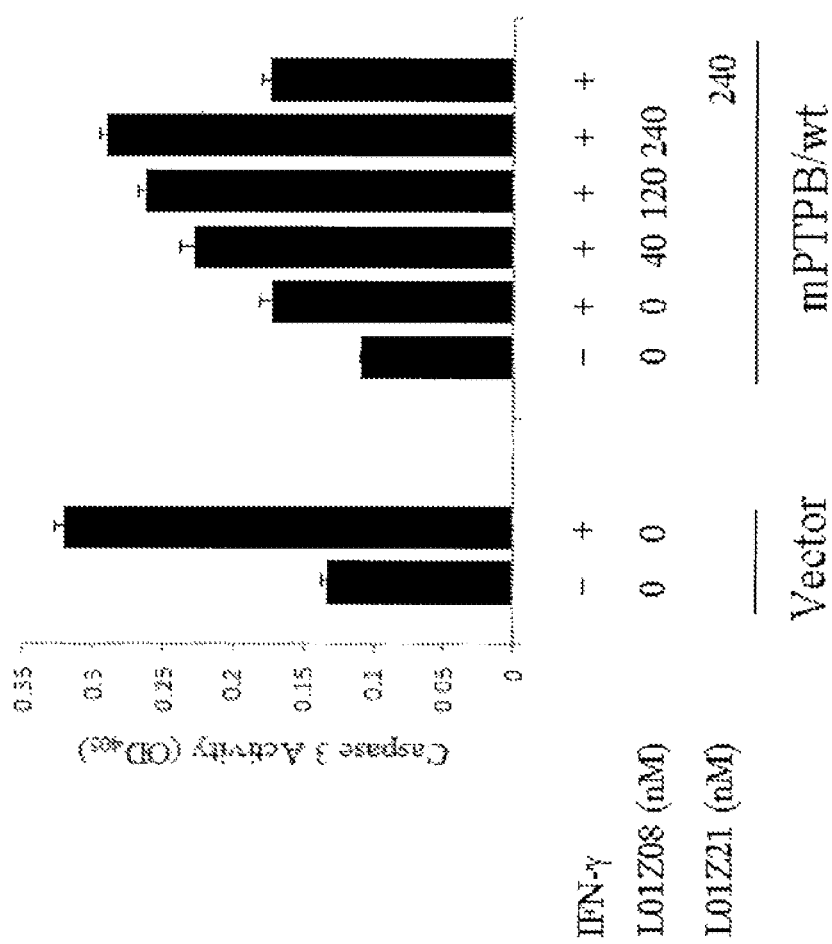
FIG. 5B. Bar graphs demonstrating the effect of compounds L01Z08 and L01Z21 on Caspase 3 activity in cells expressing mPTPB.

Referring next to FIGS. 5a and 5b, the effect of Compound 32 (L01Z08) in regard to AKT phosphorylation and caspase 3 activity is shown. With reference to FIG. 5a specifically, an increase in AKT phosphorylation is shown in macrophage cells expressing mPTPB. FIG. 5a further shows the phosphorylation decreasing with treatments of increasing concentrations of compound 32 (L01Z08). As explained above, AKT phosphorylation is associated with an increased propensity for cell survival (thus reduced apoptosis in Mtb infected cells).

Referring specifically to FIG. 5b, a reduction of Caspase 3 activity is shown for macrophage cells expressing mPTPB. As explained above, caspase 3 plays an important role in orchestrating cell death, or apoptosis. Thus, reduced caspase 3 activity also is associated with an increased propensity for cell survival. As is also demonstrated in FIG. 5b, however, treatment of the cells with Compound 32 (L01Z08), especially at 120 and 240 nM concentrations returns caspase 3 activity to near normal levels. Further, treatment of the cells with the structurally similar but inactive compound, L01Z21, the response to Compound 32 (L01Z08) is specific.

The exemplary data presented herein demonstrates that Compound 32 (L01Z08), compound 31 (L01Z06) and compound 33 (L01Z09) are highly selective for the protein tyrosine phosphatase mPTPB (see Tables 9-12). These data further demonstrate that Compound 32 (L01Z08) selectively reverses the effects of mPTPB in regard to ERK and AKT phosphorylation (see FIGS. 4a and 5a). Additionally, the ability of this novel compound to reverse the decrease in IL-6 secretion and caspase 3 activity, resulting from expression of mPTPB, is also demonstrated (in FIGS. 4b and 5b). As such, Compound 32 (L01Z08), Compound 31 (L01Z06) and Compound 33 (L01Z09) and pharmaceutical acceptable salts thereof, as disclosed herein provide new compounds for selectively inhibiting the effects of mPTPB in human and animal cells.

Example 3

Targeting of Lyp PTP with Salicylic Acid Derivatives

Protein tyrosine phosphorylation mediates multiple signal transduction pathways that play key roles in innate and acquired immunity. The level of tyrosine phosphorylation is controlled by the coordinated action of protein tyrosine kinases (PTKs) and protein tyrosine phosphatases (PTPs). The importance of the PTKs in the immune system are well recognized and widely appreciated. However, the functional significance of the PTPs in regulating various immune responses is far from clear. The lymphoid-specific tyrosine phosphatase (Lyp) has received enormous attention because of the finding that a single-nucleotide polymorphism (SNP) in the gene (PTPN22) encoding Lyp is associated with several autoimmune diseases, including type I diabetes (Bottini N, Musumeci L, Alonso A, Rahmouni S, Nika K, Rostamkhani M, MacMurray J, Meloni G F, Lucarelli P, Pellecchia M, et al. (2004) Nat Genet. 36:337-338.), rheumatoid arthritis (Begovich A B, Carlton V E, Honigberg L A, Schrodi S J, Chokkalingam A P, Alexander H C, Ardlie K G, Huang Q, Smith A M, Spoerke J M, et al. (2004) Am J Hum Genet 75:330-337; Carlton V E, Hu X, Chokkalingam A P, Schrodi S J, Brandon R, Alexander H C, Chang M, Catanese J J, Leong D U, Ardlie K G, et al. (2005) Am J Hum Genet 77:567-581.), Graves disease (Smyth D, Cooper J D, Collins J E, Heward J M, Franklyn J A, Howson J M, Vella A, Nutland S, Rance H E, Maier L, et al. (2004) Diabetes 53:3020-3023.), and systemic lupus erythematosus (Kyogoku C, Langefeld C D, Ortmann W A, Lee A, Selby S, Carlton V E, Chang M, Ramos P, Baechler E C, Batliwalla F M, et al. (2004) Am J Hum Genet 75:504-507.). Lyp is a 110-kDa protein consisting of an N-terminal PTP domain and a noncatalytic C-terminal segment with several Prorich motifs. Lyp belongs to a subfamily of PTPs, which include PTP-PEST (PTPN12), PTP-HSCF/BDP1 (PTPN18), and Lyp/PEP (PTPN22) (Alonso A, Sasin J, Bottini N, Friedberg I, Friedberg I, Osterman A, Godzik A, Hunter T, Dixon J, Mustelin T (2004) *Cell* 117:699-711.). Biochemical studies suggest that Lyp inhibits T cell activation, likely through dephosphorylation of the T cell receptor (TCR)-associated Lck and ZAP-70 kinases (Gjorloff-Wingren A, Saxena M, Williams S, Hammi D, Mustelin T (1999) *Eur J Immunol* 29:3845-3854. Cloutier J-F, Veillette A (1999) *J Exp Med* 189:111-121. Wu J, Katrekar A, Honigberg L A, Smith A M, Conn M T, Tang J, Jeffery D, Mortara K, Sampang J, Williams S R, et al. (2006) *J Biol Chem* 281:11002-11010.). Interestingly, the disease-causing SNP (a C-to-T substitution at position 1858 in the coding region of Lyp) produces an amino acid substitution (R620W) within the first Pro-rich region in the C terminus, thereby impairing Lyp binding to the Src homology 3 (SH3) domain of Csk (Bottini N, Musumeci L, Alonso A, Rahmouni S, Nika K, Rostamkhani M, MacMurray J, Meloni G F, Lucarelli P, Pellecchia M, et al. (2004) *Nat Genet.* 36:337-338. Begovich A B, Carlton V E, Honigberg L A, Schrodi S J, Chokkalingam A P, Alexander H C, Ardlie K G, Huang Q, Smith A M, Spoerke J M, et al. (2004) *Am J Hum Genet.* 75:330-337.). Moreover, it has been shown that the autoimmune predisposing variant of Lyp is actually a gain-of-function mutation, generating a more active phosphatase that is more effective in inhibiting T cell signaling than the wild-type enzyme (Nang T, Congia M, Macis M D, Musumeci L, Orru V, Zavattari P, Nika K, Tautz L, Tasken K, Cucca F, et. al. (2005) *Nat Genet.* 37:1317-1319.). Given the strong association of the C1858T polymorphism with various autoimmune disorders and the elevated phosphatase activity associated with the resultant Lyp/R620W variant, Lyp represents a potential target for a broad spectrum of autoimmune diseases. Small-molecule Lyp inhibitors may have therapeutic value for treating these disorders.

Example 3.1

Synthesis of Lyp Specific Salicylic Acid Derivatives

Described herein is a plurality of novel compounds having good affinity and selectivity for the PTP Lyp. The novel compounds disclosed herein were discovered through the creation of a PTP-directed library, and screening thereof. One embodiment of the disclosed method of synthesising the disclosed compounds comprises extensively exploring substitution patterns of the 2-position and 3-position of compound 24 (Core 1).

Compound 24 (Core 1) was designed as a p-tyr binding site directed scaffold. Empirical evidence suggests that Compound 24 (Core 1) binds to the Lyp active site. As disclosed herein, the 2-phenyl ring has been modified according to the instant disclosure. Modifications to Compound 24 (Core 1) include: modifications to the 2-phenyl ring; modifications to the 3-phenylethynyl group; the introduction of different aryl substituents at the 3-ethynyl position; and different amides substituted for the 2-phenyl ring.

One example of a novel compound, compound 127 (I-C11), produced through the modification of Compound 24 (Core 1) was disclosed in International Patent Application Publication No. WO 2009/049098 A2.

Compound 127

(I-C11)

Figure 6:
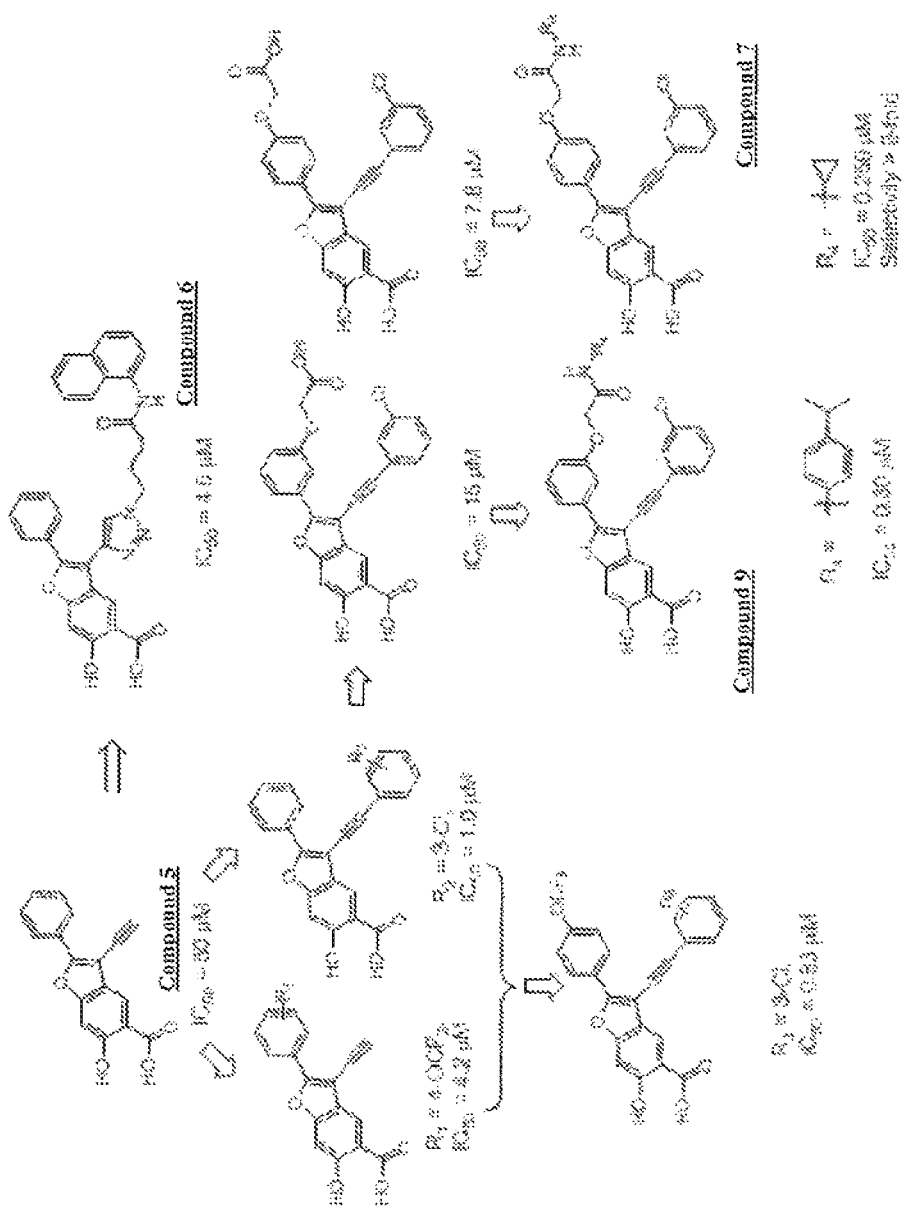
FIG. 6. A schematic illustrating select compounds which may be generated from Compound 5.

Compound 127 (I-C11) was identified through the creation of a PTP-directed library, and the screening thereof. As disclosed in International Patent Application Publication No. WO 2009/049098 A2, the creation of the subject PTP-directed library involved the coupling of Compound 24 (Core 1) and 80 azides. Compound 127 (I-C11) exhibits moderate affinity and selectivity (IC$_{50}$=4.6 µM) for PTP Lyp. Referring now to FIG. 6, a schematic illustrate that various compounds can be generated starting with Compound 5 in FIG. 6. For example, Compound 5 in FIG. 6 can be modified in order to synthesize Compound 24 (Compound 6 in FIG. 6). Additional compounds generated as a result of the modifications disclosed herein are reported in Tables 13-15.

Compound 128 (L75N04) is an example of a compound disclosed herein that exhibits potent and selective inhibition of Lyp (IC$_{50}$=259 nM). This compound exhibits a 9-fold selectivity for Lyp over other PTPs that have been examined. Additionally, as disclosed herein, the in vivo activity of Compound 128 (L75N04) demonstrates that Compound 128 (L75N04) has the potential to be used to treat autoimmune diseases.

Compound 128

(L75N04)

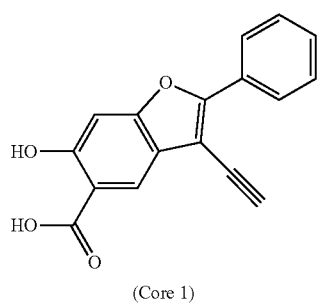

(Core 1)

The exemplary compound 129 and some of its derivatives (e.g. Compounds 129 a-e) are made and assayed according to the methods disclosed herein.

the compounds 5 (Y═H) with trimethylsilylacetylene produced the desired compounds labelled as 129a-e in Table 13 upon additional deprotection.

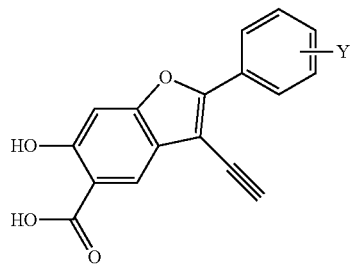

Compound 129

TABLE 13

| Compd # | | $IC_{50}$ (μM) |
|---|---|---|
| 129a | naphthalen-1-yl | 8.4 ± 0.3 |
| 129b | 4-biphenyl | 1.82 ± 0.06 |
| 129c | 3-chlorophenyl | 10.0 ± 1 |
| 129d | 4-(trifluoromethoxy)phenyl | 4.2 ± 0.6 |
| 129e | 4-phenoxyphenyl | 5.2 ± 0.2 |

The compounds labelled 129a-e in Table 13 were prepared according to Scheme 2. According to Scheme 2, presented below, the compound labelled as Compound 3 in Scheme 2 was prepared according to the literature (Zhou, B., He, Y., Zhang, X., Xu, J., Luo, Y., Wang, Y., Franzblau, S. G., Yang, Z., Chan, R. J., Liu, Y., Zheng, J. and Zhang, Z.-Y. "Targeting *Mycobacterium* Protein Tyrosine Phosphatase B for Anti-Tuberculosis Agents", *Proc. Natl. Acad. Sci. USA*, 107, 4573-8 (2010).).

The compounds labelled as Compounds 4 (Y═H) in Scheme 2 is prepared according to Sonogashira coupling of compound 3 and the appropriate alkyne, then subjected to cyclization with $I_2$ to yield the benzofuran compounds labelled in Scheme 2 as compounds 5 (Y═H). Coupling of

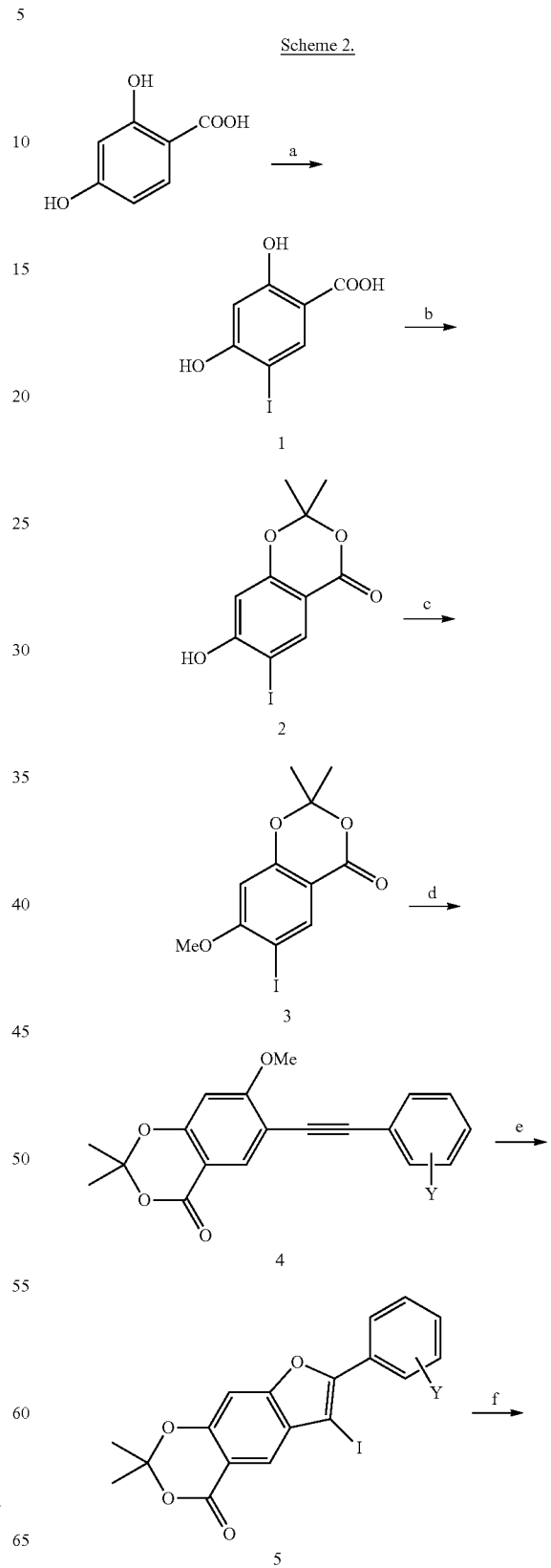

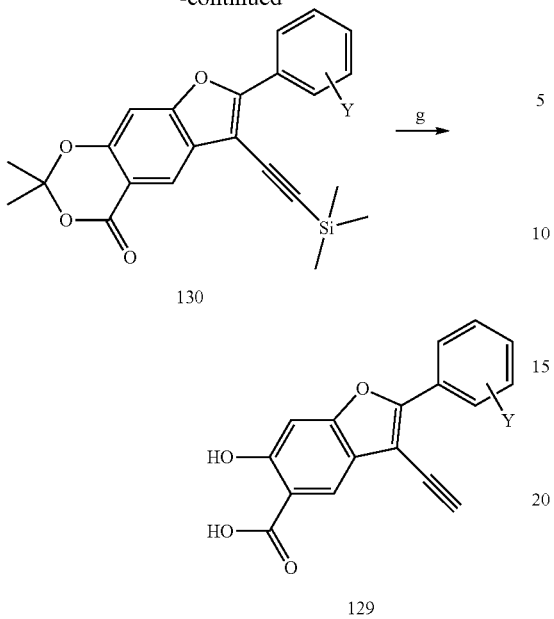

130

Reagents and conditions: a) ICl, AcOH, rt; b) Acetone, TFA, TFAA, rt; c) MeI, K₂CO₃, DMSO, rt; d) Pd(PPh₃)₂Cl₂, CuI,, DMF, rt; e) I₂, NaHCO₃, MeCN; f) Trimethylsilylacetylene, Pd(PPh₃)₂Cl₂, CuI, DMF, rt; g) KOH, THF/H₂O, reflux As is demonstrated by the values in Table 14, the potency of inhibition improved from 5 to 27.5 folds for the compounds in Table 14 as compared to the compound 127 (I-C11) (IC$_{50}$=50 μM). And only compound 129c, as labelled in Table 14, had a moderate selectivity against PTPs other than Lyp.

Through the introduction of different aryl groups to the 3-ethynyl of the Compound 24 (Core 1) scaffold, another set of PTP-target compounds is produced. These compounds were also assayed for Lyp inhibition (IC$_{50}$), leading to the identification of the compound labelled 131c (IC$_{50}$=1.0 μM) and the compound labelled 131i (IC$_{50}$=0.68 μM) in Table 13. Table 14 presents the IC$_{50}$ values of the 9 compounds derived in this manner, and demonstrates that the compounds labelled as 131c and 131i in Table 14 possess greater than a 50-fold increase in potent over Compound 24 (Core 1).

Compound 131

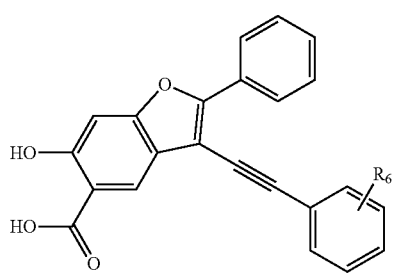

TABLE 15

| Cmpd# | R₆ = | IC$_{50}$ (μM) |
|---|---|---|
| 131a | H | 4.9 ± 0.3 |
| 131b | 3-F | 3.9 ± 0.2 |
| 131c | 3-Cl | 1.0 ± 0.07 |
| 131d | 3-OCH₃ | 17 ± 1 |
| 131e | 2,4-di-F | 3.5 ± 0.2 |
| 131f | 3,5-di-F | 1.3 ± 0.1 |
| 131g | 3-CF₃ | 2 ± 0.1 |
| 123h | 4-OCF₃ | 2 ± 0.1 |
| 131i | 4-OC₆H₅ | 0.63 ± 0.03 |

The analogues 131a-i (see Table 15) are prepared according to Scheme 3. The compound labelled 4 in Scheme 3 is prepared according to the literature (Zhou, B., He, Y., Zhang, X., Xu, J., Luo, Y., Wang, Y., Franzblau, S. G., Yang, Z., Chan, R. J., Liu, Y., Zheng, J. and Zhang, Z.-Y; and "Targeting *Mycobacterium* Protein Tyrosine Phosphatase B for Anti-Tuberculosis Agents", *Proc. Natl. Acad. Sci. USA*, 107, 4573-8 (2010).). Coupling of compound 5 with appropriate alkyne groups yielded the compounds in Scheme 3 labelled as compounds 132(a-i). Finally, deportation of compounds 132(a-i) in the presence of KOH generated the final compound (labelled 131(a-i) in Table 15).

Scheme 3

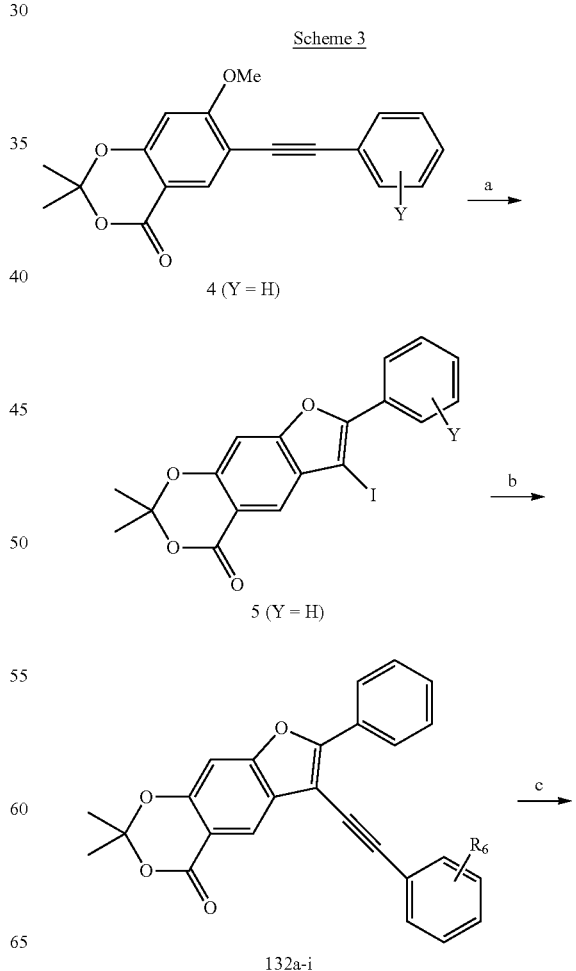

-continued

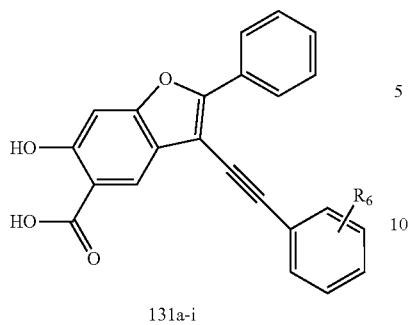

131a-i

Reaction Conditions: a) I₂, Na₂HCO₃, MeCN, 65%; b) Pd(PPh₃)₂Cl₂, CuI, Et₃N, 82%; c) KOH, THF/H₂O; 90%.

Another embodiment of the compounds disclosed herein includes Compound 133, comprising a merging of the compounds labelled 129d and 131c (in Tables 14 and 15 respectively) into one structure.

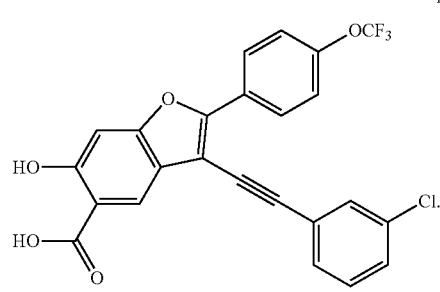

Compound 133

As is shown in Table 16, compound 133 comprises an IC$_{50}$ value of approximately 0.68 µM. Additionally, three analogues of compound 133 (labelled 134, 135 and 136 in Table 16) were generated and the respective IC$_{50}$ values are disclosed for each in Table 16. As can be determined from the IC$_{50}$ values presented in Table 16, these compounds resulted in minor changes to the IC$_{50}$ values when compared to compound 133.

TABLE 16

| Cmpd # | Structure | IC$_{50}$ (µM) |
| --- | --- | --- |
| 133 | 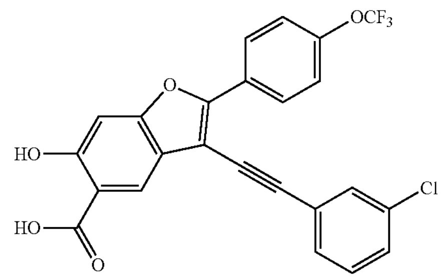 [SMILES: O=C(O)c1cc2c(C#Cc3cccc(Cl)c3)c(-c3ccc(OC(F)(F)F)cc3)oc2cc1O] | 0.68 ± 0.08 |
| 134 | 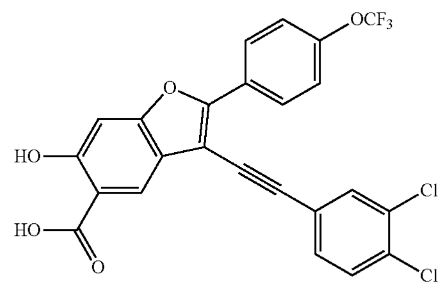 [SMILES: O=C(O)c1cc2c(C#Cc3ccc(Cl)c(Cl)c3)c(-c3ccc(OC(F)(F)F)cc3)oc2cc1O] | 0.61 ± 0.03 |
| 135 | 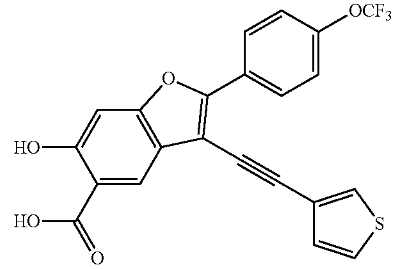 [SMILES: O=C(O)c1cc2c(C#Cc3ccsc3)c(-c3ccc(OC(F)(F)F)cc3)oc2cc1O] | 2.1 ± 0.3 |

TABLE 16-continued

| Cmpd # | Structure | IC$_{50}$ (µM) |
|---|---|---|
| 136 | 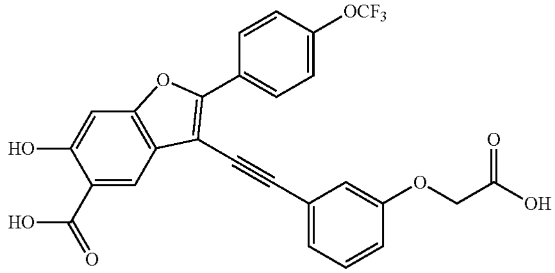 [SMILES: O=C(O)COc1cccc(C#Cc2c(-c3ccc(OC(F)(F)F)cc3)oc3cc(O)c(C(=O)O)cc23)c1] | 2.5 ± 0.2 |

Another embodiment of the present disclosure includes introducing further modifications at the β-benzene ring of formula 16 (labelled as Y in Formula 16 below) with a chloride atom affixed at the 3-benzene ring (labelled R$_6$ in Formula 16).

Formula 16

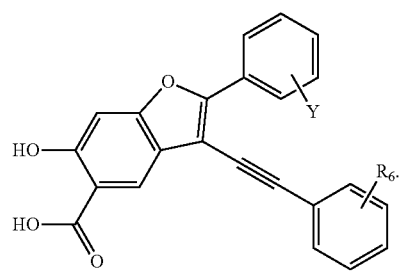

Referring now to Table 17, embodiments of compounds are depicted in which a side chain to the β-benzene ring at meta- or para-positions was introduced to 131c (IC50=1.0 µM), producing the compounds labelled as 49 (Core 74) and 50 (Core 75) in Table 16. As demonstrated by Table 16, the compounds 49 (Core 74) (IC50=15 µM for Lyp) and 50 (Core 75) possess 15 and 7.8-fold loss of activity compare with compound 133 for Lyp, respectively.

TABLE 17

| Cmpd # | Structure | IC$_{50}$ (µM) |
|---|---|---|
| Core 75 | 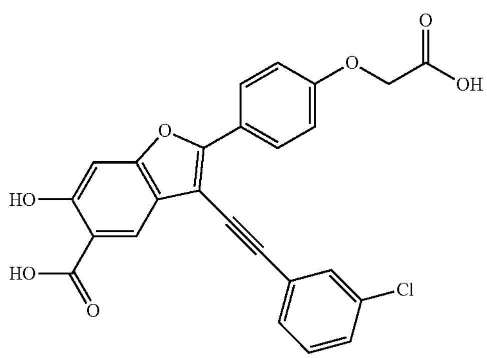 [SMILES: O=C(O)COc1ccc(-c2oc3cc(O)c(C(=O)O)cc3c2C#Cc2cccc(Cl)c2)cc1] | 7.6 ± 0.4 |
| L75N01 | 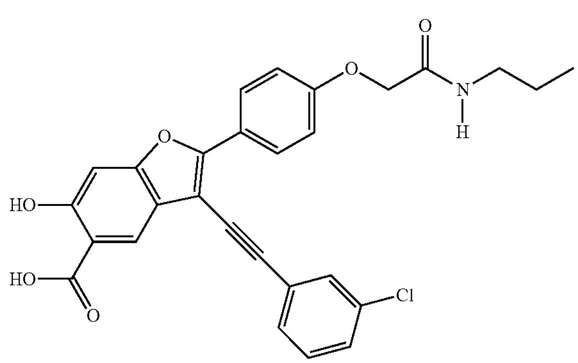 [SMILES: CCCNC(=O)COc1ccc(-c2oc3cc(O)c(C(=O)O)cc3c2C#Cc2cccc(Cl)c2)cc1] | 0.171 ± 0.004 |

TABLE 17-continued

| Cmpd # | Structure | IC$_{50}$ (μM) |
|---|---|---|
| L75N04 | 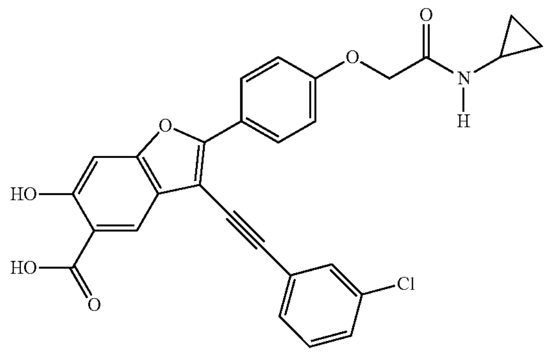 [SMILES: O=C(COc1ccc(-c2oc3cc(O)c(C(=O)O)cc3c2C#Cc2cccc(Cl)c2)cc1)NC1CC1] | 0.259 ± 0.007 |
| L75N05 | 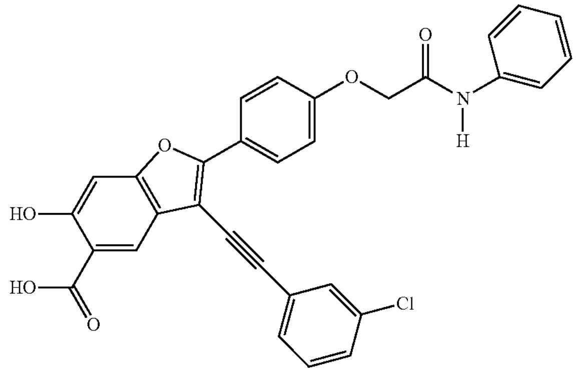 [SMILES: O=C(COc1ccc(-c2oc3cc(O)c(C(=O)O)cc3c2C#Cc2cccc(Cl)c2)cc1)Nc1ccccc1] | 0.263 ± 0.006 |
| L75N29 | 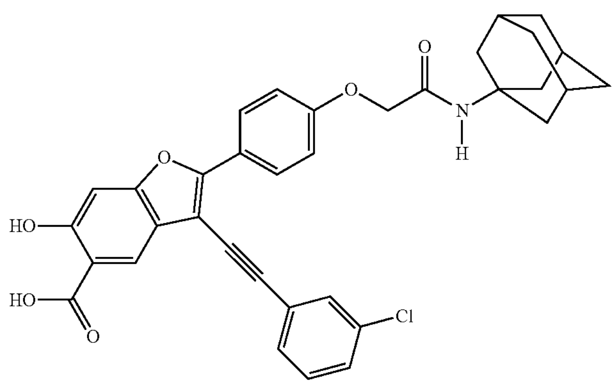 [SMILES: O=C(COc1ccc(-c2oc3cc(O)c(C(=O)O)cc3c2C#Cc2cccc(Cl)c2)cc1)NC12CC3CC(CC(C3)C1)C2] | 0.31 ± 0.008 |
| L75N47 | 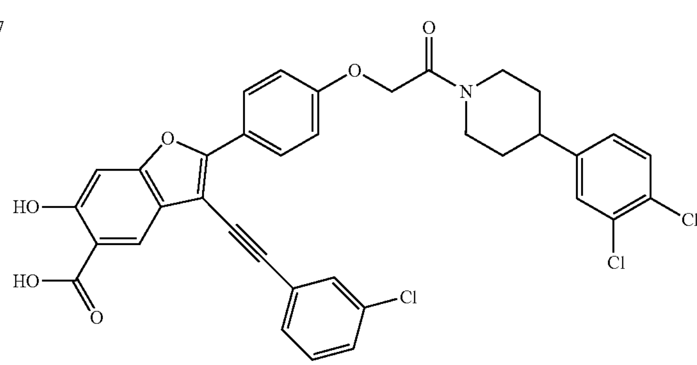 | 0.55 ± 0.03 |

TABLE 17-continued

| Cmpd # | Structure | IC$_{50}$ (µM) |
|---|---|---|
| L75N76 | 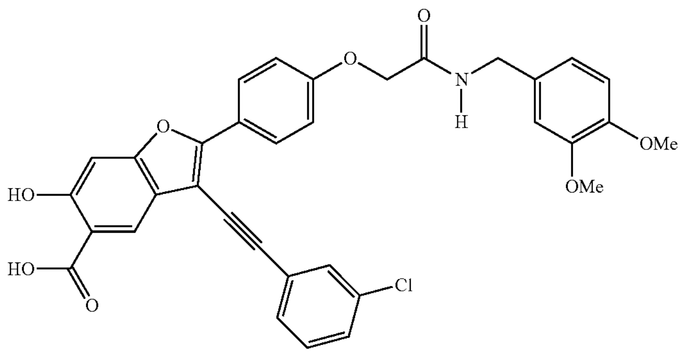 [SMILES: COc1ccc(CNC(=O)COc2ccc(-c3oc4cc(O)c(C(=O)O)cc4c3C#Cc3cccc(Cl)c3)cc2)cc1OC] | 0.259 ± 0.008 |
| L75N77 | 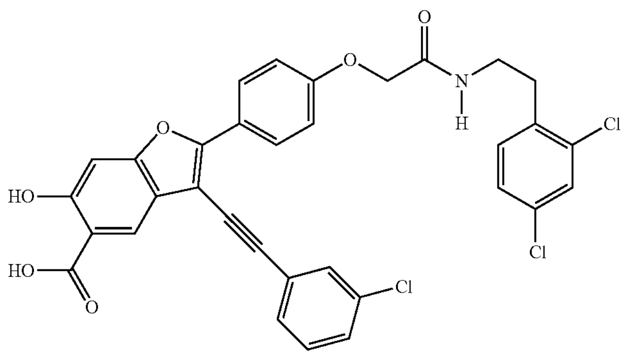 [SMILES: O=C(COc1ccc(-c2oc3cc(O)c(C(=O)O)cc3c2C#Cc2cccc(Cl)c2)cc1)NCCc1ccc(Cl)cc1Cl] | 0.67 ± 0.03 |

Further, as determined by the disclosure herein, the substituent at para-position of the β-phenyl ring (represented by compound 50 (core 75 in Table 16) has more activity than that at meta-position of β-phenyl ring (represented by compound 50 (Core 74 in Table 16).

Figure 8:
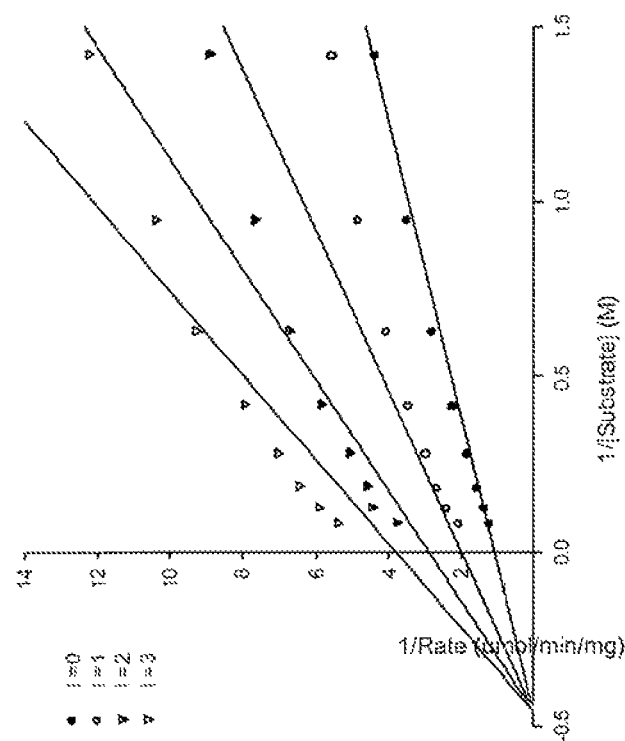
FIG. 8. Lineweaver Burke plot for Compound 207a mediated mPTPB inhibition. Non-competitive inhibition measured at concentrations of 0 (●), 1.0 µM (○), 2.0 µM (▼), and 3.0 µM (∇).

Referring now to FIG. 8, amide substitutions on the carboxylic acid of the compounds labelled 49 (Core 74) and 50 (Core 75) (in FIG. 8 and Table 17) were also introduced through amide coupling reactions of appropriate amines and the carboxylic acid group. The amide substitution reactions resulted in formation of compounds 137 and 128 (FIG. 8) respectively (where Compound 137 comprises an amide substitution at the carboxylic acid of the compound 49 (Core 74) in Table 16 and compound 128 comprises an amide substitution of the carboxylic acid of compound 50 (Core 75) of Table 1).

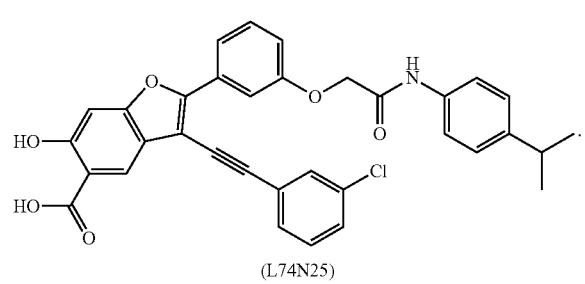

Compound 137

(L74N25)

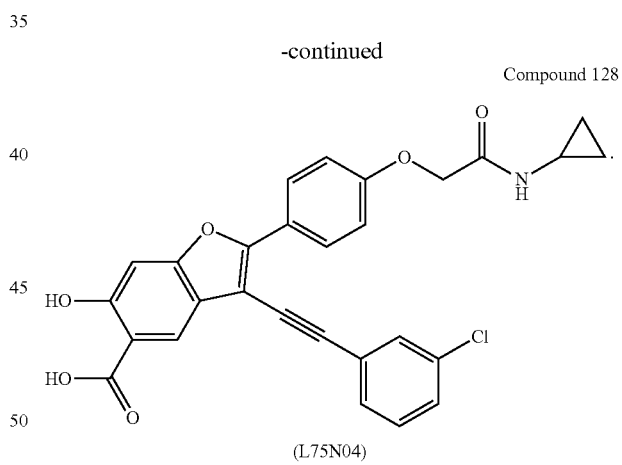

Compound 128

(L75N04)

After synthesis, the amide substitution libraries including compounds 137 and 128, respectively, were screened and it was determined that the library comprising compound 128 generated more potent inhibitors than the library comprising Compound 137. Base on the screening data, it was determined that the amide at the 4-position may only tolerate small aliphatic groups, otherwise either activity or selectivity of the compounds in the libraries were lost.

Further, the IC$_{50}$ values of some of the most potent inhibitors from both libraries were detected. As a result of this assay, the compound labelled L75N04 (Compound 128) in Table 16 was determined to better selective inhibit or Lyp, than are the other analogues that are tested.

Example 4.1

Synthesis and Characterization of Indole Salicylic Derivatives

Referring now to Table 18. Indole salicylic acid compounds were assayed for their effect on three different tyrosine phosphatases: mPTPB, PTP1B and SHP2-D2C.

The indole salicylic acid moieties that included an acetyl linking group exhibited markedly lower $K_i$ values than a similar compound that lacked such a group. Moreover, the compounds listed in Table 18 demonstrate at least one order of magnitude greater specificity for the enzyme mPTPB than they do for the other two enzymes that were tested using these compounds.

TABLE 18

| Structure | ID | mPTPB | PTP1B | SHP2-D2C |
|---|---|---|---|---|
| 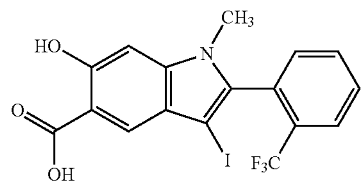 [SMILES: Cn1c(-c2ccccc2C(F)(F)F)c(I)c2cc(C(=O)O)c(O)cc21] | L02Z10 | 1.18 ± 0.09 | 700 ± 100 | 87 ± 4 |
| 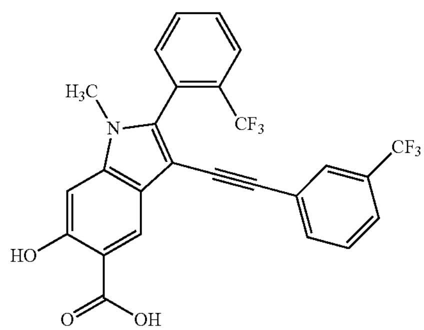 [SMILES: Cn1c(-c2ccccc2C(F)(F)F)c(C#Cc2cccc(C(F)(F)F)c2)c2cc(C(=O)O)c(O)cc21] | L84Z01 | 0.23 ± 0.04 | 5.6 ± 0.2 (Lyp) | 6.4 ± 0.1 |
| 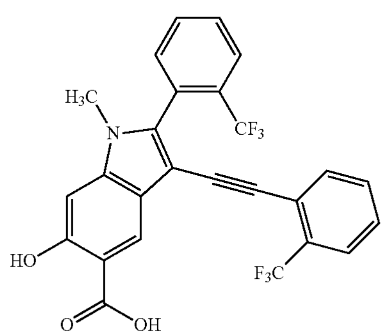 [SMILES: Cn1c(-c2ccccc2C(F)(F)F)c(C#Cc2ccccc2C(F)(F)F)c2cc(C(=O)O)c(O)cc21] | L84Z02 | 0.3 ± 0.05 | 12.5 ± 0.5 | 5.66 ± 0.08 |
| 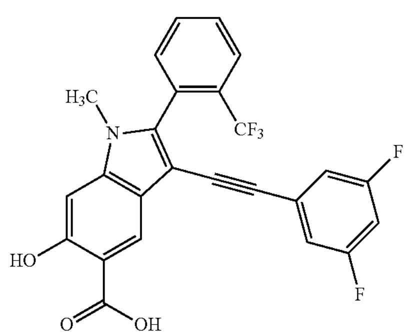 [SMILES: Cn1c(-c2ccccc2C(F)(F)F)c(C#Cc2cc(F)cc(F)c2)c2cc(C(=O)O)c(O)cc21] | L84Z03 | 0.21 ± 0.05 | 21 ± 1 | 6.28 ± 0.05 |

TABLE 18-continued

| Structure | ID | mPTPB | PTP1B | SHP2-D2C |
|---|---|---|---|---|
| 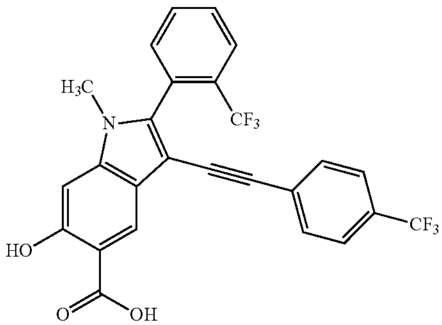 [SMILES: Cn1c(-c2ccccc2C(F)(F)F)c(C#Cc2ccc(C(F)(F)F)cc2)c2cc(C(=O)O)c(O)cc21] | L84Z04 | 0.6 ± 0.10 | 9.3 ± 0.5 | 5.44 ± 0.09 |
| 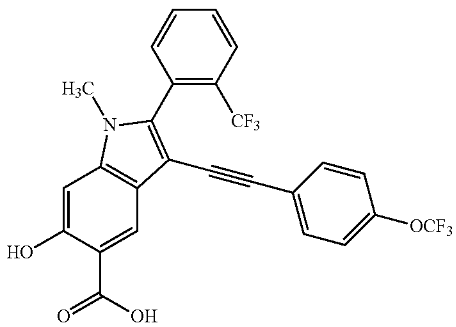 [SMILES: Cn1c(-c2ccccc2C(F)(F)F)c(C#Cc2ccc(OC(F)(F)F)cc2)c2cc(C(=O)O)c(O)cc21] | L84Z05 | 0.85 ± 0.2 | 9.2 ± 0.5 | 5.4 ± 0.1 |
| 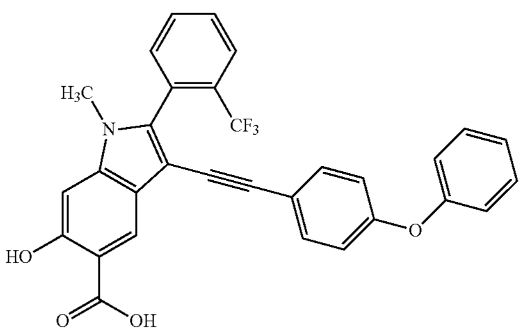 [SMILES: Cn1c(-c2ccccc2C(F)(F)F)c(C#Cc2ccc(Oc3ccccc3)cc2)c2cc(C(=O)O)c(O)cc21] | L84Z06 | 0.46 ± 0.06 | 4.27 ± 0.07 | 3.4 ± 0.1 |

As discussed above, mPTPB is a promising target for the treatment of TB. However, the highly conserved active site feature makes it a significant challenge for the discovery of selective mPTPB inhibitor. Most of the mPTPB inhibitors reported are pTyr mimetic, which usually bear two or more acid group. The poly negative charge property makes these inhibitors lack of cell permeability and thus not drug-like. Although different kinds of mPTPB inhibitors have been reported to inhibit the enzyme at micromolar or submicromolar level, most of the inhibitors' in vivo activity has not been disclosed.

However, it has been recognized that the binding affinity of the pTyr for the PTP active site is modest. The residues flanking pTyr also make significant contribution to PTP substrate recognition. A highly efficient strategy for PTP inhibitor design was proposed to bind both active site and nearby non-conserved binding pocket for enhanced activity and selectivity. Zhang, Z.-Y. Protein tyrosine phosphatases: structure and function, substrate specificity, and inhibitor development. Annu. Rev. Pharmacol. Toxicol. 2002, 42, 209-234. Using this strategy, it has been possible to produce numerous potent and selective PTP inhibitors. Tan, L. P.; Wu, H.; Yang, P. Y.; Kalesh, K. A.; Zhang, X.; Hu, M.; Srinivasan, R.; Yao, S. Q. High-throughput discovery of Mycobacterium tuberculosis protein tyrosine phosphatase B (MptpB) inhibitors using click chemistry. Org. Lett. 2009, 11, 5102-5105; Zhang, S.; Zhang, Z.-Y. PTP1B as a drug target: recent development in PTP1B inhibitor discovery. Drug Discovery Today 2007, 12, 373-381; and Zhang, X., He, Y., Liu, S., Yu, Z., Jiang, Z.-X., Yang, Z., Dong, Y., Nabinger, S. C., Wu, L., Gunawan, A. M., Wang, L., Chan, R. J., and Zhang, Z.-Y. Salicylic acid-based small molecule inhibitor for the oncogenic Src homology-2 domain containing protein tyrosine phosphatase-2 (SHP2), *J. Med. Chem.*, 2010, 53, 2482-2493.

In silico virtual screening, indicated that salicylic acid can serve as a pTyr mimic. Furthermore, it was demonstrated that polyaromatic salicylic acid derivatives exhibit enhanced affinity towards PTPs compared to salicylic acid derivatives. Indole is versatile structural scaffold found in nature products and precursor of many pharmaceuticals. Horton, D. A.; Bourne, G. T.; Smythe, M. L. The combinatorial synthesis of bicyclic privileged structures. Chem. Rev. 2003, 103, 893-930. Substituted indoles are structural elements of tryptophan-derived tryptamine alkaloids like the neurotransmitter serotonin, and melatonin. A previous study identified indole salicylic acid as pTyr mimic. Through click chemistry, a peripheral binding scaffold was attached to the indole salicylic acid core to provide potent Shp2 inhibitor. Zhang, et al., *J. Med. Chem.*, 2010.

Identification of Indole Salicylic Acid 207a as Potent and Selective Core Structure Targeting mPTPB.

Figure 9A:
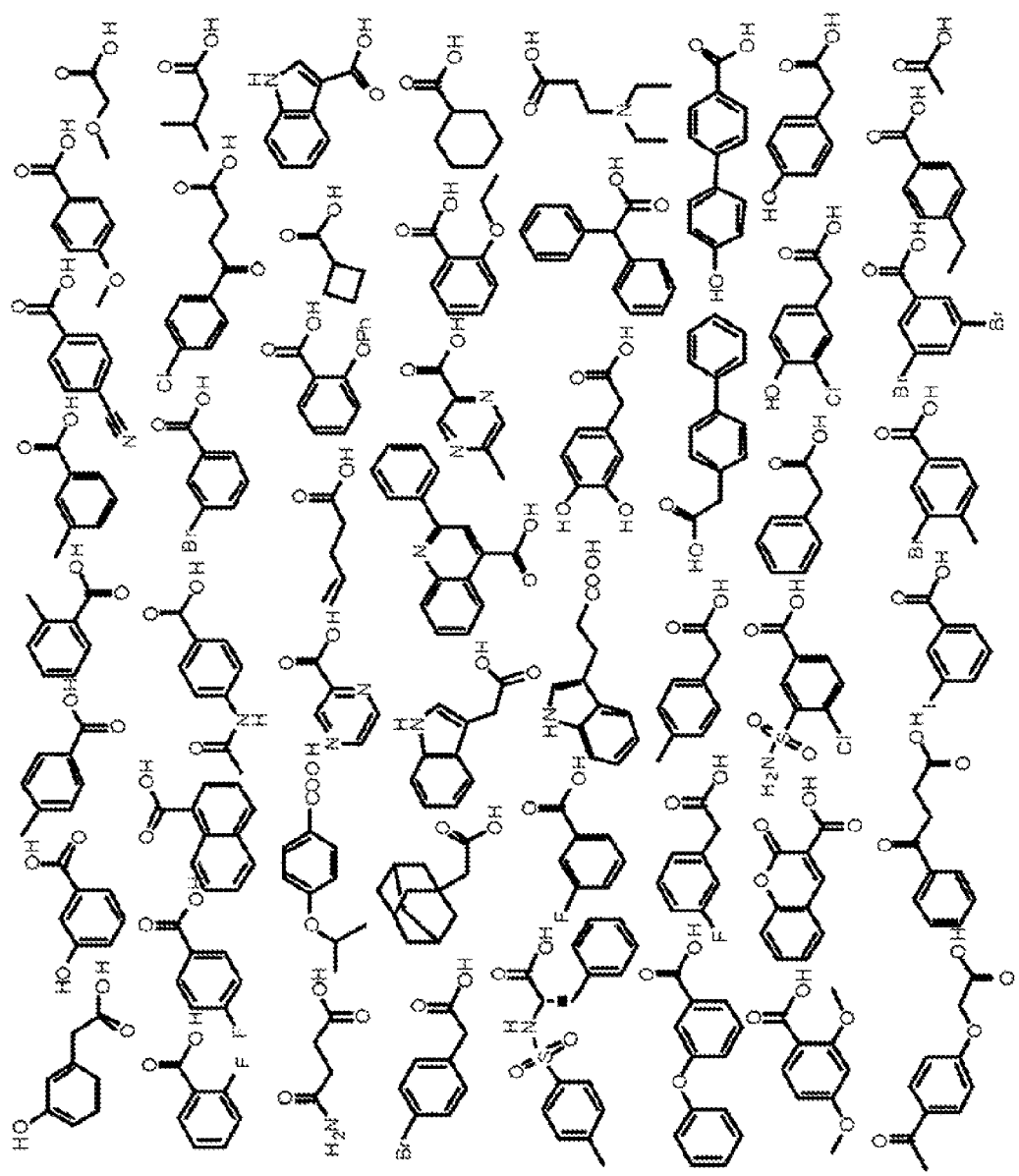
FIG. 9A. Chemical structures of 102 acids using to create combinatorial library number 13.
Figure 9B:
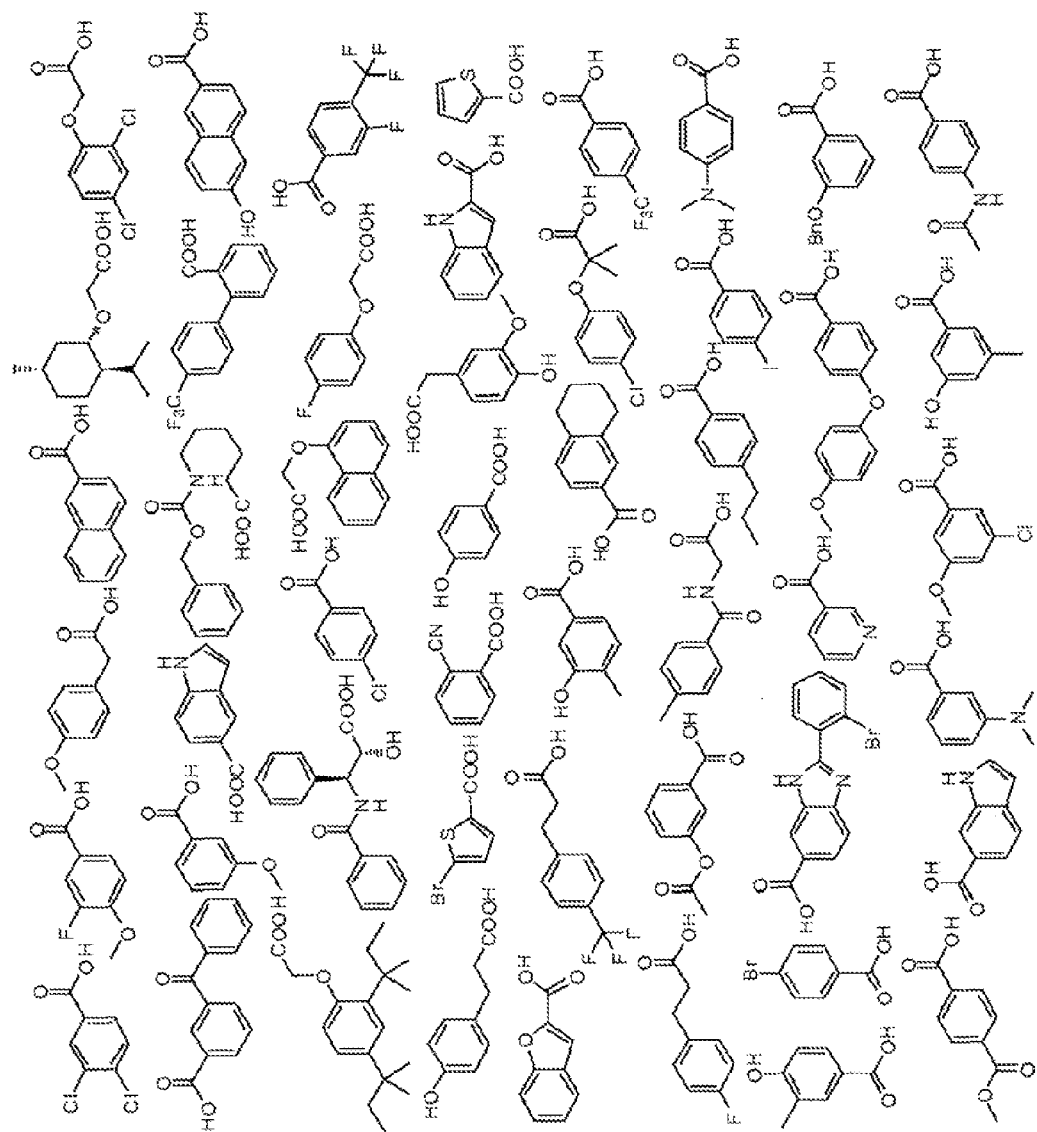
FIG. 9B. Chemical structures of 102 acids using to create combinatorial library number 13.
Figure 10:
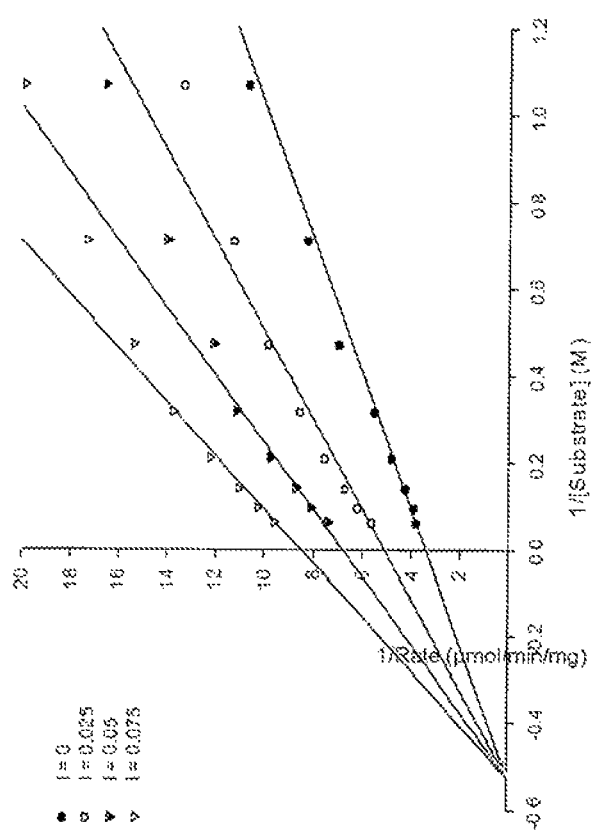
FIG. 10. Lineweaver-Burk plot for Compound 213a mediated mPTPB inhibition. Non-competitive inhibitor of mPTPB measured at concentrations of 0 (●), 0.025 µM (○), 0.05 µM (▼), and 0.075 µM (∇).

One approach disclosed herein is to first optimize the indole-based salicylic acid as a pTyr mimetic to find potent and selective core structure targeting mPTPB active site. After identification of a useful core structure, diverse scaffolds are attached to the core to yield highly potent and selective inhibitors of mPTPB. As shown in FIG. 7, six phenylacetylenes are coupled to optimized indole-based salicylic acid to afford a focused library; at the same time an additional diversity element (102 member library see FIGS. 9A and 9B) was introduced to the core through the use of proper linker to the indole salicylic acid core by a combinatorial approach. The goal of both approaches is to create compounds that exhibit enhanced binding affinity, enzyme selectivity and other desirable pharmacological properties.

In order to characterize the indole salicylic acid based core structure's targeting of the active site of mPTPB, a series of analogues of indole salicylic acid modified a the C2 position was designed and synthesized. As shown in Scheme 4, the focused indole salicylic acid derivatives were prepared. Compound 201 in methanol in the presence of concentrated sulfuric acid was refluxed for overnight provide compound 202 in 81.4% yields. Compound 202 was treated with paraformaldehyde and NaCNBH$_3$ overnight to give product 203 with 78% yield. Iodination of compound 203 in ether and water yield the desired isomer 204, which was then coupled with the corresponding commercially available alkynes by Sonogashira coupling to afford compound 205a-k with high yield. Electrophilic cyclizations of 205a-k by I$_2$ provide 206a-k in 80-90% yield. After hydrolysis of 206a-k in 3.5 N NaOH for 2 days, 207a-k was purified by pre-HPLC in 50-80% yield with over 95% purity.

Scheme 4.

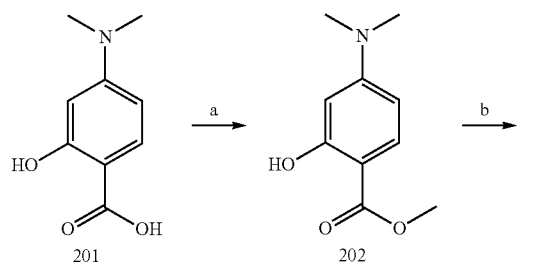

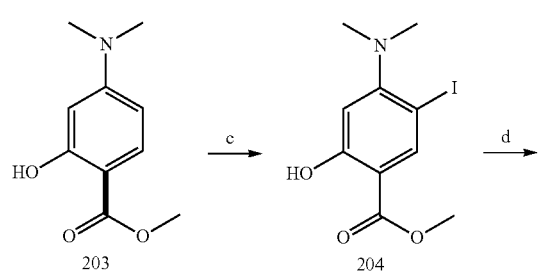

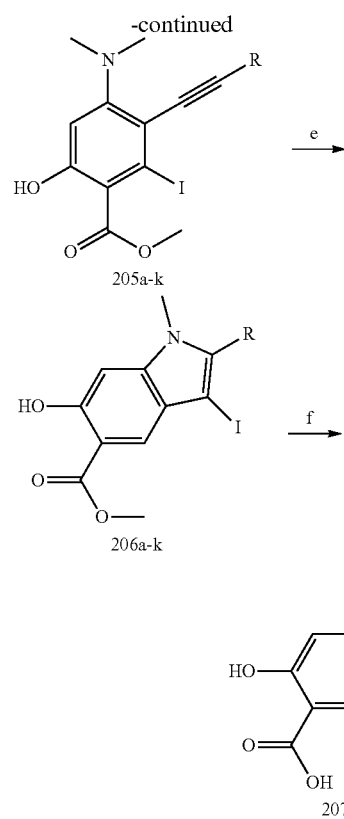

Conditions: (a) Cat. conc. H$_2$SO$_4$, CH$_3$OH, reflux, 24 h, 81.4%; (b) (CHO)n, NaCNBH$_3$, AcOH, rt, 24 h, 78%; (c) I$_2$, K$_2$CO$_3$, water, ether, rt, 4 h, 42%; (d) corresponding Phenylacetylene, Pd(PPh$_3$)$_2$Cl$_2$, CuI, Et$_3$N, DMF, 80-90%; (e) I$_2$, CH$_2$Cl$_2$, rt, 80-90%; (f) 3.5N NaOH, THF/H$_2$O, rt, 48 h, 50-80%.

As shown in Table 19, the electro-withdrawing group trifluoromethyl is introduced into different positions of the C2 phenyl ring, to render compounds 207a, 207b and 207f. An extra phenyl ring is added to the C2 phenyl ring to yield a bulky compound 207c. In order to investigate the effect of an aliphatic ring on the C2 position, a C2 phenyl ring to cyclohexyl, as compound 207d is displayed. Trifluoromethoxyl and hydroxyl group are introduced to C2 phenyl ring, in compound 207e and 207k respectively. The effect of halogen substitution on C2 phenyl ring is considered, in compound 207h, 207i and 207j.

The inhibitory of compounds 207a-k towards mPTPB was tested by the inhibition of mPTPB catalyzed hydrolysis of p-nitrophenyl phosphate (pNPP) at pH 7 and 25° C. (Table 1). Out of the 11 member small library, the most potent Compound 207a has an IC$_{50}$ of 1.2±0.1 μM towards mPTPB.

TABLE 19

IC$_{50}$ values (μM) of 207a-k for mPTPB

| ID | Structure | IC$_{50}$ (μM) |
|---|---|---|
| 207a | 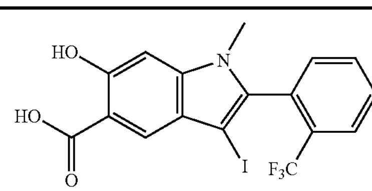 | 1.2 ± 0.1 |

TABLE 19-continued

IC$_{50}$ values (µM) of 207a-k for mPTPB

| ID | Structure | IC$_{50}$ (µM) |
|---|---|---|
| 207b | (6-OH, 5-COOH, 3-I indole, N-Me, 2-(3-CF$_3$-phenyl)) | 2.2 ± 0.2 |
| 207c | (6-OH, 5-COOH, 3-I indole, N-Me, 2-(4-biphenyl)) | 2.4 ± 0.2 |
| 207d | (6-OH, 5-COOH, 3-I indole, N-Me, 2-cyclohexyl) | 3.6 ± 0.1 |
| 207e | (6-OH, 5-COOH, 3-I indole, N-Me, 2-(4-OCF$_3$-phenyl)) | 5.5 ± 0.5 |
| 207f | (6-OH, 5-COOH, 3-I indole, N-Me, 2-(4-CF$_3$-phenyl)) | 7 ± 1 |
| 207g | (6-OH, 5-COOH, 3-I indole, N-Me, 2-phenyl) | 11 ± 1 |
| 207h | (6-OH, 5-COOH, 3-I indole, N-Me, 2-(3-F-phenyl)) | 11 ± 1 |
| 207i | (6-OH, 5-COOH, 3-I indole, N-Me, 2-(4-F-phenyl)) | 12 ± 2 |
| 207j | (6-OH, 5-COOH, 3-I indole, N-Me, 2-(2-F-phenyl)) | 16 ± 2 |
| 207k | (6-OH, 5-COOH, 3-I indole, N-Me, 2-(3-OH-phenyl)) | 18 ± 1 |

As shown in Table 20, Selectivity study showed that Compound 207a exhibits 47-fold selectivity for mPTPB over the other 10 PTPs, including bacterial PTPs, mPTPA and YopH, a panel of mammalian PTPs including cytosolic PTPs, Fap-1, HePTP, Lyp, PTP1B, Shp1 and Shp2, the receptor-like PTPs, CD45, the dual specificity phosphatases VHX. Kinetic analyses indicated that 207a is a reversible and noncompetitive inhibitor for mPTPB, its K$_i$ value is 1.21±0.04 µM (FIG. 2). Hence, Compound 207a was chosen for the core for the acquisition of more potent and selective inhibitor.

TABLE 20

Selectivity of compound 207a measured against a panel of PTPs

| PTP: | IC$_{50}$ (µM) |
|---|---|
| mPTPB | 1.18 ± 0.09 |
| mPTPA | 82 ± 1 |
| YopH | 220 ± 20 |
| CD45 | 227 ± 4 |
| Fap-1 | 84 ± 1 |
| HePTP | 86 ± 6 |
| LYP | 75 ± 4 |
| PTP1B | 700 ± 100 |
| SHP1-D1C | 86.8 ± 0.4 |
| SHP2-D2C | 87 ± 4 |
| VHX | 56 ± 1 |

Modification of Compound 207a Through a Focused Library, Compound 209a is Identified as Potent and Selective mPTPB Inhibitor.

In order to improve the potency and selectivity of the indole salicylic acid core 207a, a focused library 209a-f were prepared as Scheme 5. Compound 206a was coupled with the corresponding alkynes by Sonogashira coupling to afford Compound 208a-f with high yield. After hydrolysis of 208a-f in 20% NaOH for 2 days, 209a-f was purified by pre-HPLC in 80-90% yield.

Scheme 5

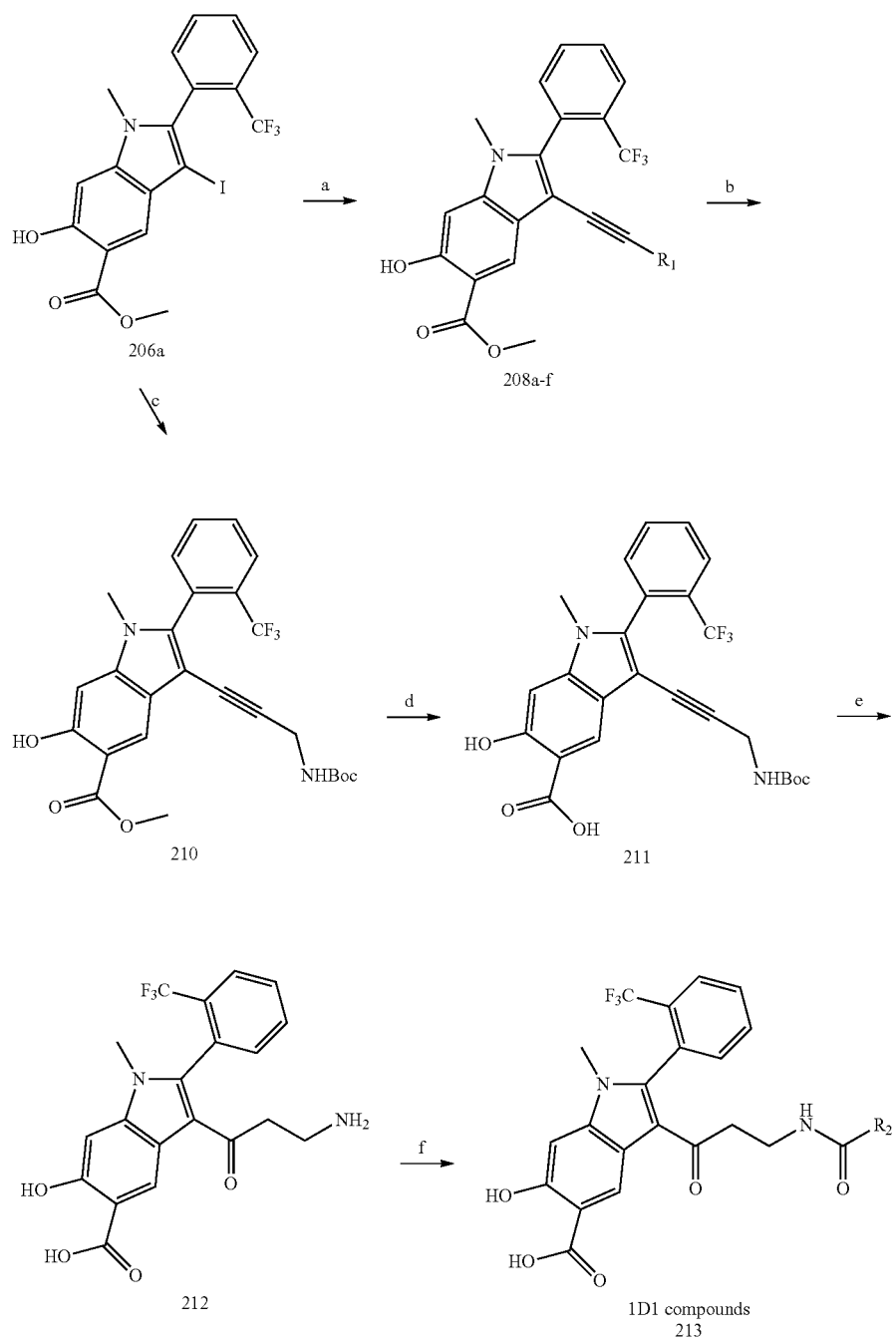

Conditions: (a) corresponding phenylaceteylene, Pd(PPh₃)₂Cl₂, CuI, Et₃N, DMF, 80 deg. 4-16 h, 80-90%; (b) 20% NaOH, methanol, THF/H₂O, rt, 48 h, 80-90%; (c) tert-butyl prop-2-yn-1-ylcarbamate, Pd(PPh₃)₂Cl₂, CuI, Et₃N, DMF, 24 h, 68%; (d) 20% NaOH, methanol, THF/H₂O, rt, 48 h, 87%; (e) 20% TFA in DCM, rt, 24 h, 91.5%; (f) 102 acids, HOBT, HBTU, TEA, DMF, rt, 2 h.

In this focused library, different ethynyl trifluoromethylbenzenes were coupled to compound 207a, after hydrolysis provided 209b, 209c and 209e (Table 21). 3,5-difluoroethynyl ethynyl attached to compound 207a provided compound 209a. phenoxyphenyl ethynyl and trifluoromethylphenyl ethynyl were introduced to the core 207a yield 209d and 209f respectively.

The IC$_{50}$ of 209a-f against mPTPB was listed in Table 21. Among the six compounds, the best compound 209a has an IC$_{50}$ of 0.21±0.05 μM against mPTPB. Compound 209a is 5 times potent than its mother compound 207a. Further selectivity study showed compound 209a is 100 fold and 30 fold selective towards PTP1B and Shpt respectively.

TABLE 21

Inhibition of 209a-f against mPTPB.

| ID | Structure | IC$_{50}$(µM) |
|---|---|---|
| 209a | 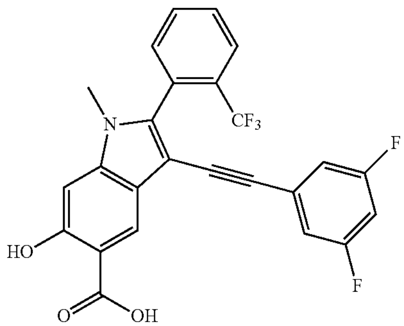 [SMILES: Cn1c(-c2ccccc2C(F)(F)F)c(C#Cc2cc(F)cc(F)c2)c2cc(C(=O)O)c(O)cc21] | 0.21 ± 0.05 |
| 209b | 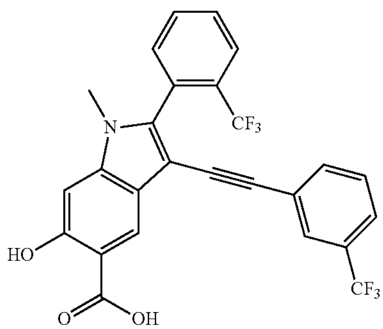 [SMILES: Cn1c(-c2ccccc2C(F)(F)F)c(C#Cc2cccc(C(F)(F)F)c2)c2cc(C(=O)O)c(O)cc21] | 0.23 ± 0.04 |
| 209c | 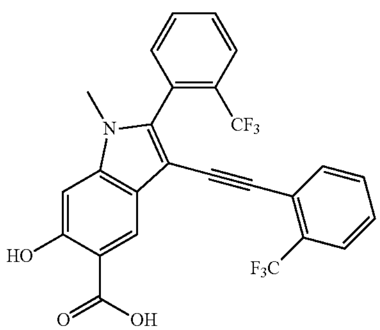 [SMILES: Cn1c(-c2ccccc2C(F)(F)F)c(C#Cc2ccccc2C(F)(F)F)c2cc(C(=O)O)c(O)cc21] | 0.3 ± 0.05 |
| 209d | 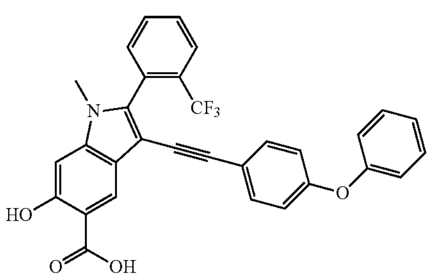 [SMILES: Cn1c(-c2ccccc2C(F)(F)F)c(C#Cc2ccc(Oc3ccccc3)cc2)c2cc(C(=O)O)c(O)cc21] | 0.46 ± 0.06 |
| 209e | 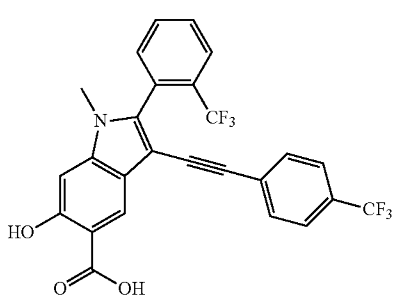 [SMILES: Cn1c(-c2ccccc2C(F)(F)F)c(C#Cc2ccc(C(F)(F)F)cc2)c2cc(C(=O)O)c(O)cc21] | 0.6 ± 0.1 |
| 209f | 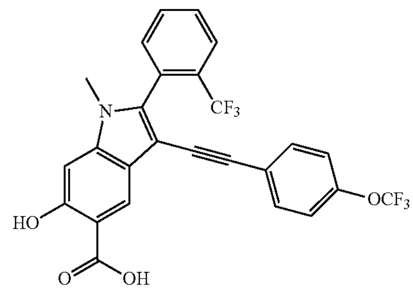 [SMILES: Cn1c(-c2ccccc2C(F)(F)F)c(C#Cc2ccc(OC(F)(F)F)cc2)c2cc(C(=O)O)c(O)cc21] | 0.85 ± 0.2 |

Combinatorial Library Approach, Synthesis of Compound 213a and it Identification as Potent and Selective mPTPB Inhibitor.

Compound 209a is highly potent inhibitor synthesized from core 207a by a 2 step process followed by an HPLC based purification process. In order to streamline the process of making additional inhibitors a combinatorial library approach and screen in situ was followed; this approach obviated the need for a tedious purification step. In order to construct the 102-member combinatorial library, compound 206a was coupled with tert-butyl prop-2-yn-1-ylcarbamate in presence of Pd(PPh$_3$)$_2$Cl$_2$ and CuI to afford compound 210 (Scheme 5). Compound 210 hydrolyzed by 20% NaOH for 2 days to provide compound 211. Compound 211 was treated with 20% TFA in DCM to afford Compound 212. Compound 212 reacted with 102 acids (FIGS. 9A and 9B) respectively in the presence of HOBT, HBTU and TEA in DMF overnight to assemble the combinatorial amide library 13 in 96 well plates. 10 of the reactions were monitored by LC-MS, indicating the good quality of library 13. About 70% of compound 212 is converted in to the target molecules.

This library was screened directly at a concentration of about 1 µM as an inhibitor of mPTPB. Two of the inhibitors at 1 µM inhibit over 50% of mPTPB activity (Table 22). The best compound 213a has 81% inhibition at 1 µM. Compound 213b has 52% inhibition at 1 µM and rank the second in this library. In order to validate the screening result, 3 low inhibition compounds 213c, 213d and 213e are used as references. These five compounds were re-synthesized, purified by HPLC and tested for IC$_{50}$ against mPTPB (Table 4). The most potent compound 213a has an IC$_{50}$ value of 0.079±0.01 µM against mPTPB. Compound 213b has an IC$_{50}$ value of 0.68±0.04 µM against mPTPB. The IC$_{50}$ value of the other there compounds were higher as expected. The consistency of the tendency between the screening data and IC$_{50}$ data indicated success of our approach.

TABLE 22
Inhibition at 1 μM and IC$_{50}$ of selected compounds from library 13 against mPTPB
| ID | Structure | In % @ 1 μM | IC$_{50}$ (μM) |
|---|---|---|---|
| 213a | 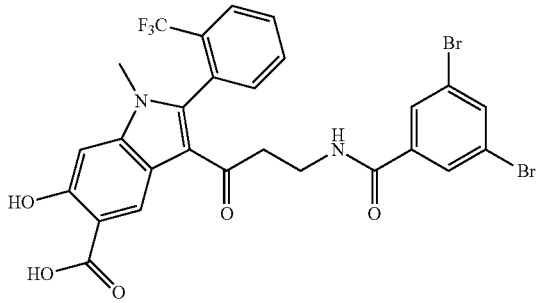 [SMILES: Cn1c(-c2ccccc2C(F)(F)F)c(C(=O)CCNC(=O)c2cc(Br)cc(Br)c2)c2cc(C(=O)O)c(O)cc21] | 81 | 0.079 ± 0.01 |
| 213b | 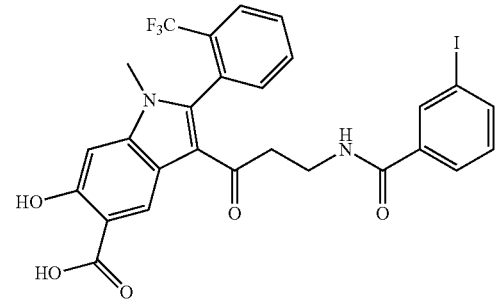 [SMILES: Cn1c(-c2ccccc2C(F)(F)F)c(C(=O)CCNC(=O)c2cccc(I)c2)c2cc(C(=O)O)c(O)cc21] | 52 | 0.68 ± 0.04 |
| 213c | 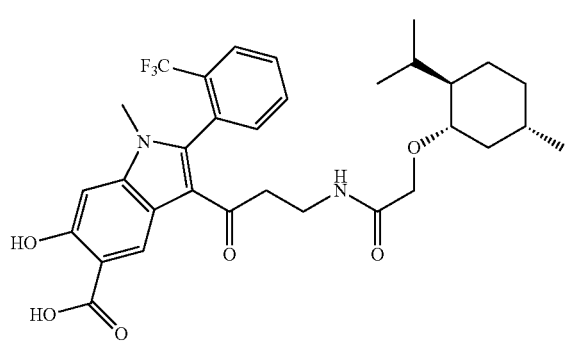 [SMILES: CC(C)[C@H]1CC[C@H](C)C[C@@H]1OCC(=O)NCCC(=O)c1c(-c2ccccc2C(F)(F)F)n(C)c2cc(O)c(C(=O)O)cc12] | 5 | 3.3 ± 0.1 |
| 213d | 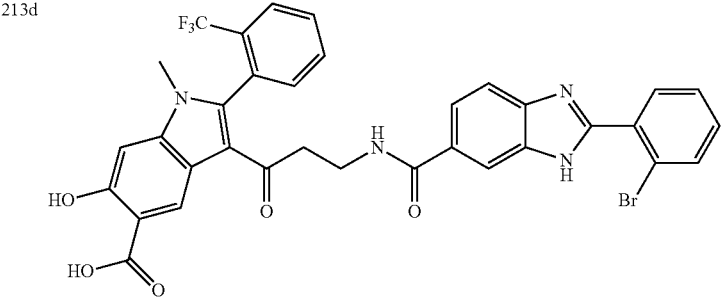 | 10 | 5.2 ± 0.2 |

TABLE 22-continued

Inhibition at 1 µM and IC$_{50}$ of selected compounds from library 13 against mPTPB

| ID | Structure | In % @ 1 µM | IC$_{50}$ (µM) |
|---|---|---|---|
| 213e | *(structure shown)* | 0 | >20 |

Selectivity of Compound 213a towards other ten PTPs mentioned above was investigated (Table 23). Compound 213a exhibits over 90 fold selectivity for mPTPB over the other ten PTPs tested. Compared to its parent compound 207a, compound 213a is 14 fold more potent and 43 fold more selective. Kinetic analyses indicated that 213a is a reversible and noncompetitive inhibitor for mPTPB, its K$_i$ value is 50±2 nM (FIGS. 4a-4b). It appears as that, compound 213a is the most potent and selective mPTPB inhibitor identified to date.

TABLE 23

Selectivity of 213a measured against a panel of various PTPs.

*(structure shown)*

| PTP | 213a IC$_{50}$(µM) |
|---|---|
| mPTPB | 0.079 ± 0.01 |
| mPTPA | 10.9 ± 0.5 |
| YopH | 13 ± 1 |
| CD45 | 27.7 ± 0.7 |
| Fap-1 | 8.0 ± 0.7 |
| HePTP | 10.7 ± 1.3 |
| LYP | 12.2 ± 3.2 |
| PTP1B | 14.0 ± 0.8 |
| SHP1-D1C | 7.1 ± 0.3 |
| SHP2-D2C | 11.4 ± 0.4 |
| VHX | 9.5 ± 0.7 | mPTPB Inhibitor 213a Restores ERK1/2 Activity and Blocks Akt Activation in Activated Macrophages Cells Overexpressing mPTPB.

Figure 11:
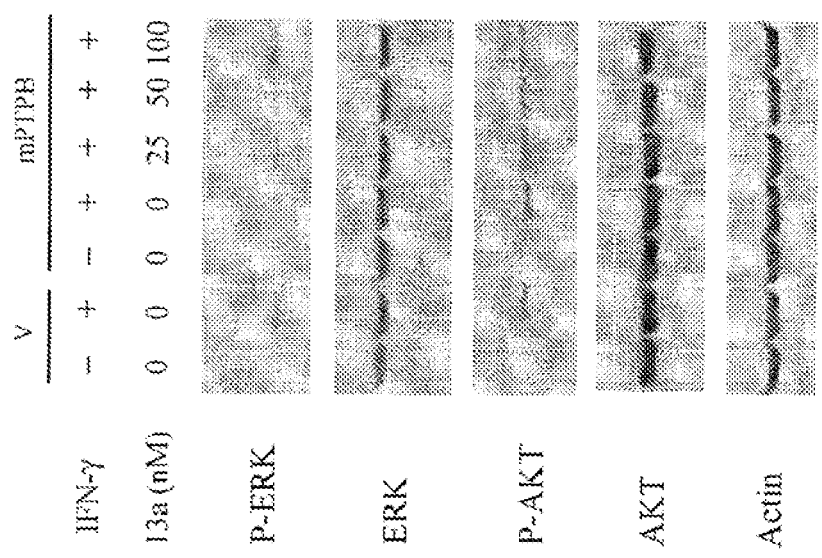
FIG. 11. Western blots illustrating that Compound 213a restores ERK1/2 activity and blocks Akt activation in activated macrophages.

Referring now to FIG. 11. Western blots illustrating that, mPTPB inhibitors 213a restore ERK1/2 activity and blocks Akt activation in activated macrophages. Cells overexpressing mPTPB have decreased ERK1/2 activity and increased Akt activity, and these can be reversed by treatment with mPTPB inhibitors 213a.

A previous study demonstrated that mPTPB suppresses the innate immune responses by blocking the ERK1/2 and p38 mediated IL-6 production and promoting host cell survival by activating the Akt pathway. Raw264.7 cells expressing mPTPB display decreased ERK1/2 activity and increased Akt activation, and these can be reversed by treatment with mPTPB inhibitor I-A09 (IC$_{50}$=1.26±0.22 µM). The reversible and noncompetitive inhibitor 213a reported herein has with higher potency and better selectivity. It is tested for the cellular activity. This proof-of-concept mPTPB inhibitor 213a increased the ERK activity FIG. 4a and decreased the Akt activity FIG. 5a in overexpressing mPTPB macrophages cells, validating that our mPTPB inhibitor 213a is cell permeable and may be a potential candidate compound for improved TB treatment.

Inhibition Mode Study of Compound 213a Against mPTPB.

Indole salicylic acid 213a is a highly potent, selective and noncompetitive mPTPB inhibitor by using focused library design and combinatorial library approach. Cellular activity study showed compound 213a can reversed the altered immune response induced by mPTPB in macrophages cells. Thus, our compound 213a is a promising candidate for TB treatment. The successful of our combinatorial library approach indicate that it may serve the purpose of discovery of novel, highly potent and selective inhibitors for other PTPs in future.

The compound p-Nitrophenyl phosphate (pNPP) was purchased from Fluke Co. For organic synthesis, reagents were used as purchased (Aldrich, Acros, Alfa Aesar, TCI), except where noted. $^1$H and $^{13}$C NMR spectra were obtained on Brucker 500 spectrometers with TMS or residual solvent as standard. All column chromatography was performed using Dynamic Adsorbents 230-400 mesh silica gel (SiO$_2$) with the indicated solvent system unless otherwise noted. TLC analysis was performed using 254 nm glass-backed plates and visualized using UV light (254 nm), low-resolution mass spectra and purity data were obtained using an Agilent Technologies 6130 Quadrupole LC/MS. HPLC purification was carried out on a Waters Delta 600 equipped with a Sunfire Prep C18 OBD column (30 mm*150 mm, 5 µm) with methanol-water (both containing 0.1% TFA) as mobile phase. The purity of all final tested compounds was established to be >95% by Agilent Technologies 6130 Quadrupole LC/MS (UV, λ=254 nm).

Methyl 4-amino-2-hydroxybenzoate (202)

Concentrated sulfuric acid (10 mL) was added to a solution of 4-aminosalicylic acid (30.6 g, 0.2 mol) in methanol (500 ml). The reaction mixture was then heated to reflux for 24 h, after which the solvent was removed. The residue was partitioned between EtOAc (1 L) and water (1 L). The organic phase was dried over $Na_2SO_4$ and evaporated to provide pale solid 202 (27.7 g, 81.4%). LC-MS (ESI): 168.0 $(M+H)^+$; Purity: >95% (UV, $\lambda$=254 nm).

Methyl 4-(dimethylamino)-2-hydroxybenzoate (203)

Paraformaldehyde (15.3 g, 0.51 mol) and $NaCNBH_3$ (16 g, 0.254 mol) were added portionwise to the solution of 202 (8.5 g, 50.8 mmol) in the acetic acid (150 mL) at 0° C., and the mixture was stirred at room temperature overnight. After evaporation, the residue was extracted with ethyl acetate, washed with saturated $NaHCO_3$, brine, and dried over $Na_2SO_4$. After evaporation, the residue was purified by silica gel column chromatography (Hex/EtOAc=30:1 then 20:1) to afford 203 (7.74 g, 78%). $^1$HNMR (500 MHz, $CDCl_3$) δ 10.93 (s, 1H), 7.63 (d, J=9.05 Hz, 1H), 6.19 (dd, J=9.05, 2.5 Hz, 1H), 6.11 (d, J=2.5 Hz, 1H), 3.86 (s, 3H), 2.99 (s, 6H); $^{13}$C NMR (125M, $CDCl_3$) δ 170.67, 163.27, 155.61, 131.01, 104.13, 100.82, 97.87, 51.53, 39.93.

Methyl 4-(dimethylamino)-2-hydroxy-5-iodobenzoate (204)

A solution of iodine (2.9 g, 11.4 mmol) in ether (15 mL) was added dropwise to a mixture of compound 3 (2.5 g, 12.8 mmol), $K_2CO_3$ (2.6 g, 18.8 mmol) and water (15 mL) at room temperature over 2 h. The reaction mixture was then stirred at room temperature for 4 h. After which, 2 M HCl was added to the reaction mixture to pH 3 then extracted with diethyl ether. The organic fractions were washed with brine, dried over $Na_2SO_4$ and concentrated in vacuo. Purification by flash silica chromatography afforded compound 204 (1.73 g, 42%). $^1$H NMR (500M Hz, $CDCl_3$) δ 10.73 (s, 1H), 8.22 (s, 1H), 6.55 (s, 1H), 3.91 (s, 3H), 2.84 (s, 6H); $^{13}$C NMR (125M, $CDCl_3$) δ 169.28, 162.82, 161.29, 141.68, 108.55, 108.11, 80.07, 52.24, 44.26.

General Method for the Synthesis of (205a-k)

A mixture of Methyl 4-(dimethylamino)-2-hydroxy-5-iodobenzoate 4 (6.5 g, 20.2 mmol), corresponding phenylacetylene (30.4 mmol) and bis(triphenylphosphine)palladium(II) chloride (0.288 g, 0.41 mmol) and CuI (0.155 g, 0.81 mmol) were loaded in a flask, which was degassed and back-filled with nitrogen. Solvent DMF and $Et_3N$ (40.4 mmol) were added. The resulting mixture was stirred under a nitrogen atmosphere at room temperature from 4 h to overnight. The reaction was monitored by TLC to establish completion. The solution was partitioned between EtOAc and water. The residue was purified by flash silica chromatography (Hex/EtOAc=60:1 then 40:1; 20:1) to afford pale solid 205a-k (80%-90%).

Methyl 4-(dimethylamino)-2-hydroxy-5-((2-(trifluoromethyl)phenyl)ethynyl)benzoate (205a)

$^1$H NMR (500 MHz, $CDCl_3$): δ 11.0 (s, 1H), 7.98 (s, 1H), 7.69 (d, J=7.9 Hz, 1H), 7.65 (d, J=7.8 Hz, 1H), 7.52 (m, 1H), 7.41 (m, 1H), 6.33 (s, 1H), 3.93 (s, 6H), 3.16 (s, 3H); $^{13}$C NMR (125 MHz, $CDCl_3$): δ 169.8, 162.9, 158.9, 138.0, 133.3, 131.3, 130.5 (q, J=30.3 Hz), 127.4, 125.8 (m), 123.7 (q, J=271.3 Hz), 122.2, 103.9, 103.5, 102.7, 94.4, 88.4, 52.0, 42.5; LC-MS (ESI): 364.0 $(M+H)^+$, 362.0 $(M-H)^-$; Purity: >95% (UV, $\lambda$=254 nm).

Methyl 4-(dimethylamino)-2-hydroxy-5-((3-(trifluoromethyl)phenyl)ethynyl)benzoate (205b)

$^1$H NMR (500 MHz, $CDCl_3$): δ 10.97 (s, 1H), 7.99 (s, 1H), 7.74 (m, 1H), 7.66 (m, 1H), 7.57 (m, 1H), 7.48 (m, 1H), 6.35 (s, 1H), 3.94 (s, 3H), 3.16 (s, 6H); LC-MS (ESI): 364.0 $(M+H)^+$, 362.0 $(M-H)^-$; Purity: >95% (UV, $\lambda$=254 nm).

Methyl 5-([1,1'-biphenyl]-4-ylethynyl)-4-(dimethylamino)-2-hydroxybenzoate (205c)

LC-MS (ESI): 372.2 $(M+H)^+$; Purity: >95% (UV, $\lambda$=254 nm).

Methyl 5-(cyclohexylethynyl)-4-(dimethylamino)-2-hydroxybenzoate (205d)

LC-MS (ESI): 302.0 $(M+H)^+$, 300.0 $(M-H)^-$; Purity: >95% (UV, $\lambda$=254 nm).

Methyl 4-(dimethylamino)-2-hydroxy-5-((4-(trifluoromethoxy)phenyl)ethynyl)benzoate (205e)

LC-MS (ESI): 380.0 $(M+H)^+$.

Methyl-4-(dimethylamino)-2-hydroxy-5-((4-(trifluoromethoxy)phenyl)ethynyl)benzoate (205f)

LC-MS (ESI): 364.2 $(M+H)^+$, 362.0 $(M-H)^-$; Purity: >95% (UV, $\lambda$=254 nm).

Methyl 4-(dimethylamino)-2-hydroxy-5-(phenylethynyl)benzoate (205g)

$^1$H NMR (500 MHz, $CDCl_3$) δ 10.93 (s, 1H), 7.94 (s, 1H), 7.48 (m, 2H), 7.31 (m, 3H), 6.31 (s, 1H), 3.90 (s, 3H), 3.12 (s, 6H).

Methyl 4-(dimethylamino)-5-((3-fluorophenyl)ethynyl)-2-hydroxybenzoate (205h)

LC-MS (ESI): 314.0 $(M+H)^+$, 312.0 $(M-H)^-$; Purity: >95% (UV, $\lambda$=254 nm).

Methyl 4-(dimethylamino)-5-((4-fluorophenyl)ethynyl)-2-hydroxybenzoate (205i)

LC-MS (ESI): 314.0 $(M+H)^+$, 312.0 $(M-H)^-$; Purity: >95% (UV, $\lambda$=254 nm).

Methyl 4-(dimethylamino)-5-((2-fluorophenyl)ethynyl)-2-hydroxybenzoate (205j)

LC-MS (ESI): 314.0 $(M+H)^+$, 312.0 $(M-H)^-$; Purity: >95% (UV, $\lambda$=254 nm).

Methyl 4-(dimethylamino)-2-hydroxy-5-((3-hydroxyphenyl)ethynyl)benzoate (205k)

$^1$H NMR (500 MHz, $CDCl_3$): δ 10.97 (brs, 1H), 7.91 (s, 1H), 7.16 (m, 1H), 7.02 (m, 1H), 6.95 (s, 1H), 6.79 (m, 1H), 6.29 (s, 1H), 3.89 (s, 3H), 3.08 (s, 6H); LC-MS (ESI): 312.2 $(M+H)^+$, 310.0 $(M-H)^-$; Purity: >95% (UV, $\lambda$=254 nm).

General Method for the Synthesis of (206a-k)

To a solution of 205a-k (17.6 mmol) in $CH_2Cl_2$ (100 mL) was added iodine (8.9 g, 35 mmol). The resulting mixture was stirred at room temperature for 4 h, then added 100 mL CH$_2$Cl$_2$ and washed with saturated aqueous Na$_2$SO$_3$ solution (3×50 mL), brine (50 mL), dried over Na$_2$SO$_4$ and concentrated in vacuo. The residue was purified by flash chromatography (Hex/EtOAc=60:1 then 40:1; 20:1) to afford pale solid 206a-k (80%-90%).

Methyl 6-hydroxy-3-iodo-1-methyl-2-(2-(trifluoromethyl)phenyl)-1H-indole-5-carboxylate (206a)

$^1$H NMR (500 MHz, CDCl$_3$): δ 10.88 (brs, 1H), 8.02 (s, 1H), 7.86 (d, J=7.4 Hz, 1H), 7.69 (m, 2H), 7.39 (d, J=7.4 Hz, 1H), 6.82 (s, 1H), 3.97 (s, 3H), 3.38 (s, 3H); LC-MS (ESI): 476.0 (M+H)$^+$, 474.0 (M−H)$^-$; Purity: >95% (UV, λ=254 nm).

Methyl 6-hydroxy-3-iodo-1-methyl-2-(3-(trifluoromethyl)phenyl)-1H-indole-5-carboxylate (206b)

$^1$H NMR (500 MHz, CDCl$_3$): δ 10.93 (s, 1H), 8.05 (s, 1H), 7.76 (m, 2H), 7.68 (m, 2H), 6.87 (s, 1H), 4.04 (s, 3H), 3.62 (s, 3H); LC-MS (ESI): 476.0 (M+H)$^+$, 474.8 (M−H)$^-$; Purity: >95% (UV, λ=254 nm).

Methyl 2-[1,1'-biphenyl]-4-yl)-6-hydroxy-3-iodo-1-methyl-1H-indole-5-carboxylate (206c)

$^1$H NMR (500 MHz, CDCl$_3$): δ 10.92 (s, 1H), 8.05 (s, 1H), 7.77 (m, 2H), 7.71 (m, 2H), 7.56 (m, 2H), 7.51 (m, 2H), 7.43 (m, 1H), 6.88 (s, 1H), 4.04 (s, 3H), 3.66 (s, 3H); $^{13}$C NMR (125 MHz, CDCl$_3$): δ 171.2, 158.3, 142.6, 142.5, 141.6, 140.2, 131.1, 129.9, 128.9, 127.7, 127.18, 127.16, 124.3, 124.2, 107.6, 96.2, 60.0, 52.2, 32.2; LC-MS (ESI): 484.0 (M+H)$^+$; Purity: >95% (UV, λ=254 nm).

Methyl 2-cyclohexyl-6-hydroxy-3-iodo-1-methyl-1H-indole-5-carboxylate (206d)

LC-MS (ESI): 414.0 (M+H)$^+$, 412.0 (M−H)$^-$; Purity: >95% (UV, λ=254 nm).

Methyl 6-hydroxy-3-iodo-1-methyl-2-(4-(trifluoromethoxy)phenyl)-1H-indole-5-carboxylate (206e)

$^1$H NMR (500 MHz, CDCl$_3$): δ 10.92 (s, 1H), 8.04 (s, 1H), 7.52 (d, J=8.1 Hz, 2H), 7.39 (d, J=8.1 Hz, 2H), 6.86 (s, 1H), 4.03 (s, 3H), 3.61 (s, 3H); LC-MS (ESI): 492.0 (M+H)$^+$, 489.8 (M−H)$^-$; Purity: >95% (UV, λ=254 nm).

Methyl 6-hydroxy-3-iodo-1-methyl-2-(4-(trifluoromethyl)phenyl)-1H-indole-5-carboxylate (206f)

$^1$H NMR (500 MHz, CDCl$_3$): δ 10.91 (s, 1H), 8.02 (s, 1H), 7.78 (d, J=8.1 Hz, 2H), 7.60 (d, J=8.1 Hz, 2H), 6.84 (s, 1H), 4.01 (s, 3H), 3.59 (s, 3H); LC-MS (ESI): 476.0 (M+H)$^+$, 474.8 (M−H)$^-$; Purity: >95% (UV, λ=254 nm).

Methyl 6-hydroxy-3-iodo-1-methyl-2-phenyl-1H-indole-5-carboxylate (206g)

$^1$H NMR (500 MHz, CDCl$_3$) δ 10.88 (s, 1H), 7.96 (s, 1H), 7.45 (m, 5H), 6.78 (s, 1H), 3.98 (s, 3H), 3.54 (s, 3H).

Methyl 2-(3-fluorophenyl)-6-hydroxy-3-iodo-1-methyl-1H-indole-5-carboxylate (206h)

LC-MS (ESI): 426.0 (M+H)$^+$, 423.8 (M−H)$^-$; Purity: >95% (UV, λ=254 nm).

Methyl 2-(4-fluorophenyl)-6-hydroxy-3-iodo-1-methyl-1H-indole-5-carboxylate (206i)

LC-MS (ESI): 426.0 (M+H)$^+$, 423.8 (M−H)$^-$; Purity: >95% (UV, λ=254 nm).

Methyl 2-(2-fluorophenyl)-6-hydroxy-3-iodo-1-methyl-1H-indole-5-carboxylate (206j)

LC-MS (ESI): 426.0 (M+H)$^+$, 423.8 (M−H)$^-$; Purity: >95% (UV, λ=254 nm).

Methyl 6-hydroxy-2-(3-hydroxyphenyl)-3-iodo-1-methyl-1H-indole-5-carboxylate (206k)

LC-MS (ESI): 424.0 (M+H)$^+$, 422.0 (M−H)$^-$; Purity: >95% (UV, λ=254 nm).

General Method for the Synthesis of (207a-k)

Compound 206a-k (1 mmol) was dissolved in 2 mL of THF and 2 mL of methanol. Then NaOH (2 mL, 5N) solution was added. The mixture was stirred under room temperature for 2 days, diluted by water to 50 mL, acidified to pH 3, and extracted with EtOAc three times. The organic layers were combined, washed with brine, dried over sodium sulfate and concentrated in vacuum. This crude product was purified by Pre-HPLC as describe to give pale solid 207a-k (yield 50-80%).

6-hydroxy-3-iodo-1-methyl-2-(2-(trifluoromethyl)phenyl)-1H-indole-5-carboxylic acid (207a)

1H NMR (500 MHz, DMSO): δ 11.4 (brs, 1H), 7.97 (d, J=7.6 Hz, 1H), 7.88 (m, 1H), 7.86 (s, 1H), 7.80 (m, 1H), 7.54 (d, J=7.6 Hz, 1H), 7.04 (s, 1H), 3.39 (s, 3H); $^{13}$C NMR (125 MHz, DMSO): δ 173.0, 158.3, 141.8, 140.1, 134.1, 133.3, 131.1, 130.1, 129.6 (q, J=29.6 Hz), 126.9 (m), 124.0 (q, J=272.3 Hz), 123.8, 123.4, 108.1, 96.9, 62.4, 32.2; LC-MS (ESI): 462.0 (M+H)$^+$, 460.0 (M−H)$^-$; Purity: >95% (UV, λ=254 nm).

6-hydroxy-3-iodo-1-methyl-2-(3-(trifluoromethyl)phenyl)-1H-indole-5-carboxylic acid (207b)

$^1$H NMR (500 MHz, DMSO): δ 13.90 (br, 1H), 11.46 (br, 1H), 7.90-7.81 (m, 5H), 7.07 (s, 1H), 3.61 (s, 3H); $^{13}$C NMR (125 MHz, DMSO): δ 173.0, 158.4, 142.6, 141.2, 135.1, 132.2, 130.2, 129.9 (q, J=31.6 Hz), 127.7, 126.0, 124.4 (q, J=270.5 Hz), 124.2, 123.7, 108.3, 97.1, 61.8, 31.7; LC-MS (ESI): 462.0 (M+H)$^+$, 460.0 (M−H)$^-$; Purity: >95% (UV, λ=254 nm).

2-([1,1'-biphenyl]-4-yl)-6-hydroxy-3-iodo-1-methyl-1H-indole-5-carboxylic acid (207c)

$^1$H NMR (500 MHz, DMSO): δ 7.86 (m, 3H), 7.79 (m, 2H), 7.63 (m, 2H), 7.52 (m, 2H), 7.42 (m, 1H), 7.06 (s, 1H), 3.64 (s, 3H); LC-MS (ESI): 470.0 (M+H)$^+$, 468.0 (M−H)$^-$; Purity: >95% (UV, k=254 nm).

2-cyclohexyl-6-hydroxy-3-iodo-1-methyl-1H-indole-5-carboxylic acid (207d)

$^1$H NMR (500 MHz, DMSO): δ 13.8 (br, 1H), 11.25 (brs, 1H), 7.73 (s, 1H), 6.96 (s, 1H), 3.72 (s, 3H), 2.98 (m, 1H), 2.02 (m, 2H), 1.85-1.72 (m, 4H), 1.44-1.23 (m, 4H); LC-MS (ESI): 400.0 (M+H)$^+$, 398.0 (M−H)$^-$; Purity: >95% (UV, λ=254 nm).

6-hydroxy-3-iodo-1-methyl-2-(4-(trifluoromethoxy) phenyl)-1H-indole-5-carboxylic acid (207e)

$^1$H NMR (500 MHz, DMSO): δ 13.76 (br, 1H), 11.43 (br, 1H), 7.86 (s, 1H), 7.68 (d, J=8.4 Hz, 2H), 7.56 (d, J=8.4 Hz, 2H), 7.05 (s, 1H), 3.59 (s, 3H); $^{13}$C NMR (125 MHz, DMSO): δ 173.0, 158.4, 149.0, 142.5, 141.5, 133.2, 130.4, 124.1, 123.7, 121.4, 120.5 (q, J=255.2 Hz), 108.2, 97.1, 61.3, 32.6; LC-MS (ESI): 478.0 (M+H)$^+$, 475.8 (M−H)$^−$; Purity: >95% (UV, λ=254 nm).

6-hydroxy-3-iodo-1-methyl-2-(4-(trifluoromethyl) phenyl)-1H-indole-5-carboxylic acid (207f)

$^1$H NMR (500 MHz, DMSO): δ 13.90 (br, 1H), 11.46 (br, 1H), 7.93 (d, J=8.1 Hz, 2H), 7.87 (s, 1H), 7.78 (d, J=8.1 Hz, 2H), 7.06 (s, 1H), 3.61 (s, 3H); LC-MS (ESI): 462.0 (M+H)$^+$, 460.0 (M−H)$^−$; Purity: >95% (UV, λ=254 nm).

6-hydroxy-3-iodo-1-methyl-2-phenyl-1H-indole-5-carboxylic acid (207g)

$^1$H NMR (500 MHz, DMSO): δ 13.78 (br, 1H), 11.36 (br, 1H), 7.85 (s, 1H), 7.58-7.49 (m, 5H), 7.04 (s, 1H), 3.54 (s, 3H); LC-MS (ESI): 392.0 (M−H)$^−$; Purity: >95% (UV, λ=254 nm).

2-(3-fluorophenyl)-6-hydroxy-3-iodo-1-methyl-1H-indole-5-carboxylic acid (207h)

$^1$H NMR (500 MHz, DMSO): δ 13.78 (br, 1H), 11.37 (br, 1H), 7.86 (s, 1H), 7.63-7.59 (m, 1H), 7.41-7.36 (m, 3H), 7.05 (s, 1H), 3.60 (s, 3H); $^{13}$C NMR (125 MHz, DMSO): δ 173.0, 162.3 (d, J=242.9 Hz), 158.4, 142.5, 141.5, 133.4 (d, J=8.3 Hz), 131.1 (d, J=8.6 Hz), 127.4, 124.1, 123.7, 117.9 (d, J=22.2 Hz), 116.3 (d, J=20.6 Hz), 108.2, 97.0, 61.3, 32.5; LC-MS (ESI): 412.0 (M+H)$^+$, 410.0 (M−H)$^−$; Purity: >95% (UV, λ=254 nm).

2-(4-fluorophenyl)-6-hydroxy-3-iodo-1-methyl-1H-indole-5-carboxylic acid (207i)

$^1$H NMR (500 MHz, DMSO): δ 13.74 (br, 1H), 11.46 (br, 1H), 7.84 (s, 1H), 7.58 (m, 2H), 7.41 (m, 2H), 7.04 (s, 1H), 3.58 (s, 3H); LC-MS (ESI): 412.0 (M+H)$^+$, 410.0 (M−H)$^−$; Purity: >95% (UV, λ=254 nm).

2-(2-fluorophenyl)-6-hydroxy-3-iodo-1-methyl-1H-indole-5-carboxylic acid (207j)

$^1$H NMR (500 MHz, DMSO): δ 13.6 (br, 1H), 11.5 (br, 1H), 7.88 (s, 1H), 7.62-7.38 (m, 4H), 7.04 (s, 1H), 3.54 (s, 3H); LC-MS (ESI): 412.0 (M+H)$^+$, 410.0 (M−H)$^−$; Purity: >95% (UV, λ=254 nm).

6-hydroxy-2-(3-hydroxyphenyl)-3-iodo-1-methyl-1H-indole-5-carboxylic acid (207k)

$^1$H NMR (500 MHz, DMSO): δ 13.75 (br, 1H), 11.35 (brs, 1H), 9.75 (brs, 1H), 7.84 (s, 1H), 7.35 (m, 1H), 7.02 (s, 1H), 6.89 (m, 3H), 3.66 (s, 3H); LC-MS (ESI): 410.0 (M+H)$^+$, 407.8 (M−H)$^−$; Purity: >95% (UV, λ=254 nm).

General Method for the Synthesis of (208a-f)

A mixture of 206a (47.5 mg, 0.1 mmol), tert-butyl prop-2-yn-1-ylcarbamate (0.5 mmol) and bis(triphenylphosphine) palladium(II) chloride (35.1 mg, 0.05 mmol) and CuI (11.4 mg, 0.06 mmol) were loaded in a flask, which was degassed and back-filled with nitrogen. Solvent DMF and Et$_3$N (0.76 mmol) were added. The resulting mixture was heated to 80° C. for 4 h to overnight. The reaction was monitored by TLC to establish completion. The solution was partitioned between EtOAc and water. The residue was purified by flash silica chromatography (Hex/EtOAc=30:1, 20:1 then 10:1) to afford pale solid 212a-f (80%-90%).

Methyl 3-((3,5-difluorophenyl)ethynyl)-6-hydroxy-1-methyl-2-(2-(trifluoromethyl)phenyl)-1H-indole-5-carboxylate (208a)

$^1$H NMR (500 MHz, CDCl$_3$): δ 10.94 (s, 1H), 8.32 (s, 1H), 7.92 (d, J=7.6 Hz, 1H), 7.73 (m, 2H), 7.51 (d, J=7.6 Hz, 1H), 6.90 (s, 1H), 6.83 (m, 2H), 6.72 (m, 1H), 4.04 (s, 3H), 3.43 (s, 3H); LC-MS (ESI): 486.0 (M+H)$^+$, 484.0 (M−H)$^−$; Purity: >95% (UV, λ=254 nm).

Methyl 6-hydroxy-1-methyl-2-(2-(trifluoromethyl) phenyl)-3-(2-(trifluoromethyl)phenyl)ethynyl)-1H-indole-5-carboxylate (208c)

$^1$H NMR (500 MHz, CDCl$_3$): δ 10.94 (s, 1H), 8.39 (s, 1H), 7.90 (d, J=7.6 Hz, 1H), 7.71 (m, 2H), 7.58 (d, J=7.6 Hz, 1H), 7.52 (m, 3H), 7.44 (m, 1H), 6.90 (s, 1H), 4.04 (s, 3H), 3.43 (s, 3H); LC-MS (ESI): 518.0 (M+H)$^+$, 516.0 (M−H)$^−$; Purity: >95% (UV, λ=254 nm).

Methyl 6-hydroxy-1-methyl-3-((4-phenoxyphenyl) ethynyl)-2-(2-(trifluoromethyl)phenyl)-1H-indole-5-carboxylate (208d)

$^1$H NMR (500 MHz, CDCl$_3$): δ 10.93 (s, 1H), 8.35 (s, 1H), 7.87 (m, 1H), 7.68 (m, 3H), 7.52 (m, 2H), 7.36 (m, 3H), 7.01 (m, 2H), 6.89 (s, 3H), 4.02 (s, 3H), 3.41 (s, 3H); LC-MS (ESI): 564.0 (M+Na)$^+$; Purity: >95% (UV, λ=254 nm).

Methyl-6-hydroxy-1-methyl-2-(2-(trifluoromethyl) phenyl)-3-((4-(trifluoromethyl)phenyl)ethynyl)-1H-indole-5-carboxylate (208e)

$^1$H NMR (500 MHz, CDCl$_3$): δ 10.94 (s, 1H), 8.35 (s, 1H), 7.91 (d, J=7.6 Hz, 1H), 7.72 (m, 2H), 7.52 (m, 3H), 7.40 (d, J=8.1 Hz, 2H), 6.90 (s, 1H), 4.03 (s, 3H), 3.43 (s, 3H); LC-MS (ESI): 518.0 (M+H)$^+$.

Methyl-6-hydroxy-1-methyl-3-((4-(trifluoromethoxy)phenyl)ethynyl)-2-(2-(trifluoromethyl) phenyl)-1H-indole-5-carboxylate (208f)

$^1$H NMR (500 MHz, CDCl$_3$): δ 10.93 (s, 1H), 8.33 (s, 1H), 7.89 (d, J=7.6 Hz, 1H), 7.72 (m, 2H), 7.51 (d, J=7.6 Hz, 1H), 7.29 (m, 2H), 7.12 (m, 2H), 6.90 (s, 1H), 4.03 (s, 3H), 3.43 (s, 3H); LC-MS (ESI): 534.0 (M+H)$^+$.

General Method for the Synthesis of (209a-f)

Compound 212a-f (0.1 mmol) was dissolved in 3 mL of THF and 1 mL of methanol. Then 20% NaOH (2 mL) solution was added. The mixture was stirred under room temperature for 2 days, then diluted by water to 50 mL, acidified to pH 3, and extracted with EtOAc three times. The organic layers were combined, washed with brine, dried over sodium sulfate and concentrated in vacuum. This crude product was purified by Pre-HPLC as describe to give pale solid 213a-f (80-90%).

3-((3,5-difluorophenyl)ethynyl)-6-hydroxy-1-methyl-2-(2-(trifluoromethyl)phenyl)-1H-indole-5-carboxylic acid (209a)

$^1$H NMR (500 MHz, DMSO): δ 11.80 (br, 1H), 8.20 (s, 1H), 8.01 (d, J=7.6 Hz, 1H), 7.88 (m, 2H), 7.67 (d, J=7.6 Hz, 1H), 7.22 (m, 1H), 7.13 (s, 1H), 6.95 (m, 2H), 3.42 (s, 3H); $^{13}$C NMR (125 MHz, DMSO): δ 173.1, 162.7 (dd, J=245.0, 14.1 Hz), 158.4, 142.9, 141.10, 133.6, 133.1, 131.1, 129.6 (q, J=29.7 Hz), 128.5 (m), 127.0 (m), 126.2 (t, J=12.1 Hz), 124.1 (q, J=272.3 Hz), 122.4, 120.7, 114.2 (dd, J=19.9, 6.7 Hz), 108.6, 104.6 (t, J=25.7 Hz), 97.6, 97.4, 90.7, 85.4, 31.6; LC-MS (ESI): 472.0 (M+H)$^+$, 470.0 (M−H)$^−$; Purity: >95% (UV, λ=254 nm).

6-hydroxy-1-methyl-2-(2-(trifluoromethyl)phenyl)-3-((3-(trifluoromethyl)phenyl)ethynyl)-1H-indole-5-carboxylic acid (209b)

$^1$H NMR (500 MHz, DMSO): δ 11.48 (br, 1H), 8.21 (s, 1H), 8.02 (m, 1H), 7.90 (m, 2H), 7.68 (m, 2H), 7.55 (m, 3H), 7.14 (s, 1H), 3.43 (s, 3H); $^{13}$C NMR (125 MHz, DMSO): δ 173.1, 158.4, 142.6, 141.0, 135.0, 133.7, 133.1, 131.1, 130.4, 129.9, 129.7 (q, J=29.6 Hz), 129.4 (q, J=29.3 Hz), 128.7 (m), 127.3 (m), 127.0 (m), 124.9 (m), 124.5, 123.0, 122.4, 120.8, 108.5, 98.0, 97.4, 91.2, 84.8, 31.6; LC-MS (ESI): 504.0 (M+H)$^+$, 502.0 (M−H)$^−$; Purity: >95% (UV, λ=254 nm).

6-hydroxy-1-methyl-2-(2-(trifluoromethyl)phenyl)-3-((2-(trifluoromethyl)phenyl)ethynyl)-1H-indole-5-carboxylic acid (209c)

$^1$H NMR (500 MHz, DMSO): δ 11.90 (br, 1H), 8.23 (s, 1H), 7.98 (m, 1H), 7.85 (m, 2H), 7.65 (m, 2H), 7.59 (m, 1H), 7.48 (m, 2H), 7.13 (s, 1H), 3.42 (s, 3H); $^{13}$C NMR (125 MHz, DMSO): δ 173.1, 158.5, 142.6, 141.0, 133.68, 133.6, 132.9, 132.8, 131.0, 129.7 (q, J=29.6 Hz), 129.4 (q, J=29.3 Hz), 128.6 (m), 128.4, 126.8 (m), 126.3 (m), 124.1 (q, J=272.1 Hz), 123.7 (q, J=271.3 Hz), 122.3, 121.4, 120.9, 108.6, 98.2, 97.4, 88.97, 88.9, 31.5; LC-MS (ESI): 504.0 (M+H)$^+$, 502.0 (M−H)$^−$; Purity: >95% (UV, λ=254 nm).

6-hydroxy-1-methyl-3-((4-phenoxyphenyl)ethynyl)-2-(2-(trifluoromethyl)phenyl)-1H-indole-5-carboxylic acid (209d)

$^1$H NMR (500 MHz, DMSO): δ 11.40 (br, 1H), 8.15 (s, 1H), 8.00 (m, 1H), 7.84 (m, 2H), 7.67 (m, 1H), 7.40 (m, 2H), 7.27 (m, 2H), 7.17 (m, 1H), 7.11 (s, 1H), 7.03 (m, 2H), 6.92 (m, 2H), 3.41 (s, 3H); $^{13}$C NMR (125 MHz, DMSO): δ 173.1, 158.4, 157.1, 156.3, 141.6, 141.0, 133.7, 133.18, 133.13, 131.0, 130.6, 129.6 (q, J=29.6 Hz), 128.9 (m), 126.9 (m), 124.4, 124.2 (q, J=272.0 Hz), 122.3, 121.0, 119.5, 118.9, 118.1, 108.2, 98.7, 97.2, 92.1, 81.9, 31.5; LC-MS (ESI): 528.0 (M+H)$^+$, 526.0 (M−H)$^−$; Purity: >95% (UV, λ=254 nm).

6-hydroxy-1-methyl-2-(2-(trifluoromethyl)phenyl)-3-((4-(trifluoromethyl)phenyl)ethynyl)-1H-indole-5-carboxylic acid (209e)

$^1$H NMR (500 MHz, DMSO): δ 11.48 (br, 1H), 8.20 (s, 1H), 8.01 (m, 1H), 7.87 (m, 2H), 7.68 (m, 3H), 7.44 (m, 2H), 7.14 (s, 1H), 3.43 (s, 3H); $^{13}$C NMR (125 MHz, DMSO): δ 173.1, 158.4, 142.7, 141.1, 133.6, 133.1, 131.7, 131.1, 129.6 (q, J=29.6 Hz), 128.6 (m), 128.2 (q, J=29.3 Hz), 127.7, 127.0 (m), 126.0 (m), 124.4 (q, J=270.5 Hz), 124.1 (q, J=272.0 Hz), 122.3, 120.8, 108.6, 97.9, 97.4, 91.6, 85.8, 31.6; LC-MS (ESI): 504.0 (M+H)$^+$, 502.0 (M−H)$^−$; Purity: >95% (UV, λ=254 nm).

6-hydroxy-1-methyl-3-((4-(trifluoromethoxy)phenyl)ethynyl)-2-(2-(trifluoromethyl)phenyl)-1H-indole-5-carboxylic acid (209f)

$^1$H NMR (500 MHz, DMSO): δ 11.45 (br, 1H), 8.18 (s, 1H), 8.00 (m, 1H), 7.84 (m, 2H), 7.68 (m, 1H), 7.37 (m, 2H), 7.31 (m, 2H), 7.03 (s, 1H), 3.42 (s, 3H); LC-MS (ESI): 520.0 (M+H)$^+$, 518.0 (M−H)$^−$; Purity: >95% (UV, λ=254 nm).

Methyl 3-(3-((tert-butoxycarbonyl)amino)prop-1-yn-1-yl)-6-hydroxy-1-methyl-2-(2-(trifluoromethyl)phenyl)-1H-indole-5-carboxylate (210)

A mixture of 206a (180 mg, 0.38 mmol), tert-butyl prop-2-yn-1-ylcarbamate (117 mg, 0.76 mmol) and bis(triphenylphosphine)palladium(II) chloride (27 mg, 0.04 mmol) and CuI (15.2 mg, 0.08 mmol) were loaded in a flask, which was degassed and back-filled with nitrogen. Solvent DMF and Et$_3$N (0.76 mmol) were added. The resulting mixture was stirred under a nitrogen atmosphere at room temperature overnight. The reaction was monitored by TLC to establish completion. The solution was partitioned between EtOAc and water. The residue was purified by flash silica chromatography (Hex/EtOAc=8:1, then 4:1) to afford viscous oil 10 (130 mg; 68%). $^1$H NMR (500 MHz, CDCl$_3$): δ 10.88 (s, 1H), 8.24 (s, 1H), 7.85 (m, 1H), 7.66 (m, 2H), 7.43 (m, 1H), 7.19 (m, 1H), 6.82 (s, 1H), 4.04 (m, 2H), 3.99 (s, 3H), 3.33 (s, 3H), 1.44 (s, 9H); LC-MS (ESI): 525.0 (M+Na)$^+$; Purity: >95% (UV, λ=254 nm).

3-(3-((tert-butoxycarbonyl)amino)prop-1-yn-1-yl)-6-hydroxy-1-methyl-2-(2-(trifluoromethyl)phenyl)-1H-indole-5-carboxylic acid (211)

Compound 210 (130 mg, 0.26 mmol) was dissolved in 3 mL of THF and 1 mL of methanol. Then 20% NaOH (2 mL) solution was added. The mixture was stirred under room temperature for 2 days, then diluted by water to 50 mL, acidified to pH 3, and extracted with EtOAc three times. The organic layers were combined, washed with brine, dried over sodium sulfate and concentrated in vacuum. This crude product was purified by Pre-HPLC as describe to give pale solid 211 (110 mg, 87%). $^1$H NMR (500 MHz, DMSO): δ 10.67 (s, 1H), 8.10 (s, 1H), 7.95 (m, 1H), 7.81 (m, 2H), 7.59 (m, 1H), 7.23 (m, 1H), 7.10 (s, 1H), 3.95 (s, 3H), 3.82 (m, 2H), 1.38 (s, 9H); LC-MS (ESI): 511 (M+Na)$^+$, 487.0 (M−H)$^−$; Purity: >95% (UV, λ=254 nm).

3-(3-aminopropanoyl)-6-hydroxy-1-methyl-2-(2-(trifluoromethyl)phenyl)-1H-indole-5-carboxylic acid (212)

Compound 211 (110 mg, 0.226 mmol) was dissolved in 5 mL of CH$_2$Cl$_2$ and then 1 mL of TFA was added to the solution under room temperature overnight. The solution was concentrated in vacuum. This crude product was purified by Pre-HPLC as describe to give pale solid 212 as TFA salt (102 mg, 91.5%). $^1$H NMR (500 MHz, DMSO): δ 8.74 (s, 1H), 8.02 (m, 1H), 7.87 (m, 2H), 7.68 (m, 2H), 6.94 (s, 1H), 3.31 (s, 3H), 2.94 (m, 2H), 2.61 (m, 2H); $^{13}$C NMR (125 MHz, DMSO): δ 192.2, 173.2, 158.9 (q, J=34.9 Hz, CF$_3$COOH), 158.5, 143.9, 141.5, 133.7, 132.8, 131.5, 129.5, 128.5 (q, J=29.5 Hz), 127.4 (m), 125.3, 123.9 (q, J=272.2 Hz), 119.0, 116.6 (q, J=292.0 Hz, $CF_3COOH$), 115.6, 109.9, 97.3, 38.0, 34.5, 31.3; LC-MS (ESI): 407.2 $(M+H)^+$, 405.0 $(M-H)^-$; Purity: >95% (UV, λ=254 nm).

General Method for the Synthesis of (213a-e)

Compound 212 (33.2 mg, 0.066 mmol) dissolved in 0.5 mL of DMF was added to a solution of corresponding carboxylic acids (0.33 mmol), HOBT (12 mg, 0.079 mmol), HBTU (30 mg, 0.079 mmol), and TEA (18.36 μL, 0.132 mmol) in 1 mL of DMF. The mixture was stirred under room temperature for 2 h, then diluted by water to 50 mL, acidified to pH 3, and extracted with EtOAc three times. The organic layers were combined, washed with brine, dried over sodium sulfate and concentrated in vacuum. This crude product was purified by Pre-HPLC as described to give pale solid 213a-e (50%-70%).

3-(3-(3,5-dibromobenzamido)propanoyl)-6-hydroxy-1-methyl-2-(2-(trifluoromethyl)phenyl)-1H-indole-5-carboxylic acid (213a)

$^1$H NMR (500 MHz, DMSO): δ 13.82 (br, 1H), 11.44 (brs, 1H), 8.85 (s, 1H), 8.59 (m, 1H), 8.02 (m, 2H), 7.90-7.82 (m, 4H), 7.71 (m, 1H), 7.11 (s, 1H), 3.38 (m, 2H), 3.35 (s, 3H), 2.37 (m, 2H); $^{13}$C NMR (125 MHz, DMSO): δ 193.5, 173.2, 163.6, 158.4, 143.3, 141.5, 138.4, 136.1, 133.6, 132.9, 131.3, 129.8, 129.5, 128.5 (q, J=29.4 Hz), 127.3 (m), 125.4, 124.0 (q, J=272.5 Hz), 122.9, 119.2, 116.3, 109.6, 97.2, 35.2, 31.3, 29.5; LC-MS (ESI): 668.8 $(M+H)^+$, 666.8 $(M-H)^-$; Purity: >95% (UV, λ=254 nm).

6-hydroxy-3-(3-(3-iodobenzamido)propanoyl)-1-methyl-2-(2-(trifluoromethyl)phenyl)-1H-indole-5-carboxylic acid (213b)

$^1$H NMR (500 MHz, DMSO): δ 11.46 (br, 1H), 8.85 (s, 1H), 8.45 (m, 1H), 8.02 (m, 2H), 7.90-7.70 (m, 5H), 7.25 (m, 1H), 7.11 (s, 1H), 3.33 (s, 3H), 3.29 (m, 2H), 2.38 (m, 2H); LC-MS (ESI): 637.0 $(M+H)^+$, 634.8 $(M-H)^-$; Purity: >95% (UV, λ=254 nm).

6-hydroxy-3-(3-(2-(((1S,2R,5S)-2-isopropyl-5-methylcyclohexyl)oxy)acetamido)propanoyl)-1-methyl-2-(2-(trifluoromethyl)phenyl)-1H-indole-5-carboxylic acid (213c)

$^1$H NMR (500 MHz, DMSO): δ 11.44 (brs, 1H), 8.87 (s, 1H), 8.01 (m, 1H), 7.93-7.85 (m, 2H), 7.71 (m, 1H), 7.20 (m, 1H), 6.98 (s, 1H), 3.50 (s, 2H), 3.38 (m, 2H), 3.37 (s, 3H), 2.17 (m, 2H), 2.10 (m, 3H), 1.54 (m, 2H), 1.28 (m, 4H), 0.86 (m, 10H); LC-MS (ESI): 603.2 $(M+H)^+$, 601.2 $(M-H)^-$; Purity: >95% (UV, λ=254 nm).

3-(3-(2-(2-bromophenyl)-1H-benzo[d]imidazole-6-carboxamido)propanoyl)-6-hydroxy-1-methyl-2-(2-(trifluoromethyl)phenyl)-1H-indole-5-carboxylic acid (213d)

$^1$H NMR (500 MHz, DMSO): δ 11.46 (brs, 1H), 8.85 (s, 1H), 8.35 (m, 1H), 8.05 (s, 1H), 8.02 (m, 1H), 8.00-7.75 (m, 4H), 7.70-7.45 (m, 4H), 7.52 (m, 1H), 7.12 (s, 1H), 3.34 (s, 3H), 3.29 (m, 2H), 2.41 (m, 2H); LC-MS (ESI): 705.0 $(M+H)^+$, 703.0 $(M-H)^-$; Purity: >95% (UV, λ=254 nm).

3-(3-acetamidopropanoyl)-6-hydroxy-1-methyl-2-(2-(trifluoromethyl)phenyl)-1H-indole-5-carboxylic acid (213e)

$^1$H NMR (500 MHz, DMSO): δ 11.44 (brs, 1H), 8.86 (s, 1H), 8.03 (m, 1H), 7.90 (m, 2H), 7.70 (m, 2H), 7.11 (s, 1H), 3.33 (s, 3H), 3.13 (m, 2H), 2.20 (m, 2H), 1.67 (s, 3H); LC-MS (ESI): 449.0 $(M+H)^+$, 447.0 $(M-H)^-$; Purity: >95% (UV, λ=254 nm).

Biological Evaluation.

Expression and purification of recombinant mPTPB, $IC_{50}$ test and kinetic characterization of mPTPB inhibitor were performed as described previously.[6]

Cellular Activity Evaluation.

Raw264.7 mouse macrophages were cultured in Dulbecco's modified Eagle's medium (DMEM) supplemented with 10% FBS (Invitrogen), penicillin (50 units/mL), and streptomycin (50 μg/mL) under a humidified atmosphere containing 5% $CO_2$ at 37° C. Transfected Raw264.7 cells (Vector, WT-mPTPB) were seeded in a 12-well plate at a density of $4\times10^4$ cells/well. The following day cells were treated with mPTPB inhibitor 213a for 1 hr, then stimulated with IFN-γ (200 U/ml) for 1 h. And then were stimulated for 1 h with IFN-γ (200 U/ml). Wash with ice-cold phosphate buffered saline, and lysed with lysis buffer on ice for 30 min. Cell lysate is then cleared by centrifuging at 13,000 rpm for 15 min. The phosphorylation of ERK1/2 and Akt was detected by western blotting.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A compound of Formula A, or a pharmaceutically acceptable salt thereof,

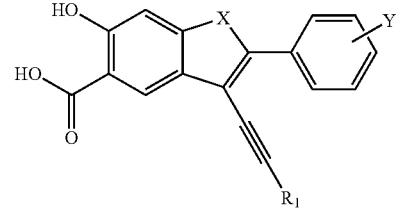

Formula A wherein X is O or $NR_2$;

$R_1$ is selected from the group consisting of:

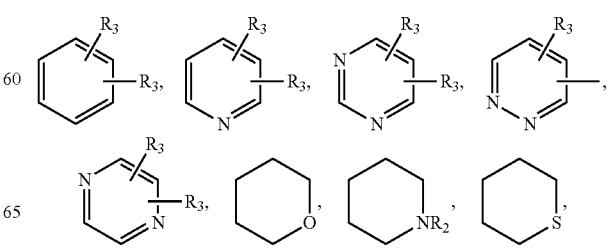

-continued

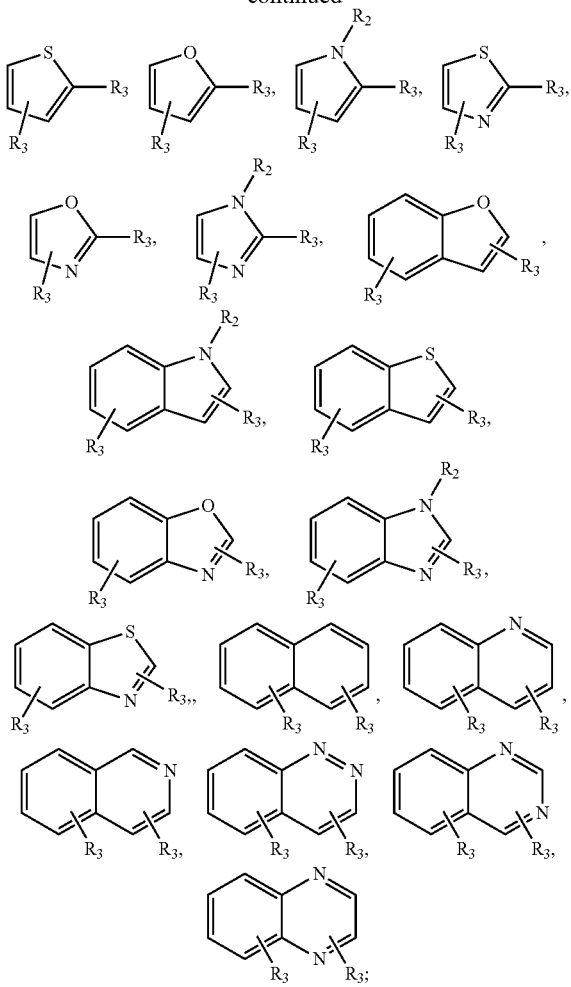

and each occurrence of $R_2$ can be the same or different and is H or $C_1$-$C_6$ alkyl; each occurrence of $R_3$ can be the same or different and is H, halogen, hydroxyl, $NR_2R_2$, substituted or unsubstituted $C_1$-$C_6$ alkyl, substituted or unsubstituted $C_1$-$C_6$ alkenyl, substituted or unsubstituted $C_1$-$C_6$ alkynyl, O-(substituted or unsubstituted $C_1$-$C_6$ alkyl), S-(substituted or unsubstituted $C_1$-$C_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, $SO_2$-(substituted or unsubstituted $C_1$-$C_6$ alkyl), $SO_2NR_2R_2$, C(O)-(substituted or unsubstituted $C_1$-$C_6$ alkyl), C(O)-(substituted or unsubstituted aryl), C(O)-(substituted or unsubstituted heteroaryl), $(CH_2)_nCO_2H$, or $O(CH_2)_nCO_2H$;

Y is H, halogen, hydroxyl, $NR_2R_2$, substituted or unsubstituted $C_1$-$C_6$ alkyl, substituted or unsubstituted $C_1$-$C_6$ alkenyl, substituted or unsubstituted $C_1$-$C_6$ alkynyl, O-(substituted or unsubstituted $C_1$-$C_6$ alkyl), S-(substituted or unsubstituted $C_1$-$C_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, $SO_2C_1$-$C_6$ alkyl, $SO_2NR_2R_2$, C(O)-(substituted or unsubstituted $C_1$-$C_6$ alkyl), C(O)-(substituted or unsubstituted aryl), C(O)-(substituted or unsubstituted heteroaryl); —$(CH_2)_nCOZ$, or —O—$(CH_2)n$-COZ;

n can be the same or different at each occurrence and is 1, 2, 3, or 4;

Z is —OH, or $N(R_4)_2$, wherein each occurrence of $R_4$ can be the same or different and is H, substituted or unsubstituted $C_1$-$C_6$ alkyl, substituted or unsubstituted $C_3$-$C_8$ cycloalkyl, substituted or unsubstituted $C_1$-$C_6$ alkenyl, substituted or unsubstituted $C_1$-$C_6$ alkynyl, substituted or unsubstituted aryl, substituted or unsubstituted heteroaryl, $OR_5$, $NHR_5$,

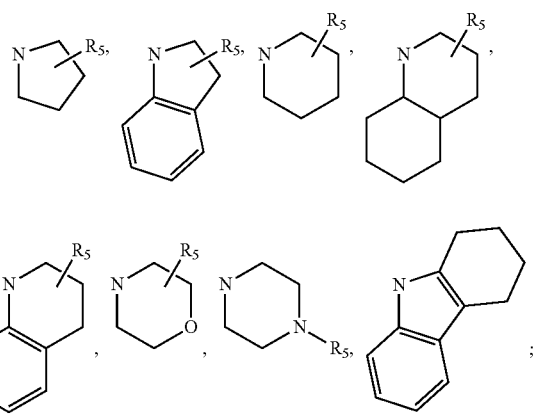

and $R_5$ is substituted or unsubstituted $C_1$-$C_6$ alkyl, substituted or unsubstituted aryl, substituted or unsubstituted heteroaryl, C(O)-(substituted or unsubstituted $C_1$-$C_6$alkyl), C(O)-(substituted or unsubstituted aryl), C(O)-(substituted or unsubstituted heteroaryl), or C(O)-(substituted or unsubstituted $C_3$-$C_8$ cycloalkyl).

2. A compound of claim 1, wherein Y is H, halogen, hydroxyl, $NR_2R_2$, substituted or unsubstituted $C_1$-$C_6$ alkyl, substituted or unsubstituted $C_1$-$C_6$ alkenyl, substituted or unsubstituted $C_1$-$C_6$ alkynyl, O-(substituted or unsubstituted $C_1$-$C_6$ alkyl), S-(substituted or unsubstituted $C_1$-$C_6$ alkyl), O-(substituted or unsubstituted aryl), O-(substituted or unsubstituted heteroaryl), S-(substituted or unsubstituted aryl), S-(substituted or unsubstituted heteroaryl), substituted or unsubstituted aryl, substituted or unsubstituted heteroaryl, cyano, $SO_2C_1$-$C_6$ alkyl, $SO_2NR_2R_2$, C(O)-(substituted or unsubstituted $C_1$-$C_6$ alkyl), C(O)-(substituted or unsubstituted aryl), or C(O)-(substituted or unsubstituted heteroaryl).

3. The compound of claim 2, wherein X is O.

4. The compound of claim 2, wherein X is $NR_2$.

5. The compound of claim 3, wherein $R_1$ is

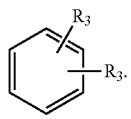

6. The compound of claim 4, wherein $R_1$ is

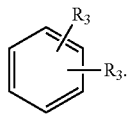

7. The compound of claim 5, wherein each occurrence of $R_3$ can be the same or different and is H, Cl, F, $OCH_3$, $CF_3$, $OCF_3$, OPh, or $OCH_2CO_2H$, and Y is H, $CF_3$, $OCF_3$, Cl, Ph, or OPh.

8. The compound of claim 6, wherein each occurrence of $R_3$ can be the same or different and is H, Cl, F, $OCH_3$, $CF_3$, $OCF_3$, OPh, or $OCH_2CO_2H$, and Y is H, $CF_3$, $OCF_3$, Cl, Ph, or OPh.

9. The compound of claim 4, wherein $R_1$ is hydrogen.

10. The compound of claim 3, wherein Y is H, Ph, Cl, $OCF_3$, or OPh.

11. The compound of claim 9, wherein Y is H, Ph, Cl, $OCF_3$, or OPh.

12. A compound of Formula C, or a pharmaceutically acceptable salt thereof,

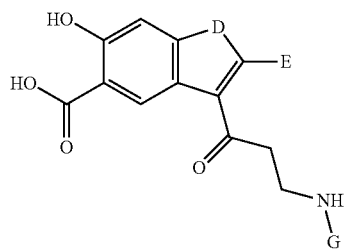

Formula C wherein D is O or $NR_8$;
$R_8$ is H or $C_1$-$C_6$ alkyl;
E is substituted or unsubstituted aryl, substituted or unsubstituted heteroaryl, or substituted or unsubstituted $C_3$-$C_8$ cycloalkyl; and
G is C(O)-(substituted or unsubstituted $C_1$-$C_6$ alkyl), C(O)-(substituted or unsubstituted $C_3$-$C_8$ cycloalkyl), C(O)-(substituted or unsubstituted $C_1$-$C_6$ alkenyl), C(O)-(substituted or unsubstituted $C_1$-$C_6$ alkynyl), C(O)-(substituted or unsubstituted aryl), or C(O)-(substituted or unsubstituted heteroaryl).

13. The compound of claim 12, wherein D is O.

14. The compound of claim 12, wherein D is $NR_8$.

15. The compound of claim 13, wherein E is cyclohexyl or

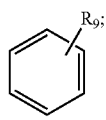

$R_9$ is H, Ph, F, $CF_3$, $OCF_3$, or OH, and G is selected from the group consisting of:

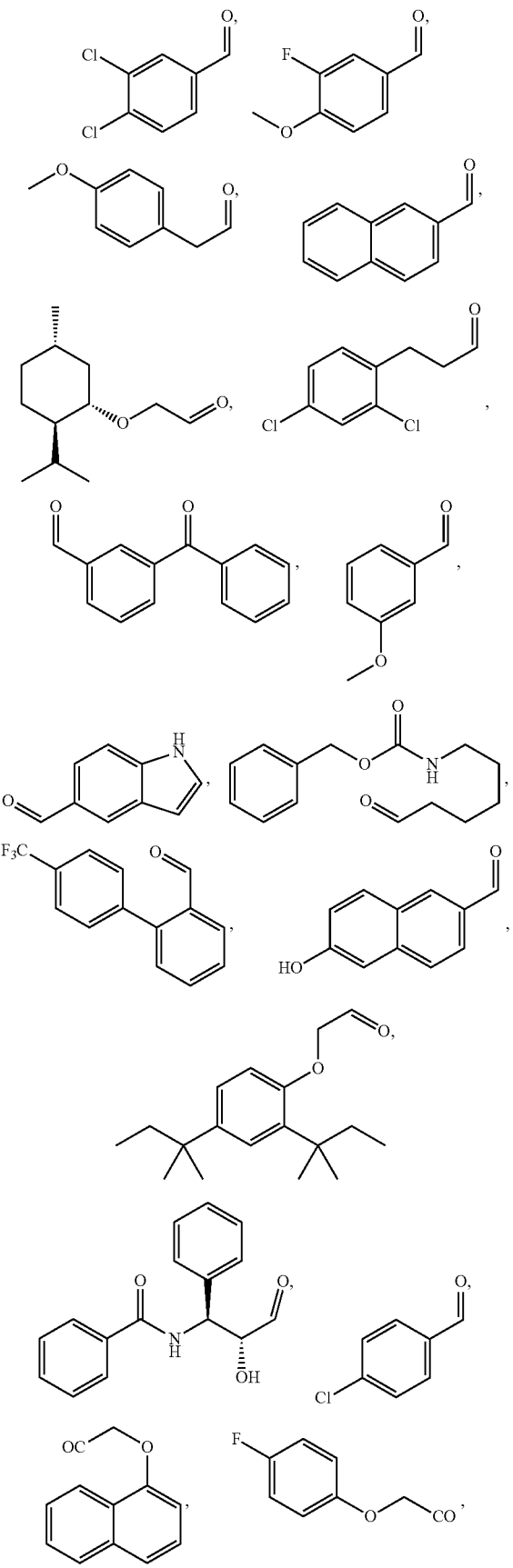

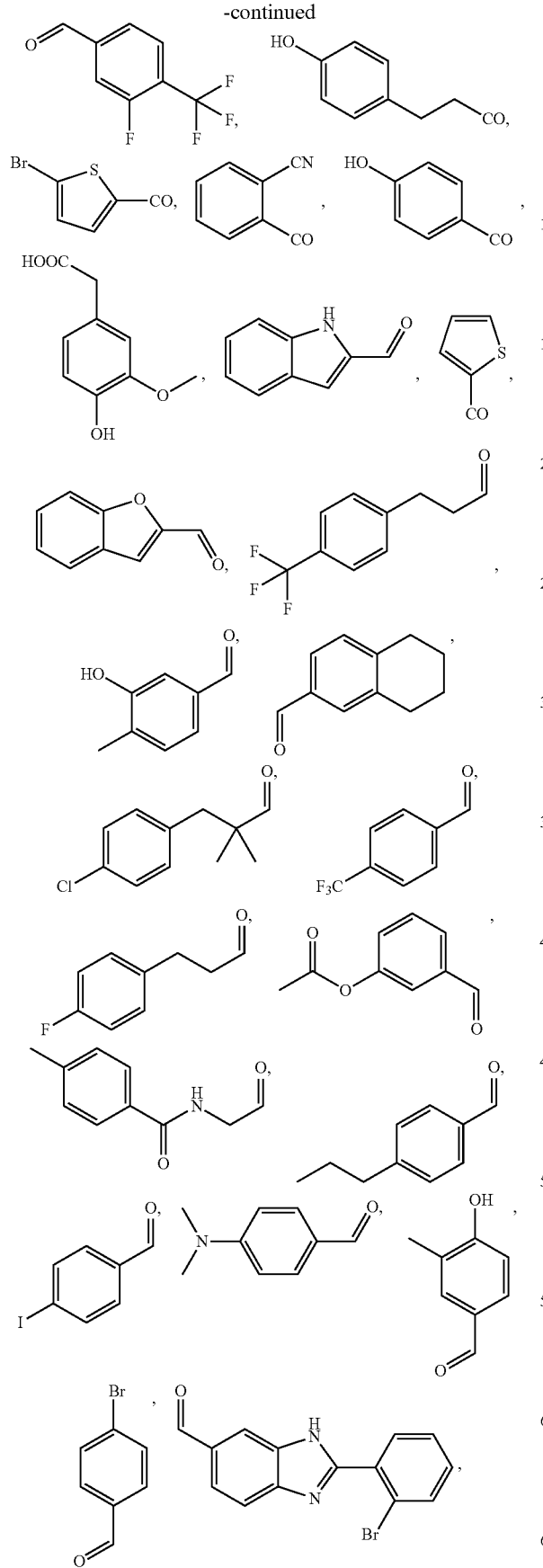
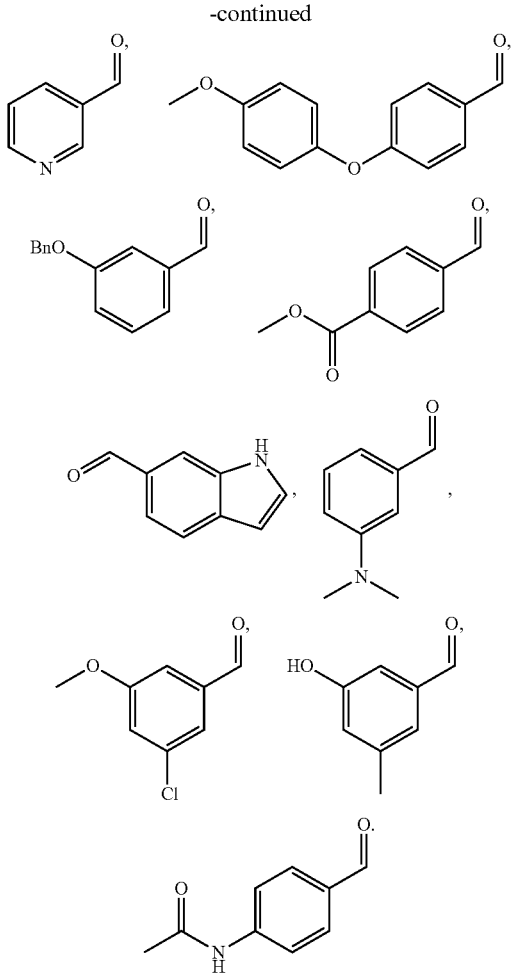
16. The compound of claim 12, wherein E is cyclohexyl or
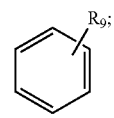
$R_9$ is H, Ph, F, $CF_3$, $OCF_3$, or OH, $NR_8$ is $CH_3$; and G is selected from the group consisting of:
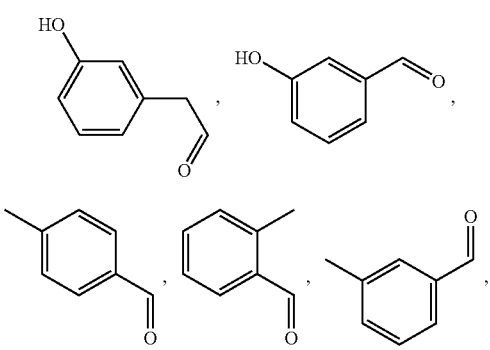

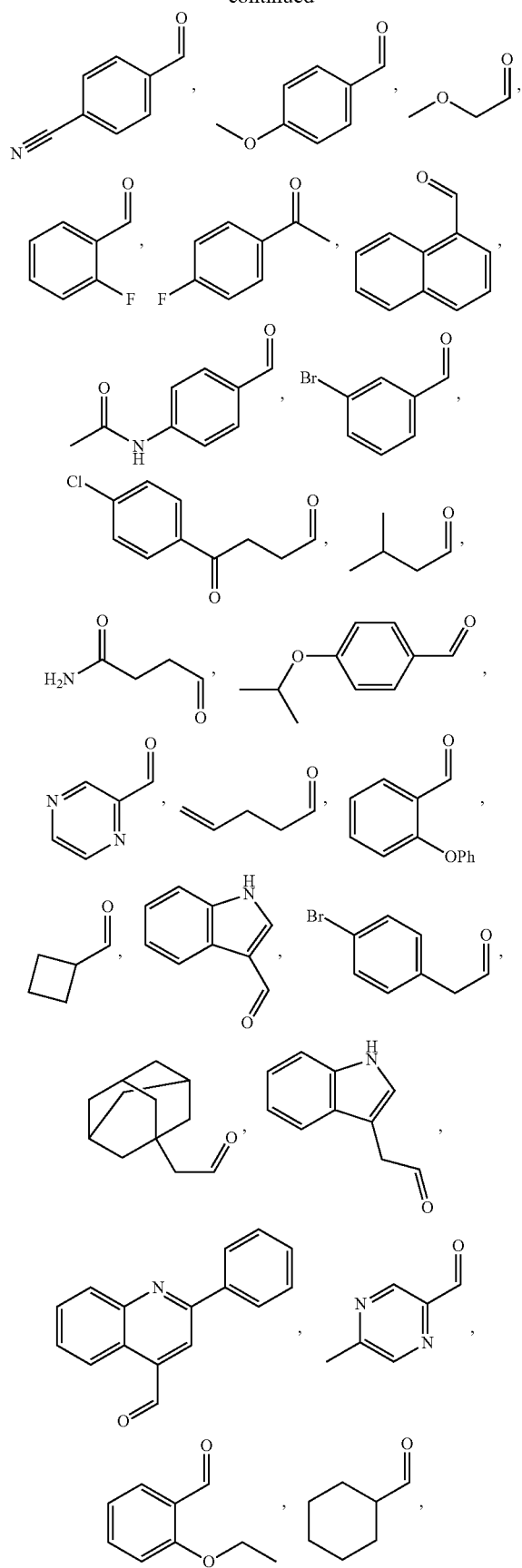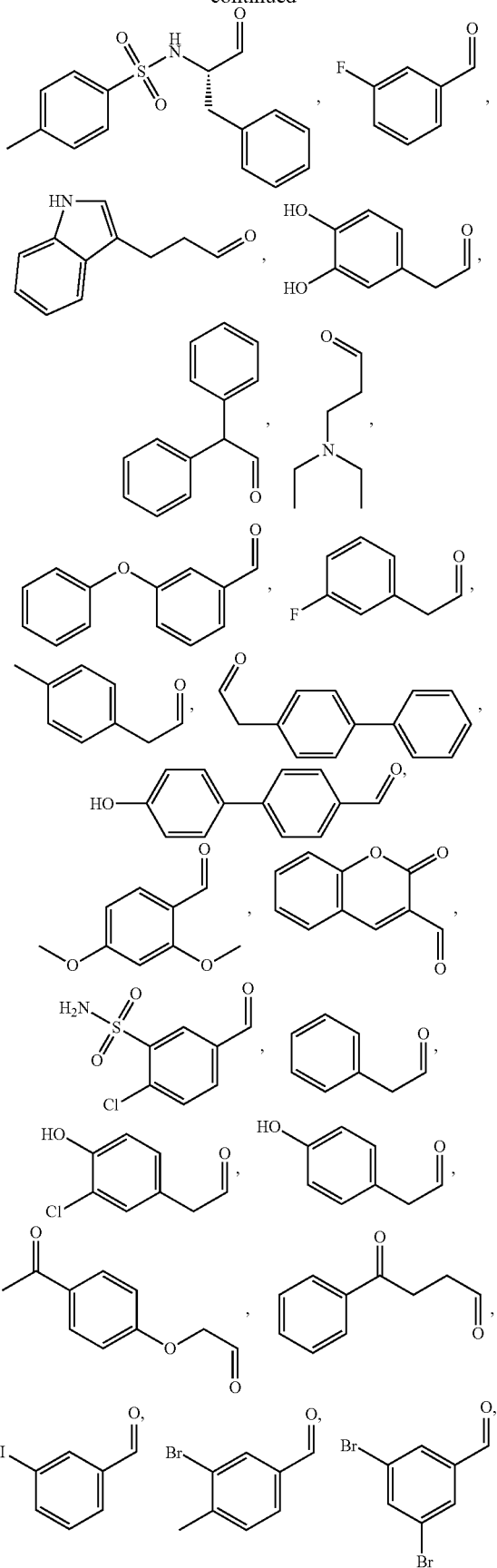

157
-continued
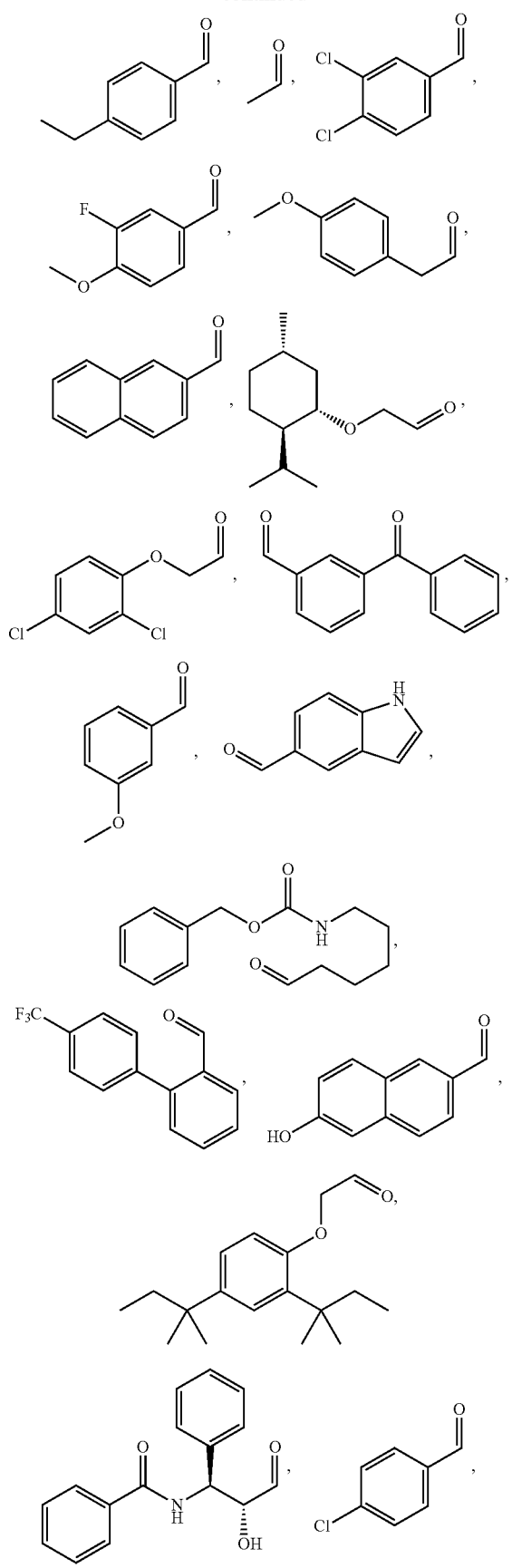
158
-continued
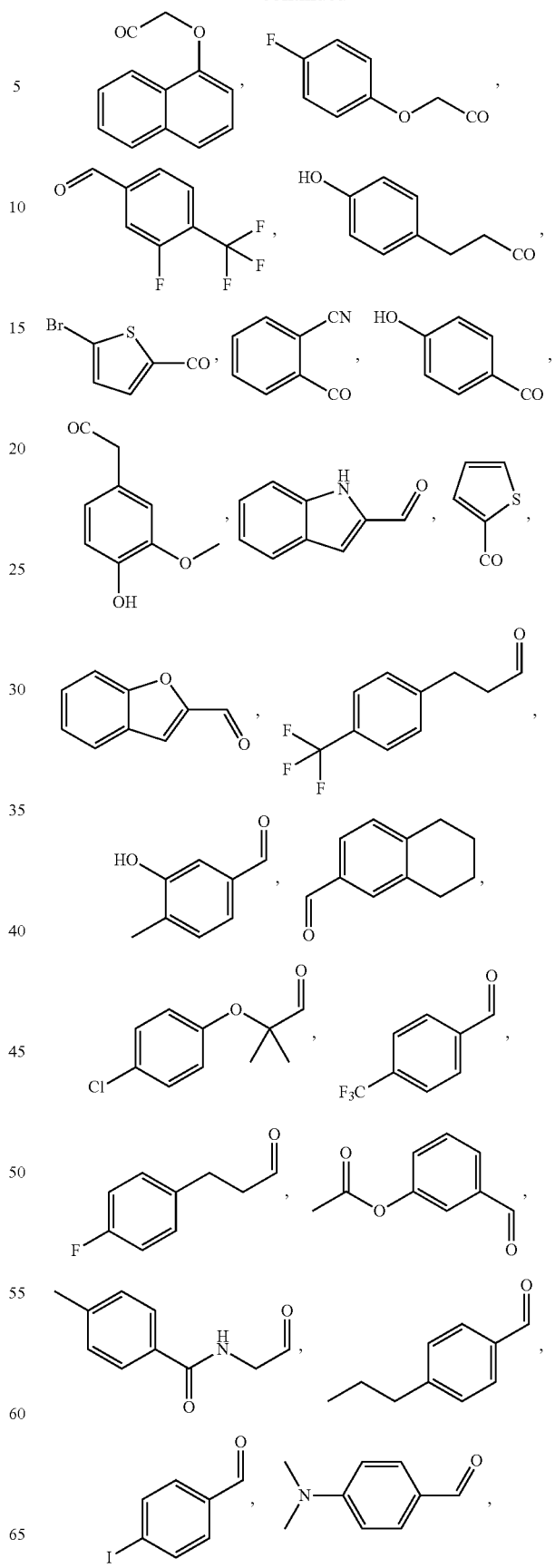

-continued

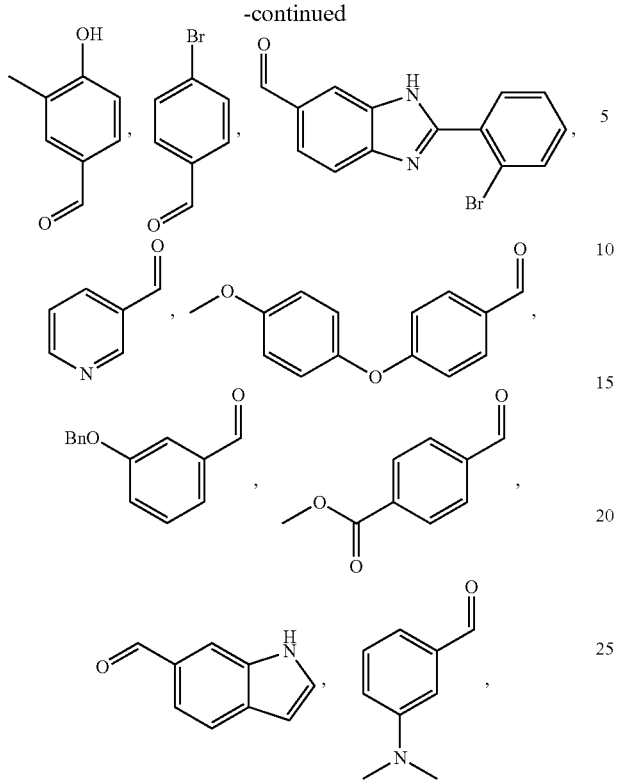

-continued

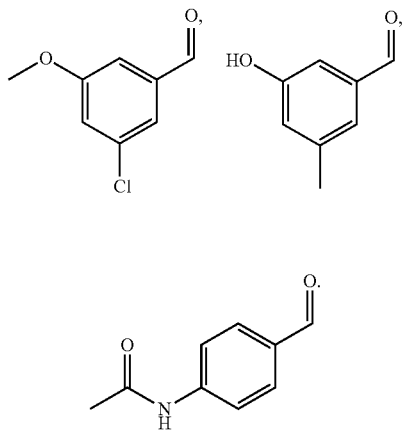

17. A method of treating a patient, comprising the step of:
administering to an individual in need thereof a therapeutically effective amount of at least one compound of claim 1 or a pharmaceutically acceptable salt thereof to a patient, where the patient has at least one disease, disorder, or condition associated with pathological activity of a protein tyrosine phosphatase wherein said disease, disorder, or condition is tuberculosis.

* * * * *